(12) United States Patent
Crawford

(10) Patent No.: US 12,297,441 B1
(45) Date of Patent: May 13, 2025

(54) **METHODS AND COMPOSITIONS FOR MODIFYING ENDOCARP STRUCTURE IN *RUBUS* PLANTS**

(71) Applicant: Pairwise Plants Services, Inc., Durham, NC (US)

(72) Inventor: Brian Charles Wilding Crawford, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 18/830,788

(22) Filed: Sep. 11, 2024

(51) Int. Cl.
*C12N 15/82* (2006.01)
*C12N 9/22* (2006.01)

(52) U.S. Cl.
CPC ........... *C12N 15/8262* (2013.01); *C12N 9/22* (2013.01); *C12N 15/8201* (2013.01); *C12N 2310/20* (2017.05)

(58) Field of Classification Search
None
See application file for complete search history.

(56) References Cited

PUBLICATIONS

Mitsuda et al. "NAC Transcription Factors, NST1 and NST3, are Key Regulators of the Formation of Secondary Walls in Woody Tissues of Arabidopsis" 2007 Plant Cell 19: 270-280. (Year: 2007).*
Mitsuda and Ohme-Takagi "NAC Transcription Factors NST1 and NST3 regulate pod shattering in a partially redundant manner by promoting secondary wall formation after the establishment of tissue identity" 2008 Plant Journal 56:768-778. (Year: 2008).*
Dai, Hongyan, et al., "Transcript Assembly and Quantification by RNA-Seq Reveals Differentially Expressed Genes between Soft-Endocarp and Hard-Endocarp Hawthorns", PLoS ONE 8(9): e72910. doi:10.1371/journal.pone.0072910, 2013.
Lyu, Xiaolong, et al., "A natural mutation of the NST1 gene arrests secondary cell wall biosynthesis in the seed coat of a hull-less pumpkin accession", Horticulture Research 9: uhac136, 2022.
Olsen, Addie Nina, et al., "NAC transcription factors: structurally distinct, functionally diverse", TRENDS in Plant Science 10(2): 79-87, 2005.
Takata, Naoki, et al., "The Arabidopsis NST3/SND1 promoter is active in secondary woody tissue in poplar", J Wood Sci 63: 396-400, 2017.

* cited by examiner

*Primary Examiner* — Matthew R Keogh
*Assistant Examiner* — Rebecca Stephens
(74) *Attorney, Agent, or Firm* — Myers Bigel, P.A.

(57) ABSTRACT

This invention relates to compositions and methods for producing *Rubus* plants exhibiting a phenotype of reduced endocarp lignification and reduced seediness or a reduced feel of seediness phenotypes through modification of endogenous NAC SECONDARY WALL THICKENING PROMOTING FACTOR1 (NST1) nucleic acids and endogenous NAC SECONDARY WALL THICKENING PROMOTING FACTOR3 (NST3) nucleic acids. The invention further relates to plants produced using the methods and compositions of the invention.

24 Claims, 2 Drawing Sheets
Specification includes a Sequence Listing.

METHODS AND COMPOSITIONS FOR MODIFYING ENDOCARP STRUCTURE IN *RUBUS* PLANTS

STATEMENT REGARDING ELECTRONIC FILING OF A SEQUENCE LISTING

A Sequence Listing in XML format, entitled 1499-153_ST26.xml, 444,433 bytes in size, generated on Sep. 4, 2024 and filed herewith, is hereby incorporated by reference into the specification for its disclosures.

FIELD OF THE INVENTION

This invention relates to compositions and methods for modifying endocarp structure in a *Rubus* plant through modification of endogenous NAC SECONDARY WALL THICKENING PROMOTING FACTOR1 (NST1) and endogenous NAC SECONDARY WAIL THICKENING PROMOTING FACTOR3 (NST3) nucleic acids. The invention further relates to plants produced using the methods and compositions of the invention.

BACKGROUND OF THE INVENTION

Fruit development normally depends on fertilization and the subsequent formation of the seed. Fruit can have hard seeds such as grapes or watermelons, or be drupes such as cherries, peaches or black raspberries. A drupe (or stone fruit) is an indehiscent fruit in which an outer fleshy part (exocarp, or skin; and mesocarp, or flesh) surrounds a single shell (the pit, stone, or pyrene) of hardened endocarp with a seed (kernel) inside. The endocarp is comprised of lignin to protect the seed. The endocarp develops from the innermost layer of the ovary. The endocarp is present in all fruit but in drupes is defined by the formation of the lignified pit which causes the sensation of 'seediness' in such plants as those from the genera of *Rubus* and *Prunus*.

Canonically, seedless fruits can develop in one of two ways: parthenocarpy and stenospermocarpy. In parthenocarpy, the fruit develops without pollination or fertilization and is desirable in fruit crops that may be difficult to pollinate or fertilize, such as fig, tomato, and summer squash. In stenospermocarpy, pollination or fertilization triggers fruit development, but the ovules or embryos abort without producing mature seeds. In *Rubus* and *Prunus*, no seedless varieties have been developed and commercially released, as it would require reduction or elimination of endocarp, as well as the enclosed seed in species with larger seeds.

The present invention overcomes the shortcomings in the art by providing improved methods and compositions for modifying plant fruit development and reduce seediness.

SUMMARY OF THE INVENTION

One aspect of the invention provides a *Rubus* plant or plant part thereof comprising at least one mutation (e.g., one or more) in at least one endogenous NAC SECONDARY WALL. THICKENING PROMOTING FACTOR1 (NST1) gene encoding a NST1 transcription factor polypeptide and at least one mutation in at least one endogenous NAC SECONDARY WALL THICKENING PROMOTING FACTOR3 (NST3) gene encoding a NST3 transcription factor polypeptide, wherein the at least one mutation in the at least one endogenous NST1 gene and/or the at least one mutation in the at least one endogenous NST3 gene is a null mutation.

A second aspect of the invention provides a method for editing a specific site in the genome of a *Rubus* plant cell, the method comprising: cleaving, in a site-specific manner, a target site within an endogenous NAC SECONDARY WALL THICKENING PROMOTING FACTOR1 (NST1) gene in the *Rubus* plant cell and a target site within an endogenous NAC SECONDARY WALL THICKENING PROMOTING FACTOR3 (NST3) gene in the *Rubus* plant cell, wherein the target site is in a region of the NST1 gene having at least 80% sequence identity to any one of the nucleotide sequences of SEQ ID NOs:84-97 or 145-171, and the target site is in a region of the NST3 gene having at least 80% sequence identity to any one of the nucleotide sequences of SEQ ID NOs:98-116 or 181-248, thereby generating an edit in the endogenous NST1 gene and in the endogenous NST3 gene of the *Rubus* plant cell and the edit results in a null mutation.

A third aspect of the invention provides a method for producing a *Rubus* plant or part thereof comprising at least one cell having a mutation in an endogenous NAC SECONDARY WALL THICKENING PROMOTING FACTOR1 (NST1) gene and a mutation in an endogenous NAC SECONDARY WALL THICKENING PROMOTING FACTOR1 (NST3) gene, the method comprising contacting a target site within the endogenous NST1 gene and a target site within the endogenous NST3 gene in the *Rubus* plant or part thereof with a nuclease comprising a cleavage domain and a nucleic acid binding domain, wherein the nucleic acid binding domain of the nuclease binds to a target site within the endogenous NST1 gene and a target site within the endogenous NST3 gene, and/or contacting a target site within the endogenous NST1 gene and a target site within the endogenous NST3 gene in the *Rubus* plant or part thereof with a first nuclease and a second nuclease each of which comprise a cleavage domain and a nucleic acid binding domain, wherein the nucleic acid binding domain of the first nuclease binds to a target site within the endogenous NST1 gene and the nucleic acid binding domain of the second nuclease binds to a target site within the endogenous NST3 gene, wherein the target site is in a region of the NST1 gene having at least 80% sequence identity to any one of the nucleotide sequences of SEQ ID NOs:84-97 or 145-171, and the target site is in a region of the NST3 gene having at least 80% sequence identity to any one of the nucleotide sequences of SEQ ID NOs:98-116 or 181-248, thereby producing a *Rubus* plant or part thereof comprising at least one cell having a mutation in the endogenous NST1 gene and in the endogenous NST3 gene, wherein the mutation in the endogenous NST1 gene and in the endogenous NST3 gene is a null mutation.

Further provided are *Rubus* plants, plant cells, and plant parts produced by the methods of the invention and comprising in their genomes at least one mutation in at least one endogenous NST1 gene and at least one mutation in at least one endogenous NST3 gene, as well as polypeptides, polynucleotides, nucleic acid constructs, expression cassettes and vectors for making a plant, plant cell, and/or plant part of this invention.

These and other aspects of the invention are set forth in more detail in the description of the invention below.

BRIEF DESCRIPTION OF THE SEQUENCES

Figure 1:
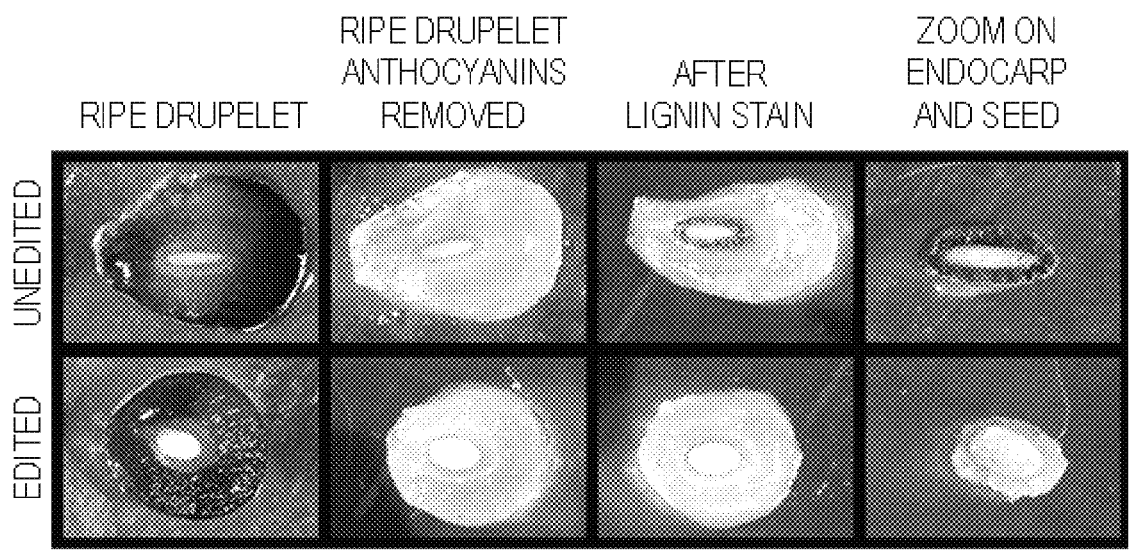
FIG. 1 provides a photograph of sectioned pits from blackberry that were exposed to phloroglucinol.

SEQ ID NOs:1-17 are exemplary Cas12a amino acid sequences useful with this invention.

SEQ ID NOs:18-20 are exemplary Cas12a nucleotide sequences useful with this invention.

SEQ ID NOs:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequence useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NOs:69, 72, 75, 256 and 258 are examples of NST1 genomic sequences.

SEQ ID NOs:70, 73, and 76 are examples of NST1 coding sequences, corresponding to genomic sequences of SEQ ID NOs:69, 72, and 75, respectively.

SEQ ID NOs:71, 74, 77, 257, 259, 274, 275, 278, and 279 are examples of NST1 polypeptide sequences.

SEQ ID NOs:78, 81, 260 and 262 are examples of NST3 genomic sequences.

SEQ ID NOs:79 and 82 are examples of NST3 coding sequences, corresponding to genomic sequences of SEQ ID NOs:78 and 81, respectively.

SEQ ID NOs:80, 83, 261, 263, 276, 277, 280 and 281 are examples of NST3 polypeptide sequences.

SEQ ID NOs:84-97 and 145-171 are example regions or portions from NST1 polynucleotides.

SEQ ID NOs:98-116 and 181-248 are example regions or portions from NST3 polynucleotides.

SEQ ID NOs:117-122 and 134-144 are example spacer sequences for nucleic acid guides useful with this invention.

SEQ ID NOs:123-129, 172-180, 264-268 and 269-273 are example regions or portions from NST1 polypeptides.

SEQ ID NOs:127, 130-133 and 249-255 are example regions or portions from NST3 polypeptides.

SEQ ID NOs:282 and 283 are example dimerization domains of NST1 and NST3 polypeptides, respectively.

DETAILED DESCRIPTION

The present invention now will be described hereinafter with reference to the accompanying examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 20%, 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In some embodiments, the reduction can result in no or essentially no (i.e., an insignificant amount, e.g., less than about 10% or even 5%) detectable activity or amount.

A "control plant" is typically the same plant as the edited plant, but the control plant has not been similarly edited and therefore is devoid of the mutation. A control plant may be an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

As used herein, the term "heterologous" refers to a nucleotide/polypeptide that originates from a foreign species, or, if from the same species, is substantially modified from its native form in composition and/or genomic locus by deliberate human intervention. A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous NST1 gene" is a NST1 gene that is naturally occurring in or endogenous to the reference organism, e.g., a plant, and may be subject to modification as described herein, after which, such a modified endogenous gene is no longer wild type. Similarly, a "wild type endogenous NST3 gene" is a NST3 gene that is naturally occurring in or endogenous to the reference organism, e.g., a plant, and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus, e.g., alternative forms of a gene that arise by mutation and are found at the same place on a chromosome.

A "recessive allele" is an allele in a gene that produces a phenotype when homozygous but the phenotype is not observable when the locus is heterozygous.

A "dominant allele" is an allele in a gene that produces a phenotype whether its paired allele is identical or different.

A "null mutation" is a mutation that results in a complete lack of production of the corresponding protein or produces a protein that is non-functional.

A "knockout mutation" is a mutation that results in a non-functional protein, but which may have a detectable transcript or protein.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypormorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wild type gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "gain-of-function" allele or mutation is a mutation that confers a new function on the encoded gene product and/or confers a new gene expression pattern. In some embodiments, a gain-of-function mutation may be dominant or semi-dominant.

As used herein, a "non-natural mutation" refers to a mutation that is generated through human intervention and differs from mutations found in the same gene that have occurred in nature (e.g., occurred naturally and not as a result of a modification made by a human).

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques Et Utilisations Des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from it's parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

A plant in which at least one (e.g., one or more, e.g., 1, 2, 3, or 4, or more) endogenous NST1 gene and at least one endogenous NST3 gene are modified as described herein (e.g., comprises a modification as described herein) may have improved or increased yield traits as compared to a plant that does not comprise (is devoid of) the modification in the at least one endogenous NST1 gene and in the at least one endogenous NST3 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, root angle, size and/or weight of root mass, or any combination thereof. In some aspects, "improved yield traits" may include, but are not limited to, increased inflorescence production, increased fruit production (e.g., increased number, weight and/or size of fruit; e.g., increased number, weight, and/or length of ears for, e.g., maize), increased fruit quality, increased number, size and/or weight of roots, and/or root angle, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous NST1 nucleic acid and/or a mutated and endogenous NST3 nucleic acid as described herein). In some aspects, improved yield traits can be expressed as quantity of grain/seed produced per area of land (e.g., bushels per acre of land). In some embodiments, a plant or part thereof comprising the at least one mutation in an endogenous NST1 gene and at least one mutation in an endogenous NST3 gene may exhibit a phenotype of improved yield traits, optionally exhibiting an increased yield (bu/acre), increased kernel size, increased kernel weight, and/or increased ear length, optionally without substantially increasing ear width, as compared to a plant that is devoid of the at least one mutation.

As used herein a "control plant" means a plant that does not contain an edited NST1 gene and/or edited NST3 gene as described herein. A control plant is used to identify and select a plant edited as described herein and that exhibits reduced endocarp lignification and reduced seediness or a reduced feel of seediness phenotypes as compared to the control plant. A suitable control plant can be a plant of the parental line used to generate a plant comprising a mutated NST1 gene and mutated NST3 gene, for example, a wild type plant devoid of an edit in an endogenous NST1 gene and/or endogenous NST3 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated NST1 gene and/or mutated NST3 gene as described herein, known as a negative segregant, or a negative isogenic line.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a NST1 gene and in a NST3 gene as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous NST1 gene and mutation in an endogenous NST3 gene as described herein relative to a plant not comprising the mutation, such as a wild type plant, or a negative segregant. In some cases, the trait modification can be evaluated quantitatively. For example, trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a plant with improved economically relevant characteristics, more specifically reduced endocarp lignification and reduced seediness or a reduced feel of seediness phenotypes. More specifically the present disclosure relates to a plant comprising a mutation(s) in a NST1 gene and a NST3 gene as described herein, wherein the plant exhibits reduced endocarp lignification and reduced seediness or a reduced feel of seediness phenotypes as compared to a control plant devoid of said mutation(s). In some embodiments, a plant of the present disclosure further exhibits an improved trait that is related to yield, including but not limited to increased nitrogen use efficiency, increased nitrogen stress tolerance, increased water use efficiency and/or increased drought tolerance, as defined and discussed infra.

Yield can be defined as the measurable product of economic value from a crop. Yield can be defined in the scope of quantity and/or quality. Yield can be directly dependent on several factors, for example, the number and size of organs (e.g., number of flowers), plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture or can occur because of modified plant architecture.

Increased yield can also manifest as increased harvest index, which is expressed as a ratio of the yield of harvestable parts, such as seeds, over the total biomass.

The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tons per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant in the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used inter-changeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the World Intellectual Property Organization (WIPO) Standard ST.26. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length (e.g., reduced by 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950 or 1000 or more nucleotides or any range or value therein) relative to a reference nucleic acid and that comprises, consists essentially of and/or consists of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild Type CRISR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment or portion may comprise, consist essentially of or consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 101, 102, 103, 104, 105, 110, 111, 112, 113, 114, 115, 120, 121, 122, 123, 124, 125, 126, 127, 128, 129, 130, 135, 140, 141, 142, 143, 144, 145, 150, 151, 152, 153, 154, 155, 160, 165, 170, 175, 176, 177, 178, 179, 180, 185, 190, 191, 192, 193, 194, 195, 200, 205, 210, 215, 216, 217, 218, 219, 220, 221, 222, 223, 224, 225, 230, 235, 240, 245, 250, 255, 256, 257, 258, 259, 260, 265, 270, 271, 272, 273, 274, 275, 280, 285, 290, 295, 300, 305, 310, 320, 330, 335, 336, 337, 338, 339, 340, 350, 360, 370, 380, 390, 395, 400, 410, 415, 420, 425, 430, 435, 440, 445, 450, 500, 550, 600, 660, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2460, 2470, 2480, 2490, 2500, 2550, or 2600, or more consecutive nucleotides or any range or value therein), of a NST1 polynucleotide (e.g., genomic DNA or coding sequence) or a NST3 polynucleotide (e.g., genomic DNA or coding sequence), optionally a fragment of a NST1 polynucleotide or a fragment of a NST3 polynucleotide may be about 20 nucleotides to about 120 nucleotides, about 20 nucleotides to about 250 nucleotides, about 20 nucleotides to about 350 nucleotides, about 100 nucleotides to about 250 nucleotides, about 100 nucleotides to about 350 nucleotides, about 150 nucleotides to about 400 nucleotides, about 60 nucleotides to about 300 nucleotides, about 60 nucleotides to about 550 nucleotides, about 60 nucleotides to about 1000 nucleotides, e.g., about 60, 80, 100, 120, 140, 160, 180, 200, 210, 220, 240, 260, 280, 300, or 350 consecutive nucleotides to about 400, 425, 450, 475, 500, 525, 550, 575, 600, 625, 650, 675, 700, 725, 750, 775, 800, 825, 850, 875, 900, 925, 950, 975, or 1000 or more consecutive nucleotides (e.g., consecutive nucleotides of any one of SEQ ID NOs:69, 70, 72, 73, 75, 76, 78, 79, 81, 82, 256, 258, 260, and/or 262, see, e.g., SEQ ID NOs:84-116, 145-171, and/or 181-248, optionally to any one of SEQ ID NOs: 84-97, 98-116, 145-171 or 181-248).

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, the polypeptide fragment comprises, consists essentially of or consists of at least about 5, 6, 7, 8, 9, 10, 11, 12, 13, 14, 15, 20, 21, 22, 23, 24, 25, 26, 27, 28, 29, 30, 35, 40, 45, 46, 47, 48, 49, 50, 55, 60, 65, 70, 75, 80, 85, 90, 95, 100, 125, 150, 175, 200, 225, 250, 300, 350, 400 or more consecutive amino acids of a reference polypeptide. In some embodiments, a fragment of a NST1 polypeptide or a fragment of a NST3 polypeptide comprises, consists essentially of or consists of at least about 5, 6, 7, 8, 9, 10, 11, 12, 13, 14, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, or 75 or more consecutive amino acids (e.g., a fragment or portion of SEQ ID NOs:71, 74, 77, 80, 83, 257, 259, 261, and/or 263).

In some embodiments, a "portion" may be related to the number of amino acids that are deleted from a polypeptide. Thus, for example, a deleted "portion" of a NST1 polypeptide or a NST3 polypeptide may comprise at least one amino acid residue (e.g., at least 1, or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more consecutive amino acid residues) deleted from the amino acid sequence of SEQ ID NOs:71, 74, 77, 80, 83, 257, 259, 261, and/or 263, (or from a sequence having at least 95% sequence identity (e.g., at least 95, 96, 97, 98, 99 or 100% identity) (e.g., at least 95% sequence identity or 100% sequence identity) to the amino acid sequence of SEQ ID NOs:71, 74, 77, 80, 83, 257, 259, 261, and/or 263) (e.g., a deletion of about 1, 2, 3, 4, 5, 6, 7, 8, 9, or 10 to about 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 295, 400, 405, 410, 415, 416, 417, 418, 419 or more residues or any range or value therein).

A "region" of a polynucleotide or a polypeptide refers to a portion of consecutive nucleotides or consecutive amino acid residues of that polynucleotide or a polypeptide, respectively. For example, a region of a NST1 polynucleotide sequence may include, but is not limited to, to any one of the nucleic acid sequences of SEQ ID NOs:84-97 and/or 145-171, optionally to any one of SEQ ID NOs:84, 85, 86, 87, 88, 89, 90, 91, 92, 93, 94, 95, 96, 97, 145, 146, 147, 148, 149, 150, 151, 152, 153, 154, 155, 156, 157, 158, 159, 160, 161, 162, 163, 164, 165, 166, 167, 168, 169, 170 and/or 171. A region of a NST3 polynucleotide sequence may include, but is not limited to, to any one of the nucleic acid sequences of SEQ ID NOs:98-116 or 181-248, optionally to any one of SEQ ID NOs:98, 99, 100, 101, 102, 103, 104, 105, 106, 107, 108, 109, 110, 111, 112, 113, 114, 115, 116, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, and/or 249. In some embodiments, a region may be a target region or target site for modification in the NST1 polynucleotide and/or NST3 polynucleotide.

In some embodiments, a "sequence-specific nucleic acid binding domain" (e.g., sequence-specific DNA binding domain) may bind to a NST1 gene (e.g., SEQ ID NOs:69, 70, 72, 73, 75, 76, 256, or 258) and/or to one or more fragments, portions, or regions of a NST1 nucleic acid (e.g., SEQ ID NOs:84-97 and/or 145-171) and/or a NST3 gene (e.g., SEQ ID NOs:78, 79, 81, 82, 260, or 262) and/or to one or more fragments, portions, or regions of a NST3 nucleic acid (e.g., SEQ ID NOs:98-116 and/or 181-248).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncated polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter than the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity; e.g., substantial complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide. In regard to a NST1 gene, a sequence may have at least 80% sequence identity to the nucleotide sequence of any one of SEQ ID NOs:69, 70, 72, 73, 75, 76, 256, and/or 258. In some embodiments, a NST1 gene may have at least 85% sequence identity to the nucleotide sequence of any one of SEQ ID NOs:69, 70, 72, 73, 75, 76, 256, and/or 258. In some embodiments, a NST1 gene may have at least 90% sequence identity to the nucleotide sequence of any one of SEQ ID NOs:69, 70, 72, 73, 75, 76, 256, and/or 258. In some embodiments, a NST1 gene may have at least 95% sequence identity (e.g., at least about 95%, 95.5%, 96%, 96.5%, 97%, 97.5%, 98%, 98.5%, 99%, 99.5%, or 100% sequence identity) to the nucleotide sequence of any one of SEQ ID NOs:69, 70, 72, 73, 75, 76, 256, and/or 258, optionally wherein the NST1 gene may have 100% sequence identity to the nucleotide sequence of any one of SEQ ID NOs:69, 70, 72, 73, 75, 76, 256, and/or 258. In regard to a NST3 gene, a sequence may have at least 80% sequence identity to the nucleotide sequence of any one of SEQ ID NOs:78, 79, 81, 82, 260, and/or 262. In some embodiments, a NST3 gene may have at least 85% sequence identity to the nucleotide sequence of any one of SEQ ID NOs:78, 79, 81, 82, 260, and/or 262. In some embodiments, a NST3 gene may have at least 90% sequence identity to the nucleotide sequence of any one of SEQ ID NOs:78, 79, 81, 82, 260, and/or 262. In some embodiments, a NST3 gene may have at least 95% sequence identity (e.g., at least about 95.5%, 96%, 96.5%, 97%, 97.5%, 98%, 98.5%, 99%, 99.5%, or 100% sequence identity) to the nucleotide sequence of any one of SEQ ID NOs:78, 79, 81, 82, 260, and/or 262, optionally wherein the NST3 gene may have 100% sequence identity to the nucleotide sequence of any one of SEQ ID NOs:78, 79, 81, 82, 260, and/or 262. A NST1 polypeptide as described herein may have at least 80% sequence identity to the polypeptide sequence of any one of SEQ ID NOs:71, 74, 77, 257, and/or 259. In some embodiments, a NST1 polypeptide may have at least 85% sequence identity to the polypeptide sequence of any one of SEQ ID NOs:71, 74, 77, 257, and/or 259. In some embodiments, a NST1 polypeptide may have at least 90% sequence identity to the polypeptide sequence of any one of SEQ ID NOs:71, 74, 77, 257, and/or 259. In some embodiments, a NST1 polypeptide may have at least 95% sequence identity (e.g., at least about 95.5%, 96%, 96.5%, 97%, 97.5%, 98%, 98.5%, 99%, 99.5%, or 100% sequence identity) to the polypeptide sequence of any one of SEQ ID NOs:71, 74, 77, 257, and/or 259, optionally wherein the NST1 polypeptide may have 100% sequence identity to the polypeptide sequence of any one of SEQ ID NOs:71, 74, 77, 257, and/or 259. A NST3 polypeptide as described herein may have at least 80% sequence identity to the polypeptide sequence of any one of SEQ ID NOs:80, 83, 261, and/or 263. In some embodiments, a NST3 polypeptide may have at least 85% sequence identity to the polypeptide sequence of any one of SEQ ID NOs:80, 83, 261, and/or 263. In some embodiments, a NST3 polypeptide may have at least 90% sequence identity to the polypeptide sequence of any one of SEQ ID NOs:80, 83, 261, and/or 263. In some embodiments, a NST3 polypeptide may have at least 95% sequence identity (e.g., at least about 95.5%, 96%, 96.5%, 97%, 97.5%, 98%, 98.5%, 99%, 99.5%, or 100% sequence identity) to the polypeptide sequence of any one of SEQ ID NOs:80, 83, 261, and/or 263, optionally wherein the NST3 polypeptide may have 100% sequence identity to the polypeptide sequence of any one of SEQ ID NOs:80, 83, 261, and/or 263. With regard to regions or portions of a NST1 gene, the region or portion may have at least 80% sequence identity to the nucleotide sequence of any one of SEQ ID NOs:84-97 and/or 145-171. In some embodiments, a region or portion of a NST1 gene may have at least 85% sequence identity to the nucleotide sequence of any one of SEQ ID NOs:84-97 and/or 145-171. In some embodiments, a region or portion of a NST1 gene may have at least 90% sequence identity to the nucleotide sequence of any one of SEQ ID NOs:84-97 and/or 145-171. In some embodiments, a region or portion of a NST1 gene may have at least 95% sequence identity (e.g., at least about 95.5%, 96%, 96.5%, 97%, 97.5%, 98%, 98.5%, 99%, 99.5%, or 100% sequence identity) to the nucleotide sequence of any one of SEQ ID NOs:84-97 and/or 145-171, optionally wherein the region or portion of a NST1 gene may have 100% sequence identity to the nucleotide sequence of any one of SEQ ID NOs:84-97 and/or 145-171. With regard to regions or portions of a NST3 gene, the region or portion may have at least 80% sequence identity to the nucleotide sequence of any one of SEQ ID NOs:98-116 and/or 181-248. In some embodiments, a region or portion of a NST3 gene may have at least 85% sequence identity to the nucleotide sequence of any one of SEQ ID NOs:98-116 and/or 181-248. In some embodiments, a region or portion of a NST3 gene may have at least 90% sequence identity to the nucleotide sequence of any one of SEQ ID NOs:98-116 and/or 181-248. In some embodiments, a region or portion of a NST3 gene may have at least 95% sequence identity (e.g., at least about 95.5%, 96%, 96.5%, 97%, 97.5%, 98%, 98.5%, 99%, 99.5%, or 100% sequence identity) to the nucleotide sequence of any one of SEQ ID NOs:98-116 and/or 181-248, optionally wherein the region or portion of a NST3 gene may have 100% sequence identity to the nucleotide sequence of any one of SEQ ID NOs:98-116 and/or 181-248. With regard to regions or portions of a NST1 polypeptide, the region or portion may have at least 80% sequence identity to the polypeptide sequence of any one of SEQ ID NOs:123-129, 172-180, 264-273, and/or 282, optionally to the polypeptide sequence of any one of SEQ ID NOs:123-127, 128, 129, 172-179, 180, 264-268 269-273, and/or 282. In some embodiments, a region or portion of a NST1 polypeptide may have at least 85% sequence identity to the amino acid sequence of any one of SEQ ID NOs: 123-129, 172-180, 264-273, and/or 282, optionally to the polypeptide sequence of any one of SEQ ID NOs:123-127, 128, 129, 172-179, 180, 264-268, 269-273, and/or 282. In some embodiments, a region or portion of a NST1 polypeptide may have at least 90% sequence identity to the amino acid sequence of any one of SEQ ID NOs:123-129, 172-180, 264-273, and/or 282, optionally to the polypeptide sequence of any one of SEQ ID NOs:123-127, 128, 129, 172-179, 180, 264-268, 269-273, and/or 282. In some embodiments, a region or portion of a NST1 polypeptide may have at least 95% sequence identity (e.g., at least about 95.5%, 96%, 96.5%, 97%, 97.5%, 98%, 98.5%, 99%, 99.5%, or 100% sequence identity) to the amino acid sequence of any one of SEQ ID NOs:123-129, 172-180, 264-273, and/or 282, optionally to the polypeptide sequence of any one of SEQ ID NOs:123-127, 128, 129, 172-179, 180, 264-268, 269-273, and/or 282. In some embodiments, a region or portion of a NST1 polypeptide may have at least 100% sequence identity to the amino acid sequence of any one of SEQ ID NOs: 123-129, 172-180, 264-273, and/or 282, optionally to the polypeptide sequence of any one of SEQ ID NOs:123-127, 128, 129, 172-179, 180, 264-268, 269-273, and/or 282. With regard to regions or portions of a NST3 polypeptide, the region or portion may have at least 80% sequence identity to the polypeptide sequence of any one of SEQ ID NOs:127, 130-133, 249-255, and/or 283, optionally to the polypeptide sequence of any one of SEQ ID NOs:127, 130-133, 249-253, 254-255, and/or 283. In some embodiments, a region or portion of a NST3 polypeptide may have at least 85% sequence identity to the amino acid sequence of any one of SEQ ID NOs:127, 130-133, 249-255, and/or 283, optionally to the polypeptide sequence of any one of SEQ ID NOs:127, 130-133, 249-253, 254-255, and/or 283. In some embodiments, a region or portion of a NST3 polypeptide may have at least 90% sequence identity to the amino acid sequence of any one of SEQ ID NOs:127, 130-133, 249-255, and/or 283, optionally to the polypeptide sequence of any one of SEQ ID NOs:127, 130-133, 249-253, 254-255, and/or 283. In some embodiments, a region or portion of a NST3 polypeptide may have at least 95% sequence identity (e.g., at least about 95.5%, 96%, 96.5%, 97%, 97.5%, 98%, 98.5%, 99%, 99.5%, or 100% sequence identity) to the amino acid sequence of any one of SEQ ID NOs:127, 130-133, 249-255, and/or 283, optionally to the polypeptide sequence of any one of SEQ ID NOs:127, 130-133, 249-253, 254-255, and/or 283. In some embodiments, a region or portion of a NST3 polypeptide may have at least 100% sequence identity to the amino acid sequence of any one of SEQ ID NOs:127, 130-133, 249-255, and/or 283, optionally to the polypeptide sequence of any one of SEQ ID NOs:127, 130-133, 249-253, 254-255, and/or 283.

As used herein, the phrase "substantially identical," or "substantial identity" in the context of two nucleic acid molecules, nucleotide sequences or polypeptide sequences, refers to two or more sequences or subsequences that have at least about 95.5%, 96%, 96.5%, 97%, 97.5%, 98%, 98.5%, 99%, 99.5%, or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more nucleotides in length, and any range therein, up to the full length of the sequence. In some embodiments, nucleotide sequences can be substantially identical over at least about 20 consecutive nucleotides (e.g., about 20, 21, 22, 23, 24, 25, 26, 27, 28, 29, 30, 31, 32, 33, 34, 35, 36, 37, 38, 39, 40, 50, 60, 70, 80, 90, 100, 200, 300, 400, 500, 600, 700, 800, 900, 1000, 1100, 1200, 1300, 1400, 1500, 1600, 1700, 1800, 1900, 2000, 2100, 2200, 2300 or more nucleotides). In some embodiments, two or more NST1 genes or two or more NST3 may be substantially identical to one another over at least about 30 or more consecutive nucleotides (e.g., 30, 31, 32, 33, 34, 35, 36, 37, 38, 39, 40, 41, 42, 43, 44, 45, 46, 47, 48, 49, 50, 51, 52, 53, 54, 54, 56, 57, 58, 59, 60, 65, 70, 75, 80, 85, 90, 95, 100, 110, 120, 130, 140, 150, 160, 170, 180, 200, 220, 240, 260, 280, 300, 320, 340, 360, 380, 400, 420, 440, 460, 480, 500, 520, 540, 560, 580, 600, or more consecutive nucleotides) of any one SEQ ID NOs:69, 70, 72, 73, 75, 76, 78, 79, 81, 82, 256, 258, 260, and/or 262 (see, e.g., SEQ ID NOs:84-116, 145-171, and/or 181-248, optionally SEQ ID NOs:84-97, 98-116, 145-171 and/or 181-248).

In some embodiments of the invention, the substantial identity exists over a region of consecutive amino acid residues of a polypeptide of the invention that is about 3 amino acid residues to about 20 amino acid residues, about 5 amino acid residues to about 10 amino acid residues, about 5 amino acid residues to about 55 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8, 9, 10, 11, 12, 13, 14, or more consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 275, 300, 325, 350, 400, 450, 500, or more amino acids in length or more consecutive amino acid residues). In some embodiments, two or more NST1 polypeptides or two or more NST3 polypeptides may be substantially identical to one another over at least about 10 to about 150 (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145 or 150 residues or more) consecutive amino acid residues of SEQ ID NOs:71, 74, 77, 80, 83, 257, 259, 261, and/or 263 (see, e.g., SEQ ID NOs:123-133, 172-180, 249-255, 264-273, 282 and/or 283). In some embodiments, a substantially identical nucleotide or protein sequence may perform substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

A polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron) (see, e.g., SEQ ID NO:21 and SEQ ID NO:22).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a DNA binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140, 150 or more amino acids in length). In some embodiments, a peptide linker may be a Gly-Ser linker.

In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon (1981) *Annu. Rev. Biochem.* 50:349). In plants, the CAAT box may be substituted by the AGGA box (Messing et al., (1983) in Genetic *Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RuBisCO small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. (2005) *Plant Cell Rep.* 23:727-735; Li et al. (2007) Gene 403:132-142; Li et al. (2010) *Mol Biol. Rep.* 37:1143-1154). PrbcS1 and Pactin are constitutive promoters and Pnr and Pdca1 are inducible promoters. Pnr is induced by nitrate and repressed by ammonium (Li et al. (2007) Gene 403:132-142) and Pdca1 is induced by salt (Li et al. (2010) *Mol Biol. Rep.* 37:1143-1154). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al. (1991) *Plant Science* 79: 87-94), maize (Christensen et al. (1989) *Plant Molec. Biol.* 12: 619-632), and *Arabidopsis* (Norris et al. (1993) *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. ((1991) *Mol. Gen. Genet.* 231: 150-160) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula (1989) *Plant Molec. Biol.* 12:579-589). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf, or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond ((1991) *FEBS* 290:103-106; EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. (2015) *Plant Biotechnol. Reports* 9(5):297-306), ZmSTK2_USP from maize (Wang et al. (2017) *Genome* 60(6):485-495), LAT52 and LAT59 from tomato (Twell et al. (1990) *Development* 109(3):705-713), Zm13 (U.S. Pat. No. 10,421,972), PLA$_2$-δ promoter from *Arabidopsis* (U.S. Pat. No. 7,141,424), and/or the ZmC5 promoter from maize (International PCT Publication No. WO1999/042587).

Additional examples of plant tissue-specific/tissue preferred promoters include, but are not limited to, the root hair-specific cis-elements (RHEs) (Kim et al. (2006) *The Plant Cell* 18:2958-2970), the root-specific promoters RCc3 (Jeong et al. (2010) *Plant Physiol.* 153:185-197) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-rnethionine synthetase (SAMS) (Vander Mijnsbrugge et al. (1996) *Plant and Cell Physiology* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: Genetic *Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989) supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain (e.g., sequence-specific DNA binding domain), a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific DNA binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific DNA binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered, or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited to, a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g., higher plant, mammalian, yeast, or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific DNA binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific DNA binding protein, the reverse transcriptase and the deaminase are expressed and the sequence-specific DNA binding protein binds to the target nucleic acid, and the reverse transcriptase and/or deaminase may be fused to either the sequence-specific DNA binding protein or recruited to the sequence-specific DNA binding protein (via, for example, a peptide tag fused to the sequence-specific DNA binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment. As described herein, a target nucleic acid may also be contacted with an RNAi molecule designed for reducing expression of the target gene, e.g., NST1 and NST3.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

As used herein, the terms "adjacent to Exon 1" and "adjacent to Exon 3" means within about 1 nucleotide to about 50 consecutive nucleotides from the 5' end or 3' end of Exon 1 or Exon 3 of the NTS1 or NTS3 gene (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, or 50 or more consecutive nucleotides from the 5' end or 3' end of Exon 1 or Exon 3 of the NTS1 or NTS3 gene, optionally about 1 nucleotide to about 112 consecutive nucleotides from the 5' or 3' end the NTS1 or NTS3 gene, optionally about 1, 5, 12, 13, 20, 22, 32, 45, 48, 52, 60, 68, 72, 100, 108, or 112 consecutive nucleotides from the 5' end or 3' end of Exon 1 or Exon 3 of the NTS1 or NTS3 gene).

The term "regulating" as used in the context of a transcription factor "regulating" a phenotype, for example, a response to illumination (e.g., a light response, e.g., a shade avoidance response), means the ability of the transcription factor to affect the expression of a gene or genes such that a phenotype, for instance, a response to illumination, is modified.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. (2013) *Nat. Biotechnol.* 31:233-239; Ran et al. (2013) *Nature Protocols* 8:2281-2308). General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska ((2002) *Cell. Mol. Biol.* Lett. 7:849-858).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior of the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention is directed to *Rubus* plants and the production of *Rubus* plants having fruit with reduced endocarp lignification and reduced seediness or a reduced feel of seediness. The development of fruit normally depends on fertilization and the subsequent formation of the seed. Many fruits have large, hard seeds which create an impediment to eating the fruit, with examples ranging from seeded grapes, apples, cherries, and peaches. For some fruits, seedless varieties have been developed which have altered development of the seed after pollination. In examples such as grape and watermelon, the result is often a seed remnant, which is smaller and softer than in seeded varieties, and in some cases this seed remnant is not detected by consumers. The fruit of *Rubus* plants is structurally similar to a stone fruit, which are botanically classified as drupes. A drupe is an indehiscent fruit in which an outer fleshy part (exocarp or skin, and mesocarp or flesh) surrounds a single shell (the pit, stone, or pyrene) of hardened endocarp with a seed (kernel) inside. The endocarp is comprised of lignin to protect the seed. The endocarp develops from the innermost layer of the ovary. The perception of seediness in drupes is caused by the presence of the endocarp-derived pit that encloses the seed. In *Rubus*, each ovary develops as a "drupelet" with a lignified endocarp containing a single seed, and the blackberry is an aggregate fruit made of many drupelets. Therefore, blackberries can have substantial seed content, with each fruit containing 40 or more pyrenes, and this is unacceptable to some consumers. Consequently, seedlessness and/or reduced feeling of 'seediness' in fruit is a desirable trait to consumers.

The feel of the seeds in the mouth is very important and blackberry cultivars having low levels of seediness are desired. The present invention addresses the issue of reducing the feeling of 'seediness' in fruit by mutating NST1 and NST3 genes in *Rubus* sp. Mutating these genes is believed to reduce or remove the endocarp layer and therefore reduce the feeling of 'seediness.'

Accordingly, the present invention provides a plant or part thereof comprising at least one mutation (e.g., one or more) in at least one endogenous NAC SECONDARY WALL THICKENING PROMOTING FACTOR1 (NST1) gene encoding a NST1 transcription factor polypeptide and at least one mutation in at least one endogenous NAC SECONDARY WALL THICKENING PROMOTING FACTOR3 (NST3) gene encoding a NST3 transcription factor polypeptide, wherein the at least one mutation in the at least one endogenous NST1 gene and/or the at least one mutation in the at least one endogenous NST3 gene is a null mutation. In some embodiments, the null mutation is a knockout mutation. In some embodiments, the null mutation results in the production of a truncated polypeptide. In some embodiments, the null mutation results in the production of a non-functional or no NST1 polypeptide and/or a non-functional or no NST3 polypeptide. In some embodiments, the at least one mutation in the at least one endogenous NST1 gene results in a mutation in a dimerization domain (located in Exon 1) and/or transactivating domain (located in Exon 3) of the NST1 transcription factor polypeptide and/or the at least one mutation in the at least one endogenous NST3 gene results in a mutation in a dimerization domain (located in Exon 1) and/or transactivating domain (located in Exon 3) of the NST3 transcription factor polypeptide. In some embodiments, the mutation in the dimerization domain results in a non-functional polypeptide that is unable to dimerize (e.g., unable to dimerize with other NTS polypeptides). In some embodiments, the dimerization domain of the NST1 polypeptide comprises a sequence of VPPGFRFHPTEEELLQYYL (SEQ ID NO:282) and the dimerization domain of the NST3 polypeptide comprises a sequence of VPPGFRFHPTEEELLHYYL (SEQ ID NO:283).

In some embodiments, an endogenous NST1 gene useful with this invention: (a) comprises a sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to the nucleotide sequence of any one of SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to any one of the nucleotide sequences of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) encodes a region having at least 80% identity to the amino acid sequence of SEQ ID NOs:123-129, 172-180, 264-273, and/or 282, optionally wherein the sequence identity of (a), (b), (c) and/or (d) may be at least 85%, or at least 90%, or it may be at least 95%, 95.5%, 96%, 96.5%, 97%, 97.5%, 98%, 98.5%, 99%, or 99.5%, optionally the sequence identity may be 100%; and wherein the endogenous gene encoding an NST3 transcription factor polypeptide: (a) comprises a nucleotide sequence having at least 80% sequence identity to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or encodes a region having at least 80% identity to the amino acid sequence of SEQ ID NOs:127, 130-133, 249-255, and/or 283, optionally wherein the sequence identity of (a), (b), (c) and/or (d) may be at least 85%, or at least 90%, or it may be at least 95%, 95.5%, 96%, 96.5%, 97%, 97.5%, 98%, 98.5%, 99%, or 99.5%, optionally the sequence identity may be 100%. Thus, a plant or plant part of the invention may comprise at least one mutation (e.g., one or more mutations) in an endogenous NST1 gene and/or NST3 gene, optionally wherein the mutation increases the expression of the NST1 gene and/or NST3, wherein the endogenous NST1 gene (a) comprises a sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to the nucleotide sequence of any one of SEQ ID NOs:69, 70, 72, 73, 75, 76, 256, and/or 258; (b) comprises a region having at least 80% sequence identity to any one of the nucleotide sequences of any one of SEQ ID NOs:84-97 and/or 145-17; (c) encodes a polypeptide comprising a sequence having at least 80% sequence identity to any one of the amino acid sequences of SEQ ID NO:71, SEQ ID NO:74, SEQ ID NO:77, SEQ ID NO:257 and/or SEQ ID NO:259; and/or (d) encodes a region having at least 80% identity to the amino acid sequence of SEQ ID NOs:123-129, 172-180, 264-273, and/or 282, optionally wherein the sequence identity of (a), (b), (c) and/or (d) may be at least 85%, or at least 90%, or it may be at least 95%, 95.5%, 96%, 96.5%, 97%, 97.5%, 98%, 98.5%, 99%, or 99.5%, optionally the sequence identity may be 100%, and wherein the endogenous gene encoding an NST3 transcription factor polypeptide: (a) comprises a nucleotide sequence having at least 80% sequence identity to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or encodes a region having at least 80% identity to the amino acid sequence of SEQ ID NOs:127, 130-133, 249-255, and/or 283, optionally wherein the sequence identity of (a), (b), (c) and/or (d) may be at least 85%, or at least 90%, or it may be at least 95%, 95.5%, 96%, 96.5%, 97%, 97.5%, 98%, 98.5%, 99%, or 99.5%, optionally the sequence identity may be 100%.

In some embodiments, an endogenous NST1 gene useful with this invention encodes a NST1 transcription factor polypeptide having the amino acid sequence of SEQ ID NO:279, optionally SEQ ID NO:274, SEQ ID NO:275 or SEQ ID NO:278. In some embodiments, an endogenous NST3 gene useful with this invention encodes a NST3 transcription factor polypeptide having the amino acid sequence of SEQ ID NO:281, optionally SEQ ID NO:276, SEQ ID NO:277 or SEQ ID NO:280.

A mutation in at least one endogenous NST1 gene and/or at least one endogenous NST3 gene in a plant may be any type of mutation including, but not limited to, a base substitution, a base deletion and/or a base insertion. In some embodiments, a mutation in at least one endogenous NST1 gene and/or a mutation in at least one endogenous NST3 gene may comprise a base substitution to an A, a T, a G, or a C. In some embodiments, a mutation useful with the invention is a non-natural mutation. In some embodiments, a NST1 gene may comprise one or more mutations (e.g., 1, 2, 3, 4, 5, 6, 7, 8, 9 or 10 or more).

In some embodiments, a mutation in at least one endogenous NST1 gene and/or at least one endogenous NST3 gene may be at least one mutation located in and/or adjacent to the first exon of the endogenous NST1 gene encoding a NST1 transcription factor polypeptide and/or at least one mutation located in and/or adjacent to the first exon of the endogenous NST3 gene encoding a NST3 transcription factor polypeptide. In some embodiments, the at least one mutation is located in the 5' region of the first exon of the endogenous NST1 gene and/or is located in the 5' region of the first exon of the endogenous NST3 gene, optionally wherein the first exon of the endogenous NST1 gene comprises a nucleotide sequence having at least 95% sequence identity (e.g., about 95%, 96%, 97%, 98%, 99% or 100% sequence identity) to SEQ ID NO:84 or SEQ ID NO:92 and/or the first exon of the endogenous NST3 gene comprises a nucleotide sequence having at least 95% sequence identity (e.g., about 95%, 96%, 97%, 98%, 99% or 100% sequence identity) to SEQ ID NO:98 or SEQ ID NO:110. In some embodiments, the 5' region of the first exon of the endogenous NST1 gene comprises a nucleotide sequence having at least about 95% sequence identity (e.g., about 95%, 96%, 97%, 98%, 99% or 100% sequence identity) to any one of SEQ ID NOs:85-91, 96 or 97 and/or the 5' region of the first exon of the endogenous NST3 gene comprises a nucleotide sequence having at least 95% sequence identity (e.g., about 95%, 96%, 97%, 98%, 99% or 100% sequence identity) to any one of SEQ ID NOs:101-104, 107-109, 112, 113, or 116. In some embodiments, the at least one mutation is located in and/or adjacent to the 5' region of the first exon of the endogenous NST1 gene and/or is located in and/or adjacent to the 5' region of the first exon of the endogenous NST3 gene, optionally wherein the location in and/or adjacent to the first exon of the endogenous NST1 gene comprises a nucleotide sequence having at least 95% sequence identity (e.g., about 95%, 96%, 97%, 98%, 99% or 100% sequence identity) to any one of SEQ ID NOs:85-97 and/or the location in and/or adjacent to the first exon of the endogenous NST3 gene comprises a nucleotide sequence having at least 95% sequence identity (e.g., about 95%, 96%, 97%, 98%, 99% or 100% sequence identity) to any one of SEQ ID NOs:98-116.

In some embodiments, a mutation in at least one endogenous NST1 gene and/or a mutation in at least one endogenous NST3 gene may be at least one mutation that is located in and/or adjacent to the third exon of the endogenous NST1 gene encoding a NST1 transcription factor polypeptide and/or may be at least one mutation that is located in and/or adjacent to the third exon of the endogenous NST3 gene encoding a NST3 transcription factor polypeptide. In some embodiments, the at least one mutation may be located in and/or adjacent to the 5' region of the third exon of the endogenous NST1 gene and/or may be located in and/or adjacent to the 5' region of the third exon of the endogenous NST3 gene, optionally wherein the third exon of the endogenous NST1 gene comprises a nucleotide sequence (e.g., a region) having at least 95% sequence identity (e.g., about 95%, 96%, 97%, 98%, 99% or 100% sequence identity) to any one of SEQ ID NOs:146-149, 152-161, 163-165, or 167-171 and/or the third exon of the endogenous NST3 gene comprises a nucleotide sequence (e.g., a region) having at least 95% sequence identity (e.g., about 95%, 96%, 97%, 98%, 99% or 100% sequence identity) to any one of SEQ ID NOs:185-188, 198-200, 202-204, 206-220, 225-228, 239, or 241-248. In some embodiments, the at least one mutation may be located in the 5' region of the third exon of the endogenous NST1 gene and/or may be located in the 5' region of the third exon of the endogenous NST3 gene, optionally wherein the 5' region of the third exon of the endogenous NST1 gene comprises a nucleotide sequence having at least 95% sequence identity (e.g., about 95%, 96%, 97%, 98%, 99% or 100% sequence identity) to any one of SEQ ID NOs:146-149, 151-161, 163-165, or 167-171 and/or the 5' region of the third exon of the endogenous NST3 gene comprises a nucleotide sequence having at least 95% sequence identity (e.g., about 95%, 96%, 97%, 98%, 99% or 100% sequence identity) to any one of SEQ ID NOs:184-188, 198-200, 202-204, 206-220, 225-228, 239, or 241-248. In some embodiments, the at least one mutation may be located in and/or adjacent to the third exon of the endogenous NST1 gene comprising a nucleotide sequence having at least 95% sequence identity (e.g., about 95%, 96%, 97%, 98%, 99% or 100% sequence identity) to any one of SEQ ID NOs:145-170 and/or may be located in and/or adjacent to the third exon of the endogenous NST3 gene comprising a nucleotide sequence having at least 95% sequence identity (e.g., about 95%, 96%, 97%, 98%, 99% or 100% sequence identity) to any one of SEQ ID NOs:183-188, 191, 192, 195, 196-220, 223-228, 231, 232, or 235-248.

In some embodiments, the endogenous NST1 gene encodes the amino acid sequence of SEQ ID NO:279 and the endogenous NST3 gene encodes the amino acid sequence of SEQ ID NO:281. In some embodiments, the endogenous NST1 gene encodes the amino acid sequence of SEQ ID NO:278 and the endogenous NST3 gene encodes the amino acid sequence of SEQ ID NO:280. In some embodiments, the endogenous NST1 gene encodes the amino acid sequence of SEQ ID NO:274 or SEQ ID NO:275 and the endogenous NST3 gene encodes the amino acid sequence of SEQ ID NO:276 or SEQ ID NO:277. In some embodiments, the endogenous NST1 gene encodes an amino acid sequence having at least 95% sequence identity (e.g., about 95%, 95.5%, 96%, 96.5%, 97%, 97.5%, 98%, 98.5%, 99%, 99.5%, or 100% sequence identity) to SEQ ID NO:71 and/or the endogenous NST3 gene encodes an amino acid sequence having at least 95% sequence identity (e.g., about 95%, 95.5%, 96%, 96.5%, 97%, 97.5%, 98%, 98.5%, 99%, 99.5%, or 100% sequence identity) to SEQ ID NO:80.

In some embodiments, the mutation of the invention is a base deletion. In some embodiments, the mutation of the invention is a base insertion. In some embodiments, the base deletion and/or base insertion may be an insertion or deletion of one to about 200 consecutive base pairs (e.g., a deletion or insertion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, 145, 150, 155, 160, 165, 170, 175, 180, 185, 190, 195 or 200 consecutive base pairs or any range or value therein), optionally a deletion or insertion of 1 base pair to about 100 consecutive base pairs (e.g., a deletion or insertion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive base pairs or any range or value therein), or a deletion or insertion of 1 base pair to about 45 consecutive base pairs (e.g., a deletion or insertion of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 base pairs, or any range or value therein). In some embodiments, a mutation in an endogenous NST1 gene and/or an endogenous NST3 gene may be a deletion of 1 base pair to about 45 consecutive base pairs, optionally a deletion of about 5 to about 30 consecutive base pairs of an endogenous NST1 gene and/or an endogenous NST3 gene (e.g., a deletion of about 5, 6, 7, 8, 9, 10, 11, 12, 13, 14, 15, 16, 17, 18, 19, 20, 21, 22, 23, 24, 25, 26, 27, 28, 29, or 30 base pairs, or any range or value therein). In some embodiments, a mutation in an endogenous NST1 gene and/or an endogenous NST3 gene may be a deletion of at least 3 consecutive base pairs (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or more, or any range or value therein, optionally a deletion of about 3 to about 10 consecutive base pairs (e.g., 3, 4, 5, 6, 7, 8, 9, or 10 consecutive base pairs, or any range or value therein).

In some embodiments, the mutation is in a region of the NST1 gene and/or NST3 gene encoding the dimerization domain having the amino acid sequence VPPGFRFHP-TEEELLQYYL (SEQ ID NO:282) or VPPGFRFHP-TEEELLHYYL (SEQ ID NO:283), e.g., a region comprising the amino acid sequence of EEELL (SEQ ID NO:127). In some embodiments, one or more of the amino acid residues (e.g., 1, 2, 3, 4, 5, 6, 7, 8, 9, 10, 11, 12, 13, 14, 15, 16, 17, 18, or 19 amino acid residues, or any range or value therein (e.g., 1 to about 3 residues, 1 to about 4 residues, 1 to about 5 residues, 1 to about 6 residues, 1 to about 8 residues, 1 to about 10 residues, 1 to about 12 residues, 1 to about 14 residues, or 1 to about 19 residues, or any other range or value therein) of the dimerization domain of the NST1 polypeptide and/or NST3 polypeptide are mutated or deleted. In some embodiments, a mutation in an endogenous NST1 gene and/or NST3 gene may be a deletion or insertion that affects the ability of the dimerization domain to dimerize. In some embodiments, a mutation in an endogenous NST1 gene and/or NST3 gene may be an out-of-frame deletion or insertion that affects the ability of the dimerization domain to dimerize. In some embodiments, a mutation in an endogenous NST1 gene and/or NST3 gene may be a deletion that truncates the C-terminus of the NST1 polypeptide and/or NST3 polypeptide, optionally wherein the mutation may be a deletion that deletes the C-terminus comprising at least the dimerization domain (e.g., SEQ ID NO:282 and/or SEQ ID NO:283) of the NST1 polypeptide and/or NST3 polypeptide.

In some embodiments, the mutation may result in an out-of-frame insertion or an in-frame deletion. In some embodiments, the mutation in at least one endogenous NST1 gene is an out-of-frame insertion or an out-of-frame deletion and/or the at least one mutation in an endogenous NST3 gene is an out-of-frame insertion or an out-of-frame deletion. In some embodiments, the at least one mutation in at least one endogenous NST1 gene is an in-frame insertion or an in-frame deletion and/or the at least one mutation in an endogenous NST3 gene is an in-frame insertion or an in-frame deletion.

In some embodiments, a NST1 gene and/or NST3 gene may comprise one mutation or more than one mutation (e.g., insertion or deletion), e.g., 1, 2, 3, 4 or 5 mutations. In some embodiments, the at least one mutation in at least one endogenous NST1 gene results in a deletion or insertion of one or more base pairs located in a region having at least 80% sequence identity (e.g., 80%, 85%, 90%, 95%, or 100% sequence identity) to any one of the nucleotide sequences of SEQ ID NOs:84-116 or 145-171, and the at least one mutation in at least one endogenous NST3 gene results in a deletion or insertion of one or more base pairs located in a region having at least 80% sequence identity (e.g., 80%, 85%, 90%, 95%, or 100% sequence identity) to any one of the nucleotide sequences of SEQ ID NOs:98-116 or 181-248. In some embodiments, an endogenous NST1 gene encoding an NST1 transcription factor polypeptide: (a) comprises a nucleotide sequence having at least 80% sequence identity to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein an endogenous NST3 gene encoding an NST3 transcription factor polypeptide: (a) comprises a nucleotide sequence having at least 80% sequence identity (e.g., 80%, 85%, 90%, 95%, or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283.

In some embodiments, a mutation (e.g., one or more mutations) in an endogenous NST1 gene and/or an endogenous NST3 gene may result in a dominant allele. In some embodiments, the mutation may be a non-natural mutation.

In some embodiments, a mutation in an endogenous NST1 gene may result in a mutated NST1 gene having at least 90% sequence identity (e.g., 90%, 91%, 92%, 93%, 94%, 95%, 95.5%, 96%, 96.5%, 97%, 97.5%, 98%, 98.5%, 99%, 99.5%, or 100% sequence identity) to a nucleotide sequence described herein and a mutation in an endogenous NST3 gene may result in a mutated NST3 gene having at least 90% sequence identity (e.g., 90%, 91%, 92%, 93%, 94%, 95%, 95.5%, 96%, 96.5%, 97%, 97.5%, 98%, 98.5%, 99%, 99.5%, or 100% sequence identity) to a nucleotide sequence as described herein.

In some embodiments, a plant or part thereof comprising a mutation in a NST1 gene and a NST3 gene as described herein may exhibit a phenotype of reduced endocarp lignification and reduced seediness or a reduced feel of seediness, wherein the reduced endocarp lignification and reduced seediness or a reduced feel of seediness is as compared to a control plant or plant part (e.g., an isogenic plant, wild type unedited plant, or a null segregant) devoid of the NST1 gene mutation and NST3 gene mutation. Reduced endocarp lignification may be characterized by a visible reduction in lignin deposition in the endocarp, e.g., as measured by staining with phloroglucinol-HCl, or the force required to crush a fruit/seed comprising the endocarp. Reduced seediness or a reduced feel of seediness may be measured by the force required to crush a fruit/seed wherein a reduced force is able to crush the seeds when the seeds have reduced seediness or a reduced feel of seediness. Force measurements may be carried out using, e.g., a texture analyzer set in compression mode. In some embodiments, reduced endocarp lignification and reduced seediness or a reduced feel of seediness is as compared to a control plant devoid of the mutation, optionally the comparison is under the same environmental conditions.

In some embodiments, a plant cell comprising an editing system is provided, the editing system comprising: (a) a CRISPR-Cas effector protein; (b) a guide nucleic acid (gRNA, gDNA, crRNA, crDNA) comprising a spacer sequence with complementarity to a region of consecutive nucleotides within an endogenous target gene encoding an NST1 polypeptide; and (c) a guide nucleic acid comprising a spacer sequence with complementarity to a region of consecutive nucleotides within an endogenous target gene encoding an NST3 polypeptide. In some embodiments, an endogenous NST1 gene, to which a spacer sequence of the guide nucleic acid shares complementarity, may encode an NST1 transcription factor polypeptide, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene, to which a spacer sequence of the guide nucleic acid shares complementarity, may encode an NST3 transcription factor polypeptide, wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%. In some embodiments, a spacer sequence useful with this invention can include, but is not limited to, a nucleotide sequence of any one of SEQ ID NOs:117-122 and/or 134-144, or reverse complement thereof, or a combination thereof.

In some embodiments, a *Rubus* plant cell is provided that comprises at least one mutation in an at least one endogenous V AC SECONDARY WALL THICKENING PROMOTING FACTOR1 (NST1) gene and at least one mutation in at least one endogenous NAC SECONDARY WALL THICKENING PROMOTING FACTOR3 (NST3) gene, wherein the at least one mutation in the NST1 gene and in the NST3 gene is a base deletion that is introduced using an editing system that comprises a nucleic acid binding domain that binds to a target site within the endogenous NST1 gene and a target site within the endogenous NST3 gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%. In some embodiments, the editing system may further comprise a nuclease, optionally wherein the nuclease is a zinc finger nuclease, transcription activator-like effector nuclease (TALEN), endonuclease (e.g., Fok1) or a CRISPR-Cas effector protein. In some embodiments, the nucleic acid binding domain of the editing system may be from a polynucleotide-guided endonuclease, a CRISPR-Cas endonuclease (e.g., CRISPR-Cas effector protein), a zinc finger nuclease, a transcription activator-like effector nuclease, a transcription activator-like effector nuclease (TALEN) and/or an Argonaute protein.

In some embodiments, a *Rubus* plant cell is provided that comprises at least one mutation in an at least one endogenous NST1 gene and at least one mutation in at least one endogenous NST3 gene, wherein the at least one mutation in the NST1 gene and in the NST3 gene is a base deletion that is introduced using an editing system that comprises a nucleic acid binding domain that binds to a target site within the endogenous NST1 gene, wherein the target site within the endogenous NST1 gene is located in a region of the endogenous NST1 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NOs:84-97 and/or 145-171, and wherein the target site within the endogenous NST3 gene is located in a region of the endogenous NST3 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NOs:98-116 and/or 181-248. In some embodiments, the at least one mutation in the endogenous NST1 gene is a null mutation and the at least one mutation in the endogenous NST3 gene is a null mutation. In some embodiments, the *Rubus* plant cell comprising a null mutation in the NST1 gene and/or a null mutation in the NST3 gene, results in a truncated NST1 polypeptide and/or NST3 polypeptide. In some embodiments, the null mutation results in the production of a non-functional or no NTS1 polypeptide and/or NTS3 polypeptide. In some embodiments, the *Rubus* plant cell comprises at least one mutation in an at least one endogenous NST1 gene and at least one mutation in at least one endogenous NST3 gene, wherein the at least one mutation in the endogenous NST1 gene and/or the endogenous NST3 gene is a base deletion. In some embodiments, the at least one mutation is an out-of-frame deletion, out-of-frame insertion, an in-frame deletion or an in-frame insertion. In some embodiments, the at least one mutation is a non-natural mutation, optionally wherein the at least one mutation results in a dominant allele.

NST1 genes and NST3 genes may be modified to generate a null mutation by any means known in the art including, but not limited to, traditional plant breeding, molecular breeding, TILLING mutagenesis, RNA interference (RNAi) (gene suppression), and through gene editing using a nuclease linked to a nucleic acid binding domain (e.g., editing system) that binds to a target sequence in the NST1 genes and NST3 genes.

In some embodiments, a nuclease of an editing system useful for generating null mutations in an NST1 gene and an NST3 gene may be a zinc finger nuclease, a transcription activator-like effector nuclease (TALEN), an endonuclease (e.g., Fok1) or a CRISPR-Cas effector protein. In some embodiments, the nucleic acid binding domain of the editing system may be from a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein as described herein and as known in the art.

In some embodiments, expression of an endogenous NST1 gene and an endogenous NST3 gene may be suppressed (reduced or eliminated) in a *Rubus* plant using RNAi. Use of RNAi to reduce or eliminate expression of an endogenous gene is well-known in the art, see e.g., Kamthan et al. (*Frontiers in Plant Science* 6: Article 208 (2015) doi.org/10.3389/fpls.2015.00208); Kleter (*Pest Manag. Sci.*

76:3333-3339 (2020)); Saurabh et al. (*Planta* 239:543-564 (2014)). RNAi, also known as RNA silencing, inhibitory RNA, and RNA inactivation and includes, but is not limited to, antisense, double stranded (dsRNA), small interfering RNA (siRNA), small hairpin RNA (or short hairpin RNA) (shRNA), microRNA (miRNA), piRNA (PIWI-interacting RNA), qiRNA (QDE-2-interacting RNA), and svRNA (small vault RNA). In some embodiments, an RNAi molecule useful for reducing expression of an NST1 gene or an NST3 gene may be a length of about 18 to 25 consecutive nucleotides, optionally a length of about 20 to 24 consecutive nucleotides (e.g., about 18, 19, 20, 21, 22, 23, 24, or 25 consecutive nucleotides in length or any range therein).

In some embodiments, the present invention provides a method of producing a *Rubus* plant having at least one NST1 gene with reduced expression (e.g., about 80%-100% reduced; e.g., about 80, 81, 82, 83, 84, 85, 86, 87, 88, 89, 90, 91, 92, 93, 94, 95, 95.5, 96, 96.5, 97, 97.5, 98, 98.5, 99, 99.5, or 100%, or any value or range therein), and at least one NST3 gene with reduced expression (e.g., about 80%-100% reduced; e.g., about 80, 81, 82, 83, 84, 85, 86, 87, 88, 89, 90, 91, 92, 93, 94, 95, 95.5, 96, 96.5, 97, 97.5, 98, 98.5, 99, 99.5, or 100%, or any value or range therein), the method comprising: contacting a population of *Rubus* plant cells comprising at least one endogenous NST1 gene and at least one endogenous NST3 with an RNAi that targets the NST1 RNA and the NST3 RNA, wherein the RNAi targets a region of the NST1 RNA and the NST3 RNA and results in suppression of expression of the at least one NST1 gene and of the at least one NST3 gene, thereby producing a *Rubus* plant with reduced expression of at least one NST1 gene and of at least one NST3 gene.

In some embodiments, reduced expression of an NST1 gene and/or an NST3 gene comprises, consists essentially of, or consists of a reduction in expression of about 85% to about 100% or a reduction in expression of about 90% to about 100%. In some embodiments, reduced expression of an NST1 gene and/or an NST3 gene comprises, consists essentially of, or consists of a reduction in expression of about 95, 95.5, 96, 96.5, 97, 97.5, 98, 98.5, 99, 99.5 to about 100% and any range therein. In some embodiments, reduced expression of an NST1 gene and/or an NST3 gene comprises, consists essentially of, or consists of a reduction in expression of the NST1 gene and the NST3 gene of about 100%. In some embodiments, a *Rubus* plant may be regenerated from *Rubus* plant cells having at having at least one NST1 gene and at least one NST3 gene with reduced expression of an NST1 gene and/or an NST3 gene as described herein.

A plant or plant part useful with this invention may be a blackberry, red raspberry, black raspberry, or artic bramble. In some embodiments, the modified plant or plant part from a plant in the *Rubus* family. Example *Rubus* plants useful with the invention can include, but are not limited to, *Rubus* spp., *Rubus occidentalis* L., *Rubus pergratus* Blanch., *Rubus oklahomus* L. H. Bailey *Rubus originalis* L. H. Bailey, *Rubus ortivus* (L. H. Bailey) L. H. Bailey, *Rubus parcifrondifer* L. H. Bailey, *Rubus odoratus* L., *Rubus parvifolius* L., *Rubus pedatus* Sm., and *Rubus phoenicolasius* Maxim. In some embodiments, the *Rubus* plant is blackberry. In some embodiments, a plant may be regenerated from a plant cell or plant part of this invention. In some aspects, a plant cell can be non-propagating plant cell that does not regenerate into a plant. Plants of this invention comprising at least one mutation in a NST1 gene and at least one mutation in a NST3 gene may comprise a reduced endocarp lignification and/or reduced seediness and/or a reduced feel of seediness as compared to a plant or part thereof not comprising the same mutations.

The term "reduced endocarp lignification" refers to a decrease in the accumulation of lignin in the berry endocarp, which typically provides a rigid protective layer surrounding the seed. Reduced endocarp lignification may be characterized by a softer pit in fruit of a mutant plant as compared to fruit of a control plant. As used herein, "reduced endocarp lignification" refers to a decrease in pit and/or seed compression, e.g., expressed as peak force (N), of about 15% to about 100% (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any value or range therein) as compared to a control plant (e.g., a plant that is devoid of the mutation or edit).

The term "reduced seediness" refers to an improvement in the number or perception of the number of seeds of a fruit by about 15% to about 100% (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any value or range therein) as compared to a control plant (e.g., a plant that is devoid of the mutation or edit).

As used herein, "reduced feel of seediness" refers to non-taste-related aspects of the pleasantness experienced by a person while chewing or swallowing a fruit. As used herein, "reduced feel of seediness" refers to a decrease in the feel of seediness of about 15% to about 100% (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or any value or range therein) as compared to a control plant (e.g., a plant that is devoid of the mutation or edit).

Also provided herein is a method of providing a plurality of plants having reduced endocarp lignification, reduced seediness and/or a reduced feel of seediness, the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants of the invention) (e.g., comprising a mutation in a NST1 gene and a mutation in a NST3 gene and having reduced endocarp lignification, reduced seediness and/or a reduced feel of seediness) in a growing area, thereby providing a plurality of plants having reduced endocarp lignification, reduced seediness and/or a reduced feel of seediness as compared to a plurality of control plants not comprising the at least one mutation (e.g., as compared to an isogenic wild type plant not comprising the mutation). A growing area can be any area in which a plurality of plants can be planted together, including, but not limited to, a field (e.g., a cultivated field, an agricultural field), a growth chamber, a greenhouse, a recreational area, a lawn, and/or a roadside, and the like.

In some embodiments, a method of producing/breeding a transgene-free genome-edited (e.g., base-edited) plant is provided, the method comprising: crossing a plant of the present invention (e.g., a plant comprising a mutation or modification in an endogenous NST1 gene and a mutation in an endogenous NST3 gene as described herein (and having reduced endocarp lignification, reduced seediness and/or a reduced feel of seediness) with a transgene-free plant, thereby introducing the mutation or modification (e.g., one or more mutations or modifications) into the plant that is transgene-free (e.g., into progeny plants); and selecting a progeny plant that comprises the mutation or modification and is transgene-free, thereby producing a transgene-free genome-edited (e.g., base-edited) plan. In some embodiments, the mutation may be a non-natural mutation.

In some embodiments, the present invention provides a method of creating a mutation in an endogenous NST1 gene and an endogenous NST3 gene in a *Rubus* plant, comprising: (a) targeting a gene editing system to a portion of the endogenous NST1 gene and the endogenous NST3 gene, wherein the portion of the endogenous NST1 gene that is targeted comprises a sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:84-97 and/or 145-171, and wherein the portion of the endogenous NST3 gene that is targeted comprises a sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:98-116 and/or 181-248; and (b) selecting a *Rubus* plant that comprises a modification located in the portion of the endogenous NST1 gene that comprises a nucleotide sequence having at least 80% sequence identity to any one of the nucleotide sequences of SEQ ID NOs:84-97 and/or 145-171 and a modification located in the portion of the endogenous NST3 gene that comprises a nucleotide sequence having at least 80% sequence identity to any one of the nucleotide sequences of SEQ ID NOs:98-116 and/or 181-248. In some embodiments, the mutation that is created results in a nucleic acid having at least 90% sequence identity to mutant NST1 gene or mutant NST3 gene.

In some embodiments, a method of generating variation in region of an endogenous NST1 gene and an endogenous NST3 gene, comprising: into a *Rubus* plant cell (a) an editing system that is targeted to a region of a NST1 gene and (b) an editing system that is targeted to a region of an NST3 gene, and contacting the region of the NST1 gene with the editing system of (a), thereby introducing a mutation into the NST1 gene and generating variation in the NST1 gene of the *Rubus* plant cell, and contacting the region of the NST3 gene with the editing system of (b), thereby introducing a mutation into the NST3 gene and generating variation in the NST3 gene of the *Rubus* plant cell. In some embodiments, the endogenous NST1 gene encodes an amino acid sequence having at least 95% sequence identity to the amino acid sequence of SEQ ID NO:71 and/or the endogenous NST3 gene encodes an amino acid sequence having at least 95% sequence identity to the amino acid sequence of SEQ ID NO:80, optionally wherein the sequence identity may be at least 95%, or at least 96%, or it may be at least 97%, 98% or 99%, optionally the sequence identity may be 100%. In some embodiments, the endogenous NST1 gene encodes the amino acid sequence of SEQ ID NO:279 (e.g., SEQ ID NO:274, SEQ ID NO:275 or SEQ ID NO:278) and/or the endogenous NST3 gene encodes the amino acid sequence of SEQ ID NO:281 (e.g., SEQ ID NO:276, SEQ ID NO:277 or SEQ ID NO:280). In some embodiments, the region of the endogenous NST1 gene that is targeted comprises a sequence having at least 80% sequence identity to any one of the nucleotide sequences of SEQ ID NOs:84-97 and/or 145-171, and the region of the endogenous NST3 gene that is targeted comprises a sequence having at least 80% sequence identity to any one of the nucleotide sequences of SEQ ID NOs:98-116 and/or 181-248. In some embodiments, contacting the region of the endogenous NST1 gene and the region of the endogenous NST3 gene in the *Rubus* plant cell with the editing system produces a *Rubus* plant cell comprising in its genome an edited NST1 gene and an edited NST3 gene. In some embodiments, the method may further comprise (a) regenerating a *Rubus* plant from the *Rubus* plant cell; (b) selfing the plant to produce progeny plants (E1); (c) assaying the progeny plants of (b) for reduced endocarp lignification, reduced seediness and/or a reduced feel of seediness; and (d) selecting the progeny plants exhibiting reduced endocarp lignification, reduced seediness and/or a reduced feel of seediness as compared to a control plant. In some embodiments, the method may further comprise (e) selfing the selected progeny plants of (d) to produce progeny plants (E2); (f) assaying the progeny plants of (e) for reduced endocarp lignification, reduced seediness and/or a reduced feel of seediness; and (g) selecting the progeny plants exhibiting reduced endocarp lignification, reduced seediness and/or a reduced feel of seediness as compared to a control plant, optionally repeating (e) through (g) one or more additional times.

In some embodiments, a method of detecting a mutant NST1 gene (a mutation in an endogenous NTS1 gene) and a mutant NTS3 gene (a mutation in an endogenous NTS3 gene) in a plant or plant part (e.g., plant cell) is provided, the method comprising detecting in the genome of the plant a NTS1 gene having at least one mutation in a region having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:84-97 and/or 145-171 and detecting in the genome of the plant a NTS3 gene having at least one mutation in a region having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:98-116 and/or 181-248, optionally wherein the mutation is a deletion and/or an insertion of at least one nucleotide (e.g., 1, 2, 3, 4, 5, 6, 7, 8, 9, 10 consecutive nucleotides to 50, 60, 70, 80, 90, 100 consecutive nucleotides to about 200 consecutive nucleotides). n some embodiments, the mutant NST1 gene and/or mutant NST3 gene that is detected comprises a nucleic acid sequence having at least 90% sequence identity to a mutant NST1 gene and/or mutant NST3 gene described herein.

In some embodiments, a method for editing a specific site in the genome of a *Rubus* plant cell is provided, the method comprising cleaving, in a site-specific manner, a target site within an endogenous NAC SECONDARY WALL THICKENING PROMOTING FACTOR1 (NST1) gene in the *Rubus* plant cell and a target site within an endogenous NAC SECONDARY WALL THICKENING PROMOTING FAC- TOR3 (NST3) gene in the *Rubus* plant cell, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, thereby generating an edit in the endogenous NST1 and in the endogenous NST3 gene of the *Rubus* plant cell, optionally wherein the sequence identity of any one of (a), (b), (c) and/or (d) may be at least 85%, or at least 90%, or it may be at least 95%, optionally the sequence identity may be 100. In some embodiments, the edit in the endogenous NST1 gene is in the 5' region of Exon 1 and/or Exon 3 of the endogenous NST1 gene and the edit in the endogenous NST3 gene is in the 5' region of Exon 1 and/or Exon 3 of the endogenous NST3 gene. In some embodiments, the edit in the endogenous NST1 gene and/or the endogenous NST3 gene results in a null allele. In some embodiments, the edit in the endogenous NST1 gene and/or the endogenous NST3 gene results in a dominant allele. In some embodiments, the edit results in a mutation, optionally a non-natural mutation, in the endogenous NST1 gene and/or endogenous NST3 gene, optionally wherein mutation results in a truncated polypeptide. In some embodiments, the plant comprising the edit in its endogenous NTS1 gene and endogenous NTS3 gene exhibits reduced endocarp lignification, reduced seediness and/or a reduced feel of seediness as compared to a control plant that is devoid of the edit. In some embodiments, the edit may be located in a region of the NST1 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally at least 90% or 95%, optionally 100%) to any one of the nucleotide sequences of SEQ ID NOs:84-97 and/or 145-171, and the edit may be located in a region of the NST3 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally at least 90% or 95%, optionally 100%) to any one of the nucleotide sequences of SEQ ID NOs:98-116 and/or 181-248. In some embodiments, an edit in an endogenous NST1 gene and edit in an endogenous NST3 gene may result in a mutated NST1 gene and mutated NST3 gene having at least 90% sequence identity (e.g., at least 90, 91, 92, 93, 94, 95, 96, 97, 98, 99 or 100%, optionally the sequence identity may be at least 95%, optionally the sequence identity may be 100%) to mutant NST1 gene and mutant NST3 gene as described herein, and/or encode a modified NST1 polypeptide and encode a modified NST3 polypeptide comprising an amino acid sequence having at least 90% sequence identity to a modified NST1 polypeptide and modified NST3 polypeptide as described herein.

In some embodiments, a *Rubus* plant may be regenerated from a plant cell comprising an edit in an endogenous NST1 gene and an edit in an endogenous NST3 gene to produce a *Rubus* plant comprising the edit in its endogenous NST1 gene and endogenous NST3 gene. In some embodiments, a *Rubus* plant is not regenerated from a plant cell. In some embodiments, a *Rubus* plant comprising an edit in its endogenous NST1 gene and endogenous NST3 gene reduced endocarp lignification, reduced seediness and/or a reduced feel of seediness as compared to a control plant that is devoid of the edit.

In some embodiments, a method for making a *Rubus* plant is provided, the method comprising: (a) contacting a population of *Rubus* plant cells that comprise an endogenous gene encoding a NAC SECONDARY WALL THICKENING PROMOTING FACTOR1 (NST1) polypeptide and an endogenous gene encoding an endogenous NAC SECONDARY WALL THICKENING PROMOTING FACTOR3 (NST3) polypeptide with a nuclease targeted to the endogenous gene encoding the NST1 polypeptide and a nuclease targeted to the endogenous gene encoding the NST3 polypeptide, wherein each nuclease is linked to a nucleic acid binding domain that binds to a target site within the endogenous gene, wherein the endogenous gene encoding an NST1 polypeptide: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (ii) comprises a region having at least 80% sequence identity to a nucleotide sequence of any one of SEQ ID NOs:84-97 and/or 145-171; (iii) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (iv) comprises a region having at least 80% sequence identity to the amino acid sequence of any one of SEQ ID NOs:123-129, 172-180, 264-273, and/or 282, optionally wherein the sequence identity of (i), (ii), (iii) and/or (iv) may be at least 85%, or at least 90%, or it may be at least 95%, optionally the sequence identity may be 100%, and wherein the endogenous gene encoding an NST3 polypeptide: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (ii) comprises a region having at least 80% sequence identity to a nucleotide sequence of any one of SEQ ID NOs:98-116 and/or 181-248; (iii) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (iv) comprises a region having at least 80% sequence identity to the amino acid sequence of any one of SEQ ID NOs:127, 130-133, 249-255, and/or 283, optionally wherein the sequence identity of (i), (ii), (iii) and/or (iv) may be at least 85%, or at least 90%, or it may be at least 95%, optionally the sequence identity may be 100%, (b) selecting a *Rubus* plant cell from the population comprising a mutation in the endogenous gene encoding a NTS1 polypeptide and a mutation in the endogenous gene encoding a NTS3 polypeptide, wherein the mutation is a deletion; and (c) growing the selected *Rubus* plant cell into a *Rubus* plant comprising the mutation in the endogenous gene encoding a NTS1 polypeptide and the mutation in the endogenous gene encoding a NST3 polypeptide. In some embodiments, the mutation in an endogenous NST1 gene and mutation in an endogenous NST3 gene may result in a mutated NST1 gene and mutated NST3 gene having at least 90% sequence identity (e.g., at least 90, 91, 92, 93, 94, 95, 96, 97, 98, 99 or 100%, optionally the sequence identity may be at least 95%, optionally the sequence identity may be 100%) to a mutant NST1 gene and mutant NST3 gene as described herein, and/or encode a modified NST1 polypeptide and encode a modified NST3 polypeptide comprising an amino acid sequence having at least 90% sequence identity to a modified NST1 polypeptide and modified NST3 polypeptide as described herein.

In some embodiments, a method for reducing endocarp lignification, seediness and/or a reducing the feel of seediness of a *Rubus* plant is provided, the method comprising (a) contacting a *Rubus* plant cell comprising an endogenous gene encoding a NAC SECONDARY WALL THICKENING PROMOTING FACTOR1 (NST1) polypeptide and comprising an endogenous gene encoding a NAC SECONDARY WALL THICKENING PROMOTING FACTOR3 (NST3) with a nuclease targeted to the endogenous gene encoding the NST1 polypeptide and a nuclease targeted to the endogenous gene encoding the NST3 polypeptide, wherein each nuclease is linked to a nucleic acid binding domain that binds to a target site within the endogenous gene, wherein the endogenous NST1 gene: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (ii) comprises a region having at least 80% sequence identity to a nucleotide sequence of any one of SEQ ID NOs:84-97 and/or 145-171; (iii) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (iv) comprises a region having at least 80% sequence identity to the amino acid sequence of any one of SEQ ID NOs:123-129, 172-180, 264-273, and/or 282, optionally wherein the sequence identity of (i), (ii), (iii) and/or (iv) may be at least 85%, or at least 90%, or it may be at least 95%, optionally the sequence identity may be 100%, and wherein the endogenous NST3 gene: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (ii) comprises a region having at least 80% sequence identity to a nucleotide sequence of any one of SEQ ID NOs:98-116 and/or 181-248; (iii) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (iv) comprises a region having at least 80% sequence identity to the amino acid sequence of any one of SEQ ID NOs:127, 130-133, 249-255, and/or 283, optionally wherein the sequence identity of (i), (ii), (iii) and/or (iv) may be at least 85%, or at least 90%, or it may be at least 95%, optionally the sequence identity may be 100%; and (b) growing the *Rubus* plant cell into a *Rubus* plant, thereby reducing endocarp lignification, seediness and/or a reducing the feel of seediness of the *Rubus* plant. In some embodiments, the regenerated plant comprises a mutated NST1 gene and a mutated NST3 gene having at least 90% sequence identity (e.g., at least 90, 91, 92, 93, 94, 95, 96, 97, 98, 99 or 100%, optionally the sequence identity may be at least 95%, optionally the sequence identity may be 100%) to a mutant nucleic acid sequence as described herein and/or encodes an amino acid sequence having at least 90% sequence identity to a mutant amino acid sequence as described herein.

In some embodiments, a method is provided for producing a *Rubus* plant or part thereof comprising at least one cell (e.g., one or more cells) having a mutation in an endogenous NST1 gene and a mutation in an endogenous NST3 gene, the method comprising contacting a target site within the endogenous NST1 gene and a target site within the endogenous NST3 gene in the *Rubus* plant or part thereof with a nuclease comprising a cleavage domain and a nucleic acid binding domain, wherein the nucleic acid binding domain of the nuclease binds to a target site within the endogenous NST1 gene and a target site within the endogenous NTS3gene, and/or contacting a target site within the endogenous NST1 gene and a target site within the endogenous NST3 gene in the *Rubus* plant or part thereof with a first nuclease and a second nuclease each of which comprise a cleavage domain and a nucleic acid binding domain, wherein the nucleic acid binding domain of the first nuclease binds to a target site within the endogenous NST1 gene and the nucleic acid binding domain of the second nuclease binds to a target site within the endogenous NTS3 gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or may be at least 90% or it may be at least 95%, optionally the sequence identity may be 100%, thereby producing a *Rubus* plant or part thereof comprising at least one cell having a mutation in the endogenous NTS1 gene and in the endogenous NTS3 gene. In some embodiments, the mutation in the endogenous NST1 gene is in the 5' region of Exon 1 and/or Exon 3 of the endogenous NST1 gene and the mutation in the endogenous NST3 gene is in the 5' region of Exon 1 and/or Exon 3 of the endogenous NST3 gene. In some embodiments, a mutation may result in a deletion, optionally wherein the deletion results in a truncated NST1 polypeptide and/or truncated NST3 polypeptide. In some embodiments, the *Rubus* plant that is produced comprises a mutated NST1 gene and NST3 gene having at least 90% sequence identity (e.g., at least 90, 91, 92, 93, 94, 95, 96, 97, 98, 99 or 100%, optionally the sequence identity may be at least 95%, optionally the sequence identity may be 100%) to a mutant nucleic acid describe herein and/or encodes a mutant amino acid sequence as described herein.

In some embodiments, a method is provided for producing a *Rubus* plant or part thereof comprising a mutation in an endogenous NST1 gene and an endogenous NST3 gene and having reduced endocarp lignification, reduced seediness and/or a reduced feel of seediness, the method comprising contacting a target site within the endogenous NST1 gene and a target site within the endogenous NST3 gene in the *Rubus* plant or part thereof with a nuclease comprising a cleavage domain and a nucleic acid binding domain, wherein the nucleic acid binding domain of the nuclease binds to a target site within the endogenous NST1 gene and a target site within the endogenous NTS3gene, and/or contacting a target site within the endogenous NST1 gene and a target site within the endogenous NST3 gene in the *Rubus* plant or part thereof with a first nuclease and a second nuclease each of which comprise a cleavage domain and a nucleic acid binding domain, wherein the nucleic acid binding domain of the first nuclease binds to a target site within the endogenous NST1 gene and the nucleic acid binding domain of the second nuclease binds to a target site within the endogenous NTS3gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of (a), (b), (c) and/or (d) may be at least 85%, or may be at least 90% or it may be at least 95%, optionally the sequence identity may be 100%, thereby producing a *Rubus* plant or part thereof having a mutated endogenous NST1 gene and a mutated endogenous NST3 gene and exhibiting reduced endocarp lignification, reduced seediness and/or a reduced feel of seediness.

In some embodiments, the nuclease may be a zinc finger nuclease, transcription activator-like effector nucleases (TALEN), endonuclease (e.g., Fok1) or a CRISPR-Cas effector protein, wherein the nuclease cleaves the endogenous NST1 gene and the endogenous NST3 gene and a mutation is introduced into the endogenous NST1 gene and into the endogenous NTS3 gene; or wherein the first nuclease cleaves the endogenous NST1 gene and a mutation is introduced into the endogenous NST1 gene and the second nuclease cleaves the endogenous NST3 gene and a mutation is introduced into the endogenous NST3 gene. In some embodiments, the target site is in a region of the NTS1 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NOs:84-97 and/or 145-171, and the target site is in a region of the NTS3 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NOs:98-116 and/or 181-248.

In some embodiments, the mutation that is introduced into the endogenous NTS1 gene may be located in the 5' region of Exon 1 and/or in the 5' region of Exon 3 of the endogenous NTS1 gene and the mutation that is introduced into the endogenous NTS3 gene may be located in the 5' region of Exon 1 and/or in the 5' region of Exon 3 of the endogenous NST3 gene. In some embodiments, the mutation may be a base deletion optionally a base deletion of at least one base, optionally a non-natural mutation. In some embodiments, a mutation may be a base deletion, wherein the base deletion may be a deletion of about one base pair to about 3 base pairs, a deletion of about 5 base pairs, a deletion of about 10 base pairs, a deletion of about 12 base pairs, a deletion of about 15 base pairs, a deletion of about 20 base pairs, a deletion of about 25 base pairs, a deletion of about 30 base pairs, a deletion of about 35 base pairs, a deletion of about 40 base pairs, a deletion of about 45 base pairs, a deletion of about 50 base pairs, optionally the base deletion may be a deletion of between 5 and 50 base pairs. In some embodiments, a NST1 gene and/or a NST3 gene may comprise more than one mutation, e.g., 1, 2, 3, 4 or 5 or more mutations, which mutations may be deletions. In some embodiments, a mutation in an endogenous NST1 gene and/or a NST3 gene may result in a dominant allele.

In some embodiments, a plant or part thereof that is produced by the methods of this invention comprises a mutated endogenous NST1 gene and a mutated endogenous NST3 gene as described herein and exhibits reduced endocarp lignification, reduced seediness and/or a reduced feel of seediness as compared to a control plant that is devoid of the mutation in the endogenous NST1 gene and devoid of the mutation in the endogenous NST3 gene.

In some embodiments, a nuclease contacting a *Rubus* plant cell, a population of *Rubus* plant cells and/or a target site cleaves an endogenous NST1 gene and an endogenous NST3 gene, thereby introducing a mutation into the 5' region of Exon 1 and/or in the 5' region of Exon 3 of the endogenous NTS1 gene and the 5' region of Exon 1 and/or in the 5' region of Exon 3 of the endogenous NTS3 gene. A nuclease useful with the invention may be any nuclease that can be utilized to edit/modify a target nucleic acid. Such nucleases include, but are not limited to, a zinc finger nuclease, transcription activator-like effector nucleases (TALEN), endonuclease (e.g., Fok1) and/or a CRISPR-Cas effector protein. Likewise, any nucleic acid binding domain (e.g., DNA binding domain) useful with the nuclease of the invention may be any nucleic acid binding domain that can be utilized to edit/modify a target nucleic acid. Such a nucleic acid binding domain includes, but is not limited to, a zinc finger, transcription activator-like DNA binding domain (TAL), an argonaute and/or a CRISPR-Cas effector DNA binding domain.

In some embodiments, a method is provided for modifying an endogenous NTS11 gene and an endogenous NTS3 gene in a *Rubus* plant or part thereof for reducing endocarp lignification, reduced seediness and/or a reduced feel of seediness in the *Rubus* plant or part thereof, the method comprising modifying a target site within the endogenous NTS1 gene and a target site within the endogenous NTS3 gene in the *Rubus* lant or a part thereof, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%, thereby modifying the endogenous NST1 gene and modifying the endogenous NST3 gene and reducing endocarp lignification, reduced seediness and/or a reduced feel of seediness in the *Rubus* plant or part thereof. In some embodiments, the target site is a region of the NST1 gene having at least 80% sequence identity to a nucleotide sequence of any one SEQ ID NOs:98-116 and/or 181-248 and/or the target site is a region of the NST3 gene having at least 80% sequence identity to a nucleotide sequence of any one SEQ ID NOs:98-116 and/or 181-248.

In some embodiments, a method of editing an endogenous NST1 gene and endogenous NST3 gene in a *Rubus* plant or plant part is provided, the method comprising contacting a target site within the NST1 gene and NST3 gene in the *Rubus* plant or plant part with a base editing system comprising a cytosine deaminase and a nucleic acid binding domain that binds to a target site within the NST1 gene and NST3 gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%, thereby producing the plant or part thereof comprising an endogenous NST1 gene having a mutation and an endogenous NST3 gene having a mutation. In some embodiments, a plant comprising the endogenous NST1 gene and an endogenous NST3 gene that comprises a mutation as described herein exhibits reduced endocarp lignification, reduced seediness and/or a reduced feel of seediness in the *Rubus* plant or part thereof as compared to a plant devoid of the mutation.

In some embodiments, a method of editing an endogenous NST1 gene and endogenous NST3 gene in a *Rubus* plant or plant part is provided, the method comprising contacting a target site within the NST1 gene and NST3 gene in the *Rubus* plant or plant part with a base editing system comprising an adenosine deaminase and a nucleic acid binding domain that binds to a target site within the NST1 gene and NST3 gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171;

(c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%, thereby producing the plant or part thereof comprising an endogenous NST1 gene having a mutation and an endogenous NST3 gene having a mutation. In some embodiments, a plant comprising the endogenous NST1 gene and an endogenous NST3 gene that comprises a mutation as described herein exhibits reduced endocarp lignification, reduced seediness and/or a reduced feel of seediness in the *Rubus* plant or part thereof as compared to a plant devoid of the mutation.

In some embodiments, the present invention provides a method of producing a plant comprising a mutation in an endogenous NST1 gene and an endogenous NST3 gene and at least one polynucleotide of interest, the method comprising crossing a plant of the invention comprising at least one mutation in an endogenous NST1 gene and an endogenous NST3 gene (a first plant) with a second plant that comprises the at least one polynucleotide of interest to produce progeny plants; and selecting progeny plants comprising at least one mutation in the NST1 gene and an endogenous NST3 gene and the at least one polynucleotide of interest, thereby producing the plant comprising a mutation in an endogenous NST1 gene and an endogenous NST3 gene and at least one polynucleotide of interest.

Further provided is a method of producing a plant comprising a mutation in an endogenous NST1 gene and an endogenous NST3 gene and at least one polynucleotide of interest, the method comprising introducing at least one polynucleotide of interest into a plant of the present invention comprising at least one mutation in a NST1 gene and an endogenous NST3 gene, thereby producing a plant comprising at least one mutation in a NST1 gene and in an endogenous NST3 gene and at least one polynucleotide of interest. In some embodiments, the polynucleotide of interest is a polynucleotide that confers herbicide tolerance, insect resistance, disease resistance, increased yield, increased nutrient use efficiency or abiotic stress resistance.

Additionally provided is a method of producing a plant comprising a mutation in an endogenous NST1 gene and a mutation in an endogenous NST3 gene exhibiting a phenotype of reduced endocarp lignification, reduced seediness and/or a reduced feel of seediness, comprising crossing a first plant, which is the plant of the present invention (e.g., comprising at least one mutation in an endogenous NST1 gene and at least one mutation in an endogenous NST3 gene), with a second plant that exhibits a phenotype of reduced endocarp lignification, reduced seediness and/or a reduced feel of seediness; and selecting progeny plants comprising the mutation in the NST1 gene and the mutation in the NST3 gene and a phenotype of reduced endocarp lignification, reduced seediness and/or a reduced feel of seediness, thereby producing the plant comprising a mutation in an endogenous NST1 gene and a mutation in an endogenous NST3 gene and exhibiting a phenotype of reduced endocarp lignification, reduced seediness and/or a reduced feel of seediness as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the present invention (e.g., comprising at least one mutation in an endogenous NST1 gene and at least one mutation in an endogenous NST3 gene) growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention (e.g., comprising at least one mutation in an endogenous NST1 gene and at least one mutation in an endogenous NST3 gene), thereby reducing insect predation on the one or more plants.

In some embodiments, a method of reducing fungal disease on a plant is provided, the method comprising applying a fungicide to one or more plants of the invention (e.g., comprising at least one mutation in an endogenous NST1 gene and at least one mutation in an endogenous NST3 gene), thereby reducing fungal disease on the one or more plants, optionally wherein the one or more plants are growing in a container, a growth chamber, a greenhouse, a field, a recreational area, a lawn, or on a roadside.

In some embodiments, a method of reducing bacterial disease on a plant is provided, the method comprising applying a bactericide to one or more plants of the invention (e.g., comprising at least one mutation in an endogenous NST1 gene and at least one mutation in an endogenous NST3 gene), thereby reducing bacterial disease on the one or more plants, optionally wherein the one or more plants are growing in a container, a growth chamber, a greenhouse, a field, a recreational area, a lawn, or on a roadside.

A polynucleotide of interest may be any polynucleotide that can confer a desirable phenotype or otherwise modify the phenotype or genotype of a plant. In some embodiments, a polynucleotide of interest may include, but is not limited to, a polynucleotide that confers herbicide tolerance, insect resistance, nematode resistance, disease resistance, increased yield, increased nutrient use efficiency and/or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

A NST1 gene useful with this invention includes any endogenous NST1 gene in which a mutation as described herein can confer reduced endocarp lignification, reduced seediness and/or a reduced feel of seediness in a plant or part thereof comprising the mutation. In some embodiments, a NST1 gene (a) comprises a sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, optionally wherein the sequence identity of (a), (b), (c) and/or (d) may be at least 85%, or at least 90%, or it may be at least 95%, optionally the sequence identity may be 100%. In some embodiments, a NST1 gene useful with this invention includes an endogenous NST1 gene encoding the amino acid sequence of SEQ ID NO:279. In some embodiments, a NST1 gene useful with this invention includes an endogenous NST1 gene encoding the amino acid sequence of SEQ ID NO:278. In some embodiments, a NST1 gene useful with this invention includes an endogenous NST1 gene encoding the amino acid sequence of SEQ ID NO:275. In some embodiments, a NST1 gene useful with this invention includes an endogenous NST1 gene encoding the amino acid sequence of SEQ ID NO:274.

A NST3 gene useful with this invention includes any endogenous NST3 gene in which a mutation as described herein can confer reduced endocarp lignification, reduced seediness and/or a reduced feel of seediness in a plant or part thereof comprising the mutation. In some embodiments, a NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of (a), (b), (c) and/or (d) may be at least 85%, or at least 90%, or it may be at least 95%, optionally the sequence identity may be 100%. In some embodiments, a NST3 gene useful with this invention includes an endogenous NST3 gene encoding the amino acid sequence of SEQ ID NO:281. In some embodiments, a NST3 gene useful with this invention includes an endogenous NST3 gene encoding the amino acid sequence of SEQ ID NO:280. In some embodiments, a NST3 gene useful with this invention includes an endogenous NST3 gene encoding the amino acid sequence of SEQ ID NO:277. In some embodiments, a NST3 gene useful with this invention includes an endogenous NST3 gene encoding the amino acid sequence of SEQ ID NO:276.

In some embodiments, a mutation in an endogenous NST1 gene and a mutation in an endogenous NST3 gene may be any mutation that results in a mutated NST1 gene and a mutated NST3 gene that can confer a reduced endocarp lignification, reduced seediness and/or a reduced feel of seediness phenotypes on a *Rubus* plant comprising the mutated NST1 gene and mutated NST3 gene, optionally wherein the mutation in the endogenous NST1 gene and mutation in the endogenous NST3 gene may be a null mutation. In some embodiments, the mutation in an endogenous NST1 gene and mutation in an endogenous NST3 gene may be a non-natural mutation. In some embodiments, a mutation (e.g., one or more mutations) in an endogenous NST1 gene and in an endogenous NST3 gene may be a point mutation. In some embodiments, a mutation may be a base deletion. In some embodiments, the at least one mutation in an endogenous NST1 gene and/or the at least one mutation in an endogenous NST3 gene may be a dominant allele. In some embodiments, the mutation in an endogenous NST1 gene and/or the mutation in an endogenous NST3 gene in a plant may be a base deletion that results in a plant having a reduced endocarp lignification, reduced seediness and/or a reduced feel of seediness phenotypes. In some embodiments, the mutation in an endogenous NST1 gene and/or the at least one mutation in an endogenous NST3 gene in a *Rubus* plant may be a deletion that results in a dominant allele. For example, the mutation may be a deletion of 1 nucleotide to about 100 nucleotides, optionally 2, 3, 4, 5 nucleotides to about 100 nucleotides or any range or value therein, optionally at least 5 nucleotides, or at least 10 nucleotides, or at least 15 nucleotides, or at least 20 nucleotides, or at least 25 nucleotides, or at least 30 nucleotides, or at least 35 nucleotides, or at least 40 nucleotides, or at least 45 nucleotides, or at least 100 nucleotides, or any range or value therein (e.g., out-of-frame deletion or an in-frame deletion). In some embodiments, the mutation in the NST1 gene and the mutation in the NST3 gene results in a truncated NST1 polypeptide and a truncated NST3 polypeptide.

In some embodiments, a plant genome or plant genomic DNA is provided that comprises at least one non-natural mutation in an endogenous NAC SECONDARY WALL THICKENING PROMOTING FACTOR1 (NST1) gene and an endogenous NAC SECONDARY WALL THICKENING PROMOTING FACTOR3 (NST3) gene that encodes a NST1 polypeptide and a NST3 polypeptide. In other embodiments, a plant genome or plant genomic DNA is provided that comprises a mutated NAC SECONDARY WALL THICKENING PROMOTING FACTOR/(NST1) gene and a mutated NAC SECONDARY WALL THICKENING PROMOTING FACTOR3 (NST3) gene having the sequence as described herein and/or encoding a mutated NST1 polypeptide and mutated NST3 polypeptide having the sequence as described herein.

In some embodiments, a guide nucleic acid (e.g., gRNA, gDNA, crRNA, crDNA) is provided that binds to a target site within an endogenous NAC SECONDARY WALL THICKENING PROMOTING FACTOR1 (NST1) gene, wherein the target site is in a region of the NTS1 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; comprising a region having at least 80% sequence identity to a nucleotide sequence of any one of SEQ ID NOs:84-97 and/or 145-171; encoding a polypeptide comprising a sequence having at least 80% sequence identity to any one of the amino acid sequences of SEQ ID NO:71, SEQ ID NO:74, SEQ ID NO:77, SEQ ID NO:257 and/or SEQ ID NO:259; and/or encoding a region having at least 80% identity to the amino acid sequence of SEQ ID NOs:123-129, 172-180, 264-273, and/or 282, optionally wherein the sequence identity may be at least 85%, or at least 90%, or it may be at least 95%, optionally the sequence identity may be 100%.

In some embodiments, a guide nucleic acid (e.g., gRNA, gDNA, crRNA, crDNA) is provided that binds to a target site within an endogenous NAC SECONDARY WALL THICKENING PROMOTING FACTOR3 (NST3) gene, wherein the target site is in a region of the NTS3 gene having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences of SEQ ID NO:78, SEQ ID NO:79, SEQ ID NO:81, SEQ ID NO:82, SEQ ID NO:260 and/or SEQ ID NO:262; comprising a region having at least 80% sequence identity to a nucleotide sequence of any one of SEQ ID NOs:98-116 and/or 181-248; encoding a polypeptide comprising a sequence having at least 80% sequence identity to any one of the amino acid sequences of SEQ ID NO:80, SEQ ID NO:83, SEQ ID NO:261 and/or SEQ ID NO:263; and/or encoding a region having at least 80% identity to the amino acid sequence of SEQ ID NOs:127, 130-133, 249-255, and/or 283, optionally wherein the sequence identity may be at least 85%, or at least 90%, or it may be at least 95%, optionally the sequence identity may be 100%. In some embodiments, a guide nucleic acid is provided that binds to a target site within an endogenous NST1 gene, wherein the guide nucleic acid comprises a spacer sequence have at least 90% (e.g., 90, 91, 92, 93, 94, 95, 96, 97, 98, 99 or 100% sequence identity) to any one of the sequences of any one of SEQ ID NOs:120-122 or 134-136.

In some embodiments, the target site within an endogenous NST1 gene to which a guide nucleic acid of the invention may bind may comprise a nucleotide sequence, or portion thereof, having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:84-97 and/or 145-171. In some embodiments, the target site within an endogenous NST3 gene to which a guide nucleic acid of the invention may bind may comprise a nucleotide sequence, or portion thereof, having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NOs:98-116 and/or 181-248. In some embodiments, a guide nucleic acid is provided that binds to a target site within an endogenous NST3 gene, wherein the guide nucleic acid comprises a spacer sequence have at least 90% (e.g., 90, 91, 92, 93, 94, 95, 96, 97, 98, 99 or 100% sequence identity) to any one of the sequences of any one of SEQ ID NOs:117-1119 or 137-144.

Example spacer sequences useful with a guide that binds to a target site within an endogenous NST1 gene may comprise complementarity to a fragment or portion of a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258, optionally at least about 80, 81, 82, 83, 84, 85, 86, 87, 88, 89, 90, 91, 92, 93, 94, 95, 96, 97, 98, 99 or 100% sequence identity (optionally at least 90% sequence identity or 95% sequence identity, or 100% sequence identity) to any one of the nucleotide sequences of SEQ ID NOs:84-97 and/or 145-171; or a fragment or portion of a nucleotide sequence encoding a polypeptide comprising a sequence having at least 80% (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) sequence identity to any one of the amino acid sequences SEQ ID NO:71, SEQ ID NO:74, SEQ ID NO:77, SEQ ID NO:257 and/or SEQ ID NO:259; and/or the amino acid sequence of SEQ ID NOs:123-129, 172-180, 264-273, and/or 282. In some embodiments, an example spacer sequence may comprise the nucleotide sequence of any one of SEQ ID NOs:120-122 or SEQ ID NOs:134-136, or a reverse complement thereof, or any combination thereof.

Example spacer sequences useful with a guide that binds to a target site within an endogenous NST3 gene may comprise complementarity to a fragment or portion of a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) to any one of the nucleotide sequences of SEQ ID NO:78, SEQ ID NO:79, SEQ ID NO:81, SEQ ID NO:82, SEQ ID NO:260 and/or SEQ ID NO:262, optionally at least about 80, 81, 82, 83, 84, 85, 86, 87, 88, 89, 90, 91, 92, 93, 94, 95, 96, 97, 98, 99 or 100% sequence identity (optionally at least 90% sequence identity or 95% sequence identity, or 100% sequence identity) to any one of the nucleotide sequences of SEQ ID NOs:98-116 and/or 181-248; or a fragment or portion of a nucleotide sequence encoding a polypeptide comprising a sequence having at least 80% (e.g., at least about 80, 81, 82, 83, 84, 85, 86, 87, 88, 89, 90, 91, 92, 93, 94, 95, 96, 97, 98, 99 or 100% sequence identity, optionally the sequence identity may be at least 85%, or at least 90%, or it may be at least 95%, optionally the sequence identity may be 100%) sequence identity to any one of the amino acid sequences SEQ ID NO:80, SEQ ID NO:83, SEQ ID NO:261 and/or SEQ ID NO:263; and/or the amino acid sequence of SEQ ID NOs:127, 130-133, 249-255, and/or 283. In some embodiments, an example spacer sequence may comprise the nucleotide sequence of any one of SEQ ID NOs:117-119 or 137-144, or a reverse complement thereof, or any combination thereof.

In some embodiments, a guide nucleic acid may comprise a spacer sequence having the nucleotide sequence of any one of SEQ ID NOs:120-122, SEQ ID NOs:134-136, SEQ ID NOs:137-144, SEQ ID NOs:117-119, or a reverse complement thereof, or any combination thereof.

In some embodiments, a system is provided that comprises a guide nucleic acid of the present invention and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site within a gene.

In some embodiments, a gene editing system is provided, the gene editing system comprising a CRISPR-Cas effector protein in association with a guide nucleic acid, wherein the guide nucleic acid comprises at least two guide nucleic acids and at least one guide nucleic acid comprises a spacer sequence that binds to a NAC SECONDARY WALL THICKENING PROMOTING FACTOR1 (NST1) gene and at least one guide nucleic acid comprises a spacer sequence that binds to a NAC SECONDARY WALL THICKENING PROMOTING FACTOR3 (NST3) gene. In some embodiments, the guide nucleic acid comprises a spacer sequence that binds to a NST1 gene. In some embodiments, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%. In some embodiments, the spacer sequence that binds to an NTS1 gene binds to a region of the NTS1 gene having at least 80% sequence identity to any one of the nucleotide sequences of SEQ ID NOs:84-97 and/or 145-171, and the spacer sequence that binds to an NTS3 gene binds to a region of the NTS3 gene having at least 80% sequence identity to any one of the nucleotide sequences of SEQ ID NOs:98-116 and/or 181-248.

In some embodiments, the guide nucleic acid of a gene editing system can comprise a spacer sequence that has complementarity to a region, portion or fragment of a NTS1 nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258 (e.g., SEQ ID NOs:84-97 and/or 145-171), or may encode a region, portion or fragment of a sequence having at least 80% sequence identity to any one of the amino acid sequences of SEQ ID NO:71, SEQ ID NO:74, SEQ ID NO:77, SEQ ID NO:257 and/or SEQ ID NO:259 and/or the amino acid sequence of SEQ ID NOs:123-129, 172-180, 264-273, and/or 282, and spacer sequence that has complementarity to a region, portion or fragment of a NTS3 nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to any one of the nucleotide sequences SEQ ID NO:78, SEQ ID NO:79, SEQ ID NO:81, SEQ ID NO:82, SEQ ID NO:260 and/or SEQ ID NO:262 (e.g., SEQ ID NOs:98-116 and/or 181-248), or may encode a region, portion or fragment of a sequence having at least 80% sequence identity to any one of the amino acid sequences of SEQ ID NO:80, SEQ ID NO:83, SEQ ID NO:261 and/or SEQ ID NO:263 and/or the amino acid sequence of SEQ ID NOs:127, 130-133, 249-255, and/or 283, optionally wherein the sequence identity may be at least 85%, or at least 90%, or it may be at least 95%, optionally the sequence identity may be 100%. In some embodiments, the spacer sequence that binds to a NAC SECONDARY WALL THICKENING PROMOTING FACTOR (NST1) gene comprises a nucleotide sequence of any one of SEQ ID NOs:120-122 or SEQ ID NOs:134-136 and the spacer sequence that binds to a NA/C SECONDARY WALL THICKENING PROMOTING FACTOR3 (NST3) gene comprises a nucleotide sequence of any one of SEQ ID NOs:117-119 or SEQ ID NOs:137-144. In some embodiments, a gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising (a) a first guide nucleic acid and a second CRISPR-Cas effector protein comprising a cleavage domain, wherein the first guide nucleic acid binds to a target site within a NAC SECONDARY WALL THICKENING PROMOTING FACTOR1 (NST1) gene and (b) a second guide nucleic acid and a second CRISPR-Cas effector protein comprising a cleavage domain, wherein the second guide nucleic acid binds to a target site within a NAC SECONDARY WALL THICKENING PROMOTING FACTOR3 (NST3) gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of (a), (b), (c) and/or (d) may be at least 90%, or it may be at least 95%, optionally the sequence identity may be 100%, wherein the cleavage domain of the first CRISPR-Cas effector protein cleaves a target strand in the NST1 gene and the cleavage domain of the second CRISPR-Cas effector protein cleaves a target strand in the NST3 gene.

Also provided herein are expression cassettes comprising a (a) a polynucleotide encoding CRISPR-Cas effector protein comprising a cleavage domain and (b) a guide nucleic acid that binds to a target site within a AC SECONDARY WALL THICKENING PROMOTING FACTOR1 (NST1), wherein the guide nucleic acid comprises a spacer sequence that is complementary to and binds to the target site within the NST1 gene, the NST1 gene: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (ii) comprises a region having at least 80% sequence identity to a nucleotide sequence of any one of SEQ ID NOs:84-97 and/or 145-171; (iii) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (iv) comprises a region having at least 80% sequence identity to the amino acid sequence of any one of SEQ ID NOs:123-129, 172-180, 264-273, and/or 282, optionally wherein the sequence identity of (i), (ii), (iii) and/or (iv) may be at least 85%, or at least 90%, or it may be at least 95%, optionally the sequence identity may be 100%.

Further, provided herein are expression cassettes comprising a (a) a polynucleotide encoding CRISPR-Cas effector protein comprising a cleavage domain and (b) a guide nucleic acid that binds to a target site within a NAC SECONDARY WALL THICKENING PROMOTING FACTOR3 (NST3), wherein the guide nucleic acid comprises a spacer sequence that is complementary to and binds to the target site within the NST3 gene, the NST3 gene: (i) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (ii) comprises a region having at least 80% sequence identity to a nucleotide sequence of any one of SEQ ID NOs:98-116 and/or 181-2481; (iii) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (iv) comprises a region having at least 80% sequence identity to the amino acid sequence of any one of SEQ ID NOs:127, 130-133, 249-255, and/or 283, optionally wherein the sequence identity of (i), (ii), (iii) and/or (iv) may be at least 85%, or at least 90%, or it may be at least 95%, optionally the sequence identity may be 100%.

In some embodiments, the target site is in a region of the NTS1 gene having at least 80% sequence identity to any one of the nucleotide sequences of SEQ ID NOs:84-97 and/or 145-171, and wherein the target site is in a region of the NTS3 gene having at least 80% sequence identity to any one of the nucleotide sequences of SEQ ID NOs:98-116 and/or 181-248.

In some embodiments, a nucleic acid is provided that encodes a mutated NAC SECONDARY WALL THICKENING PROMOTING FACTOR1 (NST1) polypeptide, optionally wherein the mutation results in a truncated NST1 polypeptide. In some embodiments, a nucleic acid is provided that encodes a mutated NAC SECONDARY WALL THICKENING PROMOTING FACTOR1 (NST3) polypeptide, optionally wherein the mutation results in a truncated NST3 polypeptide. In some embodiments, the mutated nucleic acid comprises a null mutation. In some embodiments, the mutated nucleic acid comprises a non-natural mutation.

Further provided are *Rubus* plants or parts thereof comprising a mutated NST1 nucleic acid and a mutated NST3 nucleic acid as described herein. In some embodiments, a *Rubus* plant (e.g., a blackberry plant) is provided that comprises a mutated NST1 nucleic acid and a mutated NST3 nucleic acid as described herein and exhibits a phenotype of reduced endocarp lignification, reduced seediness and/or a reduced feel of seediness as compared to a plant that is devoid of the at least one mutation. In some embodiments, a *Rubus* plant or part thereof is provided that comprises a mutation in an endogenous NST1 gene and an endogenous NST3 gene, wherein the at least one mutation is a null mutation, optionally wherein the at least one mutation is a non-natural mutation and/or a dominant mutation.

In some embodiments, a method of the present invention may further comprise regenerating a *Rubus* plant from a plant cell or plant part comprising a mutation (e.g., one or more mutations) in an endogenous NST1 gene and an endogenous NST3 gene. In some embodiments, a *Rubus* plant comprising a mutation in an endogenous NST1 gene exhibits a phenotype of reduced endocarp lignification, reduced seediness and/or a reduced feel of seediness, as compared to a plant that is devoid of the at least one mutation. In some embodiments, the mutation is a null mutation. In some embodiments, the mutation may be a non-natural mutation. In some embodiments, the mutation is a base deletion. In some embodiments, the mutation results in a dominant allele. In some embodiments, the regenerated *Rubus* plant comprises a mutated NST1 gene and a mutated NST1 gene having at least 90% sequence identity (e.g., at least about 90, 91, 92, 93, 94, 95, 96, 97, 98, 99 or 100% sequence identity, optionally the sequence identity may be at least 95%, optionally the sequence identity may be 100%) to a mutated NST1 nucleic acid and a mutated NST3 nucleic acid as described herein.

An editing system useful with this invention can be any site-specific (sequence-specific) genome editing system now known or later developed, which system can introduce mutations in target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a NST1 gene and a NST3 gene may comprise contacting a target nucleic acid (e.g., a target region of the NST1 gene and the NST3 gene) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific DNA binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a NST1 gene and a NST3 gene may comprise contacting a target nucleic acid (e.g., a target region of the NST1 gene and a target region of the NST3 gene) with a sequence-specific DNA binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific DNA binding fusion protein to the target nucleic acid and the sequence-specific DNA binding fusion protein is capable of recruiting the deaminase fusion protein to the target nucleic acid via the peptide tag-affinity polypeptide interaction, thereby editing a locus within the target nucleic acid. In some embodiments, the sequence-specific DNA binding fusion protein may be fused to the affinity polypeptide that binds the peptide tag and the deaminase may be fuse to the peptide tag, thereby recruiting the deaminase to the sequence-specific DNA binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific DNA binding fusion proteins, deaminase fusion proteins and guides may be provided as ribonucleoproteins (RNPs).

In some embodiments, methods such as prime editing may be used to generate a mutation in an endogenous NST1 gene and an endogenous NST3 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantage of the various methods of recruiting proteins for use in the editing to the target site, such methods including both non-covalent and covalent interactions between the proteins and nucleic acids used in the selected process of genome editing.

In some embodiments, the mutation or modification of an endogenous NST1 gene and an endogenous NST3 gene may be a base deletion and/or a point mutation that produces a mutated endogenous NST1 gene and a mutated endogenous NST3 gene, wherein the mutated NST1 gene encodes a null mutation and the mutated endogenous NST3 gene encodes null mutation, optionally wherein the mutated NST1 gene encodes a C-terminally truncated NST1 polypeptide and the mutated endogenous NST3 gene encodes a C-terminally truncated NST3 polypeptide, optionally wherein the mutated/modified NST1 gene and the mutated/modified NST3 gene confers a phenotype of reduced endocarp lignification, reduced seediness and/or a reduced feel of seediness on a *Rubus* plant or part thereof comprising the mutated/modified NST1 gene and mutated/modified NST3 gene. In some embodiments, a plant part may be a cell. In some embodiments, the *Rubus* plant or plant part thereof may be any *Rubus* plant or part thereof as described herein. In some embodiments, a *Rubus* plant useful with this invention may be blackberry, raspberry, or black raspberry. In some embodiments, a *Rubus* plant comprising a mutated NST1 gene may have a mutation in the dimerization domain and/or transactivating domain of the NST1 transcription factor polypeptide and comprising a mutated NST3 gene having a mutation in the dimerization domain and/or trans-activating domain of the NST3 transcription factor polypeptide, may further comprise a reduced endocarp lignification, reduced seediness and/or a reduced feel of seediness phenotypes as compared to a control plant that is devoid of the mutated NST1 gene and the mutated NST3 gene. In some embodiments, a *Rubus* plant comprising a mutated endogenous NST1 gene and mutated endogenous NST3 gene exhibits a phenotype of reduced endocarp lignification, reduced seediness and/or a reduced feel of seediness phenotypes as compared to a *Rubus* plant that is devoid of the mutation in the NST1 and in the NST3 genes.

In some embodiments, a mutation that is introduced into an endogenous NST1 gene and an endogenous NST3 gene is a null mutation. In some embodiments, a mutation that is introduced into an endogenous NST1 gene and an endogenous NST3 gene may be a non-natural mutation. In some embodiments, a mutation that is introduced into an endogenous NST1 gene and an endogenous NST3 gene may be a deletion of at least one nucleotide, at least two consecutive nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, or 140 consecutive base pairs, or any value or range therein), wherein the mutation may be located between 100 and 300 bases (or any range or value therein) upstream of the stop codon of the endogenous NST1 gene and the endogenous NST3 gene, optionally wherein the mutation may be a deletion or elimination of the dimerization domain of the NST1 polypeptide or may alter the ability of the dimerization domain to dimerize and wherein the mutation may be a deletion or elimination of the dimerization domain of the NST3 polypeptide or may alter the ability of the dimerization domain of the NST3 polypeptide to dimerize, optionally wherein the dimerization domain of the NST1 polypeptide and the NST3 polypeptide comprises the amino acid sequence VPPG-FRFHPTEEELLQYYL (SEQ ID NO:282) or VPPG-FRFHPTEEELLHYYL (SEQ ID NO:283), e.g., an amino acid sequence comprising the sequence EEELL (SEQ ID NO:127). In some embodiments, a mutation may be located in and/or adjacent to the first exon of the endogenous NST1 gene encoding a NST1 transcription factor polypeptide and/or the at least one mutation may be located in and/or adjacent to the first exon of the endogenous NST3 gene encoding a NST3 transcription factor polypeptide. In some embodiments, a mutation may be located in and/or adjacent to the third exon of the endogenous NST1 gene encoding a NST1 transcription factor polypeptide and/or the at least one mutation may be located in and/or adjacent to the third exon of the endogenous NST3 gene encoding a NST3 transcription factor polypeptide.

In some embodiments, a sequence-specific nucleic acid binding domain (sequence-specific DNA binding domains) of an editing system useful with this invention can be from, for example, a polynucleotide-guided endonuclease, a CRISPR-Cas endonuclease (e.g. CRISPR-Cas effector protein), a zinc finger nuclease, a transcription activator-like effector nuclease (TALEN) and/or an Argonaute protein.

In some embodiments, a sequence-specific nucleic acid binding domain may be a CRISPR-Cas effector protein, optionally wherein the CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain, e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., Oenococcus spp., *Pediococcus* spp., Weissella spp., and/or Olsenella spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al. (2013) *Science* 339(6121):823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al (2010) *Science* 327(5962):167-170, and Deveau et al. (2008) *J. Bacteriol.* 190(4):1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al. (2008) *J. Bacteriol.* 190(4):1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif NGRRT (R=A or G). In some embodiments, the CRISPR-Cas effector protein may be a Cas9 polypeptide derived from *S. aureus*, which recognizes the PAM sequence motif NGRRV (R=A or G). In some embodiments, the CRISPR-Cas effector protein may be a Cas9 polypeptide that is derived from *Neisseria meningitidis* and recognizes the PAM sequence motif NGATT or NGCTT (R=A or G, V=A, G or C) (See, e.g., Hou et al (2013) *Proc. Natl. Acad. Sci. USA* 110 (39):15644-15649). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., amino acid sequences of SEQ ID NOs:1-17, nucleic acid sequences of SEQ ID NOs:18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. (2019) *Nat. Biotechnol.* 37:1070-1079, each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode an uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

An "uracil glycosylase inhibitor" useful with the invention may be any protein that is capable of inhibiting an uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through an uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific DNA binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt transcription factor binding; and/or generation of point mutations in genomic DNA to disrupt splice junctions.

The nucleic acid constructs of the invention encoding a base editor comprising a sequence-specific DNA binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

In some embodiments, templated editing may be used to reduce endocarp lignification, reduce seediness or a reduce the feel of seediness in a *Rubus* plant or part thereof. Templated editing includes, but is not limited to, PRIME editing and REDRAW editing. In some embodiments, unique enzymes may be used, such as SHARC (see e.g., PCT/US2024/018165). In general, templated editing comprises a Cas polypeptide, a reverse transcriptase, a guide RNA, a primer binding site and a reverse transcriptase template. In some embodiments, the reverse transcriptase may be a DNA polymerase. These components and their exact make up can vary depending on the type of templated editing that is used. For example, a guide RNA may be an "extended" guide RNA that comprises an extended portion (in addition to a spacer) that comprises the primer binding site and an edit to be incorporated into the target nucleic acid (e.g., reverse transcriptase template). Methods for templated editing are known in the art, see for example, U.S. Pat. Nos. 11,926,834, 11,643,652, U.S. patent application Ser. No. 17/142,570, U.S. patent application Ser. No. 17/078,919 and PCT/US2024/018165.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof, wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. (2007) *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a portion of a target nucleic acid (e.g., target DNA) (e.g., protospacer). In some embodiments, the spacer sequences is complementary to a portion of consecutive nucleotides of a NST1 gene or a portion of consecutive nucleotides of a NST3 gene, wherein the endogenous NST1 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:69, SEQ ID NO:70, SEQ ID NO:72, SEQ ID NO:73, SEQ ID NO:75, SEQ ID NO:76, SEQ ID NO:256 and/or SEQ ID NO:258; (b) comprises a region having at least 80% sequence identity to a nucleotide sequence of any one of SEQ ID NOs:84-97 and/or 145-171; (c) encodes a NST1 transcription factor polypeptide having at least 80% sequence identity to the amino acid sequence of SEQ ID NO:71, SEQ ID NO:74, SEQ ID NO:77, SEQ ID NO:257 and/or SEQ ID NO:259; and/or (d) comprises a region having at least 80% sequence identity to the amino acid sequence of any one of SEQ ID NOs:123-129, 172-180, 264-273, and/or 282, and wherein the endogenous NST3 gene: (a) comprises a nucleotide sequence having at least 80% sequence identity (e.g., at least about 80, 81, 82, 83, 84, 85, 86, 87, 88, 89, 90, 91, 92, 93, 94, 95, 96, 97, 98, 99 or 100% sequence identity) to SEQ ID NO:78, SEQ ID NO:79, SEQ ID NO:81, SEQ ID NO:82, SEQ ID NO:260 and/or SEQ ID NO:262; (b) comprises a region having at least 80% sequence identity to a nucleotide sequence of any one of SEQ ID NOs:98-116 and/or 181-248; (c) encodes a NST3 transcription factor polypeptide having at least 80% sequence identity to the amino acid sequence of SEQ ID NO:80, SEQ ID NO:83, SEQ ID NO:261 and/or SEQ ID NO:263; and/or (d) comprises a region having at least 80% sequence identity to the amino acid sequence of any one of SEQ ID NOs:127, 130-133, 249-255, and/or 283, optionally wherein the sequence identity of any one of (a), (b), (c) and/or (d) may be at least 85%, or at least 90%, or it may be at least 95%, optionally the sequence identity may be 100%. A spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%)) to a target nucleic acid. In some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length. In some embodiments, a spacer sequence may comprise any one of the sequences of SEQ ID NOs:117-119, SEQ ID NOs:120-122, SEQ ID NOs:134-136, SEQ ID NOs:137-144, or any combination thereof or reverse complement thereof.

In some embodiments, the 5' region of a spacer sequence of a guide nucleic acid may be identical to a target DNA, while the 3' region of the spacer may be substantially complementary to the target DNA (such as a spacer of a Type V CRISPR-Cas system), or the 3' region of a spacer sequence of a guide nucleic acid may be identical to a target DNA, while the 5' region of the spacer may be substantially complementary to the target DNA (such as a spacer of a Type II CRISPR-Cas system), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

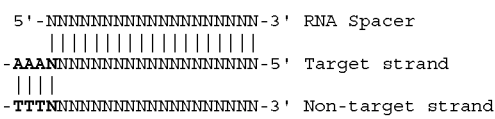

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems ((2015) *Nature Reviews Microbiology* 13:722-736). Guide structures and PAMs are described in by R. Barrangou ((2015) *Genome Biol.* 16:247).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. (2013) *Nat. Methods* 10:1116-1121; Jiang et al. (2013) *Nat. Biotechnol.* 31:233-239). In some embodiments, a computational approach can include performing BLAST searches of natural spacers to identify the original target DNA sequences in bacteriophages or plasmids and aligning these sequences to determine conserved sequences adjacent to the target sequence (Briner and Barrangou. (2014) *Appl. Environ. Microbiol.* 80:994-1001; Mojica et al. (2009) *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains, CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, an octapeptide sold under the tradename FLAG®, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO 2018/136783 and US Patent Application Publication No. 2017/0219596, which are incorporated by reference for their disclosures of peptide tags. Any epitope that may be linked to a polypeptide and for which there is a corresponding affinity polypeptide that may be linked to another polypeptide may be used with this invention as a peptide tag. A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20 or more amino acids, optionally about 3 to about 10, about 4 to about 10, about 5 to about 10, about 5 to about 15, or about 5 to about 20 amino acids, and the like, and any value or range therein. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin, see, e.g., Sha et al. (2017) *Protein Sci.* 26(5):910-924; Gilbreth (2013) *Curr. Opin. Struc. Biol.* 22(4):413-420; and U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihydrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific nucleic acid binding domain, a CRISPR-Cas effector domain, a deaminase domain, reverse transcriptase (RT), RT template and/or a guide nucleic acid, etc) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, collenchyma cells, sclerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous NST1 gene and endogenous NST3 gene, wherein when modified as described herein the modified NST1 gene and modified NST3 are capable of conferring a reduced endocarp lignification, reduced seediness and/or a reduced feel of seediness phenotypes in the plant (e.g., *Rubus* plant), is useful with this invention. Non-limiting examples of *Rubus* plants that may be modified as described herein may include blackberry, raspberry, or black raspberry.

The invention will now be described with reference to the following examples. It should be appreciated that these examples are not intended to limit the scope of the claims to the invention but rather are intended to be exemplary of certain embodiments. Any variations in the exemplified methods that occur to the skilled artisan are intended to fall within the scope of the invention.

EXAMPLES

Example 1: Targeted Editing of NST1 and NST3 Genes in *Rubus* Plants Using CRISPR-Based Gene Editing This example demonstrates the targeted mutation of the NST1 and NST3 genes in *Rubus* plant cells, resulting in a reduction in lignification of the endocarp.

A proprietary *Rubus* plant variety was selected for transformation. Multiple guide RNAs were designed to target the first exon within the NST1 and NST3 genes. gRNAs, SEQ ID NO: 120, SEQ ID NO: 121 and SEQ ID NO:122, were used to target the NST1 gene and the gRNAs, SEQ ID NO 117, SEQ ID NO:118 and SEQ ID NO 119, were used to target the NST3 gene. These gRNAs were then cloned into a CRISPR expression vector containing a Cas12a enzyme. *Rubus* plant cells were subsequently transformed using *Agrobacterium*-mediated transformation. Transformed cells were cultured on selective media containing kanamycin to encourage the growth of successfully transformed cells. After sufficient time, the regenerated shoots were transferred to rooting media.

Following transformation, genomic DNA was extracted from the regenerated plants. PCR amplification of the target regions within NST1 and NST3 was performed, and the resulting PCR products were sequenced to confirm the presence of indel mutations at the target sites, which indicated successful gene editing. The edited plants were further screened for null mutations, characterized by the introduction of stop codons due to out-of-frame mutations or disruption of the dimerization domain due to in-frame edits.

Sequencing analysis confirmed successful editing of the NST1 and NST3 loci. Indels were detected at the target sites within both genes, with no significant off-target mutations observed in predicted off-target sites.

A subset of regenerated plants with edits in NST1 and NST3 were grown to maturity, manually self-pollinated, and had fruit collected to screen for heritability of the phenotype. The seeds were germinated and progeny were screened for editing as well as for presence of the transgene. The inserted transgene, NST1 edit alleles, and NST3 edit alleles all segregated as expected. In progeny with no remaining WT NST1 or NST3 alleles, a soft endocarp phenotype was observed.

Example 2: Phenotypic Characterization of Edited *Rubus* Plants

This example demonstrates the phenotypic characterization of edited *Rubus* plants, specifically focusing on the reduction of lignification in the endocarp as measured by staining with phloroglucinol and as measured by the force required to compress blackberry pyrenes.

Phloroglucinol Staining.

Figure 2:
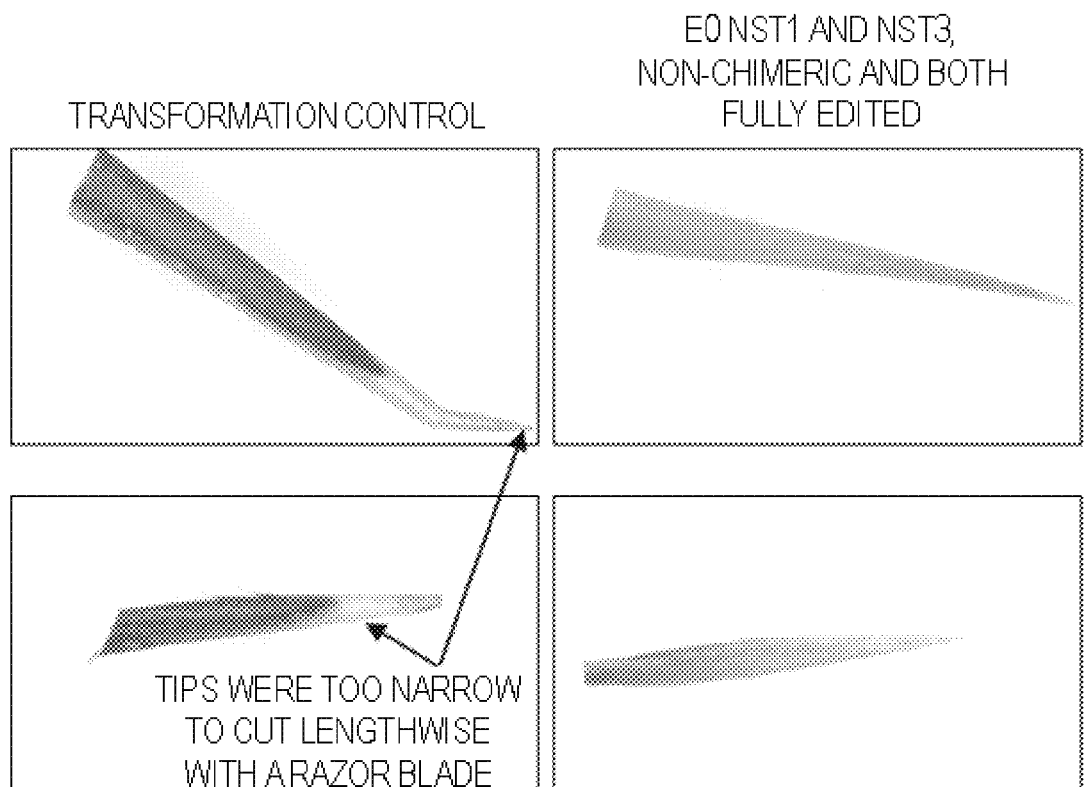
FIG. 2 provides a photograph showing the effect of the edits on prickles as measured by exposure to phloroglucinol.

Fruit was collected from edited blackberry plants, and the pits (endocarp and enclosed seed) were collected. In order to assess the impact of edits, pits were sectioned using a scalpel and exposed to phloroglucinol, which stains lignified tissues. In plants where NST1 and NST3 were edited the application of phloroglucinol to pits did not result in red pigment accumulation, indicating the edits resulted in loss of lignification in this tissue. Fruit from unedited plants developed normal pits, which when exposed to phloroglucinol exhibited strong pigmentation, indicating the tissue was lignified (FIG. 1). Plants with this loss of pit lignification phenotype also exhibited delignified prickles, where were soft to the touch, unlike unedited plants, which developed firm, sharp prickles on canes and leaves. (FIG. 2)

Absolute Positive Force.

Fresh fruit from edited blackberry plants were collected from the greenhouse and transported immediately to the NC State University small fruit lab for texture analysis. The pyrenes were extracted from the fresh fruit by gently compressing the drupelets, ensuring that any remaining mesocarp was carefully cleaned away using Kimwipes. The cleaned pyrenes were then pat-dried before proceeding with the measurements. Each pyrene was positioned horizontally on the stage of the TA.XTplus texture analyzer (Stable MicroSystem Ltd., Godalming, UK) under a 2 mm flathead probe, such that the probe would compress the pyrene centrally. The TA.XTplus Texture Analyzer from Stable Micro Systems is a precision instrument used to measure the physical properties of materials, such as texture, firmness, and compressibility. In this study, it was employed to assess the force required for 50% compression of blackberry pyrenes, using a 2 mm flathead probe to apply controlled pressure to the samples. The analyzer, coupled with Exponent Connect software, provided detailed data on the force applied and the resulting deformation of the pyrenes, allowing for precise measurement of texture changes related to lignification in the edited *Rubus* plants. Graphical profiles for each pyrene were generated, providing measurements for absolute positive force (g) at 50% compression, force at target (g), and the positive area to absolute positive force (g. see).

Figure 3:
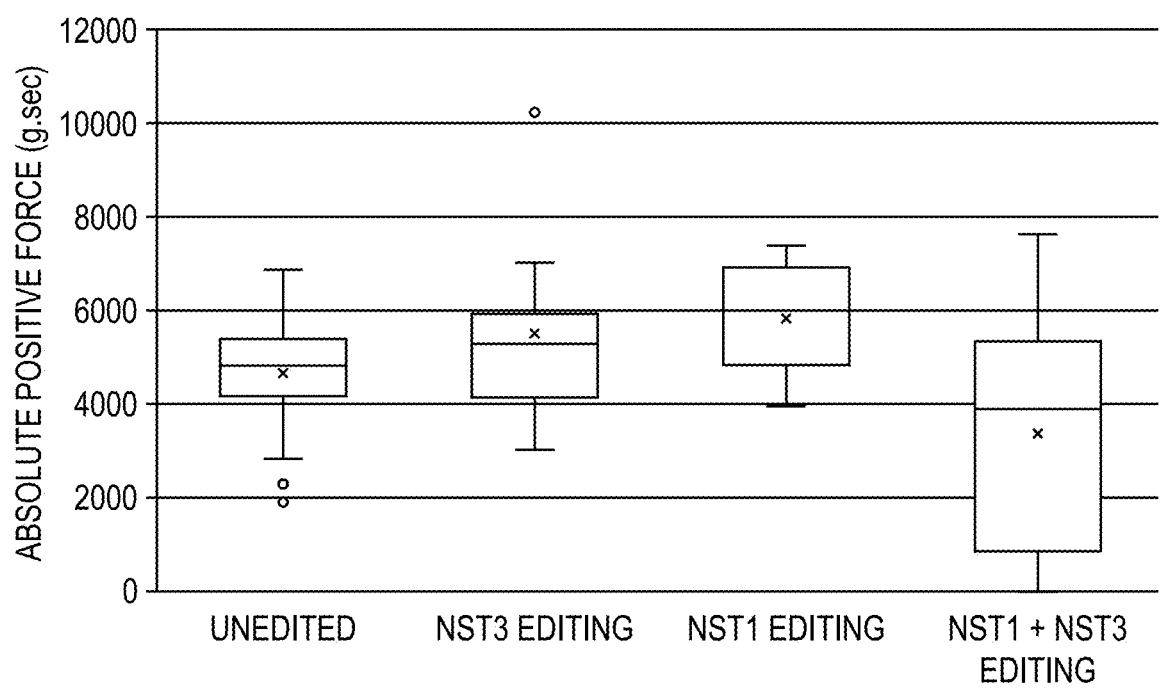
FIG. 3 provides a graph showing the effect of the edits on pit hardness as measured by absolute positive force.

The analysis revealed that the edited *Rubus* plants exhibited a significant reduction in the force required for 50% compression of the pyrenes compared to control plants (see FIG. 3). This reduction in compressive force indicates a decrease in the lignification of the endocarp, which correlates with the intended phenotypic outcome of reduced seed hardness.

The results from this phenotypic characterization provide strong evidence that the targeted editing of NST1 and NST3 genes in *Rubus* plants leads to a measurable reduction in endocarp lignification. This supports the potential of these edited plants to produce fruits with a reduced perception of seediness, making them more desirable for commercial fruit production.

In some jurisdictions, products obtained exclusively by essentially biological processes are excluded from patent protection. Accordingly, the claimed plants, plant parts and cells and their progeny can be defined as directed only to those plants, plant parts and cells and their progeny which are obtained by technical intervention (regardless of any further propagation through crossing and selection). An embodiment of the invention is directed at plants, or plant parts or progeny produced or obtainable using gene editing technology by introducing through stable or transient transformation an RNA-specific CRISPR/Cas system directed against or targeting a NST1 nucleotide sequence and targeting a NST3 nucleotide sequence, or one or more polynucleotide sequence(s) encoding said RNA-specific CRISPR/Cas system into the plant or the plant part. Alternatively, the subject matter excluded from patentability may be disclaimed. An embodiment of the invention is directed at plants, part of plants or progeny thereof comprising the alterations of the NST1 gene and the NST3 gene as elsewhere herein described, provided that the plants, parts or plants or progeny are not obtained exclusively through essentially biological processes, wherein essentially biological processes are processes for the production of plants or animals if they consist entirely of natural phenomena such as crossing or selection.

The foregoing is illustrative of the present invention and is not to be construed as limiting thereof. The invention is defined by the following claims, with equivalents of the claims to be included therein.

What is claimed is:

1. A *Rubus* plant or plant part thereof comprising at least one mutation in at least one endogenous NAC SECONDARY WALL THICKENING PROMOTING FACTOR1 (NST1) gene encoding a NST1 transcription factor polypeptide and at least one mutation in at least one endogenous NAC SECONDARY WALL THICKENING PROMOTING FACTOR3 (NST3) gene encoding a NST3 transcription factor polypeptide, wherein the at least one mutation in the at least one endogenous NST1 gene and the at least one mutation in the at least one endogenous NST3 gene is a null mutation, wherein the endogenous NST1 gene encodes the amino acid sequence of SEQ ID NO:279, SEQ ID NO:274, SEQ ID NO:275, or SEQ ID NO:278, or encodes an amino acid sequence having at least 95% sequence identity to any one of SEQ ID NO:71, SEQ ID NO:74, SEQ ID NO:77, SEQ ID NO:257 or SEQ ID NO:259; and the endogenous NST3 gene encodes the amino acid sequence of SEQ ID NO:281, SEQ ID NO:276, SEQ ID NO:277, or SEQ ID NO:280 or encodes an amino acid sequence having at least 95% sequence identity to any one of SEQ ID NO:80, SEQ ID NO:83, SEQ ID NO:261 or SEQ ID NO:263.

2. The *Rubus* plant or part thereof of claim 1, wherein the null mutation results in the production of a truncated polypeptide.

3. The *Rubus* plant or part thereof of claim 1, wherein the null mutation results in the production of a non-functional, or no, NST1 polypeptide and/or a non-functional, or no, NST3polypeptide.

4. The *Rubus* plant or part thereof of claim 1, wherein the at least one mutation is located in and/or adjacent to the first exon of the endogenous NST1 gene encoding a NST1 transcription factor polypeptide and/or the at least one mutation is located in and/or adjacent to the first exon of the endogenous NST3 gene encoding a NST3 transcription factor polypeptide.

5. The *Rubus* plant or part thereof of claim 1, wherein the at least one mutation is located in the 5' region of the first exon of the endogenous NST1 gene and/or is located in the 5' region of the first exon of the endogenous NST3 gene.

6. The *Rubus* plant or part thereof of claim 1, wherein the at least one mutation is located in and/or adjacent to the third exon of the endogenous NST1 gene encoding a NST1 transcription factor polypeptide and/or the at least one mutation is located in and/or adjacent to the third exon of the endogenous NST3 gene encoding a NST3 transcription factor polypeptide.

7. The *Rubus* plant or part thereof of claim 1, wherein the at least one mutation is located in the 5' region of the third exon of the endogenous NST1 gene and/or is located in the 5' region of the third exon of the endogenous NST3 gene.

8. The *Rubus* plant or part thereof of claim 1, wherein the at least one mutation in at least one endogenous NST1 gene and/or the at least one mutation in at least one endogenous NST3 gene comprises a base substitution, a base deletion, and/or a base insertion.

9. The *Rubus* plant or part thereof of claim 1, wherein the at least one mutation in at least one endogenous NST1 gene is an out-of-frame insertion or an out-of-frame deletion and/or the at least one mutation in an endogenous NST3 gene is an out-of-frame insertion or an out-of-frame deletion.

10. The *Rubus* plant or part thereof of claim 1, wherein the at least one mutation in at least one endogenous NST1 gene is an in-frame insertion or an in-frame deletion and/or the at least one mutation in an endogenous NST3 gene is an in-frame insertion or an in-frame deletion.

11. The *Rubus* plant or part thereof of claim 1, wherein the at least one mutation in at least one endogenous NST1 gene results in a deletion or insertion of one or more base pairs located in a region having at least 90% sequence identity to any one of the nucleotide sequences of SEQ ID NOs:84-97 or 145-171 and the at least one mutation in at least one endogenous NST3 gene results in a deletion or insertion of one or more base pairs located in a region having at least 90% sequence identity to any one of the nucleotide sequences of SEQ ID NOs:98-116 or 181-248.

12. The *Rubus* plant or plant part thereof of claim 1, wherein the at least one mutation in at least one NST1 endogenous gene and the at least one mutation in at least one endogenous NST3 gene results in the plant or part thereof that exhibits (1) reduced endocarp lignification or (2) reduced endocarp lignification and reduced seed hardness as compared to a control plant that is devoid of the at least one mutation in at least one NST1 endogenous gene and the at least one mutation in at least one endogenous NST3 gene.

13. The *Rubus* plant or part thereof of claim 1, wherein the *Rubus* plant is blackberry, black raspberry, or red raspberry.

14. A *Rubus* plant regenerated from the plant part of claim 1.

15. The *Rubus* plant of claim 14, wherein the plant exhibits (1) reduced endocarp lignification or (2) reduced endocarp lignification and reduced seed hardness as compared to a control plant that is devoid of the at least one mutation in at least one NST1 endogenous gene and the at least one mutation in at least one endogenous NST3 gene.

16. The *Rubus* plant of claim 14, wherein the *Rubus* plant is blackberry, black raspberry, or red raspberry.

17. A method for editing a specific site in the genome of a *Rubus* plant cell, the method comprising: cleaving, in a site-specific manner, a target site within an endogenous NAC SECONDARY WALL THICKENING PROMOTING FACTOR1 (NST1) gene in the *Rubus* plant cell and a target site within an endogenous NAC SECONDARY WALL THICKENING PROMOTING FACTOR3 (NST3) gene in the *Rubus* plant cell, wherein the endogenous NST1 gene encodes the amino acid sequence of SEQ ID NO:279, SEQ ID NO:274, SEQ ID NO:275, or SEQ ID NO:278, or encodes an amino acid sequence having at least 95% sequence identity to any one of SEQ ID NO:71, SEQ ID NO:74, SEQ ID NO:77, SEQ ID NO:257 or SEQ ID NO:259; and the endogenous NST3 gene encodes the amino acid sequence of SEQ ID NO:281, SEQ ID NO:276, SEQ ID NO:277, or SEQ ID NO:280 or encodes an amino acid sequence having at least 95% sequence identity to any one of SEQ ID NO:80, SEQ ID NO:83, SEQ ID NO:261 or SEQ ID NO:263, and
wherein the target site is in a region of the NST1 gene having at least 90%0 sequence identity to any one of the nucleotide sequences of SEQ ID NOs:84-97 or 145-171, and the target site is in a region of the NST3 gene having least 90% sequence identity to any one of the nucleotide sequences of SEQ ID NOs:98-116 or 181-248, thereby generating an edit in the endogenous NST1 gene and in the endogenous NST3 gene of the *Rubus* plant cell and the edit results in a null mutation.

18. The method of claim 17, wherein the edit in the endogenous NST1 gene is in the 5' region of Exon 1 and/or Exon 3 of the endogenous NST1 gene and the edit in the endogenous NST3 gene is in the 5' region of Exon 1 and/or Exon 3 of the endogenous NST3 gene.

19. The method of claim 17, wherein the edit in the endogenous NST1 gene and the endogenous NST3 gene results in a dominant allele.

20. The method of claim 17, further comprising regenerating a *Rubus* plant from the *Rubus* plant cell comprising the edit in the endogenous NST1 gene and in the endogenous NST3 gene to produce a *Rubus* plant comprising the edit in its endogenous NST1 gene and endogenous NST3 gene, wherein the plant comprising the edit in its endogenous NST1 gene and endogenous NST3 gene exhibits W11 reduced endocarp lignification or (2) reduced endocarp lignification and reduced seed hardness as compared to a control plant that is devoid of the edit.

21. A method for producing a *Rubus* plant or part thereof comprising at least one cell having a mutation in an endogenous NAC SECONDARY WALL THICKENING PROMOTING FACTOR1 (NST1) gene and a mutation in an endogenous NAC SECONDARY WALL THICKENING PROMOTING FACTOR1 (NST3) gene, wherein the endogenous NST1 gene encodes the amino acid sequence of SEQ ID NO:279, SEQ ID NO:274, SEQ ID NO:275, or SEQ ID NO:278, or encodes an amino acid sequence having at least 95% sequence identity to any one of SEQ ID NO:71, SEQ ID NO:74, SEQ ID NO:77, SEQ ID NO:257 or SEQ ID NO:259; and the endogenous NST3 gene encodes the amino acid sequence of SEQ ID NO:281, SEQ ID NO:276, SEQ ID NO:277, or SEQ ID NO:280 or encodes an amino acid sequence having at least 95% sequence identity to any one of SEQ ID NO:80, SEQ ID NO:83, SEQ ID NO:261 or SEQ ID NO:263,
the method comprising
contacting a target site within the endogenous NST1 gene and a target site within the endogenous NST3 gene in the *Rubus* plant or part thereof with a nuclease comprising a cleavage domain and a nucleic acid binding domain, wherein the nucleic acid binding domain of the nuclease binds to a target site within the endogenous NST1 gene and a target site within the endogenous NST3 gene, and/or
contacting a target site within the endogenous NST1 gene and a target site within the endogenous NST3 gene in the *Rubus* plant or part thereof with a first nuclease and a second nuclease each of which comprise a cleavage domain and a nucleic acid binding domain, wherein the nucleic acid binding domain of the first nuclease binds to a target site within the endogenous NST1 gene and the nucleic acid binding domain of the second nuclease binds to a target site within the endogenous NST3 gene,
wherein the target site is in a region of the NST1 gene having at least 90% sequence identity to any one of the nucleotide sequences of SEQ ID NOs:84-97 or 145-171, and the target site is in a region of the NST3 gene having at least 90% sequence identity to any one of the nucleotide sequences of SEQ ID NOs:98-116 or 181-248, thereby producing a *Rubus* plant or part thereof comprising at least one cell having a mutation in the endogenous NST1 gene and in the endogenous NST3 gene, wherein the mutation in the endogenous NST1 gene and in the endogenous NST3 gene is a null mutation.

22. The method of claim 21, wherein the mutation that is introduced into the endogenous NST1 gene is located in the 5' region of the endogenous NST1 gene and the mutation that is introduced into the endogenous NST3 gene is located in the 5' region of the endogenous NST3 gene.

23. A *Rubus* plant produced by the method of claim 21, wherein the *Rubus* plant exhibits (1) reduced endocarp lignification or (2) reduced endocarp lignification and reduced seed hardness as compared to a control plant.

24. The *Rubus* plant of claim 23, wherein the *Rubus* plant comprises a null mutation in an NST1 gene and in an NST3 gene.

* * * * *

UNITED STATES PATENT AND TRADEMARK OFFICE
CERTIFICATE OF CORRECTION

Page 1 of 2

PATENT NO. : 12,297,441 B1
APPLICATION NO. : 18/830788
DATED : May 13, 2025
INVENTOR(S) : Brian Charles Wilding Crawford It is certified that error appears in the above-identified patent and that said Letters Patent is hereby corrected as shown below:

In the Specification

Column 1, Line 19: Please correct "WAIL" to read --WALL--

Column 1, Line 60: Please correct "WALL. THICKENING" to read --WALL THICKENING--

Column 28, Line 5: Please correct "-rnethionine" to read -- -methionine--

Column 34, Lines 16-17: Please remove the paragraph break between "consumers." and "The feel"

Column 53, Line 20: Please correct "NTS11" to read --NTS1--

Column 58, Line 53: Please correct "FACTOR/(NST1)" to read --FACTOR1 (NST1)--

Column 59, Lines 66-67: Please correct "SEQ ID NOs:117-1119" to read --SEQ ID NOs:117-119--

Column 62, Line 39: Please correct "NA/C" to read --NAC--

Column 63, Line 30: Please correct "AC" to read --NAC--

Column 64, Line 1: Please correct "181-2481" to read --181-248--

Column 64, Line 24: Please correct "FACTOR1 (NST3)" to read --FACTOR3 (NST3)--

Column 81, Line 29: Please correct "(DHFR)." to read --(DHFR)).--

Column 83, Lines 24-25: Please correct "SEQ ID NO 117" to read --SEQ ID NO:117--

Signed and Sealed this
Sixteenth Day of September, 2025

Coke Morgan Stewart
*Acting Director of the United States Patent and Trademark Office*

CERTIFICATE OF CORRECTION (continued)
U.S. Pat. No. 12,297,441 B1

Column 83, Line 25: Please correct "SEQ ID NO 119" to read --SEQ ID NO:119--

In the Claims

Column 213, Line 31, Claim 17: Please correct "90%0" to read --90%--

Column 213, Line 53, Claim 20: Please correct "W11" to read --(1)--

```
                              SEQUENCE LISTING

Sequence total quantity: 283
SEQ ID NO: 1            moltype = AA  length = 1228
FEATURE                 Location/Qualifiers
source                  1..1228
                        mol_type = protein
                        note = Lachnospiraceae sp.
                        organism = unidentified
SEQUENCE: 1
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 2            moltype = AA  length = 1307
FEATURE                 Location/Qualifiers
source                  1..1307
                        mol_type = protein
                        organism = Acidaminococcus sp.
SEQUENCE: 2
MTQFEGFTNL YQVSKTLRFE LIPQGKTLKH IQEQGFIEED KARNDHYKEL KPIIDRIYKT   60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ VNAYLKEHP   900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI 1020
DKLNCLVLKD YPAEKVGGVL NPYQLTDQFT SFAKMGTQSG FLFYVPAPYT SKIDPLTGFV 1080
DPFVWKTIKN HESRKHFLEG FDFLHYDVKT GDFILHFKMN RNLSFQRGLP GFMPAWDIVF 1140
EKNETQFDAK GTPFIAGKRI VPVIENHRFT GRYRDLYPAN ELIALLEEKG IVFRDGSNIL 1200
PKLLENDDSH AIDTMVALIR SVLQMRNSNA ATGEDYINSP VRDLNGVCFD SRFQNPEWPM 1260
DADANGAYHI ALKGQLLLNH LKESKDLKLQ NGISNQDWLA YIQELRN              1307

SEQ ID NO: 3            moltype = AA  length = 1241
FEATURE                 Location/Qualifiers
source                  1..1241
                        mol_type = protein
                        organism = Butyrivibrio proteoclasticus
SEQUENCE: 3
MLLYENYTKR NQITKSLRLE LRPQGKTLRN IKELNLLEQD KAIYALLERL KPVIDEGIKD   60
IARDTLKNCE LSFEKLYEHF LSGDKKAYAK ESERLKKEIV KTLIKNLPEG IGKISEINSA  120
```

```
KYLNGVLYDF IDKTHKDSEE KQNILSDILE TKGYLALFSK FLTSRITTLE QSMPKRVIEN    180
FEIYAANIPK MQDALERGAV SFAIEYESIC SVDYYNQILS QEDIDSYNRL ISGIMDEDGA    240
KEKGINQTIS EKNIKIKSEH LEEKPFRILK QLHKQILEER EKAFTIDHID SDEEVVQVTK    300
EAFEQTKEQW ENIKKINGFY AKDPGDITLF IVVGPNQTHV LSQLIYGEHD RIRLLLEEYE    360
KNTLEVLPRR TKSEDARYDK FVNAVPKKVA KESHTFDGLQ KMTGDDRLFI LYRDELARYD    420
MRIKEAYGTF ERDILKSRRG IKGNRDVQES LVSFYDELTK FRSALRIINS GNDEKADPIF    480
YNTFDGIFEK ANRTYKAENL CRNYVTKSPA DDARIMASCL GTPARLRTHW WNGEEENFAIN   540
DVAMIRRGDE YYYFVLTPDV KPVDLKTKDE TDAQIFVQRK GAKSFLGLPK ALFKCILEPY    600
FESPEHKNDK NCVIEEYVSK PLTIDRRAYD IFKNGTFKKT NIGIDGLTEE KPKDDCRYLI    660
DVYKEFIAVY TRYSCFNMSG LKRADEYNDI GEFFSDVDTR LCTMEWIPVS FERINDMVDK    720
KEGLLFLVRS MFLYNRPRKP YERTFIQLFS DSNMEHTSML LNSRAMIQYR AASLPRRVTH    780
KKGSILVALR DSNGEHIPMH IREAIYKMKN NFDISSEDFI MAKAYLAEHD VAIKKANEDI    840
IRNRRYTEDK FFLSLSYTKN ADISARTLDY INDKVEEDTQ DSRMAVIVTR NLKDLTYVAV    900
VDEKNNVLEE KSLNEIDGVN YRELLKERTK IKYHDKTRLW QYDVSSKGLK EAYVELAVTQ    960
ISKLATKYNA VVVVESMSST FKDKFSFLDE QIFKAFEARL CARMSDLSFN TIKEGEAGSI   1020
SNPIQVSNNN GNSYQDGVIY FLNNAYTRTL CPDTGFVDVF DKTRLITMQS KRQFFAKMKD   1080
IRIDDGEMLF TFNLEEYPTK RLLDRKEWTV KIAGDGSYFD KDKGEYVYVN DIVREQIIPA   1140
LLEDKAVFDG NMAEKFLDKT AISGKSVELI YKWFANALYG IITKKDGEKI YRSPITGTEI   1200
DVSKNTTYNF GKKFMFKQEY RGDGDFLDAF LNYMQAQDIA V                        1241

SEQ ID NO: 4           moltype = AA  length = 1238
FEATURE                Location/Qualifiers
source                 1..1238
                       mol_type = protein
                       organism = Methanoplasma termitum
SEQUENCE: 4
MNNYDEFTKL YPIQKTIRFE LKPQGRTMEH LETFNFFEED RDRAEKYKIL KEAIDEYHKK     60
FIDEHLTNMS LDWNSLKQIS EKYYKSREEK DKKVFLSEQK RMRQEIVSEF KKDDRFKDLF    120
SKKLFSELLK EEIYKKGNHQ EIDALKSFDK FSGYFIGLHE NRKNMYSDGD EITAISNRIV    180
NENFPKFLDN LQKYQEARKK YPEWIIKAES ALVAHNIKMD IVFSLEYFNK VLNQEGIQRY    240
NLALGGYVTK SGEKMMGLND ALNLAHQSEK SSKGRIHMTP LFKQILSEKE SFSYIPDVFT    300
EDSQLLPSIG GFFAQIENDK DGNIFDRALE LISSYAEYDT ERIYIRQADI NRVSNVIFGE    360
WGTLGGLMRE YKADSININ LERTCKKVDK WLDSKEFALS DVLEAIDRTG NNDAFNEYIS    420
KMRTAREKID AARKEMKFIS EKISGDEESI HIIKTLLDSV QQFLHFFNLF KARQDIPLDG    480
AFYAEFDEVH SKLFAIVPLY NKVRNYLTKN NLNTKKIKLN FKNPTLANGW DQNKVYDYAS    540
LIFLRDGNYY LGIINPKRKK NIKFEQGSGN GPFYRKMVYK QIPGPNKNLR PVFLTSTKGK    600
KEYKPSKEII EGYEADKHIR GDKFDLDFCH KLIDFFKESI EKHKDWSKFN FYFSPTESYG    660
DISEFYLDVE KQGYRMHFEN ISAETIDEYV EKGDLFLFQI YNKDFVKAAT GKKDMHTIYW    720
NAAFSPENLQ DVVVKLNGEA ELFYRDKSDI KEIVHREGEI LVNRTYNGRT PVPDKIHKKL    780
TDYHNGRTKD LGEAKEYLDK VRYFKAHYDI TKDRRYLNDK IYFHVPLTLN FKANGKKNLN    840
KMVIEKFLSD EKAHIIGIDR GERNLLYYSI IDRSGKIIDQ QSLNVIDGFD YREKLNQREI    900
EMKDARQSWN AIGKIKDLKE GYLSKAVHEI TKMAIQYNAI VVMEELNYGF KRGRFKVEKQ    960
IYQKFENMLI DKMNYLVFKD APDESPGGVL NAYQLTNPLE SFAKLGKQTG ILFYVPAAYT   1020
SKIDPTTGFV NLFNTSSKTN AQERKEFLQK FESISYSAKD GGIFAFAFDY RKFGTSKTDH   1080
KNVWTAYTNG ERMRYIKEKK RNELFDPSKE IKEALTSSGI KYDGGQNILP DILRSNNNGL   1140
IYTMYSSFIA AIQMRVYDGK EDYIISPIKN SKGEFFRTDP KRRELPIDAD ANGAYNIALR   1200
GELTMRAIAE KFDPDSEKMA KLELKHKDWF EFMQTRGD                           1238

SEQ ID NO: 5           moltype = AA  length = 1281
FEATURE                Location/Qualifiers
source                 1..1281
                       mol_type = protein
                       organism = Eubacterium eligens
SEQUENCE: 5
MNGNRSIVYR EFVGVIPVAK TLRNELRPVG HTQEHIIQNG LIQEDELRQE KSTELKNIMD     60
DYYREYIDKS LSGVTDLDFT LLFELMNLVQ SSPSKDNKKA LEKEQSKMRE QICTHLQSDS    120
NYKNIFNAKL LKEILPDFIK NYNQYDVKDK AGKLETLALF NGFSTYFTDF FEKRKNVFTK    180
EAVSTSIAYR IVHENSLIFL ANMTSYKKIS EKALDEIEVI EKNNQDKMGD WELNQIFNPD    240
FYNMVLIQSG IDFYNEICGV VNAHMNLYCQ QTKNNYNLFK MRKLHKQILA YTSTSFEVPK    300
MFEDDMSVYN AVNAFIDETE KGNIIGKLKD IVNKYDELDE KRIYISKDFY ETLSCFMSGN    360
WNLITGCVEN FYDENIHAKG KSKEEKVKKA VKEDKYKSIN DVNDLVEKYI DEKERNEFKN    420
SNAKQYIREI SNIITDTETA HLEYDDHISL IESEEKADEM KKRLDMYMNM YHWAKAFIVD    480
EVLDRDEMFY SDIDDIYNIL ENIVPLYNRV RNYVTQKPYN SKKIKLNFQS PTLANGWSQS    540
KEFDNNAIIL IRDNKYYLAI FNAKNKPDKK IIQGNSDKKN DNDYKKMVYN LLPGANKMLP    600
KVFLSKKGIE TFKPSDYIIS GYNAHKHIKT SENFDISFCR DLIDYFKNSI EKHAEWRKYE    660
FKFSATDSYS DISEFYREVE MQGYRIDWTY ISEADINKLD EEGKIYLFQI YNKDFAENST    720
GKENLHTMYF KNIFSEENLD KIIKLNGQAE LFYRRASVKN PVKHKKDSVL VNKTYKNQLD    780
NGDVVRIPIP DDIYNEIYKM YNGYIKESDL SEAAKEYLDK VEVRTAQKDI VKDYRYTVDK    840
YFIHTPITIN YKVTARNNVN DMVVKYIAQN DDIHVIGIDR GERNLIYISV IDSHGNIVKQ    900
KSYNILNNYD YKKKLVEKEK TREYARKNWK SIGNIKELKE GYISGVVHEI AMLIVEYNAI    960
IAMEDLNYGF KRGRFKVERQ VYQKFESMLI NKLNYFASKE KSVDEPGGLL KGYQLTYVPD   1020
NIKNLGKQCG VIFYVPAAFT SKIDPSTGFI SAFNFKSIST NASRKQFFMQ FDEIRYCAEK   1080
DMFSFGFDYN NFDTYNITMG KTQWTVYTNG ERLQSEFDNA RRTGKTKSIN LTETIKLLLE   1140
DNEINYADGH DIRIDMEKMD DKKSEFFAQ LLSLYKLTVQ MRNSYTEAEE QENGISYDKI   1200
ISPVINDEGE FFDSDNYKES DDKECKMPKD ADANGAYCIA LKGLYEVLKI KSEWTEDGFD   1260
RNCLKLPHAE WLDFIQNKRY E                                             1281

SEQ ID NO: 6           moltype = AA  length = 1300
FEATURE                Location/Qualifiers
```

```
source                  1..1300
                        mol_type = protein
                        organism = Francisella tularensis
SEQUENCE: 6
MSIYQEFVNK YSLSKTLRFE LIPQGKTLEN IKARGLILDD EKRAKDYKKA KQIIDKYHQF    60
FIEEILSSVC ISEDLLQNYS DVYFKLKKSD DDNLQKDFKS AKDTIKKQIS EYIKDSEKFK   120
NLFNQNLIDA KKGQESDLIL WLKQSKDNGI ELFKANSDIT DIDEALEIIK SFKGWTTYFK   180
GFHENRKVNY SSNDIPTSII YRIVDDNLPK FLENKAKYES LKDKAPEAIN YEQIKKDLAE   240
ELTFDIDYKT SEVNQRVFSL DEVFEIANFN NYLNQSGITK FNTIIGGKFV NGENTKRKGI   300
NEYINLYSQQ INDKTLKKYK MSVLFKQILS DTESKSFVID KLEDDSDVVT TMQSFYEQIA   360
APKTVEEKSI KETLSLLFDD LKAQKLDLSK IYFKNDKSLT DLSQQVFDDY SVIGTAVLEY   420
ITQQIAPKNL DNPSKKEQEL IAKKTEKAKY LSLETIKLAL EEFNKHRDID KQCRFEEILA   480
NFAAIPMIFD EIAQNKDNLA QISIKYQNQG KKDLLQASAE DDVKAIKDLL DQTNNLLHKL   540
KIFHISQSED KANILDKDEH FYLVFEECYF ELANIVPLYN KIRNYITQKP YSDEKFKLNF   600
ENSTLANGWD KNKEPDNTAI LFIKDDKYYL GVMKKNNKI FDDKAIKENK GEGYKKIVYK   660
LLPGANKMLP KVFFSAKSIK FYNPSEDILR IRNHSTHTKN GSPQKGYEKF EFNIEDCRKF   720
IDFYKQSISK HPEWKDFGFR FSDTQRYNSI DEFYREVENQ GYKLTFENIS ESYIDSVVNQ   780
GKLYLFQIYN KDFSAYSKGR PNLHTLYWKA LFDERNLQDV VYKLNGEAEL FYRKQSIPKK   840
ITHPAKEAIA NKNKDNPKKE SVFEYDLIKD KRFTEDKFFF HCPITINFKS SGANKFNDEI   900
NLLLKEKAND VHILSIDRGE RHLAYYTLVD GKGNIIKQDT FNIIGNDRMK TNYHDKLAAI   960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSPDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
REGION                  1..1206
                        note = Lachnospiraceae sp.
source                  1..1206
                        mol_type = protein
                        organism = unidentified
SEQUENCE: 7
MYYESLTKQY PVSKTIRNEL IPIGKTLDNI RQNNILESDV KRKQNYEHVK GILDEYHKQL    60
INEALDNCTL PSLKIAAEIY LKNQKEVSDR EDFNKTQDLL RKEVVEKLKA HENFTKIGKK   120
DILDLLEKLP SISEDDYNAL ESFRNFYTYF TSYNKVRENL YSDKEKSSTV AYRLINENFP   180
KFLDNVKSYR FVKTAGILAD GLGEEEQDSL FIVETFNKTL TQDGIDTYNS QVGKINSSIN   240
LYNQKNQKAN GFRKIPKMKM LYKQILSDRE ESFIDEFQSD EVLIDNVESY GSVLIESLKS   300
SKVSAFFDAL RESKGKNVYV KNDLAKTAMS VIVFENWRTF DDLLNQEYDL ANENKKKDDK   360
YFEKRQELK KNKSYSLEHL CNLSEDSCNL IENYIHQISD DIENIIINNE TFLRIVINEH   420
DRSRKLAKNR KAVKAIKDFL DSIKVLEREL KLINSSGQEL EKDLIVYSAH EELLVELKQV   480
DSLYNMTRNY LTKKPFSTEK VKLNFNRSTL LNGWDRNKET DNLGVLLLKD GKYYLGIMNT   540
SANKAFVNPP VAKTEKVFKK VDYKLLPVPN QMLPKVFFAK SNIDFYNPSS EIYSNYKKGT   600
HKKGNMFSLE DCHNLIDFFK ESISKHEDWS KFGFKFDTQA SYNDISEFYR EVEKQGYKLT   660
YTDIDETYIN DLIERNELYL FQIYNKDFSM YSKGKLNLHT LYFMMLFDQR NIDDVVYKLN   720
GEAEVFYRPA SISEDELIIH KAGEEEIKNKN PNRARTKETS TFSYDIVKDK RYSKDKFTLH   780
IPITMNFGVD EVKRFNDAVN SAIRIDENVN VIGIDRGERN LLYVVIDSK GNILEQISLN    840
SIINKEYDIE TDYHALLDER EGGRDKARKD WNTVENIRDL KAGLYLQVVN VVAKLVLKYN   900
AIICLEDLNF GFKRGRQKVE KQVYQKFEKM LIDKLNYLVI DKSREQTSPK ELGGALNALQ   960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTDG TRDYIISPVK   1140
NKREAYFNSE LSDGSVPKDA DANGAYNIAR KGLWVLEQIR QKSEGEKINL AMTNAEWLEY  1200
AQTHLL                                                             1206

SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR    60
KIADNALCHF GTEYDFSCLG NAISKNDSKA IKKETEKVEK LLAKVLTENL PDGLRKVNDI   120
NSAAFIQDTL TSFVQDDADK RVLIQELKGK TVLMQRFLTT RITALTVWLP DRVFENFNIF   180
IENAEKMRIL LDSPLNEKIM KFDPDAEQYA SLEFYGQCLS QKDIDSYNLI ISGIYADDEV   240
KNPGINEIVK EYNQQIRGDK DESPLPKLKK LHKQILMPVE KAFFVRVLSN DSDARSILEK   300
ILKDTEMLPS KIIEAMKEAD AGDIAVYGSR LHELSHVIYG DHGKLSQIIY DKESKRISEL   360
METLSPKERK ESKKRLEGLE EHIRKSTYTF DELNRYAEKN VMAAYIAAVE ESCAEIMRKE   420
KDLRTLLSKE DVKIRGNRHN TLIVKNYFNA WTVFRNLIRI LRRKSEAEID SDFYDVLDDS   480
VEVLSLTYKG ENLCRSYITK KIGSDLKPEI ATYGSALRPN SRWWSPGELR NVKFHTIVRR   540
DGRLYYFILP KGAKPVELED MDGDIECLQM RKIPNPTIFL PKLVFKDPEA FFRDNPEADE   600
FVFLSGMKAP VTITRETYEA YRYKLYTVGK LRDGEVSEEE YKRALLVQLT AYKEFLENRM   660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS   780
RVVDRFDKDG KYIPPEVHDE LYRFFNNLLI KEKLGEKARK ILDNKKVVK VLESERVKWS   840
KFYDEQFAVT FSVKKNADCL DTTKDLNAEV MEQYSESNRL ILIRNTTDIL YYLVLDKNGK   900
```

```
VLKQRSLNII  NDGARDVDWK  ERFRQVTKDR  NEGYNEWDYS  RTSNDLKEVY  LNYALKEIAE   960
AVIEYNAILI  IEKMSNAFKD  KYSFLDDVTF  KGFETKKLAK  LSDLHFRGIK  DGEPCSFTNP  1020
LQLCQNDSNK  ILQDGVIFMV  PNSMTRSLDP  DTGFIFAIND  HNIRTKKAKL  NFLSKFDQLK  1080
VSSEGCLIMK  YSGDSLPTHN  TDNRVWNCCC  NHPITNYDRE  TKKVEFIEEP  VEELSRVLEE  1140
NGIETDTELN  KLNERENVPG  KVVDAIYSLV  LNYLRGTVSG  VAGQRAVYYS  PVTGKKYDIS  1200
FIQAMNLNRK  CDYYRIGSKE  RGEWTDFVAQ  LIN                                1233

SEQ ID NO: 9            moltype = AA  length = 1227
FEATURE                 Location/Qualifiers
source                  1..1227
                        mol_type = protein
                        note = Lachnospiraceae sp.
                        organism = unidentified
SEQUENCE: 9
MSKLEKFTNC  YSLSKTLRFK  AIPVGKTQEN  IDNKRLLVED  EKRAEDYKGV  KKLLDRYYLS   60
FINDVLHSIK  LKNLNNYISL  FRKKTRTEKE  NKELENLEIN  LRKEIAKAFK  GNEGYKSLFK  120
KDIIETILPE  FLDDKDEIAL  VNSFNGFTTA  FTGFFDNREN  MFSEEAKSTS  IAFRCINENL  180
TRYISNMDIF  EKVDAIFDKH  EVQEIKEKIL  NSDYDVEDFF  EGEFFNFVLT  QEGIDVYNAI  240
IGGFVTESGE  KIKGLNEYIN  LYNQKTKQKL  PKFKPLYKQV  LSDRESLSFY  GEGYTSDEEV  300
LEVFRNTLNK  NSEIFSSIKK  LEKLFKNFDE  YSSAGIFVKN  GPAISTISKD  IFGEWNVIRD  360
KWNAEYDDIH  LKKKAVVTEK  YEDDRRKSFK  KIGSFSLEQL  QEYADADLSV  VEKLKEIIIQ  420
KVDEIYKVYG  SSEKLFDADF  VLEKSLKKND  AVVAIMKDLL  DSVKSFENYI  KAFFGEGKET  480
NRDESFYGDF  VLAYDILLKV  DHIYDAIRNY  VTQKPYSKDK  FKLYFQNPQF  MGGWDKDKET  540
DYRATILRYG  SKYYLAIMDK  KYAKCLQKID  KDDVNGNYEK  INYKLLPGPN  KMLPKVFFSK  600
KWMAYYNPSE  DIQKIYKNGT  FKKGDMFNLN  DCHKLIDFFK  DSISRYPKWS  NAYDFNFSET  660
EKYKDIAGFY  REVEEQGYKV  SFESASKKEV  DKLVEEGKLY  MFQIYNKDFS  DKSHGTPNLH  720
TMYFKLLFDE  NNHGQIRLSG  GAELFMRRAS  LKKEELVVHP  ANSPIANKNP  DNPKKTTTLS  780
YDVYKDKRFS  EDQYELHIPI  ANINKCPKNI  FKINTEVRVL  LKHDDNPYVI  GIDRGERNLL  840
YIVVVDGKGN  IVEQYSLNEI  INNFNGIRIK  TDYHSLLDKK  EKERFEARQN  WTSIENIKEL  900
KAGYISQVVH  KICELVEKYD  AVIALEDLNS  GFKNSRVKVE  KQVYQKFEKM  LIDKLNYMVD  960
KKSNPCATGG  ALKGYQITNK  FESFKSMSTQ  NGFIFYIPAW  LTSKIDPSTG  FVNLLKTKYT  1020
SIADKKFISS  FDRIMYVPEE  DLFEFALDYK  NFSRTDADYI  KKWKLYSYGN  RIRIFRNPKK  1080
NNVFDWEEVC  LTSAYKELFN  KYGINYQQGD  IRALLCEQSD  KAFYSSFMAL  MSLMLQMRNS  1140
ITGRTDVDFL  ISPVKNSDGI  FYDSRNYEAQ  ENAILPKNAD  ANGAYNIARK  VLWAIGQFKK  1200
AEDEKLDKVK  IASNKEWLEY  AQTSVKH                                        1227

SEQ ID NO: 10           moltype = AA  length = 1264
FEATURE                 Location/Qualifiers
source                  1..1264
                        mol_type = protein
                        organism = Leptospira inadai
SEQUENCE: 10
MEDYSGFVNI  YSIQKTLRFE  LKPVGKTLEH  IEKKGFLKKD  KIRAEDYKAV  KKIIDKYHRA   60
YIEEVFDSVL  HQKKKKDKTR  FSTQFIKEIK  EFSELYYKTE  KNIPDKERLE  ALSEKLRKML  120
VGAFKGEFSE  EVAEKYNKNL  FSKELIRNEI  EKFCETDEER  KQVSNFKSFT  TYFTGPHSNR  180
QNIYSDEKKS  TAIGYRIIHQ  NLPKFLDNLK  IIESIQRRFK  DFPWSDLKKN  LKKIDKNIKL  240
TEYFSIDGFV  NVLNQKGIDA  YNTILGKSE   ESGEKIQGLN  EYINLYRQKN  NIDRKNPLNV  300
KILFKQILGD  RETKSFIPEA  FPDDQSVLNS  ITEFAKYLKL  DKKKKSIIAE  LKKFLSSFNR  360
YELDGIYLAN  DNSLASISTF  LFDDDWSFIKK  SVSFKYDESV  GDPKKKIKSP  LKYEKEKEKW  420
LKQKYYTISF  LNDAIESYSK  SQDEKRVKIR  LEAYFAEFKS  KDDAKKQFDL  LERIEEAYAI  480
VEPLLGAEYP  RDRNLKADKK  EVGKIKDFLD  SIKSLQFFLK  PLLSAEIFDE  KDLGFYNLKG  540
GYYEEIDISG  HLYNKVRNYL  TGKIYSKEKF  KLNFENSTLL  KGWDENREVA  NLCVIFREDQ  600
KYYLGVMDKE  NNTILSDIPK  VKPNELFYEK  MVYKLIPTPH  MQLPRIIFSS  DNLSIYNPSK  660
SILKIREAKS  FKEGKNFKLK  DCHKFIDFYK  ESISKNEDWS  RFDFKFSKTS  SYENISEFYR  720
EVERQGYNLD  FKKVSKFYID  SLVEDGKLYL  FQIYNKDFSI  FSKGKPNLHT  IYFRSLFSKE  780
NLKDVCLKLN  GEAEMFFRKK  SINYDEKKKR  EGHHPELFEK  LKYPILKDKR  YSEDKFQFHL  840
PISLNFKSKE  RLNFNLKVNE  FLKRNKDINI  IGIDRGERNL  LYLVMINQKG  EILKQTLLDS  900
MQSGKGRPEI  NYKEKLQEKE  IERDKARKSW  GTVENIKELK  EGYLSIVIHQ  ISKLMVENNA  960
IVVLEDLNIG  FKRGRQKVER  QVYQKFEKML  IDKLNFLVFK  EKPTEPGGV  LKAYQLTDEF  1020
QSFEKLSKQT  GFLFYVPSWN  TSKIDPRTGF  IDFLHPAYEN  IEKAKQWINK  FDSIRFNSKM  1080
DWFEFTADTR  KFSENLMLGK  NRVWVICTTN  VERYFTSKTA  NSSIQYNSIQ  ITEKLKELFV  1140
DIPFSNGQDL  KPEILRKNDA  VFFKSLLFYI  KTTLSLRQNN  GKKGEEEKDF  ILSPVVDSKG  1200
RFFNSLEASD  DEPKDADANG  AYHIALKGLM  NLLVLNETKE  ENLSRPKWKI  KNKDWLEFVW  1260
ERNR                                                                   1264

SEQ ID NO: 11           moltype = AA  length = 1373
FEATURE                 Location/Qualifiers
source                  1..1373
                        mol_type = protein
                        organism = Moraxella bovoculi
SEQUENCE: 11
MLFQDFTHLY  PLSKTVRFEL  FIDRTLEHIH  AKNFLSQDET  MADMHQKVKV  ILDDYHRDFI   60
ADMMGEVKLT  KLAEFYDVYL  KFRKNPKDDE  LQKAQLKDLQ  AVLRKEIVKP  IGNGGKYKAG  120
YDRLFGAKLF  KDGKELGDLA  KFVIAQEGES  SPKLAHLAHF  EKFSTYFTGF  HDNRKNMYSD  180
EDKHTAIAYR  LIHENLPRFI  DNLQILTTIK  QKHSALYDQI  INELTASGLD  VSLASHLDGY  240
HKLLTQEGIT  AYNTLLGGIS  GEAGSPKIQG  INELINSHHN  QHCKSERIA   KLRPLHKQIL  300
SDGMSVSFLP  SKFADDSEMC  QAVNEFYRHY  ADVFAKVQSL  FDGFDDHQKD  GIYVEHKNLN  360
ELSKQAFGDF  ALLGRVLDGY  YVDVVNPEFN  ERFAKAKTDN  AKAKLTKEKD  KFIKGVHSLA  420
SLEQAIEHYT  ARHDDESVQA  GKLGQYFKHG  LAGVDNPIQK  IHNNHSTIKG  FLERERPAGE  480
```

```
RALPKIKSGK NPEMTQLRQL KELLDNALNV AHFAKLLTTK TTLDNQDGNF YGEFGVLYDE       540
LAKIPTLYNK VRDYLSQKPF STEKYKLNFG NPTLLNGWDL NKEKDNFGVI LQKDGCYYLA       600
LLDKAHKKVF DNAPNTGKSI YQKMIYKYLE VRKQFPKVFF SKEAIAINYH PSKELVEIKD      660
KGRQRSDDER LKLYRFILEC LKIHPKYDKK FEGAIGDIQL FKKDKKGREV PISEKDLFKD      720
INGIFSSKPK LEMEDFFIGE FKRYNPSQDL VDQYNIYKKI DSNDNRRKEN FYNNHPKFKK      780
DLVRYYYESM CKHEEWEESF EFSKKLQDIG CYVDVNELFT EIETRRLNYK ISFCNINADY      840
IDELVEQGQL YLFQIYNKDF SPKAHGKPNL HTLYFKALFS EDNLADPIYK LNGEAQIFYR      900
KASLDMNETT IHRAGEVLEN KNPDNPKKRQ FVYDIIKDKR YTQKDFMLHV PITMNFGVQG      960
MTIKEFNKKV NQSIQQYDEV NVIGIDRGER HLLYLTVINS KGEILEQCSL NDITTASANG     1020
TQMTTPYHKI LDKREIERLN ARVGWGEIET IKELKSGYLS HVVHQISQLM LKYNAIVVLE     1080
DLNFGFKRGR FKVEKQIYQN FENALIKKLN HLVLKDKADD EIGSYKNALQ LTNNFTDLKS     1140
IGKQTGFLFY VPAWNTSKID PETGFVDLLK PRYENIQASQ AFFGKFDKIC YNADKDYFEF     1200
HIDYAKFTDK AKNSRQIWTI CSHGDKRYVY DKTANQNKGA AKGINVNDIL KSLFARHHIN     1260
EKQPNLVMDI CQNNDKEFHK SLMYLLKTLL ALRYSNASSD EDFILSPVAN DEGVFFNSAL     1320
ADDTQPQNAD ANGAYHIALK GLWLLNELKN SDDLNKVKLA IDNQTWLNFA QNR            1373

SEQ ID NO: 12           moltype = AA   length = 1352
FEATURE                 Location/Qualifiers
source                  1..1352
                        mol_type = protein
                        note = Parcubacteria bacterium
                        organism = unidentified
SEQUENCE: 12
MENIFDQFIG KYSLSKTLRF ELKPVGKTED FLKINKVFEK DQTIDDSYNQ AKFYFDSLHQ       60
KFIDAALASD KTSELSFQNF ADVLEKQNKI ILDKKREMGA LRKRDKNAVG IDRLQKEIND     120
AEDIIQKEKE KIYKDVRTLF DNEAESWKTY YQEREVDGKK ITESKADLKQ KGADFLTAAG     180
ILKVLKYEFP EEKEKEFQAK NQPSLFVEEK ENPGQKRYIF DSFDKFAGYL TKFQQTKKNL     240
YAADGTSTAV ATRIADNFII FHQNTKVFRD KYKNNHTDLG FDEENIFEIE RYKNCLLQRE     300
IEHIKNENSY NKIIGRINKK IKEYRDQKAK DTKLTKSDFP FFKNLDKQIL GEVEKEKQLI     360
EKTREKTEED VLIERPKEFI ENNEERFTAA KKLMNAFCNG EFESEYEGIY LKNKAINTIS     420
RRWFVSDRDF ELKLPQQKSK NKSEKNEPKV KKFISIAEIK NAVEELDGDI FKAVFYDKKI     480
IAQGGSKLEQ FLVIWKYEFE YLFRDIEREN GEKLLGYDSC LKIAKQLGIF PQEKEAREKA     540
TAVIKNYADA GLGIFQMMKY FSLDDKDRKN TPGQLSTNFY AEYGDYYKDF EFIKYYNEFR     600
NFITKKPFDE DKIKLNFENG ALLKGWDENK EYDFMGVILK KEGRLYLGIM HKNHRKLFQS     660
MGNAKGDNAN RYQKMIYKQI ADASKDVPRL LLTSKKAMEK FKPSQEILRI KKEKTFKRES     720
KNFSLRDLHA LIEYYRNCIP QYSNWSFYDF QFQDTKYQN IKEFTDDVQK YGYKISFRDI      780
DDEYINQALN EGKMYLFEVV NKDIYNTKNG SKNLHTLYFE HILSAENLND PVFKLSGMAE     840
IPQRQPSVNE REKITTCKNQ CILDKGDRAY KYRRYTEKKI MPHMSLVLNT GKGEIKQVQF     900
NKIINQRISS SDNEMRVNVI GIDRGEKNLL YYSVVKQNGE IIEQASLNEI NGVNYRDKLI     960
EREKERLKNR QSWKPVVKIK DLKKGYISHV IHKICQLIEK YSAIVVLEDL NMRFKQIRGG    1020
IERSVYQQFE KALIDKLGYL VFKDNRDLRA PGGVLNGYQL SAPFVSFEKM RKQTGILFYT    1080
QAEYTSKTDP ITGFRKNVYI SNSASLDKIK EAVKKFDAIG WDGKEQSYFF KYNPYNLADE    1140
KYKNSTVSKE WAIFASAPRI RRQKGEDGYW KYDRVKVNEE FEKLLKVWNF VNPKATDIKQ    1200
EIIKKIKAGD LQGEKELDGR LRNFWHSFIY LFNLVLELRN SFSLQIKIKA GEVIAVDEGV    1260
DFIASPVKPF FTTPNPYIPS NLCWLAVENA DANGAYNIAR KGVMILKKIR EHAKKDPEFK    1320
KLPNLFISNA EWDEAARDWG KYAGTTALNL DH                                  1352

SEQ ID NO: 13           moltype = AA   length = 1260
FEATURE                 Location/Qualifiers
source                  1..1260
                        mol_type = protein
                        organism = Porphyromonas crevioricanis
SEQUENCE: 13
MDSLKDFTNL YPVSKTLRFE LKPVGKTLEN IEKAGILKED EHRAESYRRV KKIIDTYHKV       60
FIDSSLENMA KMGIENEIKA MLQSFCELYK KDHRTEGEDK ALDKIRAVLR GLIVGAFTGV     120
CGRRENTVQN EKYESLFKEK LIKEILPDFV LSTEAESLPF SVEEATRSLK EFDSFTSYFA     180
GFYENRKNIY STKPQSTAIA YRLIHENLPK FIDNILVFQK IKEPIAKELE HIRADFSAGG    240
YIKKDERLED IFSLNYYIHV LSQAGIEKYN ALIGKIVTEG DGEMKGLNEH INLYNQQRGR    300
EDRLPLFRPL YKQILSDREQ LSYLPESFEK DEELLRALKE THDHIAEDIL GRTQQLMTSI    360
SEYDLSRIYV RNDSQLTDIS KKMLGDWNAI YMAREREAYDH EQAPKRITAK YERDRIKALK    420
GEESISLANL NSCIAFLDNV RDCRVDTYLS TLGQKEGPHG LSNLVENVFA SYHEAEQLLS    480
FPYPEENNLI QDKDNVVLIK NLLDNISDLQ RFLKPLWGMG DEPDKDERFY GEYNYIRGAL    540
DQVIPLYNKV RNYLTRKPYS TRKVKLNFGN SQLLSGWDRN KEKDNSCVIL RKGQNFYLAI    600
MNNRHKRSFE NKMLPEYKEG EPYFEKMDYK FLPDPNKMLP KVFLSKKGIE IYKPSPKLLE    660
QYGHGTHKKG DTFSMDDLHE LIDFFKHSIE AHEDWKQFGF KFSDTATYEN VSSFYREVED    720
QGYKLSFRKV SESYVYSLID QGKLYLFQIY NKDFSPCSKG TPNHLTLYWR MLFDERNLAD    780
VIYKLDGKAE IFFREKSLKN DHPTHPAGKP IKKKSRQKKG EESLFEYDLV KDRRYTMDKF    840
QPHVPITMNF KCSAGSKVND MVNAHIREAK DMHVIGIDRG ERNLLYICVI DSRGTILDQI    900
SLNTINDIDY HDLLESRDKD RQQEHRNWQT IEGIKELKQG YLSQAVHRIA ELMVAYKAVV    960
ALEDLNMGFK RGRQKVESSV YQQFEKQLID KLNYLVDKKK RPEDIGGLLR AYQFTAPFKS   1020
FKEMGKQNGF LFYIPAWNTS NIDPTTGFVN LFHVQYENVD KAKSFFQKFD SISYNPKKDW   1080
FEFAFDYKNF TKKAEGSRSM WILCTHGSRI KNFRNSQKNG QWDSEEFALT EAFKSLFVRY   1140
EIDYTADLKT AIVDEKQKDF FVDLLKLFKL TVQMRNSWKE KDLYLISPVA GADGRFFDT    1200
REGNKSLPKD ADANGAYNIA LKGLWALRQI RQTSEGGKLK LAISNKEWLQ FVQERSYEKD   1260

SEQ ID NO: 14           moltype = AA   length = 1324
FEATURE                 Location/Qualifiers
source                  1..1324
                        mol_type = protein
```

```
                        organism = Prevotella disiens
SEQUENCE: 14
MENYQEFTNL FQLNKTLRFE LKPIGKTCEL LEEGKIFASG SFLEKDKVRA DNVSYVKKEI    60
DKKHKIFIEE TLSSFSISND LLKQYFDCYN ELKAFKKDCK SDEEEVKKTA LRNKCTSIQR   120
AMREAISQAF LKSPQKKLLA IKNLIENVFK ADENVQHFSE FTSYFSGFET NRENFYSDEE   180
KSTSIAYRLV HDNLPIFIKN IYIFEKLKEQ FDAKTLSEIF ENYKLYVAGS SLDEVFSLEY   240
FNNTLTQKGI DNYNAVIGKI VKEDKQEIQG LNEHINLYNQ KHKDRRLPFF ISLKKQILSD   300
REALSWLPDM FKNDSEVIDA LKGFYIEDGF ENNVLTPLAT LLSSLDKYNL NGIFIRNNEA   360
LSSLSQNVYR NFSIDEAIDA QNAELQTFNN YELIANALRA KIKKETKQGR KSFEKYEEYI   420
DKKVKAIDSL SIQEINELVE NYVSEFNSNS GNMPRKVEDY FSLMRKGDFG SNDLIENIKT   480
KLSAAEKLLG TKYQETAKDI FKKDENSKLI KELLDATKQF QHFIKPLLGT GEEADRDLVF   540
YGDFLPLYEK FEELTLLYNK VRNRLTQKPY SKDKIRLCFN KPKLMTGWVD SKTEKSDNGT   600
QYGGYLFRKK NEIGEYDYFL GISSKAQLFR KNEAVIGDYE RLDYYQPKAN TIYGSAYEGE   660
NSYKEDKKRL NKVIIAYIEQ IKQTNIKKSI IESISKYPNI SDDDKVTPSS LLEKIKKVSI   720
DSYNGILSFK SFQSVNKEVI DNLLKTISPL NKAEFLDLI  NKDYQIFTEV QAVIDEICKQ   780
KTFIYFPISN VELEKEMGDK DKPLCLFQIS NKDLSFAKTF SANLRKKRGA ENLHTMLFKA   840
LMEGNQDNLD LGSGAIFYRA KSLDGNKPTH PANEAIKCRN VANKDKVSLF TYDIYKNRFY   900
MENKFLFHLS IVQNYKAAND SAQLNSSATE YIRKADDLRN IGIDRGERNL LYYSVIDMKG   960
NIVEQDSLNI IRNNDLETDY HDLLDKREKE RKANRQNWEA VEGIKDLKKG YLSQAVHQIA  1020
QLMLKYNAII ALEDLGQMFV TRGQKIEKAV YQQFEKSLVD KLSYLVDKKR PYNELGGILK  1080
AYQLASSITK NNSDKQNGFL FYVPAWNTSK IDPVTGFTDL LRPKAMTIKE AQDFFGAFDN  1140
ISYNDKGYFE FETNYDKFKI RMKSAQTRWT ICTFGNRIKR KKDKNYWNYE EVELTEEFKK  1200
LFKDSNIDYE NCNLKEEIQN KDNRKFFDDL IKLLQLTLQM RNSDDKGNDY IISPVANAEG  1260
QFFDSRNGDK KLPLDADANG AYNIARKGLW NIRQIKQTKN KDDLNLSISS TEWLDFVREK  1320
PYLK                                                              1324

SEQ ID NO: 15           moltype = AA   length = 1484
FEATURE                 Location/Qualifiers
VARIANT                 1073
                        note = Xaa can be any naturally occurring amino acid
source                  1..1484
                        mol_type = protein
                        note = Peregrinibacteria bacterium
                        organism = unidentified
SEQUENCE: 15
MSNFFKNFTN LYELSKTLRF ELKPVGDTLT NMKDHLEYDE KLQTFLKDQN IDDAYQALKP    60
QFDEIHEEFI TDSLESKKAK EIDFSEYLDL FQEKKELNDS EKKLRNKIGE TFNKAGEKWK   120
KEKYPQYEWK KGSKIANGAD ILSCQDMLQF IKYKNPEDEK IKNYIDDTLK GFFTYFGGFN   180
QNRANYYETK KEASTAVATR IVHENLPKFC DNVIQFKHII KRKKDGTVEK TERKTEYLNA   240
YQYLKNNNKI TQIKDAETEK MIESTPIAEK IFDVYYFSSC LSQKQIEEYN RIIGHYNLLI   300
NLYNQAKRSE GKHLSANEKK YKDLPKFKTL YKQIGCGKKK DLFYTIKCDT EEEANKSRNE   360
GKESHSVEEI INKAQEAINK YFKSNNDCEN INTVPDFINY ILTKENYEGV YWSKAAMNTI   420
SDKYFANYHD LQDRLKEAKV FQKADKKSED DIKIPEAIEL SGLFGVLDSL ADWQTTLFKS   480
SILSNEKLKI ITDSQTPSEA LLKMIFNDIE KNMESFLKET NDIITLKKYK GNKEGTEKIK   540
QWFDYTLAIN RMLKYFLVKE NKIKGNSLDT NISEALKTLI YSDDAEWFKW YDALRNYLTQ   600
KPQDEAKENK LKLNFDNPSL AGGWDVNKEC SNFCVILKDK NEKKYLAMIK KGENTLFQKE   660
WTEGRGKNLT KKSNPLFEIN NCEILSKMEY DFWADVSKMI PKCSTQLKAV VNHFKQSDNE   720
FIFPIGYKVT SGEKFREECK ISKQDFELNN KVFNKNELSV TAMRYDLSST QEKQYIKAFQ   780
KEYWELLFKQ EKRDTKLTNN EIFNEWINFC NKKYSELLSW ERKYKDALTN WINFCKYFLS   840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT   960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKQAGI   1200
MLYTRANYTS QTDPATGWRK TIYLKAGPEE TTYKKDGKIK NKSVKDQIIE TFTDIGFDGK   1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 16           moltype = AA   length = 1245
FEATURE                 Location/Qualifiers
source                  1..1245
                        mol_type = protein
                        organism = Porphyromonas macacae
SEQUENCE: 16
MKTQHFPEDF TSLYSLSKTI RFELKPIGKT LENIKKNGLI RRDEQRLDDY ELKKKVIDEY    60
HEDFIANILS SFSFSEEILQ SYIQNLSISE ARAKIEKTMR DTLAKAFSED ERYKSIFKKE   120
LVKKDIPVWC PAYKSLCKKF DNFTTSLVPF HENRKNLYTS NEITASIPYR IVHVNLPKFI   180
QNIEALCELQ KKMGADLYLE MMENLRNVWP SFVKTPDDLC NLKTYNHLMV QSSISEYNRF   240
VGGYSTEDGT KHQGINEWIN IYRQRNKEMR LPGLVFLHKQ ILAKVDSSSF ISDTLENDDQ   300
VFCVLRQFRK LFWNTVSSKE DDAASLKDLF CGLSGYDPEA IYVSDAHLAT ISKNIFDRWN   360
YISDAIRRKT EVLMPRKKES VERYAEKISK QIKKRQSYSL AELDDLLAHY SEESLPAGFS   420
LLSYFTSLGG QKYLVSDGEV ILYEEGSNIW DEVLIAFRDL QVILDKDFTE KKLGKDEEAV   480
SVIKKALDSA LRLRKFFDLL SGTGAEIRRD SSFYALYTDR MDKLKGLLKM YDKVRNYLTK   540
KPYSIEKFKL HFDNPSLLSG WDKNKELNNL SVIFRQNGYY YLGIMTPKGK NLFKTLPKLG   600
AEEMFYEKME YKQIAEPMLM LPKVFFPKKT KPAFAPDQSV VDIYNKKTFK TGQKGFNKKD   660
LYRLIDFYKE ALTVHEWKLF NFSFSPTEQY RNIGEFFDEV REQAYKVSMV NVPASYIDEA   720
```

```
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI 1020
LFFVDPWNTS LTDPSTGFVN LLGRINYTNV GDARKFFDRF NAIRYDGKGN ILFDLDLSRF 1080
DVRVETQRKL WTLTTFGSRI AKSKKSGKWM VERIENLSLC FLELFEQFNI GYRVEKDLKK 1140
AILSQDRKEF YVRLIYLFNL MMQIRNSDGE EDYILSPALN EKNLQFDSRL IEAKDLPVDA 1200
DANGAYNVAR KGLMVVQRIK RGDHESIHRI GRAQWLRYVQ EGIVE                1245

SEQ ID NO: 17           moltype = AA  length = 1250
FEATURE                 Location/Qualifiers
source                  1..1250
                        mol_type = protein
                        organism = Smithella sp.
SEQUENCE: 17
MQTLFENFTN QYPVSKTLRF ELIPQGKTKD FIEQKGLLKK DEDRAEKYKK VKNIIDEYHK   60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTKKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI 1020
FYVPAWNTSK TDPATGFIDF LKPRYENLNQ AKDFFEKFDS IRLNSKADYF EFAFDFKNFT 1080
EKADGGRTKW TVCTTNEDRY QWNRALNNNR GSQEKYDITA ELKSLFDGKV DYKSGKDLKQ 1140
QIASQESADF FKALMKNLSI TLSLRHNNGE KGDNEQDYIL SPVADSKGRF FDSRKADDDM 1200
PKNADANGAY HIALKGLWCL EQISKTDDLK KVKLAISNKE WLEFVQTLKG            1250

SEQ ID NO: 18           moltype = DNA  length = 3987
FEATURE                 Location/Qualifiers
source                  1..3987
                        mol_type = other DNA
                        organism = synthetic construct
SEQUENCE: 18
atggccggga gcaagaagcg ccggataaag caggacacgc agttcgaggg cttcaccaac   60
ctgtaccaag tctccaagac gctccggttc gagcttatcc cgcaagggaa gaccctgaaa  120
cacatccagg aacaaggttt catcgaggag gacaaggccg gcaacgacca gctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcgggc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgcccttcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcaa catcttcacg  660
cgcctgatta cagccgtacc ttcacttcgt gagcacttcg agaacgtcaa aaaggccatc  720
gggatcttcg tctccacgtc catcgaggag gtattctctt tccgttccta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc 1020
attcagtctt tctgcaagta caagacgctc tacggaatgg agaatgtgct ggagaccgcg 1080
gaggcactct tcaatgagct gaactccatt gacctgaccc acatcttcat tagccacaag 1140
aaactggaga cgatctccag cgccctgtgc gaccactggg acactctccg caactgcctc 1200
tacgaacgcc ggatctccga acttaccggc aagataacta agtcggctaa ggagaaggtg 1260
caacggagcc tcaagcacga ggacatcaac cttcaggaaa tcatctcagc cgcgggcaag 1320
gagctgagcg aggcgtttaa gcagaaaaca tcggagatac tgaccacgc gcacgcggcc 1380
ctggatcaac cgctgccgac gactctcaag agcaagaggg agaaggaaat ccttaagtcc 1440
cagctcgact cgctgctcgg cctctatcac ttgctcgatt ggttcgcggt tgatgagtcc 1500
aacgaggtgg acccgagtt ctccgcgcgc ctcacgggta ttaagctgga gatggagcca 1560
agcttaagct tctacaacaa ggccgcaac tacgcgacca aaaaccgta ctcagtcgag 1620
aaattcaagc tgaatttcca gatgcctaca ttggcgaggg ggtgggacgt gaaccgcgag 1680
aagaacaatg gagccatcct gttcgtcaaa atgggttgt actacctggg catcatgccc 1740
aagcaaggc gccgttacaa ggcctgtca ttcgagccta ccgagaagac ctcgagggc 1800
ttcgacaaga tgtactacga ctatttcccg gacgccgcca agatgatccc gaagtgctcc 1860
acgcagctca agccgtcac ggcccactca cagacgcata ccacgccgat acttctgagc 1920
aacaacttca ttgagccgct agagatcacg aaggagatat acgacctaaa caaccccgaa 1980
aaggagccca agaagttcca gacagcctac gctaagaaga caggtgatca agggggatat 2040
aggggaggcac tctgcaagtg gatcgacttc acgcgcgact cctgtcgaa atatacaaag 2100
```

-continued

```
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctataccgtg tccaaatata taacaaggac  2280
ttcgctaaag gcaccacgg gaagcccaac ctgcacacac tctactggac gggcttgttt  2340
tcgccagaaa atttggccaa gacttcgatc aagctcaacg accagcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ccccgaagc tccgtgagaa cgacgactcg  3660
cacgctattg acacgatggt cgccctcata cggagcgtgc ttcagatgcg gaacagtaac  3720
gctgccacgg gcgaggacta cattaactcc ccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                      3987
```

```
SEQ ID NO: 19          moltype = DNA   length = 3987
FEATURE                Location/Qualifiers
source                 1..3987
                       mol_type = other DNA
                       organism = synthetic construct
SEQUENCE: 19
atggcgggaa gcaaaaagcg ccggattaag caagacacgc agttcgaggg cttcacgaac    60
ctctaccaag tcagcaagac cctccggttc gagctgatac cacagggaaa gacgctcaag   120
cacatccagg aacagggctt catcgaggag acaaggcgc gcaacgacca ctacaaggag   180
ttgaaaccga tcatcgaccg catctacaag acgtacgccg accagtgcct ccagctcgtg   240
cagctcgact gggagaacct ctccgccgcc attgactcgt accggaagga gaagactgag   300
gagaccgcca acgccctgat cgaggagcaa gcaacctacc ggaacgccat ccacgactac   360
ttcatcggcc gcaccgacaa cctcaccgac gcgatcaaca agcggcacgc ggagatatac   420
aaagggctgt tcaaggcgga gctgttcaac ggcaaggtgc tcaagcagct agggacggtg   480
accacgaccg agcacgagaa cgcgctcctc cgcagcttcg acaagttcac cacctacttc   540
agcggcttct accggaaccg caagaatgtg ttcagcgcgg aggacatcag cacggccatc   600
ccgcaccgca tcgtccagga caacttcccg aagttcaagg agaactgcca catcttcacc   660
cgcctgataa ccgccgtccc ctccctgcgg gagcactttg agaacgtcaa aaaggcaatt   720
gggatcttcg tctcgaccag cattgaggag gtgttcagct tccccttcta caaccagctc   780
ctcacccaga cgcagatcga cctgtacaat cagttgctcg gcgggataag ccgcgaggcg   840
ggaaccgaaa aaatcaaggg gctgaacgaa gtgttgaacc tcgccatcca gaagaacgac   900
gagaccgcgc acatcatcgc ctccctgccc caccggttca tcccgctgtt caagcagatc   960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgtc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg acgaaatcc tgtcccacgc gcacgcggcc  1380
ctggatcagc tctgccgac gaccctcaag aaacaagaag aaaaggaaat cctcaagtcg  1440
cagctcgact cgctgctggg cctgtaccat ctcctcgcct ggttcgccgt ggacgagagc  1500
aacgaggtgg acccccgagtt ctccgcgcgc cttacgggga tcaagctgga gatggagccc  1560
agcctgtcct tctacaacaa ggcgcgcaac tacgccacca gaagcctca cagcgtggag  1620
aagttcaagc tcaacttcca gatgccact ctcgcacgtg gtgggacgt caaccgcgaa  1680
aaaaataatg gggcgatcct gttcgtcaag aacgccgtgt actacttggg catcatgccg  1740
aaacagaagg gccgctacaa ggccctgagc ttcgaaccga cgcgagaaaac gagcgagggg  1800
ttcgacaaga tgtactacga ctacttcccc gacgccgcga agatgattcc aaagtgctcc  1860
acgcagctta aggccgtgac ggcccacttt cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggagcccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctataccctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
```

```
cggcccaagt cccgcatgaa gcggatggcc caccggctcg gggagaaaat gctcaacaag 2460
aaattgaagg accaaaaaac gccgatacccc gacaccctat accaggagct gtacgactat 2520
gtgaaccacc gcctgagcca cgacctcagc gacgaggcgc gggccctcct gccgaacgtc 2580
atcacaaagg aggtcagcca cgagatcatc aaggaccggc gcttcacctc cgacaagttc 2640
ttctttcacg tgcccatcac gctcaactac caggccgcca actgccgtc caagttcaac 2700
cagcgcgtga acgcctacct caaggagcac cccgagaccc cgatcatcgg gattgaccga 2760
ggggagcgga acctcatcta catcaccgtc atcgacagca ccgggaagat ccttgaacag 2820
cggtcgctca acaccatcca gcagttcgac taccagaaga aactcgacaa ccgggagaag 2880
gagagagtgg cggcccgcca ggcttggtcc gtcgtcggga cgattaagga cttgaaacaa 2940
ggttacctgt cgcaagtgat ccacgagatc gttgacctga tgatccacta ccaagccgtc 3000
gtggtcctgg agaacctcaa cttcggcttc aagagcaaac gaaccggcat cgcggagaag 3060
gccgtgtacc agcagttcga aaaaatgctg atcgacaagc tgaactgcct cgtgctcaag 3120
gactaccccg ctgagaaggt cggcggggtg ctgaacccgt accagctcac tgaccagttc 3180
accagcttca caaagatggg caccagtcc ggcttcctgt tctacgtgcc tgcgccatac 3240
acctcgaaga tcgacccgct caccgggttc gtggacccct tcgtctggaa gaccatcaag 3300
aaccacgaga gccgcaagca cttcctggag ggcttcgact tcctccacta cgacgtcaag 3360
accggggact tcatcctgca cttcaagatg aaccgcaacc tcagtttcca gcgcggcctg 3420
ccggggttca tgcccgcttg ggatatagtc ttcgagaaga atgagacgca gttcgacgcg 3480
aagggcaccc cgttcatcgc cgggaagcgc atcgtgccgg tcatcgagaa ccaccggttc 3540
accgggcgct accgcgacct ataccccggcg aacgagttga tcgccctcct ggaggagaag 3600
ggcatccgtgt tccgcgacgg ctccaacatc ctccccgaagc tgctcgaaaa cgacgactcc 3660
cacgccatcg acacgatggt cgcgctgatc cggtcggtgc tccagatgcg gaactccaac 3720
gccgcgacgg gcgaggacta catcaacagt ccggtccgcg atctgaacgg cgtctgcttc 3780
gactccggt tccagaaccc cgagtggccg atggacgcgg acgcgaacgg cgcataccac 3840
atcgccctaa aagggcaatt gctgctcaac cacctcaagg aatccaaaga cctaaagctc 3900
cagaacggca tctccaacca ggactggctg gcgtacatcc aggaactgcg gaacgggagc 3960
aaaaaacgtc ggatcaagca agattga 3987
```

```
SEQ ID NO: 20          moltype = DNA   length = 3987
FEATURE                Location/Qualifiers
source                 1..3987
                       mol_type = other DNA
                       organism = synthetic construct
SEQUENCE: 20
atggcgggct ccaagaaacg ccggattaag caagatacccc agttcgaggg gttcacgaac 60
ctctaccaag tgagcaagac cctccgattc gaactgattc ctcaggggaa gacccctcaag 120
cacatccagg agcaagggtt catcgaggag gacaaggcgc ggaacgacca ctacaaggaa 180
ctcaaaccca tcatcgaccg catctacaag acctacgccg atcagtgcct ccagctcgtg 240
cagttggact gggagaacct cagcgcggcc attgactcct accggaagga gaaaacggag 300
gagacgcgca acgcgctcat cgaggaacag gcaacctatc gcaacgccat ccacgactac 360
ttcatcggga ggactgacaa cctcactgac gcgattaaca agcgcacgc ggagatatac 420
aagggactct tcaaagcgga gctgtttaac ggcaaggttc tcaagcaact cggcactgtg 480
accacgaccg agcatgagaa cgccctgctc cgctccttcg acaagttcac cacctacttc 540
tccgggttct accgcaaccg caagaatgtc ttcagcgcgg aggacatcag cacggccatt 600
ccacatcgaa tcgtccaaga taacttcccg aagttcaagg agaactgcca catcttcacc 660
cgactcatta ctgctgtacc gtcgttacgc gaacacttcg agaacgtcaa gaaggcaatt 720
ggaatcttcg tctctacgtc aatagaggag tgttcagtc tcccttttcta caaccagctc 780
cttacgcaga cccagataga cctgtacaat cagctcctcg gtgggatcag ccggaggcg 840
gggactgaga agattaaagg gctcaacgag gtcttgaacc tggccatcca aaaaaacgat 900
gagacggcgc acatcatcgc ctcgctgccc caccggttca tcccgctgtt caagcagatc 960
ctcagtgaca ggaacacctt gagctttatc ctagaggagt tcaagagcga cgagagggtg 1020
atccagagct tctgcaagta caaaacccctg ctgaggaacg agaacgtcct ggagacggcc 1080
gaggcgctgt tcaacgagct gaactctatc gacttaactc acatattcat ctcgcacaag 1140
aagctggaga ctattagctc tgcactctgc gaccactggg acaccctccg caacgcgctc 1200
tacgacgcc gcatctcgga gctgaccggg aagatccaca atccgcgaa ggaaaaggtc 1260
cagcgttccc tcaaaacga ggatattaac ttacaggaga ttatctcagc ggctgggaag 1320
gagttgtcag aggcgttcaa gcagaaaact tccgagatcc tgagcacgc gcacgcagcg 1380
ctcgaccagc tctgcccac cacccctaa aagcaggaag aaaagagat cctcaagagc 1440
cagttggact ccctgctggg gctctatcac ctttctcgact ggttcgccgt cgatgagtcg 1500
aacgaggtgg accccgagtt ctccgccccg ctgaccggca tcaagctaga tgatgagccg 1560
tccctcagct tctacaataa ggcccgcaac tacgcgacca aaaaaccccta cagcgtggag 1620
aagttcaagc tgaacttcca gatgccgacc ttagcacgcg gttgggacgt aaacagggag 1680
aagaacaatg gagccatcct gttcgtcaag acgggctttt actacctcgg gataatgccc 1740
aagcagagga gccgctacaa ggccccttcc ttcgagccgg cggagaaaac ctccgagggg 1800
ttcgacaaga tgtactacga ctacttcccc gacgccgcca agatgatccc gaagtgctca 1860
acgcagctaa aagccgtgac cgcccacttc cagacccaca cgacgccgat cctgctgagc 1920
aacaacttca tcgagcccct tgagatcact aaggagatat acgacctgaa caaccccgag 1980
aaggagccca agaagtttca aaccgcctac gccaaaaaaa ctggccgacca aaagggctac 2040
agggaggcgc tgtgtaagtg gatcgacttc acacgcgact tcctttccgaa gtatacgaag 2100
acaacctcta ttgacctgag cagcctgcgt cctagctccc agtacaaaga tttgggcgag 2160
tactacgcgg agcttaatcc actactctac cacatctcat tccagcgcat cgctgagaag 2220
gaaatcatga cgcggtgga cacaggcaaa ctgtacctct tccagatata aacaaagac 2280
ttcgctaagg ggcaccacgg gaagcccaac cttcatacgc tctactggac gggcctattc 2340
agccccgaaa atctggccaa cctccatc aagctgaagc tggttctac 2400
agacccaaga gccggatgaa gcggatggcc cacaggctcg gcgagaaaat gcttaacaaa 2460
aagttgaagg accagaaaac ccctatcccc gacaccctct accaggaact gtacgactac 2520
gtgaaccaca ggctctcgca cgacctttcc gacgaggccc gtgccctact cccgaacgtc 2580
attaccaaag aggtttcgca cgagatcatc aaggaccggc ggttcacgag cgacaagttt 2640
ttctttcacg tcccccatcac cctttaactac caggcggcca actcccccatc caagttcaac 2700
```

```
cagcgtgtga atgcctacct caaggagcac ccagagaccc cgatcattgg gatcgaccgg    2760
ggcgagcgga acctgatcta catcaccgtc atcgactcga cgggcaagat tcttgagcag    2820
agatcgttga ataccataca gcagttcgac taccagaaga aactcgacaa ccgcgagaag    2880
gagcgcgtgg cggcccgcca ggcgtggtcc gtcgttggga cgattaagga cttgaaacaa    2940
ggttatctgt cccaagtcat ccacgagatc gttgatctga tgatccacta tcaggcagtg    3000
gtggtgctgg agaatctcaa cttcggcttc aagagtaagc ggacgggaat cgccgagaag    3060
gccgtgtacc agcagttcga gaagatgctg atcgacaagc tcaactgcct tgtgctgaaa    3120
gactacccgg ccgagaaggt cggcggcgtc ctcaacccgt accaacttac cgaccagttc    3180
acctccttcg ccaagatggg cactcagtcc gggttcttgt tctacgtccc cgcaccttac    3240
acctctaaga tcgaccctct gactggcttc gtagatccat tcgtgtggaa gaccattaag    3300
aaccacgaga gccgcaagca cttcctggag ggcttcgact tcctgcacta cgacgtgaag    3360
accgggggact tcatccttca cttcaagatg aaccggaacc tcagcttcca gcggggcctg    3420
ccggggttca tgcccgcctg ggacatcgtg ttcgagaaga acgagaccca gttcgacgcg    3480
aagggcacgc ccttcatcgc cgggaagcgt atcgtgcctg tgatcgagaa ccatcgtttc    3540
acgggtcgct accgtgacct ctacccggcg aacgagctta tcgcactcct ggaggagaag    3600
ggcatcgtct tccgggacgg ctccaacatc ctcccgaaac tgctgaaaaa cgacgactct    3660
cacgccatcg acacgatggt ggccctcatc cggtccgtgc tccaaatgcg gaacagcaac    3720
gccgccaccg gtgaggacta catcaacagc ccggtccggg atctgaacgg ggtgtgcttc    3780
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                        3987

SEQ ID NO: 21           moltype = DNA  length = 1592
FEATURE                 Location/Qualifiers
source                  1..1592
                        mol_type = other DNA
                        organism = Medicago truncatula
SEQUENCE: 21
actgttaata attttttaaac gtcagcgcac taaaaaaacg aaaagacgga cacgtgaaaa    60
taaaaaacac acactagttt atgacgcaat actatttttac ttatgatttg ggtacattag    120
acaaaaccgt gaaagagatg tatcagctat gaaacctgta tacttcaata cagagactta    180
ctcatatcgg atacgtacgc acgaagtatc atattaatta tttttaatttt taataaaatat    240
tttatcggat acttatgtga tactctacat atacacaagg atatttctaa gatactttat    300
agatacgtat cctagaaaaa catgaagagt aaaaaagtga gacaatgttg taaaaattca    360
ttataaatgt atatgattca atttttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttttaa tgatgtttct ctcaatatca catcatatga    540
aaatgtaata tgattttataa gaaaatttttt aaaaaattta ttttaataat cacatgtact    600
attttttaaa aattgtatct tttataataa tacaataata aagagtaatc agtgttaatt    660
tttcttcaaa tataagttttt attataaatc attgttaacg tatcataagt cattaccgta    720
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga tttttgctat aaaagcaaat caggtaaact aaacttcttc attctttttct    1020
tccccatcgc tacaaaaccg gttccttttgg aaaagagatt cattcaaacc tagcacccaa    1080
ttccgtttca aggtataatc tactttctat tcttcgatta ttttattatt attagctact    1140
atcgtttaat cgatcttttc ttttgatccg tcaaatttaa attcaattag ggttttgttc    1200
ttttctttca tctgattgaa atccttctga attgaaccgt ttacttgatt ttactgttta    1260
ttgtatgatt taatccttttg ttttttcaaag acagtcttta gattgtgatt aggggttcat    1320
ataaattttt agatttggat ttttgtattg tatgattcaa aaaatacgtc ctttaattag    1380
attagtacat ggatatttt tacccgattt attgattgtc agggagaatt tgatgagcaa    1440
gttttttttga tgtctgttgt aaattgaatt gattataatt gctgatctgc tgcttccagt    1500
tttcataacc catattcttt taaccttgtt gtacacacaa tgaaaaattg gtgattgatt    1560
catttgtttt tctttgttttt ggattataca gg                                 1592

SEQ ID NO: 22           moltype = DNA  length = 2000
FEATURE                 Location/Qualifiers
source                  1..2000
                        mol_type = other DNA
                        organism = Zea mays
SEQUENCE: 22
gtcgtgcccc tctctagaga taaagagcat tgcatgtcta aagtataaaa aattaccaca    60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
atacttcatc cattttatta gtacatccat ttaggattta gggttgatgg tttcatataga    360
ctaattttta gtacatccat ttattctttt ttagtctcta aatttttttaa aactaaaact    420
ctattttagt ttttttattta ataatttaga tataaaatga aataaaataa attgactaca    480
aataaaacaa atacccttta agaaataaaa aaactaagca acattttttc ttgtttcgag    540
tagataatga caggctgttc aacgccgtcg acgagtctaa cggacaccaa ccagcgaacc    600
agcagcgtgc cgtcgggcca agcgaagcag acggcacggc atctctgtag ctgcctctgg    660
accctctctg agagttccgc tccaccgttg gacttgctcc gctgtcggca tccagaaatt    720
gcgtggcgga gcgcagacg tgaggcggca cggcaggcgg cctcttcctc ctctcacggc    780
accggcagct acgggggatt cctttcccac cgctccttcg cttcccttc ctcgcccgcc    840
gtaataaaata gacaccccct ccacaccctc ttccccaac ctcgtgttcg ttcggagcgc    900
acacacacgc aaccagatct ccccccaaatc cagccgtcgg cacctccgct tcaaggtacg    960
```

-continued

```
ccgctcatcc tcccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct tttttctcg cttggttgtg atgatatggt    1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt ttaagatgat    1500
ggatggaaat atcgatctag gataggtata catgttgatg cgggttttac tgatgcatat    1560
acagagatgc ttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt    1920
agccctgcct tcatacgcta tttatttgct tggtactgtt tcttttgtcc gatgctacc    1980
ctgttgtttg gtgatacttc                                                2000

SEQ ID NO: 23           moltype = AA  length = 228
FEATURE                 Location/Qualifiers
source                  1..228
                        mol_type = protein
                        organism = Rattus norvegicus
SEQUENCE: 23
SSETGPVAVD PTLRRRIEPH EFEVFFDPRE LRKETCLLYE INWGGRHSIW RHTSQNTNKH     60
VEVNFIEKFT TERYFCPNTR CSITWFLSWS PCGECSRAIT EFLSRYPHVT LFIYIARLYH    120
HADPRNRQGL RDLISSGVTI QIMTEQESGY CWRNFVNYSP SNEAHWPRYP HLWVRLYVLE    180
LYCIILGLPP CLNILRRKQP QLTFFTIALQ SCHYQRLPPH ILWATGLK                 228

SEQ ID NO: 24           moltype = AA  length = 199
FEATURE                 Location/Qualifiers
source                  1..199
                        mol_type = protein
                        organism = Homo sapiens
SEQUENCE: 24
MEASPASGPR HLMDPHIFTS NFNNGIGRHK TYLCYEVERL DNGTSVKMDQ HRGFLHNQAK     60
NLLCGFYGRH AELRFLDLVP SLQLDPAQIY RVTWFISWSP CFSWGCAGEV RAFLQENTHV    120
RLRIFAARIY DYDPLYKEAL QMLRDAGAQV SIMTYDEFKH CWDTFVDHQG CPFQPWDGLD    180
EHSQALSGRL RAILQNQGN                                                 199

SEQ ID NO: 25           moltype = DNA  length = 621
FEATURE                 Location/Qualifiers
source                  1..621
                        mol_type = other DNA
                        organism = Petromyzon marinus
SEQUENCE: 25
acagatgcag agtatgtgag aattcacgaa aagctggaca tctataccct caagaagcag     60
ttctttaaca ataagaagtc tgtgagccat aggtgctacg tgctgttcga gctgaagaga    120
aggggtgaaa gaagggcatg tttttggggg tatgctgtga acaagcccca gtctggaact    180
gagagaggca ttcacgccga aattttcagc atcagaaagg tggaggaata cctgagggat    240
aaccctggac agtttacaat taattggtat tctagctggt ctccatgcgc tgactgtgcc    300
gagaagatcc tggaatggta caaccaggag ctgagaggaa atggccatac cctgaagatt    360
tgggcctgca agctgtacta tgaaaagaac gcaagaaatc agatcggact gtggaacctg    420
agggataatg gtgtggggct gaacgtgatg gtgtccgagc actatcagtg ctgtagaaag    480
attttcattc agtcctcaca taatcagctg aacgagaata gatggctgga aaagactctg    540
aagagggctg agaagagaag gtccgaactg tcaattatga tccaggtgaa gatcctgcac    600
accactaagt cacctgccgt g                                              621

SEQ ID NO: 26           moltype = AA  length = 160
FEATURE                 Location/Qualifiers
source                  1..160
                        mol_type = protein
                        organism = synthetic construct
SEQUENCE: 26
FERNYDPREL RKETYLLYEI KWGKSGKLWR HWCQNNRTQH AEVYFLENIF NARRFNPSTH     60
CSITWYLSWS PCAECSQKIV DFLKEHPNVL EIYVARLYYH EDERNRQGLR DLVNSGVTIR    120
IMDLPDYNYC WKTFVSDQGG DEDYWPGHFA PWIKQYSLKL                          160

SEQ ID NO: 27           moltype = AA  length = 207
FEATURE                 Location/Qualifiers
source                  1..207
                        mol_type = protein
                        organism = synthetic construct
SEQUENCE: 27
TDAEYVRIHE KLDIYTFKKQ FSNNKKSVSH RCYVLFELKR RGERRACFWG YAVNKPQSGT     60
ERGIHAEIFS IRKVEEYLRD NPGQFTINWY SSWSPCADCA EKILEWYNQE LRGNGHTLKI    120
WVCKLYYEKN ARNQIGLWNL RDNGVGLNVM VSEHYQCCRK IFIQSSHNQL NENRWLEKTL    180
KRAEKRRSEL SIMFQVKILH TTKSPAV                                        207
```

```
SEQ ID NO: 28            moltype = AA   length = 228
FEATURE                  Location/Qualifiers
source                   1..228
                         mol_type = protein
                         organism = synthetic construct
SEQUENCE: 28
SSKTGPVAVD PTLRRRIEPH EFEVFFDPRE LRKETCLLYE INWGGRHSIW RHTSQNTNKH    60
VEVNFIEKFT TERYFCPNTR CSITWFLSWS PCGECSRAIT EFLSRYPNVT LFIYIARLYH   120
LANPRNRQGL RDLISSGVTI QIMTEQESGY CWHNFVNYSP SNESHWPRYP HLWVRLYVLE   180
LYCIILGLPP CLNILRRKQS QLTSFTIALQ SCHYQRLPPH ILWATGLK               228

SEQ ID NO: 29            moltype = AA   length = 162
FEATURE                  Location/Qualifiers
source                   1..162
                         mol_type = protein
                         organism = synthetic construct
SEQUENCE: 29
SFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YPENERNRQG LRDLVNSGVT   120
IRIMDLPDYN YCWKTFVSDQ GGDEDYWPGH FAPWIKQYSL KL                     162

SEQ ID NO: 30            moltype = AA   length = 166
FEATURE                  Location/Qualifiers
source                   1..166
                         mol_type = protein
                         organism = Escherichia coli
SEQUENCE: 30
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTD                 166

SEQ ID NO: 31            moltype = AA   length = 166
FEATURE                  Location/Qualifiers
source                   1..166
                         mol_type = protein
                         organism = synthetic construct
SEQUENCE: 31
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM PRQVFNAQKK AQSSTD                 166

SEQ ID NO: 32            moltype = AA   length = 166
FEATURE                  Location/Qualifiers
source                   1..166
                         mol_type = protein
                         organism = synthetic construct
SEQUENCE: 32
SEVEFSHEYW MRHALTLAKR AWDEREVPVG AVLVLNNRVI GEGWNRSIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM RRQVFNAQKK AQSSTD                 166

SEQ ID NO: 33            moltype = AA   length = 166
FEATURE                  Location/Qualifiers
source                   1..166
                         mol_type = protein
                         organism = synthetic construct
SEQUENCE: 33
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM RRQVFNAQKK AQSSTD                 166

SEQ ID NO: 34            moltype = AA   length = 166
FEATURE                  Location/Qualifiers
source                   1..166
                         mol_type = protein
                         organism = synthetic construct
SEQUENCE: 34
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM PRQVFNAQKK AQSSTD                 166

SEQ ID NO: 35            moltype = AA   length = 1763
FEATURE                  Location/Qualifiers
source                   1..1763
                         mol_type = protein
                         organism = synthetic construct
SEQUENCE: 35
SEVEFSHEYW MRHALTLAKR AWDEREVPVG AVLVHNNRVI GEGWNRPIGR HDPTAHAEIM    60
```

```
ALRQGGLVMQ  NYRLIDATLY  VTLEPCVMCA  GAMIHSRIGR  VVFGARDAKT  GAAGSLMDVL   120
HHPGMNHRVE  ITEGILADEC  AALLSDFFRM  RRQEIKAQKK  AQSSTDSGGS  SGGSSGSETP   180
GTSESATPES  SGGSSGGSSE  VEFSHEYWMR  HALTLAKRAR  DEREVPVGAV  LVLNNRVIGE   240
GWNRAIGLHD  PTAHAEIMAL  RQGGLVMQNY  RLIDATLYVT  FEPCVMCAGA  MIHSRIGRVV   300
FGVRNAKTGA  AGSLMDVLHY  PGMNHRVEIT  EGILADECAA  LLCYFFRMPR  QVFNAQKKAQ   360
SSTDSGGSSG  GSSGSETPGT  SESATPESSG  GSSGGSDKKY  SIGLAIGTNS  VGWAVITDEY   420
KVPSKKFKVL  GNTDRHSIKK  NLIGALLFDS  GETAEATRLK  RTARRYTRR   KNRICYLQEI   480
FSNEMAKVDD  SFFHRLEESF  LVEEDKKHER  HPIFGNIVDE  VAYHEKYPTI  YHLRKKLVDS   540
TDKADLRLIY  LALAHMIKFR  GHFLIEGDLN  PDNSDVDKLF  IQLVQTYNQL  FEENPINASG   600
VDAKAILSAR  LSKSRRLENL  IAQLPGEKKN  GLFGNLIALS  LGLTPNFKSN  FDLAEDAKLQ   660
LSKDTYDDDL  DNLLAQIGDQ  YADLFLAAKN  LSDAILLSDI  LRVNTEITKA  PLSASMIKRY   720
DEHHQDLTLL  KALVRQQLPE  KYKEIFFDQS  KNGYAGYIDG  GASQEEFYKF  IKPILEKMDG   780
TEELLVKLNR  EDLLRKQRTF  DNGSIPHQIH  LGELHAILRR  QEDFYPFLKD  NREKIEKILT   840
FRIPYYVGPL  ARGNSRFAWM  TRKSEETITP  WNFEEVVDKG  ASAQSFIERM  TNFDKNLPNE   900
KVLPKHSLLY  EYFTVYNELT  KVKYVTEGMR  KPAFLSGEQK  KAIVDLLFKT  NRKVTVKQLK   960
EDYFKKIECF  DSVEISGVED  RFNASLGTYH  DLLKIIKDKD  FLDNEENEDI  LEDIVLTLTL  1020
FEDREMIEER  LKTYAHLFDD  KVMKQLKRRR  YTGWGRLSRK  LINGIRDKQS  GKTILDFLKS  1080
DGFANRNFMQ  LIHDDSLTFK  EDIQKAQVSG  QGDSLHEHIA  NLAGSPAIKK  GILQTVKVVD  1140
ELVKVMGRHK  PENIVIEMAR  ENQTTQKGQK  NSRERMKRIE  EGIKELGSQI  LKEHPVENTQ  1200
LQNEKLYLYY  LQNGRDMYVD  QELDINRLSD  YDVDHIVPQS  FLKDDSIDNK  VLTRSDKNRG  1260
KSDNVPSEEV  VKKMKNYWRQ  LLNAKLITQR  KFDNLTKAER  GGLSELDKAG  FIKRQLVETR  1320
QITKHVAQIL  DSRMNTKYDE  NDKLIREVKV  ITLKSKLVSD  FRKDFQFYKV  REINNYHHAH  1380
DAYLNAVVGT  ALIKKYPKLE  SEFVYGDYKV  YDVRKMIAKS  EQEIGKATAK  YFFYSNIMNF  1440
FKTEITLANG  EIRKRPLIET  NGETGEIVWD  KGRDFATVRK  VLSMPQVNIV  KKTEVQTGGF  1500
SKESILPKRN  SDKLIARKKD  WDPKKYGGFD  SPTVAYSVLV  VAKVEKGKSK  KLKSVKELLG  1560
ITIMERSSFE  KNPIDFLEAK  GYKEVKKDLI  IKLPKYSLFE  LENGRKRMLA  SAGELQKGNE  1620
LALPSKYVNF  LYLASHYEKL  KGSPEDNEQK  QLFVEQHKHY  LDEIIEQISE  FSKRVILADA  1680
NLDKVLSAYN  KHRDKPIREQ  AENIIHLFTL  TNLGAPAAFK  YFDTTIDRKR  YTSTKEVLDA  1740
TLIHQSITGL  YETRIDLSQL  GGD                                             1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW  MRHALTLAKR  ARDEREVPVG  AVLVLNNRVI  GEGWNRAIGL  HDPTAHAEIM    60
ALRQGGLVMQ  NYRLIDATLY  VTFEPCVMCA  GAMIHSRIGR  VVFGVRNSKR  GAAGSLMNVL   120
NYPGMNHRVE  ITEGILADEC  AALLCDFYRM  PRQVFNAQKK  AQSSINSGGS  SGGSSGSETP   180
GTSESATPES  SGGSSGGSDK  KYSIGLAIGT  NSVGWAVITD  EYKVPSKKFK  VLGNTDRHSI   240
KKNLIGALLF  DSGETAEATR  LKRTARRYT   RRKNRICYLQ  EIFSNEMAKV  DDSFFHRLEE   300
SFLVEEDKKH  ERHPIFGNIV  DEVAYHEKYP  TIYHLRKKLV  DSTDKADLRL  IYLALAHMIK   360
FRGHFLIEGD  LNPDNSDVDK  LFIQLVQTYN  QLFEENPINA  SGVDAKAILS  ARLSKSRRLE   420
NLIAQLPGEK  KNGLFGNLIA  LSLGLTPNFK  SNFDLAEDAK  LQLSKDTYDD  DLDNLLAQIG   480
DQYADLFLAA  KNLSDAILLS  DILRVNTEIT  KAPLSASMIK  RYDEHHQDLT  LLKALVRQQL   540
PEKYKEIFFD  QSKNGYAGYI  DGGASQEEFY  KFIKPILEKM  DGTEELLVKL  NREDLLRKQR   600
TFDNGSIPHQ  IHLGELHAIL  RRQEDFYPFL  KDNREKIEKI  LTFRIPYYVG  PLARGNSRFA   660
WMTRKSEETI  TPWNFEEVVD  KGASAQSFIE  RMTNFDKNLP  NEKVLPKHSL  LYEYFTVYNE   720
LTKVKYVTEG  MRKPAFLSGE  QKKAIVDLLF  KTNRKVTVKQ  LKEDYFKKIE  CFDSVEISGV   780
EDRFNASLGT  YHDLLKIIKD  KDFLDNEENE  DILEDIVLTL  TLFEDREMIE  ERLKTYAHLF   840
DDKVMKQLKR  RRYTGWGRLS  RKLINGIRDK  QSGKTILDFL  KSDGFANRNF  MQLIHDDSLT   900
FKEDIQKAQV  SGQGDSLHEH  IANLAGSPAI  KKGILQTVKV  VDELVKVMGR  HKPENIVIEM   960
ARENQTTQKG  QKNSRERMKR  IEEGIKELGS  QILKEHPVEN  TQLQNEKLYL  YYLQNGRDMY  1020
VDQELDINRL  SDYDVDHIVP  QSFLKDDSID  NKVLTRSDKN  RGKSDNVPSE  EVVKKMKNYW  1080
RQLLNAKLIT  QRKFDNLTKA  ERGGLSELDK  AGFIKRQLVE  TRQITKHVAQ  ILDSRMNTKY  1140
DENDKLIREV  KVITLKSKLV  SDFRKDFQFY  KVREINNYHH  AHDAYLNAVV  GTALIKKYPK  1200
LESEFVYGDY  KVYDVRKMIA  KSEQEIGKAT  AKYFFYSNIM  NFFKTEITLA  NGEIRKRPLI  1260
ETNGETGEIV  WDKGRDFATV  RKVLSMPQVN  IVKKTEVQTG  GFSKESILPK  RNSDKLIARK  1320
KDWDPKKYGG  FDSPTVAYSV  LVVAKVEKGK  SKKLKSVKEL  LGITIMERSS  FEKNPIDFLE  1380
AKGYKEVKKD  LIIKLPKYSL  FELENGRKRM  LASAGELQKG  NELALPSKYV  NFLYLASHYE  1440
KLKGSPEDNE  QKQLFVEQHK  HYLDEIIEQI  SEFSKRVILA  DANLDKVLSA  YNKHRDKPIR  1500
EQAENIIHLF  TLTNLGAPAA  FKYFDTTIDR  KRYTSTKEVL  DATLIHQSIT  GLYETRIDLS  1560
QLGGD                                                                  1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW  MRHALTLAKR  ARDEREVPVG  AVLVLNNRVI  GEGWNRAIGL  HDPTAHAEIM    60
ALRQGGLVMQ  NYRLYDATLY  STFEPCVMCA  GAMIHSRIGR  VVFGVRNAKT  GAAGSLMDVL   120
HHPGMNHRVE  ITEGILADEC  AALLCRFFRM  PRRVFNAQKK  AQSSTDSGGS  SGGSSGSETP   180
GTSESATPES  SGGSSGGSDK  KYSIGLAIGT  NSVGWAVITD  EYKVPSKKFK  VLGNTDRHSI   240
KKNLIGALLF  DSGETAEATR  LKRTARRYT   RRKNRICYLQ  EIFSNEMAKV  DDSFFHRLEE   300
SFLVEEDKKH  ERHPIFGNIV  DEVAYHEKYP  TIYHLRKKLV  DSTDKADLRL  IYLALAHMIK   360
FRGHFLIEGD  LNPDNSDVDK  LFIQLVQTYN  QLFEENPINA  SGVDAKAILS  ARLSKSRRLE   420
NLIAQLPGEK  KNGLFGNLIA  LSLGLTPNFK  SNFDLAEDAK  LQLSKDTYDD  DLDNLLAQIG   480
DQYADLFLAA  KNLSDAILLS  DILRVNTEIT  KAPLSASMIK  RYDEHHQDLT  LLKALVRQQL   540
```

```
PEKYKEIFFD QSKNGYAGYI DGGASQEEFY KFIKPILEKM DGTEELLVKL NREDLLRKQR    600
TFDNGSIPHQ IHLGELHAIL RRQEDFYPFL KDNREKIEKI LTFRIPYYVG PLARGNSRFA    660
WMTRKSEETI TPWNFEEVVD KGASAQSFIE RMTNFDKNLP NEKVLPKHSL LYEYFTVYNE    720
LTKVKYVTEG MRKPAFLSGE QKKAIVDLLF KTNRKVTVKQ LKEDYFKKIE CFDSVEISGV    780
EDRFNASLGT YHDLLKIIKD KDFLDNEENE DILEDIVLTL TLFEDREMIE ERLKTYAHLF    840
DDKVMKQLKR RRYTGWGRLS RKLINGIRDK QSGKTILDFL KSDGFANRNF MQLIHDDSLT    900
FKEDIQKAQV SGQGDSLHEH IANLAGSPAI KKGILQTVKV VDELVKVMGR HKPENIVIEM    960
ARENQTTQKG QKNSRERMKR IEEGIKELGS QILKEHPVEN TQLQNEKLYL YYLQNGRDMY   1020
VDQELDINRL SDYDVDHIVP QSFLKDDSID NKVLTRSDKN RGKSDNVPSE EVVKKMKNYW   1080
RQLLNAKLIT QRKFDNLTKA ERGGLSELDK AGFIKRQLVE TRQITKHVAQ ILDSRMNTKY   1140
DENDKLIREV KVITLKSKLV SDFRKDFQFY KVREINNYHH AHDAYLNAVV GTALIKKYPK   1200
LESEFVYGDY KVYDVRKMIA KSEQEIGKAT AKYFFYSNIM NFFKTEITLA NGEIRKRPLI   1260
ETNGETGEIV WDKGRDFATV RKVLSMPQVN IVKKTEVQTG GFSKESILPK RNSDKLIARK   1320
KDWDPKKYGG FDSPTVAYSV LVVAKVEKGK SKKLKSVKEL LGITIMERSS FEKNPIDFLE   1380
AKGYKEVKKD LIIKLPKYSL FELENGRKRM LASAGELQKG NELALPSKYV NFLYLASHYE   1440
KLKGSPEDNE QKQLFVEQHK HYLDEIIEQI SEFSKRVILA DANLDKVLSA YNKHRDKPIR   1500
EQAENIIHLF TLTNLGAPAA FKYFDTTIDR KRYTSTKEVL DATLIHQSIT GLYETRIDLS   1560
QLGGD                                                              1565

SEQ ID NO: 38         moltype = AA   length = 364
FEATURE               Location/Qualifiers
source                1..364
                      mol_type = protein
                      organism = synthetic construct
SEQUENCE: 38
SEVEFSHEYW MRHALTLAKR AWDEREVPVG AVLVHNNRVI GEGWNRPIGR HDPTAHAEIM     60
ALRQGGLVMQ NYRLIDATLY VTLEPCVMCA GAMIHSRIGR VVFGARDAKT GAAGSLMDVL    120
HHPGMNHRVE ITEGILADEC AALLSDFFRM RRQEIKAQKK AQSSTDSGGS SGGSSGGSETP   180
GTSESATPES SGGSSGGSSE VEFSHEYWMR HALTLAKRAR DEREVPVGAV LVLNNRVIGE    240
GWNRAIGLHD PTAHAEIMAL RQGGLVMQNY RLIDATLYVT FEPCVMCAGA MIHSRIGRVV    300
FGVRNAKTGA AGSLMDVLHY PGMNHRVEIT EGILADECAA LLCYFFRMPR QVFNAQKKAQ    360
SSTD                                                                364

SEQ ID NO: 39         moltype = AA   length = 167
FEATURE               Location/Qualifiers
source                1..167
                      mol_type = protein
                      organism = synthetic construct
SEQUENCE: 39
MSEVEFSHEY WMRHALTLAK RARDEREVPV GAVLVLNNRV IGEGWNRAIG LHDPTAHAEI     60
MALRQGGLVM QNYRLYDATL YSTFEPCVMC AGAMIHSRIG RVVFGVRNAK TGAAGSLMDV    120
LHHPGMNHRV EITEGILADE CAALLCRFFR MPRRVFNAQK KAQSSTD                  167

SEQ ID NO: 40         moltype = AA   length = 167
FEATURE               Location/Qualifiers
source                1..167
                      mol_type = protein
                      organism = synthetic construct
SEQUENCE: 40
MSEVEFSHEY WMRHALTLAK RARDEREVPV GAVLVLNNRV IGEGWNRAIG LHDPTAHAEI     60
MALRQGGLVM QNYRLIDATL YVTFEPCVMC AGAMIHSRIG RVVFGVRNSK RGAAGSLMNV    120
LNYPGMNHRV EITEGILADE CAALLCDFYR MPRQVFNAQK KAQSSIN                  167

SEQ ID NO: 41         moltype = AA   length = 83
FEATURE               Location/Qualifiers
source                1..83
                      mol_type = protein
                      note = Bacillus phage AR9
                      organism = unidentified
SEQUENCE: 41
TNLSDIIEKE TGKQLVIQES ILMLPEEVEE VIGNKPESDI LVHTAYDEST DENVMLLTSD     60
APEYKPWALV IQDSNGENKI KML                                            83

SEQ ID NO: 42         moltype = AA   length = 24
FEATURE               Location/Qualifiers
source                1..24
                      mol_type = protein
                      organism = synthetic construct
SEQUENCE: 42
EELLSKNYHL ENEVARLKKG SGSG                                           24

SEQ ID NO: 43         moltype = AA   length = 241
FEATURE               Location/Qualifiers
source                1..241
                      mol_type = protein
                      organism = synthetic construct
SEQUENCE: 43
EEELLSKNYH LENEVARLKK GSGSGEELLS KNYHLENEVA RLKKGSGSGE ELLSKNYHLE     60
NEVARLKKGS GSGEELLSKN YHLENEVARL KKGSGSGEEL LSKNYHLENE VARLKKGSGS    120
```

```
GEELLSKNYH LENEVARLKK GSGSGEELLS KNYHLENEVA RLKKGSGSGE ELLSKNYHLE    180
NEVARLKKGS GSGEELLSKN YHLENEVARL KKGSGSGEEL LSKNYHLENE VARLKKGSGS    240
G                                                                    241

SEQ ID NO: 44               moltype = AA    length = 277
FEATURE                     Location/Qualifiers
source                      1..277
                            mol_type = protein
                            organism = synthetic construct
SEQUENCE: 44
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG    120
GGGSGGGGSS GGGSEVKLLE SGGGLVQPGG SLKLSCAVSG FSLTDYGVNW VRQAPGRGLE    180
WIGVIWGDGI TDYNSALKDR FIISKDNGKN TVYLQMSKVR SDDTALYYCV TGLFDYWGQG    240
TLVTVSSYPY DVPDYAGGGG GSGGGGSGGG GSGGGGS                             277

SEQ ID NO: 45               moltype = DNA    length = 66
FEATURE                     Location/Qualifiers
source                      1..66
                            mol_type = other DNA
                            organism = Saccharomyces bayanus
SEQUENCE: 45
ttcttgtcgt acttatagat cgctacgtta tttcaattt gaaaatctga gtcctgggag     60
tgcgga                                                               66

SEQ ID NO: 46               moltype = AA    length = 605
FEATURE                     Location/Qualifiers
source                      1..605
                            mol_type = protein
                            organism = Homo sapiens
SEQUENCE: 46
MSGWESYYKT EGDEEAEEEQ EENLEASGDY KYSGRDSLIF LVDASKAMFE SQSEDELTPF    60
DMSIQCIQSV YISKIISSDR DLLAWFYGTE KDKNSVNFKI YVLQELDNPG AKRILELDQF    120
KGQQGQKRFQ DMMGHGSDYS LSEVLWVCAN LFSDVQFKMS HKRIMLFTNE DNPHGNDSAK    180
ASRARTKAGD LRDTGIFLDL HLKKPGGFDI SLFYRDIISI AEDEDLRVHF EESSKLEDLL    240
RKVRAKETRK RALSRLKLKL NKDIVISVGI YNLVQKALKP PPIKLYRETN EPVKTKTRTF    300
NTSTGGLLLP SDTKRSQIYG SRQIILEKEE TEELKRFDDP GLMLMGFKPL VLLKKHHYLR    360
PSLFVYPEES LVIGSSTLFS ALLIKCLEKE VAALCRYTPR RNIPPYFVAL VPQEEELDDQ    420
KIQVTPPGFQ LVFLPFADDK RKMPFTEKIM ATPEQVGKMK AIVEKLRFTY RSDSFENPVL    480
QQHFRNLEAL ALDLMEPEQA VDLTLPKVEA MNKRLGSLVD EFKELVYPPD YNPEGKVTKR    540
KHDNEGSGSK RPKVEYSEEE LKTHISKGTL GKFTVPLKEA CRAYGLKSGL KKQELLEALT    600
KHFQD                                                                605

SEQ ID NO: 47               moltype = AA    length = 482
FEATURE                     Location/Qualifiers
source                      1..482
                            mol_type = protein
                            organism = synthetic construct
SEQUENCE: 47
MVRSGNKAAW LCMDVGFTMS NSIPGIESPF EQAKKVITMF VQRQVFAENK DEIALVLFGT    60
DGTDNPLSGG DQYQNITVHR HLMLPDFDLL EDIESKIQPG SQQADFLDAL IVSMDVIQHE    120
TIGKKFEKRH IEIFTDLSSR FSKSQLDIII HSLKKCDISE RHSIHWPCRL TIGSNLSIRI    180
AAYKSILQER VKKTTWDAKT LKKEDIQKET VYCLNDDDET EVLKEDIIQG FRYGSDIVPF    240
SKVDEEQMKY KSEGKCFSVL GFCKSSQVQR RFFMGNQVLK VFAARDDEAA AVALSSLIHA    300
LDDLDIWAIV RYAYDKRANP QVGVAFPHIK HNYECLVYQ LPFMEDLRQY MFSSLKNSKK    360
YAPTEAQLNA VDALIDSMSL AKKDEKTDTL EDLFPTTKIP NPRFQRLFQC LLHRALHPRE    420
PLPPIQQHIW NMLNPPAEVT TKSQIPLSKI KTLFPLIEAK KKDQVTAQEI FQDNHEDGPT    480
AK                                                                   482

SEQ ID NO: 48               moltype = DNA    length = 10
FEATURE                     Location/Qualifiers
source                      1..10
                            mol_type = other DNA
                            organism = Methanobacterium thermoautotrophicum
SEQUENCE: 48
aattttgga                                                            10

SEQ ID NO: 49               moltype = AA    length = 83
FEATURE                     Location/Qualifiers
source                      1..83
                            mol_type = protein
                            organism = Methanobacterium thermoautotrophicum
SEQUENCE: 49
GSVIDVSSQR VNVQRPLDAL GNSLNSPVII KLKGDREFRG VLKSFDLHMN LVLNDAEELE    60
DGEVTRRLGT VLIRGDNIVY ISP                                            83

SEQ ID NO: 50               moltype = DNA    length = 25
FEATURE                     Location/Qualifiers
source                      1..25
```

```
                              isolate = Escherichia phage MS2
                              mol_type = other DNA
                              organism = Emesvirus zinderi
SEQUENCE: 50
gcgcacatga ggatcaccca tgtgc                                              25

SEQ ID NO: 51                 moltype = AA   length = 116
FEATURE                       Location/Qualifiers
source                        1..116
                              mol_type = protein
                              note = Escherichia phage MS2
                              organism = Emesvirus zinderi
SEQUENCE: 51
MASNFTQFVL VDNGGTGDVT VAPSNFANGI AEISSNSRSQ AYKVTCSVRQ SSAQNRKYTI        60
KVEVPKGAWR SYLNMELTIP IFATNSDCEL IVKAMQGLLK DGNPIPSAIA ANSGIY           116

SEQ ID NO: 52                 moltype = DNA   length = 26
FEATURE                       Location/Qualifiers
source                        1..26
                              isolate = Bacteriophage PP7
                              mol_type = other DNA
                              organism = Pepevirus rubrum
SEQUENCE: 52
ataaggagtt tatatggaaa ccctta                                             26

SEQ ID NO: 53                 moltype = AA   length = 127
FEATURE                       Location/Qualifiers
source                        1..127
                              mol_type = protein
                              note = Bacteriophage PP7
                              organism = Pepevirus rubrum
SEQUENCE: 53
MSKTIVLSVG EATRTLTEIQ STADRQIFEE KVGPLVGRLR LTASLRQNGA KTAYRVNLKL        60
DQADWDCSTS VCGELPKVRY TQVWSHDVTI VANSTEASRK SLYDLTKSLV ATSQVEDLVV       120
NLVPLGR                                                                 127

SEQ ID NO: 54                 moltype = DNA   length = 19
FEATURE                       Location/Qualifiers
misc_feature                  1..19
                              note = Shigella phage
source                        1..19
                              mol_type = other DNA
                              organism = unidentified
SEQUENCE: 54
ctgaatgcct gcgagcatc                                                     19

SEQ ID NO: 55                 moltype = AA   length = 62
FEATURE                       Location/Qualifiers
REGION                        1..62
                              note = Shigella phage
source                        1..62
                              mol_type = protein
                              organism = unidentified
SEQUENCE: 55
MKSIRCKNCN KLLFKADSFD HIEIRCPRCK RHIIMLNACE HPTEKHCGKR EKITHSDETV        60
RY                                                                       62

SEQ ID NO: 56                 moltype = AA   length = 1367
FEATURE                       Location/Qualifiers
source                        1..1367
                              mol_type = protein
                              organism = synthetic construct
SEQUENCE: 56
DKKYSIGLAI GTNSVGWAVI TDEYKVPSKK FKVLGNTDRH SIKKNLIGAL LFDSGETAEA        60
TRLKRTARRR YTRRKNRICY LQEIFSNEMA KVDDSFFHRL EESFLVEEDK KHERHPIFGN       120
IVDEVAYHEK YPTIYHLRKK LVDSTDKADL RLIYLALAHM IKFRGHFLIE GDLNPDNSDV       180
DKLFIQLVQT YNQLFEENPI NASGVDAKAI LSARLSKSRR LENLIAQLPG EKKNGLFGNL       240
IALSLGLTPN FKSNFDLAED AKLQLSKDTY DDDLDNLLAQ IGDQYADLFL AAKNLSDAIL       300
LSDILRVNTE ITKAPLSASM IKRYDEHHQD LTLLKALVRQ QLPEKYKEIF FDQSKNGYAG       360
YIDGGASQEE FYKFIKPILE KMDGTEELLV KLNREDLLRK QRTFDNGSIP HQIHLGELHA       420
ILRRQEDFYP FLKDNREKIE KILTFRIPYY VGPLARGNSR FAWMTRKSEE TITPWNFEEV       480
VDKGASAQSF IERMTNFDKN LPNEKVLPKH SLLYEYFTVY NELTKVKYVT EGMRKPAFLS       540
GEQKKAIVDL LFKTNRKVTV KQLKEDYFKK IECFDSVEIS GVEDRFNASL GTYHDLLKII       600
KDKDFLDNEE NEDILEDIVL TLTLFEDREM IEERLKTYAH LFDDKVMKQL KRRRYTGWGR       660
LSRKLINGIR DKQSGKTILD FLKSDGFANR NFMQLIHDDS LTFKEDIQKA QVSGQGDSLH       720
EHIANLAGSP AIKKGILQTV KVVDELVKVM GRHKPENIVI EMARENQTTQ KGQKNSRERM       780
KRIEEGIKEL GSQILKEHPV ENTQLQNEKL YLYYLQNGRD MYVDQELDIN RLSDYDVDHI       840
VPQSFLKDDS IDNKVLTRSD KNRGKSDNVP SEEVVKKMKN YWRQLLNAKL ITQRKFDNLT       900
KAERGGLSEL DKAGFIKRQL VETRQITKHV AQILDSRMNT KYDENDKLIR EVKVITLKSK       960
```

-continued

```
LVSDFRKDFQ FYKVREINNY HHAHDAYLNA VVGTALIKKY PKLESEFVYG DYKVYDVRKM   1020
IAKSEQEIGK ATAKYFFYSN IMNFFKTEIT LANGEIRKRP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD                 1367

SEQ ID NO: 57           moltype = AA   length = 1367
FEATURE                 Location/Qualifiers
source                  1..1367
                        mol_type = protein
                        organism = synthetic construct
SEQUENCE: 57
DKKYSIGLAI GTNSVGWAVI TDEYKVPSKK FKVLGNTDRH SIKKNLIGAL LFDSGETAEA     60
TRLKRTARRR YTRRKNRICY LQEIFSNEMA KVDDSFFHRL EESFLVEEDK KHERHPIFGN    120
IVDEVAYHEK YPTIYHLRKK LVDSTDKADL RLIYLALAHM IKFRGHFLIE GDLNPDNSDV    180
DKLFIQLVQT YNQLFEENPI NASGVDAKAI LSARLSKSRR LENLIAQLPG EKKNGLFGNL    240
IALSLGLTPN FKSNFDLAED AKLQLSKDTY DDDLDNLLAQ IGDQYADLFL AAKNLSDAIL    300
LSDILRVNTE ITKAPLSASM IKRYDEHHQD LTLLKALVRQ QLPEKYKEIF FDQSKNGYAG    360
YIDGGASQEE FYKFIKPILE KMDGTEELLV KLNREDLLRK QRTFDNGSIP HQIHLGELHA    420
ILRRQEDFYP FLKDNREKIE KILTFRIPYY VGPLARGNSR FAWMTRKSEE TITPWNFEEV    480
VDKGASAQSF IERMTNFDKN LPNEKVLPKH SLLYEYFTVY NELTKVKYVT EGMRKPAFLS    540
GEQKKAIVDL LFKTNRKVTV KQLKEDYFKK IECFDSVEIS GVEDRFNASL GTYHDLLKII    600
KDKDFLDNEE NEDILEDIVL TLTLFEDREM IEERLKTYAH LFDDKVMKQL KRRRYTGWGR    660
LSRKLINGIR DKQSGKTILD FLKSDGFANR NFMQLIHDDS LTFKEDIQKA QVSGQGDSLH    720
EHIANLAGSP AIKKGILQTV KVVDELVKVM GRHKPENIVI EMARENQTTQ KGQKNSRERM    780
KRIEEGIKEL GSQILKEHPV ENTQLQNEKL YLYYLQNGRD MYVDQELDIN RLSDYDVDHI    840
VPQSFLADDS IDNKVLTRSD KNRGKSDNVP SEEVVKKMKN YWRQLLNAKL ITQRKFDNLT    900
KAERGGLSEL DKAGFIKRQL VETRQITKHV AQILDSRMNT KYDENDKLIR EVKVITLKSK    960
LVSDFRKDFQ FYKVREINNY HHAHDAYLNA VVGTALIKKY PALESEFVYG DYKVYDVRKM   1020
IAKSEQEIGK ATAKYFFYSN IMNFFKTEIT LANGEIRKAP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD                 1367

SEQ ID NO: 58           moltype = DNA   length = 4101
FEATURE                 Location/Qualifiers
source                  1..4101
                        mol_type = other DNA
                        organism = synthetic construct
SEQUENCE: 58
gacaagaagt acagcatcgg gctggcgatc gggaccaact ccgtcggctg ggctgtgatt     60
accgacgagt acaaggtgcc atccaagaag ttcaaggtcc tcggcaacac tgaccggcac    120
agcattaaga agaacctgat tggggcgctg ctgttcgatt cgggggagac tgcggagggc    180
accaggctga gcggactgcg cgcgccgagg tacaccagga ggaagaatcg gatctgctac    240
ctccaggaga tttttctcga atgagatggc aaggtggacg attccttctt ccatcgcctg    300
gaggagtcgt tcctcgttga ggaggacaag aagcatgaga ggcatcccat tttcgggaat    360
atcgttgacg aggtggctta ccatgagaag tacccgacta tctaccatct gcggaagaag    420
ctcgtcgatt cgaccgataa ggccgacctg cggctgatct acctggccct cgcgcacatg    480
attaagttcc ggggccattt cctcatcgag ggcgacctca cccgacaa ctcggacgtg      540
gataagctct tcattcagct cgtgcagaca tacaaccagc tcttgaggga gaatcccatt    600
aacgcctcgg gggtcgacgc taaggctatt ctctcggtc gcgtgtcgaa gtcgcgccgg     660
ctggagaatc tcattgccca gctcccaggc gagaagaaga acggcctctt cggcaacctg    720
attgccctgt cgctggggct cacaccgaat ttcaagtcga acttcgacct cgccgaggac    780
gctaagctcc agctcagcaa ggatacttac gatgatgacc tcgataacct gctcgcccag    840
attggggatc agtacgcgga tctgttcctc gcggccaaga atctcagcga tgctattctc    900
ctgtcggaca ttctccgcgt caacacagag attactaagg ccccactgtc ggcgagcatg    960
attaagaggt acgatgagca tcatcaggac ctgacactgc tcaaggcgct ggtccggcag   1020
cagctccccg agaagtacaa ggagattttt ttcgatcagt caaagaatgg gtacgcgggc   1080
tacattgatg gcggcgcgtc ccaggaggag ttctacaagt tcattaagcc catcctggag   1140
aagatggacg ggaccgaaga gctgctggtg agctcaatcg ggggactaag gctccggaaa   1200
cagcgcacat cgacaatggg ctcgattcct caccagattc acctgggcga gctgcacgcc   1260
attctccgca ggcaggagga cttctacccg ttcctcaagg acaaccgcga aagatcgag    1320
aagatcctga ccttccggat tccatactac gtggggccgc tcgcgcgggg gaactcccgg   1380
ttcgcgtgga tgactcgcaa gtccgaagaa acgattacac cgtggaattt cgaggaggtc   1440
gtcgacaagg gcgctagtgc gcagtcattc attgagaagg taagcaatt cgataagaac    1500
ctgcctaacg agaaggtgct gccgaagcat tcgctgctct acgagtactt caccgtttac   1560
aatgagctga ccaaggtgaa gtatgtgact gagggcatga ggaagccagc gttcctgagc   1620
ggcgagcaga gaaggctat cgtggacctg ctcttcaaga ctaaccggaa ggtgactgtg    1680
aagcagctca aggaggacta cttcaagaag attgagtgct cgattccgt tgagattagc    1740
ggggtgaggg atcggttcaa tgcttcgctc gggacatacc acgatctgct gaagatcatt   1800
aaggataagg acttcctcga caacgaggag aacgaggaca ttctcgaaga tattgtcctg   1860
accctcaccc tcttcgagga tcgggagatg atcgaggaga ggctcaagac atacgctcat   1920
ctgttcgatg ataaggtcat gaagcagctg aagcgcaggc ggtacacagg gtggggcgg    1980
ctgagccgga agctgatcaa cgggattcgg gataagcagt ccgggaagac aattctcgac   2040
ttcctcaagt ccgacgggtt cgctaaccgg aacttcatgc agctcattca tgatgactcg   2100
```

```
ctgacattca aggaggatat tcagaaggcg caggtttcgg ggcagggcga ctcgctccac    2160
gagcatattg cgaatctggc gggctccccc gcgattaaga agggcattct gcaaaccgtc    2220
aaggtggttg atgagctggt caaggtcatg gggcggcata agccagagaa tattgtcatc    2280
gagatggcgc gggagaatca gaccacacag aaggggcaga agaactcacg ggagcggatg    2340
aagcgcatcg aggagggcat caaggagctg gggtcgcaga tcctgaagga gcatcccgtc    2400
gagaacactc agctgcaaaa tgagaagctg tacctctact acctccagaa cggagggac     2460
atgtatgtgg atcaggagct ggatattaat aggctgagcg attacgatgt cgaccacatt    2520
gtcccacagt cgttcctgaa ggacgacagc attgacaaca aggtgctgac ccgctcggat    2580
aagaacaggg gcaagagcga taatgttcca agcgaggagg ttgtgaagaa gatgaagaac    2640
tactggcgc agctcctgaa cgcgaagctc atcacacagc ggaagttcga caacctcacc     2700
aaggctgagc gcgggggcct gagcgagctg gacaaggcgg ggttcattaa gaggcagctg    2760
gtcgagacac ggcagattac aaagcatgtt gcgcagattc tcgattcccg gatgaacacc    2820
aagtacgatg agaacgataa gctgattcgg gaggtcaagg taattaccct gaagtccaag    2880
ctggtgtccg acttcaggaa ggacttccaa ttctacaagg ttcgggagat caacaactac    2940
caccacgcgc atgatgccta cctcaacgcg gtcgtgggga ccgctctcat caagaagtac    3000
ccaaagctgg agtcagagtt cgtctacggg gattacaagg tttacgacgt gcggaagatg    3060
atcgctaaga gcgagcagga gattggcaag gctaccgcta agtacttctt ctactccaac    3120
atcatgaact tcttcaagac agagattacc ctcgcgaatg gcgagatccg gaagaggccc    3180
ctcatcgaga caaatgggga gacagggag attgtctggg ataagggcg ggatttcgcg      3240
accgtccgga aggtcctgtc gatgcccag gttaatattg tcaagaagac tgaggtccag     3300
actggcggct tctcaaagga gtcgattctc caaagagga actccgataa gctcattgct    3360
cggaagaagg attgggaccc caagaagtcg ggggattcg actccccac tgttgcttac     3420
tctgttctgg ttgttgctaa ggtgagaag gggaagtcga agaagctgaa gagcgtgaag    3480
gagctgctcg ggattacaat tatggagagg tcatccttcg agaagaatcc catcgacttc    3540
ctggaggcca agggctacaa ggaggtgaag aaggacctga ttattaagct gcccaagtac    3600
tcgctcttcg agctggagaa tgggcggaag cggatgctgg cgtccgcggg ggagctgcaa    3660
aaggggaacg agctggcgct cccctccaag tatgtgaact tcctctacct ggcgtcgcac    3720
tacgagaagc tgaaggggtc cccagaggat aatgagcaga agcagctctt cgtcgagcag    3780
cataagcact acctggacga gattatcgag cagattagcg agttctcgaa gcgggtcatc    3840
ctcgcggatg cgaacctgga taaggtgctc agcgcctaca ataagcaccg ggacaagccg    3900
attcgggagc aggcggagaa tattattcac ctcttcacac tcaccaacct cggggcacca    3960
gctgcgttca agtacttcga cactactatc gaccggaagc ggtacacctc gacgaaggag    4020
gtgctcgacg ccaccctcat tcaccagtcg atcacaggcc tgtacgagac acggattgac    4080
ctgtcccagc tcgggggcga c                                              4101
```

SEQ ID NO: 59          moltype = DNA   length = 4101
FEATURE                 Location/Qualifiers
source                  1..4101
                        mol_type = other DNA
                        organism = synthetic construct
SEQUENCE: 59

```
gacaagaagt actccattgg cctggcgatt gggacaaact cggtggggtg ggccgtgatt    60
acggatgagt acaaggttcc aagcaagaag ttcaaggtcc tcgggaacac agatcggcat    120
tcgattaaga agaatctcat tggggcgctc ctcttcgact cggggagac agcggaggct     180
accaggctca gcggacagc caggcggcgg tacacaaggc ggaagaatcg catctgctac    240
ctccaggaga ttttctcgaa tgagatggcg aaggtggacg acagcttctt ccatcggctg    300
gaggagtcct tcctggtgga ggaggataag aagcacgaga ggcatccaat tttcgggaac    360
atcgtggacg aggttgcgta ccatgagaag taccctacaa tctaccatct gcggaagaag    420
ctggttgact ccacagacaa ggcggacctg aggctgatct acctcgctct ggcccacatg    480
attaagttcc gcgggcattt cctgatcgag ggggacctga tcccgacaa ttcggatgtg    540
gacaagtct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga tgggctctct cgggaatctg    720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcgggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcccctgc tcaaggccct cgtgcggcag     1020
cagctgcccg agaagtacaa ggagattttc ttcgaccaga gcaagaatgg gtacgctggc    1080
tacattgacg gcggggcctc acaggaggag ttctacaagt tcatcaagcc aatcctggag    1140
aagatggatg gaacagagga gctgctggtg aagctcaacc gggaggatct gctcaggaag    1200
cagcggacgt tcgacaacgg gtcgattccc atcagatcc acctggggga gctgcacgcg     1260
atcctgcgcc ggcaggagga tttctaccct tcctgaagg ataatcggga gaagatcgag      1320
aagattctca ccttccggat tccctactac gtcgggccac ttcgcgggg caatagcagg    1380
ttcgcctgga tgacacgaa gagcgaggag acaatcaccc cctggaactt cgaggaggtt    1440
gtcgacaagg gggcgtccgc ccagtcattc attgagcgga tgaccaattt cgacaagaat    1500
ctgccaaatg agaaggttct cccaaagcat agcctcctct acgagtactt cactgttta     1560
aacgagctga ccaaggtgaa gtatgtgacc gagggcatgc ggaagcccgc gttcctgtcc    1620
ggcgagcaga agaaggccat tgtggacctc tgttcagaa ccaatcgcaa ggtcacagtc     1680
aagcagctca aggaggatta cttcaagaag atcgagtgct tcgactcggt tgagattagc    1740
ggggtggagg atcggttcaa cgcgagcctc ggcacttacc acgacctcct gaagatcatc    1800
aaggataagg acttcctcga caacgaggag aacgaggata ttctggagga catcgtgctc    1860
accctgacgc tgttcgagga tcgggagatg atcgaggagc gcctgaagac ctacgctcat    1920
ctcttcgatg ataaggtcat gaagcagctg aagagaggc ggtacaccgg gtgggggcgc    1980
ctgagcagga agctcattaa cgggatcagg gacaagcaga gcggcaagac catcctggac    2040
ttcctcaaga gcgatggctt cgccaaccgg aatttcatgc agctcatcca cgacgactcc    2100
ctcaccttca aggaggacat tcagaaggct caggtcagcg gccagggcga ctcgctgcat    2160
gagcacatcg ctaacctggc gggcagccca gccatcaaga agggcatcct ccagacagtg    2220
aaggtcgtgg atgagctggt gaaggtcatg ggccggcata agcccgagaa tattgtgatt    2280
```

```
gagatggcgc gggagaatca gaccactcag aagggccaga agaactcgcg ggagcgcatg   2340
aagaggatcg aggaggggat taaggagctg ggcagccaga ttctcaagga gcaccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatcgcg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttcggaa  ggacttccag ttctacaagg tgcgggagat taacaactac   2940
catcatgcgc acgatgcgta cctcaatgcg gtggtgggca cagccctgat taagaagtac   3000
cccaagctgg agagcgagtt cgtctacggg gactacaagg tgtacgatgt tcggaagatg   3060
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
ctcatcgaga ctaacgggga gactggcgag attgtgtggg acaaggggcg cgacttcgct   3240
accgtgcgca aggtcctctc gatgcccag  gttaatattg ttaagaagac agaggtgcag   3300
acggggcggt tctccaagga gtctatcctg ccgaagcgga actcggacaa gctgatcgcc   3360
cgcaagaagg attgggaccc caagaagtac gggggattcg atagcccaac cgtggcttac   3420
agcgtcctgg tggtcgccaa ggttgagaag gggaagtcga agaagctcaa gagcgttaag   3480
gagctgctgg gcatcaccat catggagcgg tccagcttcg agaagaatcc tatcgacttc   3540
ctggaggcta aggggtacaa ggaggtcaag aaggacctga tcattaagct gcccaagtac   3600
tctctgttcg agctggagaa cgggaggaag cggatgctgg cgtctgctgg cgagctacag   3660
aagggcaatg agctggcgct cccctcgaag tatgtcaact tcctctacct ggcttcccat   3720
tacgagaagc tgaagggctc gcccgaggat aatgagcaga agcagctctt cgtggagcag   3780
cacaagcact acctcgacga gatcattgag cagattttcg agttctcgaa gcgggtcatt   3840
ctcgcgacg  cgaacctcga caaggtcctc tcggcgtaca caagcaccg  ggacaagccc   3900
atccgggagc aggccgagaa cattatccac ctcttcacac tgaccaacct cggcgctccc   3960
gccgcgttca gtacttcga  caccaccatt gaccgcaaga gatacacatc caccaaggag   4020
gtgctggacg cgaccctcat ccaccagagc atcacaggcc tctacgagac acggatcgac   4080
ctctcgcagc tcggggcga  t                                             4101

SEQ ID NO: 60           moltype = DNA  length = 4092
FEATURE                 Location/Qualifiers
source                  1..4092
                        mol_type = other DNA
                        organism = synthetic construct
SEQUENCE: 60
gacaagaagt actcgatcgg cctggcgatt ggcacaaaca gcgtgggggtg ggctgtgatc    60
actgatgagt acaaggtgcc atcgaagaag ttcaaggtgc tggggaatac agaccggcat   120
tcgatcaaga agaatctcat tggcgctctc ctcttcgatt ccggcgagac tgctgaggcg   180
acccgcctga agcgcaccgc ccggcggcgc tacactcggc ggaagaatag gatttgctac   240
ctccaggaga ttttctcgaa tgagatggcc aaggtgatg  acagctttct ccaccgcctg   300
gaggagtcgt tcctggtcga ggaggacaag aagcatgagc ggcaccctat cttcgggaat   360
atcgttgatg aggtcgccta ccacgagaag taccccacta tctaccatct ccgcaagaag   420
ctcgtggaca gcacagataa ggccgacctc cgcctgatct acctgcccct cgcgcacatg   480
attaagttcc gggggcacttcctcattgag ggggatctga atcccgataa ctccgacgtg   540
gacaagctgt tcatccagct ggtgcagaca taaccagc  tgttcgagga gaatcccatc   600
aacgcgagcg cgtggacgc  taaggccatt ctgtcggcta ggctctcgaa gtcgaggcgg   660
ctggagaacc tgattgcgca gctccccggc gagaagaaga acgggctgtt cgggaatctc   720
atcgccctct ccctcggcct cacaccaaac ttcaagaca atttcgacct ggctgaggac   780
gctaagctgc aactctcaaa ggatacatac gatgacgacc tggacaatct cctggctcag   840
atcggcgacc agtacgctga cctgttcctc gcgccaaga  atctgtcgga cgcgattctc   900
ctcagcgaca tcctgcgcgt caataccgag attacgaagg ctccactgtc tgcgtcaatg   960
attaagcggt acgatgagca tcaccaggat ctgacctcc  tgaaggcgct cgtgcggcag  1020
cagctgcccg agaagtacaa ggagattttc ttcgatcaga gcaagaatgg ctacgccggc  1080
tacatcgacg gggcgcgag  ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc actcggcga  gctgcatgcg  1260
attctgcggc ggcaggagga tttctaccct ttcctgaagg acaaccggga gaagatccga  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctcccaacg  agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga gaaggccat  tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg gggacttacc acgacctgct gaagattatt  1800
aaggacaagg acttcctgga taacgaggag aatgaggaca tcctggaaga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg ggcagggaga ctcactccac  2160
gagcatattg ccaatctggc cggctctcca gctatcaaga agggcatcct gcaaacagtt  2220
aaggttgttg acgagctggt taaggtcatg ggcggcata  agcccgagaa cattgtcatc  2280
gagatggctc gggagaacca gacaactcag aagggccaga agaactccag ggagcgcatg  2340
aagcggatt  aggagggcat taaggagctg gggtcccaga tcctcaagga gcaccctgtc  2400
gagaacactc agctgcaaaa cgagaagctc tacctgtact acctccagaa cgggcgggat  2460
```

```
atgtatgtgg atcaggagct ggacatcaac aggctctccg actacgacgt ggatcacatt    2520
gtcccacagt ctttcctcaa ggatgattcc atcgacaaca aggtgctgac gcgcagcgac    2580
aagaataggg ggaagtcgga caacgttccg agcgaggagg tcgtgaagaa gatgaagaat    2640
tactggaggc agctcctgaa tgcgaagctg atcactcaga ggaagttcga caatctgaca    2700
aaggcggaga ggggcgggct ctcggagctg gataaggcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagcg acttcaggaa ggatttccag ttctacaagg ttcgggagat taacaactac    2940
caccacgcgc atgatgcgta cctgaacgct gtttgtcggca ctgctctcat caagaagtac    3000
ccaaagctgg agtccgagtt cgtctacggg gactacaagg tctacgatgt ccggaagatg    3060
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattg ttaagaagac agaggtgcag    3300
actgggggct tctcgaagga gagcattctc ccaaagcgga acagcgataa gctcatcgcg    3360
cgcaagaagg attgggaccc taagaagtac ggcggcttcg attctcccac tgtggcctac    3420
tccgttctcg tggttgccaa ggttgagaag gggaagtcga agaagctgaa gtcggtcaag    3480
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aaggggaatg agctggccct cccgtcgaag tatgtgaatt tcctgtacct cgcgtcgcac    3720
tacgaagagc tcaagggcag cccggaggat aatgagcagg agcagctcct cgtggagcag    3780
cataagcact acctggacga gatcattgag cagatcagcg agttctcgaa gcgggttatt    3840
ctggctgatg ctaacctgga caaggttctg agcgcctaca ataagcatcg cgacaagccg    3900
attcgcgagc aggcggagaa tattatccac ctgttcaccc tcactaacct cggggctccc    3960
gcggccttca agtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092
SEQ ID NO: 61       moltype = DNA   length = 4101
FEATURE             Location/Qualifiers
source              1..4101
                    mol_type = other DNA
                    organism = synthetic construct
SEQUENCE: 61
gacaagaagt attccatagg cctggctatc ggcaccaaca gcgtgggctg ggccgtcatc      60
accgacgagt acaaagtgcc gagtaaaaag ttcaaagtgc tcggcaacac cgaccgccac     120
tccataaaga aaaacctgat cggggcgctc tgttcgaca gcggcgagac ggcggaggcc      180
acccgcttga aacgcacggc ccgacgcgcg tacacgcgga gcaagaaccg gatctgttac     240
ctacaggaga ttttctctaa cgagatggcc aaggtggacg actcgttctt tcaccgcctc     300
gaagagtcct tcctcgtgga ggaggacaag aaacacgagc gccacccgat cttcggcaac     360
atcgtggacg aggtggccta ccacgagaag taccccgacca tctaccacct ccggaagaaa     420
ctcgtggaca gcacggacaa ggccgacctg aggctcatct acctcgccct ggcgcacatg     480
attaagttcc ggggccactt cctgatcgag ggcgacctga accggacaa cagcgacgtg     540
gacaagctgt tcatccagct agtccagacc tacaaccagc ttttcgagga aaaccccatc     600
aacgccagcg gggtggacgc gaaggcgatc ctgtccgccc ggctgagcaa gtcccggcgg     660
ctggagaacc tcatcgcgca gttgcccggc gagaagaaga acgggctgtt cgggaacctg     720
atcgccctct ccctggggct caccccgaac ttcaagtcca acttcgacct cgccgaggac    780
gccaaactac agctgagcaa ggacacctac gacgacgacc tcgacaacct gctggccag     840
atcggggacc agtacgcaga cctgttcctc gccgccaaga acctctccga cgccatcctg    900
ctgtcggaca tcctgcgggt gaacacggag atcacgaagg ccccgctctc ggcctcgatg    960
attaaacgct acgacgagca ccaccaggac ttgaccctcc tcaaggcgct ggtccgccag   1020
cagcttcccg agaagtacaa ggaaatcttt tcgatcaga gcaagaacgg gtacgccggg    1080
tacatcgacg gcgggcgtc ccaggaggag ttctacaagt tcatcaagcc catcctggag    1140
aaaatggaca ggaccgagga gctgctcgtg aagctcaacc gcgaagattt gctccgcaag    1200
cagcgcacgt tcgacaacgg gtcgatcccc caccagatcc acctgggcga gctgcacgcg    1260
atcctcaggc gtcaggaaga cttctacccc ttcctcaagg acaaccgcga gaagatagag    1320
aagattctga ccttcagaat tccttattac gtgggcccgc tggctcgggg caactcgcgc    1380
ttcgcctgga tgacgcgcaa gtccgagagg accatcaccc cgtggaactt cgaggaggtg    1440
gtggataagg gtgcctcggc ccagtccttc atcgagcgga tgaccaactt cgacaagaac    1500
ctgccgaacg agaaggtgct ccccaagcac agcctgctct acgaatattt cacggtgtac    1560
aacgagctga cgaaggtcaa gtacgtgacc gagggaatga ggaaacctgc attcctctcc    1620
ggggagcaga agaaagccat agtcgacctc ctgttcaaga ccaaccggaa ggtcaccgtc    1680
aagcagctca aggaggacta cttcaagaag atcgagtgct tcgattcagt ggagatcagc    1740
ggcgtcgagg accggttcaa cgccagcctg ggcacctacc acgacctgct caagatcatc    1800
aaggacaagg acttcctcga caacgaggag aacgaggaca tcctggagga catcgtgctg    1860
accctgacgc tcttcgagga ccgcgagatg atcgaggagc gcctcaagac ctacgcccac    1920
ctgttcgacg acaaggtgat gaagcagctc aagcggcgga gatatactgg gtgggccgc    1980
ctctcccgga agctcattaa cggtatcagg gataagcagt cctccggaag gatcctcgac    2040
ttcctcaagt cggacgggtt cgccaaccgc aacttcatgc agctcatcca cgacgactcc    2100
ctgacgttca aggaggacat ccagaaggcc aagtgtctg gtcaaggtga ctcgctccac    2160
gagcacatcc caaccctcgc gggcagcccg gccatcaaga agggaatact ccagaccgtc    2220
aaggtggtgg acgagctggt gaaggtcatg ggccgccaca gccggagaa catcgtcatc    2280
gagatgggga gggaaccga gaccacgca agggggcag aaaatagcc tgagcgcatg    2340
aagcgcatcg aggaggggat taaggagttg ggcagccaga tcctcaagga gcaccctgtg    2400
gagaacacgc agttgcaaaa cgagaagctc tacctgtact acctccagaa cgggagggat    2460
atgtacgtgg accaagaact ggacatcaac cgcctgtccg actacgacgt ggaccacatc    2520
gtgccgcaga gcttcctcaa ggacgacagc atcgacaaca aggtgctcac ccggtccgac    2580
aagaatcggg gcaagtccga caacgtgccc agcgaggagg tcgtcaaaaa gatgaaaaac    2640
```

```
tactggcgac aactactgaa cgccaagctc atcacccagc gcaagttcga caacctcaca  2700
aaagccgagc gcggcgggtt gagcgagctg acaaggccg ggttcatcaa gcgccagctc   2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtcgacg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga atacttctt ctacagcaac   3120
atcatgaact tcttcaagac cgagatcacc ctcgccaacg gcgagatccg caagcgcaac  3180
ctcatcgaga cgaacgggga gaccggcgag atcgtctggg acaaggggcg cgacttcgcc  3240
actgtgcgga aggtgctgtc gatgcccag gtcaacatcg tcaagaagac ggaggtccag    3300
acgggcgggt tcagcaagga gagcatcctg ccgaagcgca acagcgacaa gctgatcgcc  3360
cgcaaaaagg actgggatcc aaaaaagtac ggcggcttcg cagcccac cgtcgcctca    3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cgggcgcaag cggatgctgc gtcggccgg agagctccaa   3660
aagggcaacg agctggcgct gccgacaag tacgtgaact tcctctacct gggcgtccac    3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca caagcaccg cgacaagccg    3900
atccgcgagc aagccgagaa catcatccac ctgttcaccc tcacgaaccg tggggcaccg  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                             4101
```

SEQ ID NO: 62          moltype = DNA   length = 4101
FEATURE                Location/Qualifiers
source                 1..4101
                       mol_type = other DNA
                       organism = synthetic construct
SEQUENCE: 62

```
gacaagaagt acagtattgg attggccatc gggacgaaca cgtgggctg ggccgtcatc    60
accgacgagt acaaggtgcc atccaagaag tttaaggttc tggggaatac cgaccgccac   120
tcgatcaaga aaatctcat cggggcgctg cttttcgaca gcggcgagac gcggaagcg    180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccaccccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacg agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagcccc cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccc caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggccgcggg caactcccgg  1380
ttcgcctgga tgaccgtaa gagcgaggag acgatcaccc cgtgaacctt cgaggagtc    1440
gtggacaagg gcgcgagcgc gcagagcttc atcgagcgca tgaccaactt cgacaagaac  1500
ctccccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt gggagataagc  1740
ggcgtggagg accgattcaa cgcctccctc ggcacctacc acgacctcct taagatcatc  1800
aaggacaagg acttcctgga caacgaggag aacgaggaca tctggagga catcgtgctc  1860
accctgaccc tcttcgagga ccggggagatg atcgaggagc gcctcaagac gtacgcccac  1920
ttgttcgacg acaaggtgat gaagcagctc aagcggcggc gatacaccgg tgggccgcc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc aagtgagcg gtcaagggga cagcctccac   2160
gagcacattg cgaaccttgc tgggagccct gcgatcagta aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctcacagaa cggggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcagtccga caacgtgccc tcgaggagg tggtcaagaa atgaaaaac     2640
tactggcggc agttgctgaa cgccaagctc attacgcagc ggaagttcga caacctgacg  2700
aaggctgaac gtggtgggct cagcgagcta acaaggcgg ggttcatcaa gcggcagctc    2760
gtcgagaccc ggcagatcac caagcacgtg gcgcagatcc tggactcgcg catgaacacc  2820
```

```
aagtacgacg agaacgacaa gctcatccgt gaggtgaagg tcatcaccct taagtctaag    2880
ctggtcagtg acttccgcaa ggacttccag ttctacaagg tccgggagat caacaactac    2940
caccacgcgc acgacgccta cctcaacgcg gtggtgggga cggcgcttat taagaaatat    3000
cccaagctgaa aaagcgagtt cgtttacggc gactacaagg tgtacgacgt ccgcaagatg    3060
atcgcaaagt cggaacagga aatcggaaag gcgacggcca aatatttctt ttactccaac    3120
atcatgaatt tttttaagac ggagatcacc ctggcgaacg gggagatccg caagcggccc    3180
ctcatcgaga ccaacgggga gacgggcgag atcgtctggg acaagggccg ggacttcgcc    3240
accgtgcgga aggtgctttc tatgcctcaa gtcaatatcg tcaaaaagac agaggtgcag    3300
accggcgggt tcagcaagga gtctatcctg ccgaagcgca actcggacaa gctcatcgcg    3360
cgcaagaaag actgggaccc caaaaaatat ggcgggttcg actcgccgac cgtcgcctac    3420
agcgtcctcg tggtggctaa ggtcgagaag ggcaagagca aaaagctaaa gtcggtgaag    3480
gagctgctgg gcatcaccat catggagcgc tcgtctttcg agaagaatcc aatcgacttc    3540
ctagaggcga agggtacaa ggaggtcaaa aaggatctta tcatcaaact gccgaagtac    3600
agtctgttcg agctggagaa cgggcggaag cggatgctgg ctagtgcggg cgagttgcag    3660
aagggcaacg agttggcact gccctccaag tacgtgaact tcctgtacct ggcctcccac    3720
tacgagaagc tcaaggggag ccccgaggac aacgagcaga agcagctatt cgtcgagcag    3780
cacaagcact acctggacga gatcatcgag cagatcagtg agttctccaa gcgggtcatc    3840
ctcgcggacg ccaacctgga caaggtgctg agcgcgtaca acaagcacag ggacaagcca    3900
atcagggaac aggccgagaa catcatccac ctgttcaccc tgaccaacct gggtgcaccg    3960
gctgccttca agtactttga cacgaccatc gaccggaagc gctacacctc cacgaaggag    4020
gtgctggacg ccacgctgat ccaccagagc atcaccgggc tctacgagac acggatcgac    4080
ctgagccagc ttggcgggga c                                               4101

SEQ ID NO: 63        moltype = DNA   length = 4092
FEATURE              Location/Qualifiers
source               1..4092
                     mol_type = other DNA
                     organism = synthetic construct
SEQUENCE: 63
gacaaaaagt attccattgg actcgctatc ggcacgaaca gcgtcgggtg ggcggtcatc    60
actgacgagt acaaggtgcc gagcaagaag tttaaggtgc tgggaaacac cgacaggcac    120
tcgatcaaga aaaatcttat cggggcccta ctcttcgact ccggagaaac cgccgaggcc    180
acccggttga agcgcacggc ccgccgtcgc tacaccaggc gcaagaaccg gatctgctac    240
ctccaggaga tattcagcaa tgagatggcg aaggtcgacg actcgttttt tcacaggcta    300
gaggagtctt tcctcgtgga ggaggacaag aaacacgagc gccacccccat cttcggcaac    360
atcgtggatg aggtggcata tcacgagaag tacccaacca tctaccacct ccgcaaaaag    420
ctcgtggact ctaccgacaa ggccgacctc cgtctgatct acctcgcgct ggcccacatg    480
attaagttcc gaggacactt tctgatcgag ggcgacctga cccgacaa cagcgacgtg    540
gacaagtgt tcatccaact tgtccagacc tacaatcagc tcttcgagga gaaccctatc    600
aacgcctcgg gcgtggacgc gaaggccatc ctgtccgccc gctgagcaa gtcgcggcgg    660
ctggagaacc tgatcgccca gctccccggc gaaaaaaaga acggcctctt cggcaacctc    720
atcgcgttgt cgctggggct caccccgaac ttcaagtcca acttcgacct ggccgaggac    780
gctaaactcc agctctcgaa ggatacctac gacgacgacc tgacaacct gctgccccag    840
atcggcgacc agtacgcgga ccttttcctg gcgccaaga acctgagcga cgcgatcctc    900
cttagcgaca tactccgtgt gaacaccgag atcacgaagg ccccgctctc cgcgtccatg    960
attaagcgct acgacgagca ccaccaagac cttccctgc ttaaggcgct ggtcaggcag    1020
cagttaccgg agaagtacaa ggagatcttt tttgatcaat ctaagaacgg ttacgcggga    1080
tacatcgacg gcggcgcgtc ccaggaggag ttctacaagt tcatcaagcc gatcttggag    1140
aaaatggacg gaccgagga gctgctcgtg aagctcaacc gcgaagacct cctccgcaag    1200
cagcgcacct tcgacaacgg gagcatcccg caccagatcc acctgggaga gctgcacgcg    1260
atcctgcgga gacaaggga cttctacccc ttcctcaaga acaaccggga gaagattgaa    1320
aaaatactta ctttttcgtat cccgtactac gtcgggcccc ttgcgagggg caactccaga    1380
ttcgcgtgga tgacccgcaa gtccgaggag accatcaccc cgtggaactt cgaggaggtg    1440
gtggacaagg gcgcgtcggc ccagtcgttc atcgagcgca tgaccaactt cgacaagaac    1500
cttccgaacg agaaggtgct cccgaagcac agcctgctct acgaatattt tactgtgtac    1560
aacgagctga cgaaggtcaa gtacgttacg gaggggatga ggaagccgc cttcctctcc    1620
ggcgagcaga agaaagccat tgtggatctc ctgttcaaga ccaaccgcaa ggtgacggtg    1680
aaacagctca agaggacta cttcaagaag atcgagtgct tcgactccgt agagatcagc    1740
ggggtcgagg accgcttcaa cgcctcgctg ggcacgtac acgacctgct aaagattatc    1800
aaggacaaag acttcctaga caatgacgga aacgggaca ttctggagga catcgtgctg    1860
actctgacgc tgttcgaaga ccgcgagatg atcgaggagc ggcttaagac gtacgccac    1920
ctgttcgacg acaaggtgat gaagcagttg aaacggcggc gctacaccgg tgggggccgc    1980
ctctcccgca gctcatcaa cggcatccgc gacaagcagt cggggaagac gatcctggac    2040
ttcctcaaga gcgacggctt cgccaaccga aacttcatgc agctaatcca cgacgacagc    2100
ctgacgttca aggaggacat ccagaaggcc caagtgagcg gccagggaga ctcgctacc    2160
gagcatatcg ccaacctggc tggcagcccg gcgattaaga aggaatcct ccaaaccgtc    2220
aaagtggtgg acgagctggt gaaggtgatg ggccgccaca gcccgagaa cattgtgatc    2280
gagatggcgc gggagaacca gacgacgcag aagggccaaa aaaatagcag ggaaaggatg    2340
aagcgaatag aggaggggat caaggagctg gggagccaga ttctgcaga gcacccgtc    2400
gagaacacac agctcccgaa cgagaagctg tacctctact acctccaaaa cggccgcgat    2460
atgtacgtgg accaggaact agacatcaac cggctgagcg actatgacgt ggaccacatc    2520
gtgccgcagt ccttcctcaa ggacgactcg attgacaaca agtgctcac tagatccgac    2580
aagaacagag gcaagagcga taacgtcccg tcggaggagg tcgtcaagaa atgaaaaac    2640
tactgcctaa acgccaagtc atcacgcag gtaagttcga caactgtg caacctgaag    2700
aaggcggagc ggggcgggct gagcgagctg gacaaagcgg ggttcatcaa cggcagctc    2760
gttgagacgc ggcagatcac aaagcacgtc gcgcaaatcc tcgactccg catgaacacc    2820
aagtacgacg agaacgacaa gctcatccgg gaggtgaagg tcattaccct taatcgaag    2880
ctcgtcagcg actttcgtaa ggacttccag ttctacaagg tcagagagat caacaactac    2940
caccacgccc acgacgccta tctgaacgcc gtggtgggca ccgcgcttat taagaagtac    3000
```

```
cccaagctgg agtccgagtt cgtgtacggc gactacaagg tttatgacgt caggaagatg    3060
atcgccaagt cggaacagga gatcggaaaa gctaccgcca aatatttctt ctatagcaac    3120
atcatgaact tcttcaaaac cgagatcacc ctcgccaacg gcgagatccg gaagcgcccg    3180
ctcatcgaga ccaacgggga gaccggggag atcgtctggg acaaggggcg ggacttcgct    3240
actgtccgaa aggtgctctc catgccacaa gtgaatatcg tcaagaaaac agaggtgcag    3300
accggagggt tcagtaagga gtccatcctg cccaagcgga actccgacaa gctaattgct    3360
cgcaaaaagg attgggatcc taaaaaatat ggcggcttcg actcgcccac ggtcgcctac    3420
tctgtgctgt tcgtggcgaa ggtggagaag ggcaagtcca agaagctcaa gagcgtcaag    3480
gagctgctgg ggatcacgat catggagcgt agttcgtttg agaagaatcc catcgacttc    3540
ctggaggcta agggctacaa ggaggtcaaa aaggacctca tcattaagct gccgaagtac    3600
agcctcttcg agctggagaa cgggcggaag cgtatgctcg cctccgctgg ggagttacaa    3660
aaggggaacg agctggcgct gccgtctaag tacgtcaact tcctgtacct ggcctcccac    3720
tacgagaagc tcaaggggtc gccggaggac aacgagcaga agcagctctt cgtagagcag    3780
cacaagcact acctggacga gatcatcgaa cagatttcag agttctcaaa ggcgggtcatc   3840
ctcgccgacg ccaacctgga caaggtgctc tcggcctaca caagcaccgg gacaagccca    3900
atccgcgaac aggccgaaaa catcatccac ctgttcacgc tcaccaacct cggtgccccg    3960
gcggccttca agtactttga cacgaccatc gaccggaagc gctatacctc gacgaaggag    4020
gtgctggacg ccaccctgat ccaccagtcc atcaccgggc tttacgagac ccggatcgac    4080
ctctcgcagc ta                                                       4092

SEQ ID NO: 64          moltype = DNA  length = 4101
FEATURE                Location/Qualifiers
source                 1..4101
                       mol_type = other DNA
                       organism = synthetic construct
SEQUENCE: 64
gacaagaagt atagtattgg actcgccatc ggaaccaact ctgtggggtg ggctgttatt     60
acagatgaat ataaggtgcc atccaaaaag tttaaagttc tgggcaatac tgatagacac    120
tcaatcaaga agaatctgat aggtgcactt ctgtttgata gtggagagac tgccgaggca    180
accagactta aaaggactgc aaagaagaga tataccagaa gaaagaatag gatttgctat    240
ttgcaggaaa tcttcagcaa cgaaatggcc aaggttgatg actcattttt ccataggttg    300
gaggagagtt ttcttgtgga ggaagataag aagcacgaaa gacacccaat tttcgggaat    360
atagtggacg aggtggctta tcatgagaag tatcccacta tctaccacct gagaaagaaa    420
cttgtggact caaccgataa ggctgatctt aggctatatat acttggccct tgcacatatg    480
atcaaattca ggggccattt tctttatcga ggcgatctta atcccgataa ctcagatgtg    540
gacaagctgt ttatcaaact tgtgcaaacc tacaatcaac tcttcgagga gaatcccatt    600
aacgcctccg gcgtggatgc aaaagccata ctgtcagcca gactgagcaa agtaggagaa    660
ctggagaatc ttatagccca actgccccgt gaaaagaaga tgggctctt cggaaatctg    720
atcgctcttt cattggggtt gacacccaac tttaagagta actttgactt ggcagaagat    780
gcaaagttgc agctcagtaa agacacatat gacgatgacc ttgacaatct cttggcacaa    840
ataggggatc aatacgctga cctttttcctc gctgccaaga acctcagcga cgctatactg    900
ttgtccgaca ttcttagggt taataccgaa attacaaagg cccctcttag tgcaagtatg    960
atcaaaaggt atgatgagca tcaccaagac cttacactgt gaaggctct ggttagacag    1020
caactccctg aaaagtataa ggaaatattc tccgaccaaa gtaagaacgg gtacgccggt    1080
tatattgatg ggggcgcaag tcaagaagaa ttttacaaat tcatcaagcc aattcttgaa    1140
aagatgacg ggactgagga attgctggtg aaactgaata gagaggacct tcttagaaaa    1200
cagaggacat ttgacaatgg gtccatccca caccagattc atctgggga actccacgca    1260
atattgagga gacaagaaga cttttaccca ttccttaagg ataatagaga gaaaatcgaa    1320
aaaatcctga ctttcaggat tccttactat gttgggccac tggccagggg gaactcaaga    1380
ttcgcttgga tgacaaggaa gtcagaagaa accataaccc cttggaattt tgaagaggtg    1440
gttgataagg gggcatcagc ccagtctttc atagagagga tgaccaactt tgataaaaat    1500
cttccaaatg agaaggtttt gccaaaacat agtctttgt acgagtactt tactgtttat    1560
aacgaattga ccaaggtgaa gtatgtgacc gagggaatga ggaagccagc attttttgtcc    1620
ggggagcaaa agaaagcaat cgttgatctt ctcttcaaga ccaacagaaa agtgaccgtg    1680
aaacaactga aggaagacta cttcaaaaag atagaatgtt tcgattcagt tgaaaattgc    1740
ggtgttgaag acaggttcaa tgcttcattg gtacttacc acgacctgtt gaagataatc    1800
aaagacaagg actttctcga taatgaggag aacgaagaca tcttggaaga cattgtgctt    1860
acactcactt tgtttgagga cagggaaatg attgaggaaa gactcaaaac ttacgctcat    1920
ttgtttgatg ataaggttat gaaacaacta aaaagaagaa ggtacaccgg ctggggaaga    1980
ttgagtagga aactgatcaa cggtattaga gataaacaat ccggaaagac tatcctcgat    2040
ttccttaaga gtgatggctt tgcaaatagg aattttatgc agctgattca tgacgactca    2100
cttaccttca aagaagacat ccaaaaagct caggtgtctg gcaaggcga cagtctgcat    2160
gaacatatag ctaacttggc tgggagtccc gccatcaaga aggggatact tcaaacagtt    2220
aaagttgtgg acgaattggt gaaggtaatg gaaaggccca agcctgaaaa tatagtgata    2280
gaaatggcaa gggaaaatca aacacccag aagggacaga gaacagtag ggaaaggatg    2340
aaaaggatag aagagggat caaagagctt ggtagccaga tcctcaagga acatccagtg    2400
gagaatacc aacttcaaaa cgagaaactc tatttgtact acttgcagaa cggaagagat    2460
atgtatgtgg accaagagct tgatattaac aggctgagcg attatgacgt tgaccacata    2520
gtgccccaat cattcctcaa ggatgactct attgataata aggtgctgac aaggagtgac    2580
aagaatagag ggaatccga caacgttcca tccgaggaag ttgtgaagaa gatgaagaac    2640
tactggaggc agttgctgaa cgctaagctc attcccaga ggaaattcga taacctgacc    2700
aaagcagaga gaggcgggct gagcgaactc gataaagcag gtttcatcaa gagacaactc    2760
gtggagacta ggcaaattac taagcacgtg gctcaaatac tcgacagcag gatgaacaca    2820
aagtacgacg agaacgacaa gctcattaga gaggttaagg ttattactct gaaagtaaa    2880
ttggttagcg atttcagaaa ggatttccaa ttctataagg ttagagagat caacaattat    2940
catcatgcac atgatgccta tctgaatgct gtggttggta cagcccttat caagaagtac    3000
cctaagctag agagcgagtt tgtgtacgga gattataagg tgtatgatgt gaggaaaatg    3060
atcgctaaaa gtgagcaaga gattggaaag gctaccgcca aatacttctt ttattccaat    3120
attatgaatt tcttcaagac agaaatcacc ctggctaacg cgagataag gaagaggccg    3180
```

```
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtgggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca caaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                          4101

SEQ ID NO: 65         moltype = DNA length = 4101
FEATURE               Location/Qualifiers
source                1..4101
                      mol_type = other DNA
                      organism = synthetic construct
SEQUENCE: 65
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaacctgat aggcgcactg ttgttcgact ccgggaaac agccgaagct  180
accaggctga agagaactgc aagaagaagg tacaccagaa gaaaaaacag aatatgttat  240
ctccaagaga tttctctaa cgagatggcc aaggtggacg actcattctt tcacagactg  300
gaagaatctt tccttgtgga agaagataag aaacacgaga ggcacccat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagattga accccgacaa cagtgatgtt  540
gataagctct ttattcagct cgtgcagact acaatcagt tgtttgagga aaaccccatt  600
aatgcttccg gggtggcagc caaggcaatc ctttctgaca gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcaggt taataccgag attacaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaacgg ctacgccggc  1080
tatatagacg ggggagcatc ccaagaagaa ttttataagt tcataaaacc tatattggag  1140
aagatggacg gacagagga attgctcgtg aaactgaaca gggaggatct cctcaggaaa  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cggaaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa acgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
ttttgaaat cagacgggtt cgcaaatagg aatttcatgc agcttataca cgacgattca  2100
cttacttta aagaggacat tcaaaaggct caagttagtg gacaaggtga ctccctccaa  2160
gaacacatcg caaatctcgc tggcagccct gcaattaaga agggtatact ccagacagtg  2220
aaggttgttg acgagctggt taaagtgatg ggaagacaca aacccgagaa catagtgata  2280
gagatggcca gggaaaacca aaccactcaa aaagggcaga aaattccag agagaggatg  2340
aaaaggattg aagaaggtat caaggagctg ggtagcaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgctcaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagt gtacgacgt tagaaaatg  3060
attgcaaagt cagagcagga gataggaaa gccactgcaa aatatttctt ttatagcaat  3120
atcatgaatt tctttaagac agaaatcaca ctgccaatg ggaaataag gaagaggccc  3180
ctgatcgaaa ctaatggcga gacagggag attgtgtggg ataaaggtag ggactttgca  3240
acagtgagga aagtgctgag catgccccaa gttaatatcg ttaaaaagac cgaggttcaa  3300
acaggggggct ttagtaagga aagcattttg cccaagagga atagtgacaa attgattgct  3360
```

```
aggaaaaaag attgggaccc caaaaagtat ggcggatttg atagccccac tgttgcttac   3420
tccgtgctcg tggttgcaaa ggtgagaag ggaaagagca agaaactgaa gtcagttaag   3480
gaactccttg gtatcactat catggaaaga agctcctttg agaagaaccc tattgacttc   3540
ctggaggcta aagggtacaa agaggttaag aaagacctta tcattaaatt gcccaaatat   3600
agtcttttcg agcttgaaaa cggaagaaag aggatgctcg catccgctgg cgaattgcaa   3660
aagggcaatg agcttgctct cccttccaag tatgtgaact tcctttatct tgcctcacac   3720
tatgaaaaac tcaaaggttc ccccgaagac aacgaacaaa agcaactatt tgtgaacaa    3780
cacaagcact acctggacga aatcattgag caaatttctg agttttcaaa aagggtaatc   3840
ttggctgacg caaatctcga caaagttttg tcagcttaca acaaacatag agataagcaa   3900
attagagagc aagctgagaa tatcatccat ctgtttaccc tgactaacct tggagcgcct   3960
gctgctttta aatatttcga caccacaatc gacaggaaga ggtacactag cactaaggaa   4020
gttctcgacg ccaccctcat ccaccagagt attacaggcc tgtacgagac aagaattgat   4080
cttctcaac ttggtggtga c                                             4101

SEQ ID NO: 66         moltype = DNA   length = 4101
FEATURE               Location/Qualifiers
source                1..4101
                      mol_type = other DNA
                      organism = synthetic construct
SEQUENCE: 66
gataagaagt actcaatcgg tctggcaatc ggaaccaact ctgtgggttg ggcagtgatt     60
acagatgagt ataaggtgcc aagcaaaaaa ttcaaggtgc tgggtaatac cgacagacac    120
agcattaaga agaatttgat tggagcactc ctctttgact caggggaaac agcgagagca    180
acaaggctga gaggacagc aaggcggagg tacacaaggc ggaaaaacag gatatgctac     240
ctccaggaaa tctttagcaa cgagatggct aaagtggatg atagcttttt ccatagactc    300
gaagaatcct ttcttgttga agaggacaaa aagcatgaaa ggcatcccat cttcggcaat    360
atagttgatg aggttgcata ccatgagaag taccccacaa tctaccacct cagaaagaaa    420
cttgtggact ccacagataa agcagacctg aggctcatat acctcgcact cgcacacatg    480
atcaagttca gagggcactt tctcatcgaa ggtgacctga atccagataa ttcagatgtg    540
gataaactgt ttatacagct ggtgcaaaca tacaaccaac ttttcgagga aaacccaatc    600
aatgcctccg gtgttgatgc aaaggccatc ctgtcagcaa gactcagcaa agcaggcgg    660
ctcgaaaacc tcatcgccca gcttccccggt gaaaagaaga cgggctctt tggtaatctc    720
atcgcattga gccttggtct tactccaaac ttcaagagca attttgatct ggcagaggat    780
gctaaactgc aactctcaaa ggacacatat gacgatgacc ttgacaatct gttggcccag    840
atcgggacc aatatgcaga cctcttcctg gccgcaaaga atctgtcaga tgcaatcctc    900
ttgtccgaca tactgagagt taacactgag atcacaaagg cacctctgtc cgcctccatg    960
attaagagat acgatgagca tcaccaggat ctgactttgc tcaaagccct cgttagacag   1020
cagttgccag aaaagtacaa agaaatattc tttgatcaat caaaaacgg atatgcaggg   1080
tacatcgacg gtggggcaag ccaggaagag ttctacaaat tcatcaaacc ttcctggaa    1140
aagatggatg ggacagaaga gctgctggtt aagctgaata gggaagacct cctcagaaag   1200
cagaggacat ttgataacgg gagcatccct catcaaatcc acctcggtga actccatgct   1260
atcctgagaa ggcaggaaga ctttttatcca tttttgaagg acaataggga gaaatcgaa    1320
aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga gaaagccagc attcctttcc   1620
ggggaacaga agaaagctat tgtgaccctc ctgttcaaga caaatagaaa agtgacagtt   1680
aagcaactca agaggatta cttcaaaaag atcgaatgtt ttgactctgt ggagatcagc   1740
ggggtggagg atagattcaa cgccagcctg gtacatatcc atgatctcct gaaaatcatt   1800
aaagacaagg acttccttga caacgaagg aacgaggaca ttctggaaga cattgttctg   1860
accctcacac tctttgagga taggagatg attgaggaaa gactgaagac ctacgcccac   1920
ctctttgacg ataaagtgat gaaacagctc aagagaagaa ggtatacagg ttggggagaa   1980
ctgagcagga gttgatcaa tgggattagg acaaacagt ccgggaaaac aatcctcgat    2040
tttctgaagt cagacggttt cgcaaacaga aattttatgc agctcattca cgatgacagc   2100
ttgacattca aggaagacat ccaaaggct caagtgagcg gccaagggga tagcctccac   2160
gagcatattg caaatctggc aggttcacca gccatcaaaa agggcatact tcagacagtt   2220
aaggttgtgg acgaattggt taagttatgg gcaggcata agccagagaa tatcgttatc   2280
gaaatggcaa gggagaacca acaactcaa aaagggcaga aaatagcag agagaggatg   2340
aaaagaatcg aggaagggat caaggaactt gggtcccaaa tcctcaagga gcaccagtt    2400
gaaaatactc aactgcaaaa cgagaagctc tatctctact atctccaaaa cgggagggat   2460
atgtatgttg accaggagct ggatattaac agactgtcag attatgatgt tgatcatatc   2520
gtgccccagt cattcctgaa ggacgattcc atcgacaaca agttctcac aaggtccgat   2580
aaaaacaggg gcaagtccga taacgttcca agcgaagtga tggtgaaaaa gatgaaaaac   2640
tattggagac aacttctgaa tgcaaagttg attactcaga gaaagtttga caacctcaca   2700
aaagcagaaa gaggcgggct tagcgaactc gataaggcag ggtttatcaa agacagctg    2760
gttgagacaa ggcagatcac aaaacatgtg gcacagatcc ttgactcaag gatgaatacc   2820
aagtatgatg agaatgataa gttgatcagg gaggttaaag ttatcacact caaatccaaa   2880
ctggtgtcag acttcaggaa agactttcaa ttttataagg tgagggagat caataactac   2940
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta gtatttctt ttacagtaat    3120
atcatgaatt tctttaaaac tgagattact ctggcaaacg gggagatcag gaaaagaccc   3180
ctcatcgaga ctaatggtga acaggtgag atccatcaag gatttttgct   3240
actgttagaa aagttctgag tatgccacaa gtgaatattg tgaaaagac agaagttcag   3300
acaggtgggt tctccaaaga atccatcctg cccaagagaa attcagacaa gctcatcgca   3360
agaaagaagg actgggaccc taagaagtac ggaggatttg acagcccac cgtgccctat   3420
tccgtgcttg ttgtggcaaa ggtggagaaa gggaagagca aaaaactgaa atccgtgaaa   3480
gaactgctgg gaattaccat catggaaaga agctcctttg agaagaaccc aatcgacttc   3540
```

```
ctggaagcaa aaggatataa ggaagtgaaa aaggacctca ttatcaagct cccaaaatac   3600
tcacttttcg agttggagaa cggtagaaag aggatgctgg caagcgcagg ggaacttcag   3660
aaaggcaatg agctggcatt gccatcaaag tatgtgaact tcctctactt ggccagccat   3720
tacgagaaac ttaaaggtag cccagaagat aacgagcaaa aacagctctt tgtggaacag   3780
cataagcatt atctggatga gatcatagaa caaatctcag agttttccaa gagagtttatc  3840
ctcgcagatg caaacctgga taaggttctc tcagcctata ataagcatag agacaagcca   3900
attagagagc aagcagagaa cattatccac ttgttcactc ttacaaacct gggggccaca   3960
gccgccttca aatatttcga tacaacaata gacagaaaga ggtataccag caccaaagaa   4020
gttctcgacg ccacactgat ccatcaatca atcacaggcc tttacgaaac taggatcgac   4080
ttgtcacaac tgggtgggga t                                             4101

SEQ ID NO: 67           moltype = DNA   length = 3307
FEATURE                 Location/Qualifiers
source                  1..3307
                        mol_type = other DNA
                        organism = synthetic construct
SEQUENCE: 67
gagcaaggac acctacgacg acgacttgga caacctattg gcccagatag gtgaccagta   60
tgcagacctc ttccttgcgg ccaagaactt gagtgacgct atactgctca gtgacatcct   120
gagggtgaac actgagatca ctaaggcccc tctctctgcc tcaatgatta agcgttacga   180
cgagcatcac caggatctca ccctgcttaa ggcccttgtt cggcagcagc tccctgagaa   240
gtacaaggag atatttttg accagtctaa gaacggctac gccggttaca ttgacggtgg   300
ggcaagccag gaggagttct acaagttcat caagccgatc cttgagaaga tggacggcac   360
cgaggagcta cttgtcaagt tgaaccggga gacctgctc cggaaacagc gtacattcga    420
caacggcagc atccctcacc agatccacct gggcgaacta cacgccatcc tccgacgtca   480
ggaggacttc tatccattct tgaaagataa caggggaaaa atcgaaaaaa tacttacgtt   540
tcgaataccct tactacgtgg ggcccttgc tcggggaaac tccagattcg catgggatgac 600
caggaagtca gaggagacca tcacaccctg gaactttgag gaggtggttg acaaaggtgc   660
ttctgcccag tccttcattg agcggatgac taacttcgac aagaacctgc ccaacgaaaa   720
ggtgctgcca aagcacagcc tgctctacga atacttact gtgtacaatg agctgacgaa    780
ggtgaagtac gtgacagagg ggatgcggaa gcccgctttc ctgagcggcg agcaaaaaaa   840
agcaatcgtg gacctactgt tcaagaccaa ccgaaaggtg acagtgaagc agctcaagga   900
ggactacttc aaaaaaatcg agtgcttcga ctctgttgag ataagcggcg tggaggaccg   960
attcaacgcc tcattgggaa cctatcacga cctgctcaag atcattaagg acaaggactt   1020
cctggataat gaggagaatg aggacatcct ggaggatatt gtgctgaccc ttactctatt   1080
cgaggacagg gagatgatcg aggagcgact caagacctac gctcacctgt tcgacgacaa   1140
ggttatgaag caattgaagc gtaggcgata cacgggtggg ggaagactct cccgaaaact   1200
gataaacggc atcagggaca agcagtcagg gaagacgatc ttggacttcc tgaaatccga   1260
cgggtcgcc aaccgcaact tcatgcagct cattcacgac gactcactaa cgttcaaaga    1320
ggacattcag aaggctcaag tcagtggaca aggcgactcc ctgcacgagc acattcaaa    1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
gaaccgagact acccagaagg gtcagaagaa ctctcggaca cgtatgaagc gtattgagga   1560
gggattaag gagttgggct ctcaaatcct caaggagcac cctgtggaga cactccagct    1620
ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac acagcatcg acaacaaggt tctgacgagg aggacaaga atcgagggaa     1800
aagtgacaat gttccatccg aggaggtggt caagaaaatg aagaactatt ggcgtcagct   1860
tctgaacgcc aagctcatca cccagcggaa attgacaaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgaaga   2040
cgacaagctc atcagggagg tgaaggtcat tacccttaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtacccca gttggagtc    2220
ggagttcgtt tacggggact acaaggtgta cgacgttcgg aagatgatcg ccaagtctga   2280
acaggagatc gggaaagcaa ccgccaagta tttcttctat agcaacatca tgaacttctt   2340
taaaaccgag atcacacttg ccaatggcga gatcctgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaaagactg   2580
ggatccaaag aaatacggcg ggttcgactc gccgacagtc gcatactccg tgttagtggt   2640
ggctaaagtg gaaagggga gtccaagaa gctcaagtcc gtcaaggagt gctcggat      2700
caccattatg gaacggtcct cattcgagaa gaatcccatt gacttcctag aggcgaaggg   2760
ctacaaagag gtcaaaaagg acctaattat taagctcccc aagtattcac tcttcgaact   2820
tgaaaatggt cgtaagcgga tgttggcaag cgctgagag cttcagaagg ggaacgagct   2880
tgcactgcct tccaagtacg tgaacttcct gtacctcgcc tctcattacg agaagttgaa   2940
gggctcaccg gaggacaacg agcagaagca gttgttcgtg gagcagcaca gcactacct    3000
cgacgagatc attgagcaga taagtgagtt cagcaaacgg gtgatccttg ccgacgctaa   3060
cctggacaag gtgctgagcg cctacaacaa gcacagagac aagccgatcc gagagcaagc   3120
ggagaacatc atacacctgt tcaccctcac gaacctcggg gctcccgcag ccttcaaata   3180
ttttgacacg accatcgacc gtaaacgcta cactagcacg aaggaggtgc tggacgctac   3240
ccttatccac cagtccatca ccggcctgta cgagacgaga atcgacttgt cgcagctcgg   3300
tggtgac                                                             3307

SEQ ID NO: 68           moltype = DNA   length = 4101
FEATURE                 Location/Qualifiers
source                  1..4101
                        mol_type = other DNA
                        organism = synthetic construct
```

```
SEQUENCE: 68
gacaaaaaat actcaattgg tctggcaatt gggaccaaca gtgtcggatg ggccgtgatt      60
accgacgagt acaaggtgcc gtccaaaaaa ttcaaggtgc ttgggaacac cgaccgccac     120
tcgatcaaga aaaacctaat cggtgcgttg cttttcgaca gtggggagac cgccgaggca     180
acacgcttaa aacgcacagc taggaggaga tatacacggc gcaagaaccg aatatgctac     240
ttacaggaga tatttctccaa tgagatggcg aaggtggacg actctttctt ccatcggctt    300
gaggaatcct tcctggtcga ggaggacaag aagcacgagc gacacccgat attcgggaac    360
atcgttgatg aggtggcgta ccacgagaag tacccaacga tataccactt acgcaagaag    420
ctcgtggact ctacggacaa ggccgacttg cgccttatct acttggcact ggcccacatg    480
attaagttcc gaggccactt ccttatcgag ggtgacctga accccgataa ctccgacgtg    540
gacaagctct tcatccaact cgtccagaca tacaaccagc tattcgagga gaatcctatc    600
aacgcctctg gggtggacgc taaagctatc ctctcagccc gcctgtcaaa gtcgaggagg    660
ttggagaacc taatcgccca gcttccaggc gagaagaaaa atgggctgtt cggaaacctt    720
atcgcactct cactgggcct aaccccgaac ttcaagtcca acttcgacct ggcagaggac    780
gcgaaattgc agttgtcgaa agacacctat gacgatgacc tggacaacct gttggcccag    840
ataggggacc agtacgccga cctgttccta gcggccaaga acctgtccga cgccatcttg    900
ctgtcggata tactgcgggt gaacaccgag atcactaaag cacctctctc cgccagcatg    960
attaagcgtt acgacgagca ccaccaagat ttgacccgtc taaaggcact tgtacggcag   1020
cagcttcccg agaagtacaa ggagatcttt ttcgaccaaa gcaagaacgg ctacgccggg   1080
tacatcgacg gaggtgccag ccaggaggag ttctacaagt tcattaagcc catcctggag   1140
aagatggacg ggactgagga actacttgtg aagctgaacc gggaagactt actacggaag   1200
cagcgtacct tcgacaacgg ttctatccca catcagatcc acttgggga gttgcacgcg   1260
atcctgcgac gccaggagga cttttacccc ttcctgaaag acaaccgcga gaaaatcgag   1320
aagatactga ccttcagaat accttactac gtcggacccc ttgcgcgagg caactcaaga   1380
ttcgcgtgga tgaccaggaa atcagaggag accatcacac cctggaattt cgaggaggtg   1440
gttgacaagg gtgcctccgc ccagtccttt atcgaacgaa tgccaacctt cgacaagaac   1500
ttgcccaacg agaaggtgct ccccaaacac agcctcctct acgaatattt cacagtgtac   1560
aacgagctta ctaaagttaa gtatgttact gagggcatga ggaaacccgc cttcctgtca   1620
ggcgagcaga agaaagctat tgtggacctc ctttttcaaga ccaaccggaa ggtgacagtg   1680
aagcagctca aggaggacta cttcaagaag atagagtgct tcgacagcgt ggagatcgac   1740
ggggtggagg acagattcaa tgcctctctc ggaacatacc acgacttgct taagatcatc   1800
aaggacaagg acttcctcga caacgaggaa aacgaggata ttctggagga tattgttctg   1860
actcttaccc tgttcgagga ccgggagatg atcgaggagc gtctcaagac ctacgcccac   1920
ctgttcgacg acaaagttat gaagcagctc aagcgtcgga gatataccgg atgggccgt    1980
ctgtctcgga agctcatcaa cgggatcagg gacaagcagt cagggaagac gatcttagac   2040
ttccttaagt ctgacggctt cgccaacagg aacttcatgc agttgatcca cgacgacagc   2100
cttaccttca aggaggacat ccagaaggcc aagtgagtg gccagggtga cagcctccac    2160
gagcatattg ctaatcttgc gggttcccca gcgattaaaa agggcatact tcaaaccgtt   2220
aaggtggtgg acgagcttgt caaggtgatg gggcgacaa agcccgagaa catcgtgatc    2280
gagatggcca gggagaacca gaccacccag aagggcaga agaatagccg agaacgcatg    2340
aagcgcatcg aggaggggat taaggagcta gggagccaga tcctcaagga acatcccgtc   2400
gagaacaccc agctccagaa cgagaagcta tacctctact acttgcaaaa cgggagggat   2460
atgtacgtgg atcaggagtt ggacattaac cgcctaagcg actacgacgt agatcacatc   2520
gtgcctcagt cattcctcaa agacgacagc attgacaaca aagtcttgac ccgatccgac   2580
aagaaccgag gaaaatccga caatgtgccc tcagaggagg tcgtcaagaa aatgaagaac   2640
tattggaggc agctacttaa cgccaaactc ataaccagc ggaagttcga caacctgaca    2700
aaggctgagc ggggtgggct cagcgagctt gacaaggctg gcttcatcaa gcggcagttg   2760
gtggagacaa gacagataac gaagcacgtg gctcagatcc tggactctcg catgaacacg   2820
aagtacgacg agaacgacaa attgatccgc gaggtcaagg ttattacgct caagagcaaa   2880
cttgtcagcg atttccgcaa ggacttccag ttctacaagg tgagggagat taacaactac   2940
caccatcgcac atgatgccta cttgaacgca gtggtgggga ccgcgcttat taaaaagtac   3000
cctaagttgg agtcagagtt cgtttatggg gactacaagg tgtacgacgt ccggaagatg   3060
attgcaaagt ctgaacagga aatcgggaag gccaccgcca aatattcc ctacagtaac     3120
attatgaatt tttttaagac tgaaattact ctcgcaaacg cgagatcag gaagcgtccc     3180
ctcatcgaga caaacgggga gaccggggga atagtctgag acaagggcg ggacttcgct   3240
acggtgagga aggtgctctc gatgccacaa gtgaacatcg tcaaaaagac agaggtgcag   3300
accggtggct tctcaaagga gtcaatcctg ccaaaacgta acagcgacaa gctcatcgcc   3360
cgcaagaaag actgggaccc taagaagtat ggtgggttcg actcaccgac ggtcgcatac   3420
tccgttctgg tcgtggcaaa ggtggaaaag ggcaagtcca aaaactgaag atccgtgaag   3480
gagttgcttg gcattaccat catggaacgc agcagcttcg agaagaaccc cattgacttc   3540
ctggaggcta aagggtacaa ggaggtcaag aaagatttaa ttattaagct acctaagtac   3600
agcttgttcg agctggagaa cggccgaaaa cgaatgctcg catccgccgg ggaacttcaa   3660
aagggcaacg agcttgcgct gccctccaag tacgtgaact tcctgtactt ggcatccac    3720
tacgagaaac tcaaggtgtag cccagaggac aacgagcaga agcagctatt cgtggagcag  3780
cacaagcact acctcgacga gataatcgag cagatcagtg agttcagtaa gcggtgata    3840
ctcgcggacg ccaacttgga caaggtgctt agtgcctaca caagcaccg tgacaagccc    3900
atccgagaac aggctgagaa catcatccac cttttcactc tgacaaacct cggtgctccc    3960
gccgccttca aatacttcga cactaccatc gacaggaagc gctacacatc tacgaaggaa   4020
gttcttgacg ctacgcttat tcatcagtct atcacagggc tgtacgagac aaggatcgac   4080
cttagccaac tcggcgggga t                                             4101

SEQ ID NO: 69          moltype = DNA  length = 4684
FEATURE                Location/Qualifiers
source                 1..4684
                       mol_type = genomic DNA
                       organism = Rubus sp.
SEQUENCE: 69
gtatagtcgt gctagctagc ttacacgatt tttatcgtac cgtttaaatt cttgtttatc      60
ttttttgatct cgtagactct agtctcgtaa ttagaacctt ttttttttta attctttgtt    120
```

```
taatgatcat ttttataaat tcaattaaat aagatactct tatagttatt tgaaatcaag    180
tagaaattcg ttatttgagc ctaaatggtt tattggtgtt tgtttttttt ttttttttt    240
tgagggggc  taaataacag aatttgatta cataaaaaca aaatttaaca ggtaatgtag    300
aaaatacatt tacatacata ttgcaacata aatacatatt gcaatacaac aattaacaca    360
ctacataaaa ttctagctcc atgagagtca tctctcctgt aaaactctag tccctatgat    420
attcctcagt agcgcctatg tgcgtatcaa atctaatagc atcttcgtgt gctatcctcc    480
tagcatatgg cttcattcta tacttttcat tatgcaaatc ctagcgccgt caactatcgt    540
tgatgcggct tcttatggtg aggatggttt tggtctctct cactcacaat gacgactttg    600
tatgtcatgc tcttttcaag cctatggtgg ttatgcttt  gtagggtctc ccttagattc    660
tcagagatgg ttggcacctt gcttagatct aattttattg tcggttctat tgggtgtcaa    720
tcaaatccaa ggattcaaga tctgagatcc aggtgagttt tgaatgctcg tttatgacga    780
ctcaacaatc ttgctgtttc aagtcgacaa ctttattact ggtggggtgt tgttaaagtt    840
taacatacgt caaatttttgt tatttgattt gggttttttt attttattgt ttaagcataa    900
gcatgatatg ttgtaagttt caattgtgat tttactttat ttttcatggg ttctccttaa    960
attaaattga atttattggt ctcaatgtca atatttgctg aattttttct attggttgtt   1020
gacagtagtg atgcacgctg tatgtattgt tttaaatttc gaatatttga ttagagttct   1080
aggtttagat tcttcaataa agtcacttgt gtggtctata atcctcattt ttaggatgtc   1140
catattaagt attgtaatcc tctattgatt aataaaaatt ttatttaaaa aaaaaaaatt   1200
aatacaccat atgaggtgtg taatcttccg tctcaatata ttatcgtatt ctcattgaaa   1260
aaaaaacaca tacacactag acggagtgga agtgagagaa gaaaaattat actctcgctt   1320
aatctttgat tcgccaagaa agaaaccgat ctggttacat cgggttagct agccctcatg   1380
catgcttgta taaagagatt tcttttctcta gaacgtacag tggttttctt tctctagaag   1440
gccaatgtca ttttacgtca catttttttt tcaccttcac atctaacgga ccatgaaaga   1500
gcaatccta  cgtaccccac tatcttcttt cttgtcgcgg tggttgcaca gagagagaga   1560
gagagagaga gagggtgg   tccatattag ttgtttaaga ggagctttg  tatggagatt   1620
ttaaggtcgt gggtctttgt tgtaagatgt gagcttcccc ccttgcactt ggtgtgtatt   1680
tctaacgagc cggatcctct atgcagtgtt gatacccaca ttcgtggacc ctacgtaggt   1740
ctttctacgt ctattttgta atgcagtgat gatattgtag gtgaggtggc tcttctcgga   1800
ccatagtaaa acaaaaccca tactaaaaaa ataaaactgt ataccatgtg tcccatgaga   1860
accattcttt cacacatata tatagtcgtc ccctacatac tccttttgcg tacaacttgt   1920
tattgagctc tctctgtctc tctctctgtg atctccacaa attgtgtgga gtagtctgga   1980
taaattatct tttgatattc aaaatgactg aaaacgtgag tatatctgtg aatgggcaat   2040
ctcaagtccc tcctggtttc agatttcatc caactgaaga ggagctcttg cagtactact   2100
tgaggaagaa ggtctccaat cagagcattg atctcgatgt catctgcgat gtcgatctca   2160
ataagcttga gccatgggat ataccaaggta cgtacgtaca taaatgatat gggaaatatt   2220
taatttagtc tagtagttct ccaacaagtt atgcatcaca ataaatatga attaatccaa   2280
gttctgatgt tggttttgca gagaagtgta agataggaac cacaccgcaa aatgattggt   2340
atttcttcag ccacaaagac aagaaatacc ctaccggaac acgtacaaac cgtgcaacgg   2400
ctgccggatt ctggaaggcc accggccgtg ataagatgat aagcagcaac tgcaggcgga   2460
tcggtatgag gaagactctt gtgttctaca aaggccgagc tccccacggc caaaagtccg   2520
attggatcat gcacgagtat agactcgacg acaacactag caacatcact aatgtaagtc   2580
atttaattca aaccagagtt tctgtcctcg ggaaatgttc aagtgcggac tttgcagacc   2640
ttgtgtctac agaacgtttg cacagtctgc agtctgcact acagatgtcc acacttgaca   2700
atttgagtt  tatagacata tcgatcgatt gttattgaac agtttccttt tatttgaatc   2760
aggtctcgat caccgttgtg ggagaggcag cggaggaggg gtgggtggtt tgcagaatct   2820
tcaagaagaa aaatctccac aagagcttga gtagtccaat catgagcact tctatttctt   2880
catctatcac agaagaaatt acaagaagct caagccaaca gtttgatgat gatcatgagg   2940
gagcttttga ggaaatgctt cagtacatag gatcaaggac ctgcaaggaa gagaataatg   3000
aacattatca tcttcatccc atcaacacag gtaaagtgaa taagattaat ggctaccatg   3060
atcatggtga taggttcttg aaacttccga gccttgagag ccccaactcc accagtagcc   3120
aaaacggtta tcagccaatt atcagtcatg aagacatggt catagatcag aatgagggca   3180
caattgctaa ccagcatctg ggttatcagc acgtggacga ctcagccagc ctcaccaact   3240
gggcagccct tgatcgtttg gtggcttcac aactcaatgg agtccatgaa acgggggtcgt  3300
ctaggcaatt ttcttgctta attgagccca ttcgtgatgt ttactgcact agtattactg   3360
ataatgagct tcagttaccg agtacattac gatcgtcaac ttcttcgaat tcatccagca   3420
aatcataccca cgccactcaa ccggaatgca acaatagcga gattgacctg tggactactt   3480
ttgctgctgc tcgactacaa tcatcattcc ctttgtcatc ctccgacgca ctatgccacg   3540
tgtcgaacgc tcctatataa cagaacgatc cattacacaa taatataaga attacacctt   3600
gaatcgaaag tcagaggagt ataatttat  gtgacataat attattacat gattgctaat   3660
atatatgtaa gataaataaa ggttatggtt ttaatgaaaa tgtctagcat taaagttttt   3720
tctgtttgtg actgttagtg gtccagatcg atcatgatta tctctttcca actgcaatta   3780
tagttttttcc aactttttttc tcttctaaga tgatcaagta ggcaaagtat atatggacca   3840
tatatacata atcatcatcg atcgccaatt ggtatctttg ggtcacgtgg tttgtcggtc   3900
tgtttgaaga aactagtcca tggctcaacc aatctgacca ctaaaaaact gatcattgtg   3960
atcgatgaag attcaagggt ttcatgtata tattagatag ccagctagcc agagaaagat   4020
cgatagagag atggcacatt tgtcctactt ttacgaagtc aaatgaataa gaattaatta   4080
agaaggaatc aagtcgtata taggtttcac atatagtcta gttttttcacg aagaaaaatt   4140
tgtctctgag aggatctaaa tatatctagc ttttacttac tttcttggtg ctgatcaatc   4200
ttgtatatat gcctcgatca atagaccata aatgtaaaac gttttaacat taaaccctca   4260
aaagattgtc ggaaaaatca atcataaaaa gatattgctt tggagttaat caagtagatg   4320
atcaacacca gaaaaatcaa ttttcagagt agcaccattt aaaatctatt aataattgat   4380
gcaattaata aagcgcgcca tgcacacaat atggattcca ataagactgc ttgtttgtgt   4440
ttattgtgat ttaagctaag taaattcaat tgtgtgcttt tgtttgtata tatttgttgt   4500
ttgtgatcta ttggcgagtt tagccttag  gcttatcat  gtataacatg accgtacaca   4560
tatgcatgct atgagagcat atgtcattta tcatattttta agcctttatt tatgatttat   4620
ccattgacta gctcccacgg attgaaattg ccttctttttt tgaaaaccc  tagctatcat   4680
acaa                                                                4684

SEQ ID NO: 70       moltype = DNA   length = 1254
```

| FEATURE | Location/Qualifiers |
|---|---|
| source | 1..1254<br>mol_type = other DNA<br>organism = Rubus sp. |

SEQUENCE: 70

```
atgactgaaa acgtgagtat atctgtgaat gggcaatctc aagtccctcc tggtttcaga   60
tttcatccaa ctgaagagga gctcttgcag tactacttga ggaagaaggt ctccaatcag  120
agcattgatc tcgatgtcat ctgcgatgtc gatctcaata agcttgagcc atgggatata  180
caagagaagt gtaagatagg aaccacaccg caaaatgatt ggtatttctt cagccacaag  240
gacaagaaat accctaccgg aacacgtaca aaccgtgcaa cggctgccgg attctgaag   300
gccaccgggc gtgataagat gataagcagc aactgcaggc ggatcggtat gaggaagact  360
cttgtgttct acaaaggccg agctccccac ggccaaaagt ccgattggat catgcacgag  420
tatagactcg acgacaacac tagcaacatc actaatgtct cgatcaccgt tgtgggagag  480
gcagcggagg aggggtgggt ggtttgcaga atcttcaaga agaaaaatct ccacaagagc  540
ttgagtagtc caatcatgag cacttctatt tcttcatcta tcacagaaga aattacaaga  600
agctcaagcc aaatgtttga tgatgatcat gagggagctt tgaggaaat gcttcagtac   660
ataggatcaa ggacctgcaa ggaagagaat aatgaacatt atcatcttca tcccatcaac  720
acaggtaata gtgataagat taatggctac catgatcagt gtgataggtt cttgaaactt  780
ccgagccttg agagccccaa ctccaccagt agccaaaacg gttatcagcc aattatcagt  840
catgaagaca tggtcataga tcagaatgag ggcacaattg ctaaccagca tctgggttat  900
cagcacgtgg acgactcagc cagcctcacc aactgggcag cccttgatcg tttggtggct  960
tcacaactca atggagtcca tgaaacgggg tcgtctaagc aattttcttg cttaattgag 1020
cccattcgtg atgtttactg cactagtatt actgataatg agcttcagtt accgagtaca 1080
ttacgatcgt caacttcttc gaattcatcc agcaaatcat accacgccac tcaaccggaa 1140
tgcaacaata gcgagattga cctgtggact acttttgctg ctgctcgact acaatcatca 1200
ttccctttgt catcctccga cgcactatgc cacgtgtcga acgctcctat ataa        1254
```

| SEQ ID NO: 71 | moltype = AA length = 417 |
|---|---|
| FEATURE | Location/Qualifiers |
| source | 1..417<br>mol_type = protein<br>organism = Rubus sp. |

SEQUENCE: 71

```
MTENVSISVN GQSQVPPGFR FHPTEEELLQ YYLRKKVSNQ SIDLDVICDV DLNKLEPWDI   60
QEKCKIGTTP QNDWYFFSHK DKKYPTGTRT NRATAAGFWK ATGRDKMISS NCRRIGMRKT  120
LVFYKGRAPH GQKSDWIMHE YRLDDNTSNI TNVSITVVGE AAEEGWVCR IFKKKNLHKS   180
LSSPIMSTSI SSSITEEITR SSSQMFDDDH EGAFEEMLQY IGSRTCKEEN NEHYHLHPIN  240
TGNSDKINGY HDHGDRFLKL PSLESPNSTS SQNGYQPIIS HEDMVIDQNE GTIANQHLGY  300
QHVDDSASLT NWAALDRLVA SQLNGVHETG SSRQFSCLIE PIRDVYCTSI TDNELQLPST  360
LRSSTSSNSS SKSYHATQPE CNNSEIDLWT TFAAARLQSS FPLSSSDALC HVSNAPI     417
```

| SEQ ID NO: 72 | moltype = DNA length = 4808 |
|---|---|
| FEATURE | Location/Qualifiers |
| source | 1..4808<br>mol_type = genomic DNA<br>organism = Rubus sp. |

SEQUENCE: 72

```
aataactgat tttctcttga agagaaaagt ttcttatata tatacatgta taattgtata   60
gtcgtgctaa cacaatttt atcgtaccgt ttaaattctt gtttatcttt ttgatctcgt  120
agctagactc tagacttgta attagaactt ctttttattt ttttgaattc tttgtttaat  180
gatcatttt ataaattcaa ttaaataaga tactcttaga ttattttgaa atcaagtaga   240
aatttgttat ttgagcctaa atggtttatt ggcgtttgtt tgatacgatt gagtggctaa  300
ataacagaat ttgattacat aaaaacaaaa tttaacaggt aatgtagaaa atacatttac  360
atacatattg caacataaat acatattaca atacaacaat taacacacta aataaaatcc  420
tagctccatg agactatgag agtcctctct ccagtaaaac tccagtcccc atgatattcc  480
tcagtagcgc ctatgtgcat atcaaatcta gtagcatttt cgtgtgctat cctcctagca  540
tatggcttca ttctatactt ttcattatga aaagtgccgt caactatcgc tgatgcggct  600
tcttatgatg aggacggttt ttgcctctct cactcacaag gacgactttg tccgtcatgt  660
tctattcaag cctatggtgg ttatgctctt gcagggcctc ccttagattc tcagagatgg  720
ttgacacctt acttagatct aatttttgttg tcggttctat tgggtgtcaa tcaaatccaa  780
ggatttaaga tctgggatcc aggtgagtcg tgaatgctca attatggcga ctcgacaatc  840
ttgttgtttc aagtcgataa cttattact ggtgggcac tgttaaagtt taacataagt    900
caaatttatt atttgatttg ggtctttta ttttattgtt taagcataaa catgatcagg   960
tgtgtaagtt tcatttgtgg tttactttc ttttcatgg gttctcttg aactaaattg    1020
aatttattgg tctcaatggt aatatttgcc ggaattttc tattggttgt tgacagcagt  1080
gatgcacagt gtatgtattg ttttaaattt tgaatcttca attagagttc taggtttaga  1140
ttcttcaata aagtcactat gtgtagtatg taatcctcct tttgagaatg ttcatattaa  1200
gtattgtaat cctttttga ttaataaaat ttctactttt aaaaaaagta aaaaaattga   1260
tacactaaat gaagtgaaat atcatgtagta atcttccgtc ttaatatatt atcgtattcc  1320
cattgaaaaa aaaaaacaca tacacactag acgagtggga agtgagagaa aaatattata  1380
ctcgcttaat ctttgattcg ccaagaaaga aaccgatctg gttacatcgg ttagctagc   1440
cctcatgcat gcttgtataa agagattct ttctctagaa cgtacagtgg ctttctttct   1500
ctagaaggcc aatgtcattt tacgtcacat tttttttca acttcacatc taacggacca   1560
tgaaagaaga atccctacgt accccactat cttctttct gtcgcgtgc ggtggttgca    1620
cagagagaga gagagagaga gagagagaga gagagagaga gagagagaga gagagagagg  1680
gtggtccata ttagttgttt aagaggagct tttgtatgga gatttaagg tcgagggtct   1740
tagttgtaag atgtgagctt ccccccttac actaggtgtg tatttctaac gagccggatc  1800
ctctatgcag tgttgatacc cacattcgtg gaccctacgt aggtctttct acgtctatt   1860
tgtaatgcag tgataatatt gtaggtgagg tggctcttcc cggaccatag tgaaacaaac  1920
```

```
cccctactaa aaaaaaaact gtataccatg tgtcccatga gaaccattct ttcacacata   1980
tatatagtcg tctcctacat actccttttg cgtacaactt gttattgagt tctctctctc   2040
tctctctctc tctctctctc tctctctctg atcttcacaa attgtgtgga              2100
gcagtctgga taaatcacct tttgatcaaa attcaaaatg actgaaaacg tgagtatatc   2160
tgtgaatggg caatctcaag tccctcctgg tttcagattt catccaactg aagaggagct   2220
cttgcagtac tacttgagga agaaggtctc caatcagagc attgatctcg atgtcatctc   2280
cgatgtcgat ctcaataagc ttgagccatg ggatatacaa ggtacgtacg tacataaatg   2340
atatgggaaa tatttaattt agtctagtag ttctccaaca agttatgtat cacaataaat   2400
atgaattaat ccgagttttg atgttggttt tgcagagaaa tgtaagatag gaaccacacc   2460
gcaaaatgat tggtatttct tcagccacaa agacaagaaa taccctaccg gaacacgtac   2520
aaaccgtgca acgctgccg gattctgaaa ggccaccggg cgtgataagg tgataagcag    2580
caattgcagg cggatcggta tgaggaagac tcttgtgttc tacaaaggcc gagctcccca   2640
cggccaaaag tccgattgga tcatgcacga gtatagactc gacgacaaca ctagcaacat   2700
cactaatgtg agtcatttag ttcaaaccag agtttcagcc ctcgggaaat gttcaagtgc   2760
ggactttgca tatcttgtgt ctacagaacg tttgcacagt ctgtagtctg cactacagat   2820
gtccacactt gaacattttg agtttataga catatcgatc gattgttatt gaacagttaa   2880
tttcctttta tatgaatcag gtctcgatca ccgttgtggg agacgcagcg gaggaggggt   2940
gggtggtttg cagaatcttc aagaagaaaa atctccacaa gagcttgagt agtccaatca   3000
tgagcacttc tatttcttca tctatcacag aagaaattac aagaagctca agccaaatgt   3060
ttgatgatga tcatgaggga gcttttgagg aaatgcttca gtacatagga tcaaggacct   3120
gcaaggaaga gaataatgaa cattatcatc ttcatcccat caacacaggt aatagtgata   3180
acattaatga ctaccatgat catggtgata ggttcttgaa acttccgagc cttgagagcc   3240
ccaactccac cagtagccaa aacgttatc agccaattat cagtcatgaa gacttggtca    3300
tagatcagaa tgagggcaca attgctaacc agcatctggg ttatcaacac gtggacgact   3360
cagccagcct caccaactgg gcagcccttg atcgtttggg ggcttcacaa ctcaatggag   3420
gccatgaaac ggggtcgtct aggcaattta cttttcttaat tgaacccatt gctgatgttt   3480
actgcactag tactactgat aatgagcttc agttaccaag tacattacga tcgtccactt   3540
cttcgaattc atccagcaaa tcataccact ccacccaacc ggaatacaac aatagcgaga   3600
ttgacctgtg gactactttt gctgctgctc gactacaatc atcatccct ttgtcatcct    3660
ccgacgcact atgccacgtg tcgaacgctc ctatataaca gaacgatcca ttacacaata   3720
atataagaat tacaccttga atcgaaagtc agaggagtat aattttatgt gacataaat    3780
tattacatga ttgctaatac atatgtaaga taaataaagg ttatggtttt aatgaaaatg   3840
tctagcatta aagttttatc tgtttgtgac tgttagtggt ccagatcgat catgattatc   3900
tctttccaac tgcaattata gtttttccaa cttttttctc ttctaagatg atcaagtagg   3960
caaagtatat atggaccata catacataat catcatcgat cggcatttgg tatctttggg   4020
tcacgtggtt tgtcggtctg tttgaagaaa ccagtccatg gctcaaccaa tccgagcact   4080
aaaaaactga tcattgttat cgatcaaaat tcaagggttt catgtatata ttagatagcc   4140
agctagccag agaaagatcg agagagagag ggcacatttg tcctactttt acgaagtcaa   4200
atgaattata agaattaaga aggaatcaag ccgtatatag gtttcacata tagtctagtt   4260
ttccacgaag aaaaatttgt ctctgagagg atctaaatat atctagcttt tacttacttt   4320
cgtggtgctg atcaatcttg tatatatgcc tcaatcaata gaccataaat ctaaacgtt    4380
ttaacattaa acgtacccctc aaaagattgt cggaaaaacc aatcataaaa acatattgct   4440
ttggagttaa tcaagtagat gatcaacacc agaaaaatca attttcagag cagcaccatc   4500
taaaatctat taataattga tgaaattaat aaagcgcgcc atgcacacaa tatggactcc   4560
aataagactg cctatttgtg tttattgcga tttaagctaa ttaactaaat tcagttgtgt   4620
gcttttgttt gtatatattt gttgtttgtg atctattggc gggtttaggc tttaggcctt   4680
atcatgtata acatgaccgt acacatatgc atgctatgag agcatatgtc attatcata   4740
ttttaagcct ttatttatga tttatccatt gactagctcc cacggattga aattaattgc   4800
cttcttttt                                                          4808
```

```
SEQ ID NO: 73          moltype = DNA  length = 1254
FEATURE                Location/Qualifiers
source                 1..1254
                       mol_type = other DNA
                       organism = Rubus sp.
SEQUENCE: 73
atgactgaaa acgtgagtat atctgtgaat gggcaatctc aagtccctcc tggtttcaga   60
tttcatccaa ctgaagagga gctcttgcag tactacttga ggaagaaggt ctccaatcag   120
agcattgatc tcgatgtcat ctccgatgtc gatctcaata agcttgagcc atgggatata   180
caagagaagt gtaagatagg aaccacaccg caaaatgatt ggtatttctt cagccacaaa   240
gacaagaaat accctaccgg aacacgtaca aaccgtgcaa cggctgccgg attctgaag    300
gccaccgggc gtgataaggt gataagcagc aattgcaggc ggatcggtat gaggaagact   360
cttgtgttct acaaaggccg agctccccac ggccaaaagt ccgattggat catgcacgag   420
tatagactcg acgacaacac tagcaacatc actaatgtct cactcaccgt tgtgcggaa    480
gcagcggagg aggggtgggt ggtttgcaga atcttcaaga gaaaaatct ccacaagagc    540
ttgagtagtc caatcatgag cacttctatt tcttcatcta tcacagaaga aattacaaga   600
agctcaagcc aaatgtttga tgatgatcat gagggagctt ttgaggaaat gcttcagtac   660
ataggatcaa ggacctgcaa ggaagagaat aatgaacatt atcatcttca tcccatcaac   720
acaggtaata gtgataacat taatgactac catgatcatg gtgataggtt cttgaaactt   780
ccgagccttg agagcccaa ctccaccagt agccaaaacg ttatcagcc aattatcagt     840
catgaagact tggtcataga tcagaatgag ggcacaattg ctaaccagca tctgggttat   900
caacacgtgg acgactcagc cagcctcacc aactgggcag cccttgatcg tttggtggct   960
tcacaactca atggaggcca tgaaacgggg tcgtctaggc aatttacttt cttaattgaa   1020
cccattcgtg atgtttactg cactagtact actgataact accaagtaca              1080
ttacgatcgt ccacttcttc gaattcatcc agcaaatcat accactccac ccaaccgaa    1140
tacaacaata gcgagattga cctgtggact acttttgctg ctgctcgact acaatcatca   1200
tcccctttgt catcctccga cgcactatgc cacgtgtcga acgctcctat ataa         1254

SEQ ID NO: 74          moltype = AA  length = 417
```

```
FEATURE              Location/Qualifiers
source               1..417
                     mol_type = protein
                     organism = Rubus sp.
SEQUENCE: 74
MTENVSISVN GQSQVPPGFR FHPTEEELLQ YYLRKKVSNQ SIDLDVISDV DLNKLEPWDI    60
QEKCKIGTTP QNDWYFFSHK DKKYPTGTRT NRATAAGFWK ATGRDKVISS NCRRIGMRKT   120
LVFYKGRAPH GQKSDWIMHE YRLDDNTSNI TNVSITVVGD AAEEGWVVCR IFKKKNLHKS   180
LSSPIMSTSI SSSITEEITR SSSQMFDDDH EGAFEEMLQY IGSRTCKEEN NEHYHLHPIN   240
TGNSDNINDY HDHGDRFLKL PSLESPNSTS SQNGYQPIIS HEDLVIDQNE GTIANQHLGY   300
QHVDDSASLT NWAALDRLVA SQLNGGHETG SSRQFTFLIE PIRDVYCTST TDNELQLPST   360
LRSSTSSNSS SKSYHSTQPE YNNSEIDLWT TFAAARLQSS SPLSSSDALC HVSNAPI     417

SEQ ID NO: 75        moltype = DNA   length = 4892
FEATURE              Location/Qualifiers
source               1..4892
                     mol_type = genomic DNA
                     organism = Rubus sp.
SEQUENCE: 75
ggctttaata actgatttct cttgaagaga aaagtttctt atatatacat gtataattgt    60
atagtcgtgc tagctagcta acacaatttt tatcgtaccg tttaaattct tgtttatctt   120
tttgatctcg tagctagact ctagtcttgt aattagaact tcttttttaat ttttttgaatt  180
ctttgtttaa tgatcatttt tataaattca attaaataag atactcttat agttatttga   240
aatcaagtag aaattcgtta tttgagccta aatggtttat tggcgtttgt ttgatacgat   300
tgagtggcta ataacagaa tttgattata taaaaacaaa atttaacagg taatgtagaa    360
aatacattta catacatatt gcaacataaa tacatattac aatcaacaa ttaacacact    420
aaataaaatc ctagctccat gagactttga gagtcctctc tccagtaaaa ctctagtccc   480
caggatattc ctcagtagcg cctatgtgca tatcaaatct agtagcattt tcgtgtgcta   540
tcctcctagc ctatgccttc attctatact tttcattatg aaaagtgccg tcaactatcg   600
ctgatgcggc ttcttatgat gaggacggtt ttggcctctc tcactcacaa ggacgactt    660
gtccgtcatg ttctattcaa gcctatggtg gttatgctct tgcagggcct cccttagatt   720
ctcggagatg gttgacacct tactagatc taatttgtt gtcggttcta ttgggtgtca    780
atcaaatcca aggatttaag atctgggatc caggtgagtc gtgaatgctc aattatggcg   840
actcgacaat cttgttgttt caagtcgata acttattac tggtggggca ctgttaaagt   900
ttaacataag tcaattttat tatttgattt gggtcttttt atttttattgt ttaagcataa   960
gcatgatcag gtgtgtaagt ttcatttgtg gttttacttt cttttttcatg ggttctcttt  1020
gaactaaatt gaatttattg gtctcaatgg taatatttgc cggaattttt ctattggttg  1080
ttgacagcag tgatgcacgg tgtatgtatt gttttaaatt tcaaatcctc gattagagtt  1140
ctaggtttag attcttcaat aaagtcactg tgtgtagtat gtaatcctcc tttttagaat  1200
gttcatatta agtattgtaa tctttttattg attaataaag tttctacttt taaaaaaagt  1260
aaaaaaatta atacactaaa tgaggtgaaa tatcatgtgt aatcttccgt cttaatatat  1320
tatcttattc tcattgaaaa aaaaaacaca tacacactag acggagtgga agtgagagaa  1380
aaatattata ctcgcttaat ctttgattcg ccaagaaaga aaccgatctg gttacatcgg  1440
gttagctagc cctcatgcat gcttgtataa agagatttct ttctctagaa cgtacagtgg  1500
ctttctttct ctagaaggcc aatgtcattt tacgtcacat tttttttttca acttcacatc  1560
taacggacca tgaaagagca atccctacgt accccactat cttctttctt gtcgcgtcgc  1620
ggtggttgca cagagagaga gagagagaga gagagagaga gagagagaga gagagagaga  1680
gagacagaca gacagagaga gagagagggt ggtccatatt agttgtttaa gaggagcttt  1740
tgtatggaga tttaaggtc gagggtctta gttgtaagat gtgagcttcc cccttacac    1800
ttggtgtgta tttctaacga gccggatcct ctatgcagtg ttgatccca cattcgtgga   1860
ccctacgtag gtctttctac gtctatttg taatgcagtg ataatattgt aggtgaggtg  1920
gctcttctcg gaccatagtg aaacaaaccc cctactaaaa aaaaaactgt ataccatgtg  1980
tcccatgaga accattcttt cacacatata tatagtcgtc tcctacatac tccttttgcg  2040
tacaacttgt tattgagctc tctctctctc tctctctgat cttcacaaat tgtgtggagc  2100
agtctgaata aatcacctt tgatcaaaat tcaaaatgct tgaaaacgtg agtatatctg  2160
tgaatgggca atctcaagtc cctcctggtt tcagatttca tccaactgaa gaggagctct  2220
tgcagtacta cttgaggaag aaggtctcca atcagagcat tgatctcgat gtcatctccg  2280
atgtcgatct caataagctt gagccatggg atatacaagg tacgtacgta cataaatgat  2340
atgtgaaata tttaatttag tctagtagtt tctctaacag ttatgtatca caataaatat  2400
gaattaatcc aagttttgat gttggttttg cagagaagtg taagatagga accacaccgc  2460
aaaatgattg gtatttcttc agccacaaag acaagaaata ccctaccgga acacgtacaa  2520
accgtgcaac ggctgccgga ttctggaagg ccaccgggcg tgataaggtg ataagcagca  2580
actgcaggcg gatcggtatg aggaagactc ttgtgttcta caaggccga gctccccacg    2640
gccaaaagtc cgattggatc atgcaggagt atagatcga tgacaacact agcaacatca   2700
ctaatgtgag tcatttagtt caaaccagg tttcagtcct cgggaaatgt tcaagtgcgg   2760
actttgcata tcttgtgtct acagaacgtt tgcacagtct gcagtctgca ctacagatgt  2820
ccacacttga acattttgag tttatagaca tatcgatcga ttgttattga acagttaatt  2880
tccttttata tgaatcaggt ctcgatcacc gttgtgggag acgcagcgga ggaggggtgg  2940
gtggtttgca gaatcttcaa gaagaaaaat ctccacaaga gcttgagtag tccaatcatg  3000
agcacttcta tttcttcatc tatcacagaa gaaattacaa gaagctcaag ccaaatgttt  3060
gatgatgatc atgagggagc ttttgaggaa atgcttcagt acataggatc aaggacctgc  3120
aaggaagaga ataatgaaca ttatcatctt catcccatca acacaggtaa tagtgataac  3180
attaatgact accatgatca tggtgatagg ttcttgaaac ttccgagact tgagagcccc  3240
aactcccaa gtagccaaaa cggttatcag ccaattatca catgaaga catgatccata  3300
gatcagaatg agggcacaat tgctaaccag catctgggtt atcaacacgt ggacgactca  3360
gccagcctca ccaactgggc agcccttgat cgtttggtgg cttcacaact caatggagc   3420
catgaaacgg ggtcgtctag gcaatttgct ttccttaattg aacccattcg tgatgtttac  3480
tgcactagta ctactgataa tgagcttcag ttaccagta cattcgatc gtccacttct    3540
tcgaattcat ccagcaaatc ataccactcc acccaaccgg aatacaacaa tagcgagatt  3600
```

```
gacctgtgga ctactttgc  tgctgctcga ctacaatcat catccccttt gtcatcctcc  3660
gacgcactat gccacgtgtc gaacgctcct atataacaga acgatccatt acacaataat  3720
ataagaatta caccttgaat cgaaagtcag aggagtataa ttttatgtga cataatatta  3780
ttacatgatt gctaatacat atgtaagata aataaaggtt atggttttaa tgaaaatgtc  3840
tagcattaaa gttttatctg tttgtgactg ttagtggtcc agatcgatca tgattatctc  3900
tttccaactg caattatagt ttttccaact tttttctctt ctaagatgat caagtaggca  3960
aagtatatat ggaccataca tacataatca tcatcgatcg gcatttggta tctttgggtc  4020
acgtggtttg tcgtctgtt  tgaagaaacc agtccatggc tcaaccaatc cgagcactaa  4080
aaaactgatc attgttatcg atcaaaattc aagggtttca tgtatatatt agatagccaa  4140
ctagccagag aaaatcgat  agagagaggg cacatttgtc ctactttac  gaagtcaaat  4200
gaattataag aattaagaag gaatcaagcc gtatataggt ttcacatata gtctagtttt  4260
ccacgaagaa aaatttgtct ctgagaggat ctaaatatat ctagctttta cttactttcg  4320
tggtgctgat caatcttgta tatatgcctc aatcaataga ccataaatct aaaacgtttt  4380
aacattaaac gtaccctcaa aagattgtcg gaaaaaccaa tcataaaaac atattgcttt  4440
ggagttaatc aagtagatga tcaacaccag aaaaatcaat tttcagagca gcaccatcta  4500
aaatctatta ataattgatg aaaataataa agcgcgccat gcacacaata tgaactccaa  4560
taagactgcc tatttgtgtt tattgcgatt taagctaatt aagtaaattc agttgtgtgc  4620
ttttgtttgt atatatttgt tgtttgtgat ctattggcgg gtttaggctt taggcctat   4680
catgtataac atgaccgtac acatatgcat gctatgagag catatgtcat ttatcatatt  4740
ttaagccttt atttatgatt tatccattga ctagctccca cggattgaaa ttaattgcct  4800
tcttttttga aaaccctag  ctatcataca atcatgtatg tatgtgtgtg tgtgtatata  4860
tatatatata tatatgttca tgcacacata tg                                4892

SEQ ID NO: 76           moltype = DNA  length = 1254
FEATURE                 Location/Qualifiers
source                  1..1254
                        mol_type = other DNA
                        organism = Rubus sp.
SEQUENCE: 76
atgactgaaa acgtgagtat atctgtgaat gggcaatctc aagtccctcc tggtttcaga   60
tttcatccaa ctgaagagga gctcttgcag tactacttga ggaagaaggt ctccaatcag  120
agcattgatc tcgatgtcat ctccgatgtc gatctcaata gcttgagcc  atgggatata  180
caagagaagt gtaagatagg aaccacaccg caaaatgatt ggtatttctt cagccacaaa  240
gacaagaaat accctaccgg aacacgtaca aaccgtgcaa cggctgccgg attctggaag  300
gccaccgggc gtgataaggt gataagcagc aactgcaggc ggatcggtat gaggaagact  360
cttgtgttct acaaaggccg agctcccac  ggccaaaagt ccgattggat catgcacgag  420
tatagactcg acgacaacac tagcaacatc actaatgtct cgatcaccgt tgtgggagac  480
gcagcggagg aggggtgggt ggtttgcaga atcttcaaga agaaaaatct ccacaagagc  540
ttgagtagtc caatcatgag cacttctatt tcttcatcta tcacagaaga aattacaaga  600
agctcaagcc aaatgtttga tgatgatcat gagggagctt ttgaggaaat gcttcagtac  660
ataggatcaa ggacctgcaa ggaagagaat atgaacatt  atcatcttca tcccatcaac  720
acaggtaata gtgataacat taatgactac catgatcatg gtgataggtt cttgaaactt  780
ccgagacttg agagcccaa  ctccaccagt agccaaaacg gttatcagcc aattatcagt  840
catgaagaca tggtcataga tcagaatgag ggcacaattg ctaaccagca tctgggttat  900
caaacacgtgg acgactcagc cagcctcacc aactgggcag cccttgatcg tttggtggct  960
tcacaactca atggaggcca tgaaacgggg tcgtctaggc aatttgcttt cttaattgaa 1020
cccattcgtg atgtttactg cactagtact actgataagt cagttcagtt accaagtaca 1080
ttacgatcgt ccacttcttc gaattcatcc agcaaatcat accactccac ccaaccggaa 1140
tacaacaata gcgagattga cctgtggact acttttgctg ctgctcgact acaatcatca 1200
tcccctttgt catcctccga cgcactatgc cacgtgtcga acgctcctat ataa        1254

SEQ ID NO: 77           moltype = AA  length = 417
FEATURE                 Location/Qualifiers
source                  1..417
                        mol_type = protein
                        organism = Rubus sp.
SEQUENCE: 77
MTENVSISVN GQSQVPPGFR FHPTEEELLQ YYLRKKVSNQ SIDLDVISDV DLNKLEPWDI   60
QEKCKIGTTP QNDWYFFSHK DKKYPTGTRT NRATAAGFWK ATGRDKVISS NCRRIGMRKT  120
LVFYKGRAPH GQKSDWIMHE YRLDDNTSNI TNVSITVVGD AAEEGWVVCR IFKKKNLHKS  180
LSSPIMSTSI SSSITEEITR SSSQMFDDDH EGAFEEMLQY IGSRTCKEEN NEHYHLHPIN  240
TGNSDNINDY HDHGDRFLKL PRLESPNSTS SQNGYQPIIS HEDMVIDQNE GTIANQHLGY  300
QHVDDSASLT NWAALDRLVA SQLNGGHETG SSRQFAFLIE PIRDVYCTST TDNELQLPST  360
LRSSTSSNSS SKSYHSTQPE YNNSEIDLWT TFAAARLQSS SPLSSSDALC HVSNAPI     417

SEQ ID NO: 78           moltype = DNA  length = 4561
FEATURE                 Location/Qualifiers
source                  1..4561
                        mol_type = genomic DNA
                        organism = Rubus sp.
SEQUENCE: 78
gtcatagtca taattgaccc aaaacgtata tacgtaggct tttgacatta gctagctagg   60
ctattttaca atttgagata acgtctccat gtaatcttat gtatgcaaaa ccttttgtatg 120
ataaatattc acgaccccta tatattagtt tctgtgacga gtatgtactt ttatttttat  180
attgtttgat acactgaagg gggattgaat ctctgatcta gtttagtact aacttaaattt 240
tcaaagtcct ttactatttg ggataattaa ctccaaggac atagttatat ttttgtttta  300
tttttaatgt tgctaaacat atgaatttga aagattaaat aacatcaaaa ggcattcacg  360
aatccaaggt aattagtata gtaatttgac accaaaatta tttaaaaaaa tatcatgaat  420
acattcaact cacctacaat accaatatat gtgtgttatg acgtcatgag ataaaaaagg  480
```

```
cctttaccaa aaaacacgag gccttaatat cagcacatcc caccaacata tatattcatg   540
tggacgtggt gtattacctg tagcctgacc catatatgcg gccatgcatg catgtatgca   600
gctagcagta atcaagaata aggaacctgg ggcatttctc acatttttggt acgtgatcat   660
ccacattgag cttaatttcc ttacatgaaa tgtgtgttaa cgttacagct gcatgcagcc   720
atcaatttgc acagcttgtt tctgcaaaga agatgtatat gtagtacctt gatctttatg   780
agaccaatta ctcctctctta tctctctttta atttgtacca cgtacgcaat ataaatattg   840
ttataaataa gtgattatgc ggagccaaaa catccaattt atttgcagct agctaggtta   900
ataatgtgat cgagagaagt agctagctag gagatcgatt cacataagat atcgtactac   960
gcttgtgagc aaatagcctg gtgacataca tcgtcattgg atcgaacatg tggataaacc  1020
gtttaccac ataacatgaa aatcctatag tgttagaaat atcccaaaga gaatgtgaat  1080
gaacgtacat aacctgctct agaaccatgc atgtacaagg aaacaaaagg cctgcaaaga  1140
aaccaaggta aattcaatgt ttcaagatca aaagctcaaa aaacccaagg acaagaaaat  1200
cgaactcaag aactacaaca aactggccgg cgtgtatgat tgtgggattc tatttccaac  1260
ctccagaact gaattcgcac aagaagggaa gaagccatgg tgtcttttat tttttcgggg  1320
tccatgcgaa agctcagttg ctccgacccc atcatctctg tccctctctt tggcttcttg  1380
tcgttgaggt ggttgcacaa gtaaaacgag tgagtgcatg acgttttcaa tttcgcttat  1440
catggccaca gcgagagaga gagagagaga gagagagaga gagagagaga gagagagaga  1500
gagagagaga gagagagaga gagagaatta gctagaggtg cttttccatt  1560
agatattaag gtcgagtgtc acagttgaga tgtgggcgtg ccccccgcac accactgact  1620
ttataataat acttgttttg ttgcctctct aacgcatttt gctttggccc cactttcact  1680
acctataata ccagtggtgg cccacacccc cttctttgcc ctttttctctc tctctctagg  1740
ctctagtccc tctagtttag ttgggttggct tttcttcaag ggtttggacc ccatactaag  1800
tacactaata gccatgatac ctaagctttt catgcatttt tggacccttc cctgtcctac  1860
ttccattata aattatcatg actgcgctta ttgtccttcc aattcactgc tctcattcat  1920
tctctctctc tctctctctc tgaatatttg tttgctttttt attttctggg tttcagactt  1980
tcagtatctt tccaaaaaaa aaaaagtgaa aaaaagactt tcagtaggct agctaggcgc  2040
taatgtctgc agaggatcat atgaatctat ccataaatgg tcagtctcag gtccctcctg  2100
gctttcgctt ccatccaacc gaagaggagc ttcttcacta ctatctcagg aagaaagttt  2160
catatgagag gattgatctt gacgtcattc gagaggttga tcttaacaag ctcgagccat  2220
gggacattca aggtactcac ggcttcattc ccctagttct ttagcttaaa ctgattccac  2280
tttccaacga gctaatccta actatcatta gtatcgagat tcaaaagtag ttattataac  2340
atgctagacg tctgaaatg actcattagt ttgtggtttt ggcatgtaga gaagtgcaag  2400
ataggttcca ccccacagaa cgattggtat ttcttcagcc acaaagacaa gaaataccct  2460
acaggtactc gaaccaatcg cgcaaccgct gcaggggtttt ggaaggccac cggccgcgac  2520
aagatcatct acagcggcat tcgaagaatc ggattgagaa agacgcttgt gtttacaag  2580
ggacgagctc cgcacggaca aaagtcgat tggatcatgc atgaatacag actagatgaa  2640
agcagcagca gcagcagcct tgacaccaca gtatgttagc tattaatttt cgaactcttc  2700
aaatatttct catcagagat aaattatcaa acacttaatt ggaatgtact tttctttctt  2760
gcaggtttct agttcaattg gggagtcaat gtcagaagat gggtgggtgg tttgcagggt  2820
cttcaagaag aagaactacc agaaagcctt ggagagccca aaatcctcct acccgatgga  2880
ctcatcaaac aaccaaatgc taccgggtgg ttcgagaaac gacggcgttg tcgatcagat  2940
tctcttgtac atgggaagga ctagttcaa gctcgaaaac catgactcac tccatgacag  3000
attcatgcat cttccaaggc tcgagagcca aacttctctc cctctccttg cggtccactt  3060
cgatcatgac cgtagcttca aaggttgtta tcatgatcag accattgatg acatgctcat  3120
agaaacagat catcaacaac cttccaaac aacaaaaccaa cccaatgacc cggttgatca  3180
tgacgacccc aaaacaagga ttgtaaatga ctgggcttact atccatcagc tcgtggcctc  3240
tcaactcaat ggccatgaag acacttcaaa gcacttgtcc tgttcggtg acccaaacat  3300
ggcctttttgt tcttctcctc cttctaatga tgaggactta cagttgtcct atccatatct  3360
acgtccaggt agaatatcac agaatcaacc cgaagtctac aacagcgaga acgatctatg  3420
gagcttcaca aaatcgtcgc cgtcgccgtc atcatcagac ccattatgcc acctgtcggt  3480
gtaagggaag caataactaa tcaagcttga accaaacgac atatatatat atatacagt  3540
actatatagt agaagtatat aatatgtttta ctgtttacag aaaatacttg tagccaccgc  3600
aaaagaataa attaggaaat aatatagtgt ggcattgtca accctaatct ttcttaatta  3660
aaaataaata ttatgtttat tatctaagta tttgttgtct aattttggga tctgtcacgt  3720
gcatgctatc tagctgtgtg attatttctt tgggttaatt atgctccgac cctttttttt  3780
ttttttttct ttttttaaaa ctcttttgaa aagcatgagg ctggcttgag ttagtctgtg  3840
aaatgattga tcatcatatc gagaaagata tataaaacgc agtattgcag catactattg  3900
gcttagttttg gggtaacaat atattggtaa gaggtcgtta ttccaacaaa tcaattggtt  3960
attgttgagt ctagctataa ctctataatg gttaggaagc tgggttattt caaaccttca  4020
cctaacgtac gtaccagaaa agaggatgat gttgataaag ctgctgacta ccttttaccc  4080
ataaagataa gataagagcc accatgaaaa tcatatggaa ttgaactgtg aattttata   4140
tcatatggaa ttgaaccgtg tattttttatt catatatata tatatatata tatattctcc  4200
atcatatata gtctcatcct gatataacat gttacttctt aaaaaatatt gatagatagt  4260
acatgcttct tcttctctcc cttggctagc tagacgggta tcttccgata cgatctctct  4320
aaaagatttt aacttgtaat ttaaggtatg gctataattg ctcttaatta ttaaagtcat  4380
aagttctaac ataaattggg aaccaggtct ttcgttttcg gttgatgttt cggtttggcc  4440
atcgaagcta aatatttcgt tatggttcga ttcatctgca aacgttttcg gttgatatat  4500
atcacttcat atcgaacaaa tattgttgag gaaaaatatg gtttttcttg aatgaaatga  4560
a                                                                   4561
SEQ ID NO: 79          moltype = DNA   length = 1191
FEATURE                Location/Qualifiers
source                 1..1191
                       mol_type = other DNA
                       organism = Rubus sp.
SEQUENCE: 79
atgtctgcag aggatcatat gaatctatcc ataaatggtc agtctcaggt ccctcctggc    60
tttcgcttcc atccaaccga agaggagctt cttcactact atctcaggaa gaaagtttca   120
tatgagagga ttgatcttga cgtcattcga gaggttgatc ttaacaagct cgagccatgg   180
```

```
gacattcaag agaagtgcaa gataggttcc accccacaga acgattggta ttttcttcagc    240
cacaaagaca agaaataccc tacaggtact cgaaccaatc gcgcaaccgc tgcagggttt    300
tggaaggcca ccggccgcga caagatcatc tacagcggca ttcgaagaat cggattgaga    360
aagacgcttg tgttttacaa gggacgagct ccgcacggac aaaagtcaga ttggatcatg    420
catgaataca gactagatga aagcagcagc agcagcagcc ttgacaccac agtttctagt    480
tcaattgggg agtcaatgtc agaagatggg tgggtggttt gcagggtctt caagaagaag    540
aactaccaga aagccttgga gagcccaaaa tcctcctacc cgatggactc atcaaacaac    600
caaatgctac cggtggttc gagaaacgac ggcgttgtcg atcagattct cttgtacatg    660
ggaaggacta gttgcaagct cgaaaaccat gactcactcc atgacagatt catgcatctt    720
ccaaggctcg agagccaaac ttctcttcct tcacttgcgg tccacttcga tcatgaccgt    780
agcttcaaag gttgttatca tgatcagacc attgatgaca tgctcataga aacagatcat    840
caacaacctt ctccaacaac aaaccaaccc aatgacccgg ttgatcatga cgaccccaaa    900
acaaggattg taaatgactg ggctactatc catcagctcg tggcctctca actcaatggc    960
catgaagaca cttcaaagca cttgtcctgc ttcggtgacc caaacatggc cttttgttct   1020
tctcctcctt ctaatgatga ggacttacag ttgtcctatc catatctacg tccaggtaga   1080
atatcacaga atcaacccga agtctacaag agcgagaacg atctatggag cttcacaaaa   1140
tcgtcgccgt cgccgtcatc atcagaccca ttatgccacc tgtcggtgta a            1191

SEQ ID NO: 80           moltype = AA  length = 396
FEATURE                 Location/Qualifiers
source                  1..396
                        mol_type = protein
                        organism = Rubus sp.
SEQUENCE: 80
MSAEDHMNLS INGQSQVPPG FRFHPTEEEL LHYYLRKKVS YERIDLDVIR EVDLNKLEPW     60
DIQEKCKIGS TPQNDWYFFS HKDKKYPTGT RTNRATAAGF WKATGRDKII YSGIRRIGLR    120
KTLVFYKGRA PHGQKSDWIM HEYRLDESSS SSSLDTTVSS SIGESMSEDG WVVCRVFKKK    180
NYQKALESPK SSYPMDSSNN QMLPGGSRND GVVDQILLYM GRTSCKLENH DSLHDRFMHL    240
PRLESQTSLP SLAVHFDHDR SFKGCYHDQT IDDMLIETDH QQPSPTTNQP NDPVDHDDPK    300
TRIVNDWATI HQLVASQLNG HEDTSKHLSC FGDPNMAFCS SPPSNDEDLQ LSYPYLRPGR    360
ISQNQPEVYN SENDLWSFTK SSPSPSSSDP LCHLSV                              396

SEQ ID NO: 81           moltype = DNA  length = 4663
FEATURE                 Location/Qualifiers
source                  1..4663
                        mol_type = genomic DNA
                        organism = Rubus sp.
SEQUENCE: 81
tcttccagcc accacaaaca aattgtcata gtcataattg acgcaaaacg tatatacgta     60
ggcttttgac attagctagc tagactattt tccaatttga gataacatct ccatgtaatc    120
ttatgtatgc aaaacctatg tatgattaaa tattcacgac ccctttatat tagttttctgt   180
gatgagtata tataaaatgt acttttattt ttatattttt tgttatatcg aagggggatt    240
gaatctctga tctaatttag tactatctta atttccaacc tcctttacta tttgggataa    300
ttaactctaa ggacatagtt atatttgtgt tttatttta ctgttgctaa acatatgaat    360
tgaaagatc aaataacatc aagagggatt catgaatcta aggtaattaa tacagtaatt    420
taacactaaa attattcaaa aaaagatcat gaagacattc aactcgatcc ctacaatatc    480
aatatatgtg tgttatgacg tcatgagata aaaaaggcct ttaccaaaaa acacgaggcc    540
ttaatatcag cacatcccac caacatacat attcatgtgg atgtggtgta ttacctgtaa    600
cctaccccat atatgcggcc atgcatgcat atatgcagct atcaataatc aagaataagg    660
aacctggggc atttctcaca ttttggtacg tgatcatcta catcgagctt aatttcctaa    720
catatatgga atgtgtgtta accttacagc tgcatgcagc catcaattg cacagcttgt    780
ttatgtaaag aagatgtata tatagtacct tgatctttat gagaccaatt actcctcttt    840
atctctcttt aatttgtacc acgtacgcaa tataaatatt gttataaata aatgattatg    900
tggagccaaa gatccaattt atttgcagct agctaggtta ctaatgtgat cgagagaagt    960
acctagctag tagatcgatt tacataagat atcgtactac gcttgtcagc aaatagcctg   1020
gtgacatgca tcgttattgg atcaaacatg tcgataaacc gttttaccac ataacgatgaa   1080
aatcctatag tgttagaaat atcccaaaga gaatgtgaat gaacataacc tgctctagaa   1140
ccatgcatgt acaaggaaac aaaaggcctg caaagaaacc aaggtaaaat caatgtttca   1200
agatcaaaat cggctcaaaa aacccaagga caagaaaatc caactcaaga actataacaa   1260
actggccggc gtgtatgatt gtgggattct atttccaacc tccagaactg aattctcaca   1320
agaagggaag aagccatggt gtctttattt tttttggggt ccatgcgaaa gctcagttgc   1380
tccgacccca tcatctctgt ccctctctct ggcttcttgt cgttgaggtg gttgcacaag   1440
taaaacgagt gagtgcatga cgttttcaat ttcgcttatc atggcgagag agagagagag   1500
agagagagag agagagagag agagagagag agagaattag ctagaggtcg                1560
ttttccatta gatattaagg tcgagtgtca cagttgagat gtgggcgtgc ccccgcaca    1620
ccactgactt tataataata cttgttttgt tgcctctcta acgcattttg ctttggcccc   1680
actttcacta ccttataata ccagtggtgg cccacacccc cttctttgcc cttttctttc   1740
tctctagcct ctagtctctc tagtttaggt ggttggctct tcttcaaggg tttggacccc   1800
agactaagta cactaatagc catgatacct aagcttttca tgcattttg gacccttcc    1860
tgtcctactt ccattataaa ttatcatgac tgcgcttatt gtccttccaa ttcactgctc   1920
tcattctctc tctctctctc tctctctctc tctctctctc tgaatattag tttgcttttt   1980
attttctggg tttcagattt tcagtatctt tccaaaaaaa aaaagtgaa aaaaagact    2040
ttcagtaggc tagctaggcg ctaatgtctg cagaggatca tatgaatcta tccataaatg   2100
gtcagtctca ggtccctcct ggcttttcgct tcatccaac cgaagaggag cttcttcact   2160
actatctcag gaagaaagtt tcctatgaga ggattgatcc tgacgtcatt cgagaggttg   2220
atcttaacaa gctcgagcca tgggacattc aaggtactca cggcttcatt ccctcgttc   2280
tttagcttaa agtgattcca ctttccaacg agctaatcct aactatcatt agtatcgaga   2340
tcaaaaacta gttattataa catgctagac ggtctgcaat gactcattgg tttgtggttt   2400
tggcatgtag agaagtgcaa gataggttcc accccacaga acgattggta ttttcttcagc   2460
```

```
cacaaagaca agaaatacc tacaggtact cgaaccaatc gcgcaaccgc tgcagggttt  2520
tggaaggcca ccggccgcga caagatcatc tatagcggca ttcgaagaat cggattgaga  2580
aagacgcttg tgttttacaa gggacgagct ccgcacggac aaaagtcaga ttggatcatg  2640
catgaataca gactagatga aagcagcagc agcagcagca gccttgacac cacagtaagt  2700
tagctattaa ttttcgaact cttcaaatat ttctcatcag agataaatta tcaaacactt  2760
aattggaatg cacttttctt tcttgcaggt ttctagttca attggggagt caatgtcaga  2820
agatgggtgg gtggtttgca gggtcttcaa gaagaagaac taccagaaag ccttggagag  2880
cccaaaatcc tcctacccga tggactcatc aaacaaccaa atgctaccgg gtggtatgag  2940
aaacgacggc gttgtcgatc agattctctt gtacatggga aggactagtt gcaagctcga  3000
aaaccatgac tcactccatg acagattcat gcatcttcca aggctcgaga gccaaacttc  3060
tcttccttca cttgcggtcc acttcgatca tgaccgtagc ttcaaagctt gttatcatga  3120
tcagaccatt gatgacatgc tcatagaaac agatcatcaa caaccttctc aacaacaaa   3180
ccaacccaac gacccggttg atcatgacga ccccaaaaca aggattgtaa atgactgggc  3240
tactatccat cagctcgtgg cctctcaact caatggccat gaagacacat caaagcactt  3300
gtcctgcttc ggtgacccaa acatggcctt tgttcttct cctccttcta atgatgagga    3360
cttacagttg tcctatccat atctacgtcc aggtagaata tcacagaatc aacccgaagt  3420
ctacaacagc gagaacgatc tgtggagctt cacaaaatcg tcgccgtcgc cgtcatcatc  3480
agacccatta tgccacctgt cggtataagg aagcaataa ctaatcaagc ttgaaccaaa    3540
cgacatatat atatataaaa atatattata tatatacacg tactatcgta gaagtatata  3600
atatgtttac tgtttacaga aaatacttgt agccaccgca aaagaataaa ttaggaaata  3660
atatagtgtg gcattgtcaa ccctaatctt tcttaattaa aaataaatat tatgtctatt  3720
atctaagtat ttgttgtcga attttgggat ctgtcacgtg catgctagct agctgtgtga  3780
ttatttcttt gggttaatta tgctccgacc cttctttttt tttattttta aaactctttt  3840
gaaaagcatg aggctggctt gagttagtct gtgaaatgat tgatcatcat atatatcgag  3900
aaagatatat aaaacgcagt aatgcagcat acaattggct tagtttgggg taacaataat  3960
attggtaaga ggtcgttatt ccaacaaatc aattggttat cgttgagtct agctataact  4020
ctataatggt taggaagccg ggttatttca aaccttcacc taacgtacgt accagaaaag  4080
aggatgctgt tgataaagct gctgaccacc ttttacccat aaagataaga taagagccac  4140
cacgaaaatc atatggaatt gaactgtgta ttttatatc atatggaatt gaaccgtgta   4200
ttttattca tatatatata tatatataaa ttctccatca tatatagtct catcctgata   4260
taacatgtta cttcttaaaa aatattgatc gatagtacgt gctccttctt ctctccctgt  4320
gctagctaga cgggtatctt ccgatacgat ctctctaaaa gatttttact tgtaatttaa  4380
ggtatggcta taattgctct taattactca agtcacaagt tctaacataa attgggaacc  4440
aggtcttca tcttcggttg atgtttcggt ttggccatcg aagctaaata tttcgttttc   4500
gattcatctg caaacgtttt tggttgataa cttgatatat atcacttcat atcgaacaaa  4560
tattgttgag aaaaattatg atttttctcg aatggaatga agataggatt gtaacaaaat  4620
aaagatcatt aattccttag ccacgacgtg taaatctttt cat                    4663

SEQ ID NO: 82        moltype = DNA   length = 1194
FEATURE              Location/Qualifiers
source               1..1194
                     mol_type = other DNA
                     organism = Rubus sp.
SEQUENCE: 82
atgtctgcag aggatcatat gaatctatcc ataaatggtc agtctcaggt ccctcctggc    60
tttcgcttca atccaaccga agaggagctt cttcactact atctcaggaa gaaagtttcc   120
tatgagagca ttgatcttga cgtcattcga gaggttgatc ttaacaagct cgagccatgg   180
gacattcaag agaagtgcaa gataggttcc accccacaga acgattggta tttcttcagc   240
cacaaagaca agaaatacc tacaggtact cgaaccaatc gcgcaaccgc tgcagggttt    300
tggaaggcca ccggccgcga caagatcatc tatagcggca ttcgaagaat cggattgaga   360
aagacgcttg tgttttacaa gggacgagct ccgcacggac aaaagtcaga ttggatcatg   420
catgaataca gactagatga aagcagcagc agcagcagca gccttgacac cacagttttct  480
agttcaattg gggagtcaat gtcagaagat gggtggtgg tttgcagggt cttcaagaag   540
aagaactacc agaaagcctt ggagagccca aaatcctcct acccgatgga ctcatcaaac  600
aaccaaatgc taccgggtgg tatgagaaac gacggcgttg tcgatcagat tctcttgtac   660
atgggaagga ctagttgcaa gctcgaaaac catgactcac tccatgacag attcatgcat   720
cttccaaggc tcgagagcca aacttctctt ccttcacttg cggtccactt cgatcatgac   780
cgtagcttca aagcttgtta tcatgatcag accattgatg acatgctcat agaaacagat   840
catcaacaac cttctccaac aacaaaccaa cccaacgacc cggttgatca tgacgaccac   900
aaaacaagga ttgtaaatga ctgggctact atccatcagc tcgtggcctc tcaactcaat   960
ggccatgaag acatcaaa gcacttgtcc tgcttcggtg acccaaacat ggccttttgt   1020
tcttctcctc cttctaatga tgaggactta cagttgtcct atccatatct acgtccaggt  1080
agaatatcac agaatcaacc cgaagtctac aacagcgaga acgatctgtg gagcttcaca  1140
aaatcgtcgc cgtcgccgtc atcatcagac ccattatgcc acctgtcggt ataa        1194

SEQ ID NO: 83        moltype = AA    length = 397
FEATURE              Location/Qualifiers
source               1..397
                     mol_type = protein
                     organism = Rubus sp.
SEQUENCE: 83
MSAEDHMNLS INGQSQVPPG FRFHPTEEEL LHYYLRKKVS YERIDLDVIR EVDLNKLEPW    60
DIQEKCKIGS TPQNDWYFFS HKDKKYPTGT RTNRATAAGF WKATGRDKII YSGIRRIGLR   120
KTLVFYKGRA PHGQKSDWIM HEYRLDESSS SSSSLDTTVS SSIGESMSED GWVVCRVFKK   180
KNYQKALESP KSSYPMDSSN NQMLPGGMRN DGVVDQILLY MGRTSCKLEN HDSLHDRFMH   240
LPRLESQTSL PSLAVHFDHD RSFKACYHDQ TIDDMLIETD HQQPSPTTNQ PNDPVDHDDP   300
KTRIVNDWAT IHQLVASQLN GHEDTSKHLS CFGDPNMAFC SSPPSNDEDL QLSYPYLRPG   360
RISQNQPEVY NSENDLWSFT KSSPSPSSSD PLCHLSV                            397
```

-continued

| | | |
|---|---|---|
| SEQ ID NO: 84 | moltype = DNA length = 184 | |
| FEATURE | Location/Qualifiers | |
| source | 1..184 | |
| | mol_type = genomic DNA | |
| | organism = Rubus sp. | |

SEQUENCE: 84
atgactgaaa acgtgagtat atctgtgaat gggcaatctc aagtccctcc tggtttcaga 60
tttcatccaa ctgaagagga gctcttgcag tactacttga ggaagaaggt ctccaatcag 120
agcattgatc tcgatgtcat ctgcgatgtc gatctcaata agcttgagcc atgggatata 180
caag 184

| | | |
|---|---|---|
| SEQ ID NO: 85 | moltype = DNA length = 143 | |
| FEATURE | Location/Qualifiers | |
| source | 1..143 | |
| | mol_type = genomic DNA | |
| | organism = Rubus sp. | |

SEQUENCE: 85
aaaatgactg aaaacgtgag tatatctgtg aatgggcaat ctcaagtccc tcctggtttc 60
agatttcatc caactgaaga ggagctcttg cagtactact tgaggaagaa ggtctccaat 120
cagagcattg atctcgatgt cat 143

| | | |
|---|---|---|
| SEQ ID NO: 86 | moltype = DNA length = 103 | |
| FEATURE | Location/Qualifiers | |
| source | 1..103 | |
| | mol_type = genomic DNA | |
| | organism = Rubus sp. | |

SEQUENCE: 86
tatatctgtg aatgggcaat ctcaagtccc tcctggtttc agatttcatc caactgaaga 60
ggagctcttg cagtactact tgaggaagaa ggtctccaat cag 103

| | | |
|---|---|---|
| SEQ ID NO: 87 | moltype = DNA length = 63 | |
| FEATURE | Location/Qualifiers | |
| source | 1..63 | |
| | mol_type = genomic DNA | |
| | organism = Rubus sp. | |

SEQUENCE: 87
ctcaagtccc tcctggtttc agatttcatc caactgaaga ggagctcttg cagtactact 60
tga 63

| | | |
|---|---|---|
| SEQ ID NO: 88 | moltype = DNA length = 143 | |
| FEATURE | Location/Qualifiers | |
| source | 1..143 | |
| | mol_type = genomic DNA | |
| | organism = Rubus sp. | |

SEQUENCE: 88
ctgaaaacgt gagtatatct gtgaatgggc aatctcaagt ccctcctggt ttcagatttc 60
atccaactga agaggagctc ttgcagtact acttgaggaa gaaggtctcc aatcagagca 120
ttgatctcga tgtcatctgc gat 143

| | | |
|---|---|---|
| SEQ ID NO: 89 | moltype = DNA length = 103 | |
| FEATURE | Location/Qualifiers | |
| source | 1..103 | |
| | mol_type = genomic DNA | |
| | organism = Rubus sp. | |

SEQUENCE: 89
gtgaatgggc aatctcaagt ccctcctggt ttcagatttc atccaactga agaggagctc 60
ttgcagtact acttgaggaa gaaggtctcc aatcagagca ttg 103

| | | |
|---|---|---|
| SEQ ID NO: 90 | moltype = DNA length = 63 | |
| FEATURE | Location/Qualifiers | |
| source | 1..63 | |
| | mol_type = genomic DNA | |
| | organism = Rubus sp. | |

SEQUENCE: 90
ccctcctggt ttcagatttc atccaactga agaggagctc ttgcagtact acttgaggaa 60
gaa 63

| | | |
|---|---|---|
| SEQ ID NO: 91 | moltype = DNA length = 30 | |
| FEATURE | Location/Qualifiers | |
| source | 1..30 | |
| | mol_type = genomic DNA | |
| | organism = Rubus sp. | |

SEQUENCE: 91
agatttcatc caactgaaga ggagctcttg 30

| | | |
|---|---|---|
| SEQ ID NO: 92 | moltype = DNA length = 184 | |
| FEATURE | Location/Qualifiers | |
| source | 1..184 | |
| | mol_type = genomic DNA | |

```
                         organism = Rubus sp.
SEQUENCE: 92
atgactgaaa acgtgagtat atctgtgaat gggcaatctc aagtccctcc tggtttcaga      60
tttcatccaa ctgaagagga gctcttgcag tactacttga ggaagaaggt ctccaatcag     120
agcattgatc tcgatgtcat ctccgatgtc gatctcaata agcttgagcc atgggatata     180
caag                                                                  184

SEQ ID NO: 93            moltype = DNA   length = 143
FEATURE                  Location/Qualifiers
source                   1..143
                         mol_type = genomic DNA
                         organism = Rubus sp.
SEQUENCE: 93
tctctctctc tctctgatct tcacaaattg tgtggagcag tctggataaa tcaccttttg      60
atcaaaattc aaaatgactg aaaacgtgag tatatctgtg aatgggcaat ctcaagtccc     120
tcctggtttc agatttcatc caa                                             143

SEQ ID NO: 94            moltype = DNA   length = 103
FEATURE                  Location/Qualifiers
source                   1..103
                         mol_type = genomic DNA
                         organism = Rubus sp.
SEQUENCE: 94
tcacaaattg tgtggagcag tctggataaa tcaccttttg atcaaaattc aaaatgactg      60
aaaacgtgag tatatctgtg aatgggcaat ctcaagtccc tcc                       103

SEQ ID NO: 95            moltype = DNA   length = 63
FEATURE                  Location/Qualifiers
source                   1..63
                         mol_type = genomic DNA
                         organism = Rubus sp.
SEQUENCE: 95
tctggataaa tcaccttttg atcaaaattc aaaatgactg aaaacgtgag tatatctgtg      60
aat                                                                    63

SEQ ID NO: 96            moltype = DNA   length = 100
FEATURE                  Location/Qualifiers
source                   1..100
                         mol_type = genomic DNA
                         organism = Rubus sp.
SEQUENCE: 96
atcaaaattc aaaatgactg aaaacgtgag tatatctgtg aatgggcaat ctcaagtccc      60
tcctggtttc agatttcatc caactgaaga ggagctcttg                           100

SEQ ID NO: 97            moltype = DNA   length = 143
FEATURE                  Location/Qualifiers
source                   1..143
                         mol_type = genomic DNA
                         organism = Rubus sp.
SEQUENCE: 97
ctgaaaacgt gagtatatct gtgaatgggc aatctcaagt ccctcctggt ttcagatttc      60
atccaactga agaggagctc ttgcagtact acttgaggaa gaaggtctcc aatcagagca     120
ttgatctcga tgtcatctcc gat                                             143

SEQ ID NO: 98            moltype = DNA   length = 190
FEATURE                  Location/Qualifiers
source                   1..190
                         mol_type = genomic DNA
                         organism = Rubus sp.
SEQUENCE: 98
atgtctgcag aggatcatat gaatctatcc ataaatggtc agtctcaggt ccctcctggc      60
tttcgcttcc atccaaccga agaggagctt cttcactact atctcaggaa gaaagtttca     120
tatgagagga ttgatcttga cgtcattcga gaggttgatc ttaacaagct cgagccatgg     180
gacattcaag                                                            190

SEQ ID NO: 99            moltype = DNA   length = 143
FEATURE                  Location/Qualifiers
source                   1..143
                         mol_type = genomic DNA
                         organism = Rubus sp.
SEQUENCE: 99
tccaaaaaaa aaaagtgaa aaaaagactt tcagtaggct agctaggcgc taatgtctgc       60
agaggatcat atgaatctat ccataaatgg tcagtctcag gtccctcctg gctttcgctt     120
ccatccaacc gaagaggagc ttc                                             143

SEQ ID NO: 100           moltype = DNA   length = 103
FEATURE                  Location/Qualifiers
source                   1..103
                         mol_type = genomic DNA
```

```
                        organism = Rubus sp.
SEQUENCE: 100
aaaaaagactt tcagtaggct agctaggcgc taatgtctgc agaggatcat atgaatctat      60
ccataaatgg tcagtctcag gtccctcctg gctttcgctt cca                       103

SEQ ID NO: 102          moltype = DNA  length = 63
FEATURE                 Location/Qualifiers
source                  1..63
                        mol_type = genomic DNA
                        organism = Rubus sp.
SEQUENCE: 101
agctaggcgc taatgtctgc agaggatcat atgaatctat ccataaatgg tcagtctcag      60
gtc                                                                    63

SEQ ID NO: 102          moltype = DNA  length = 143
FEATURE                 Location/Qualifiers
source                  1..143
                        mol_type = genomic DNA
                        organism = Rubus sp.
SEQUENCE: 102
ctgcagagga tcatatgaat ctatccataa atggtcagtc tcaggtccct cctggctttc      60
gcttccatcc aaccgaagag gagcttcttc actactatct caggaagaaa gtttcatatg     120
agaggattga tcttgacgtc att                                             143

SEQ ID NO: 103          moltype = DNA  length = 103
FEATURE                 Location/Qualifiers
source                  1..103
                        mol_type = genomic DNA
                        organism = Rubus sp.
SEQUENCE: 103
ctatccataa atggtcagtc tcaggtccct cctggctttc gcttccatcc aaccgaagag      60
gagcttcttc actactatct caggaagaaa gtttcatatg aga                       103

SEQ ID NO: 104          moltype = DNA  length = 63
FEATURE                 Location/Qualifiers
source                  1..63
                        mol_type = genomic DNA
                        organism = Rubus sp.
SEQUENCE: 104
tcaggtccct cctggctttc gcttccatcc aaccgaagag gagcttcttc actactatct      60
cag                                                                    63

SEQ ID NO: 105          moltype = DNA  length = 143
FEATURE                 Location/Qualifiers
source                  1..143
                        mol_type = genomic DNA
                        organism = Rubus sp.
SEQUENCE: 105
tccataaatg gtcagtctca ggtccctcct ggctttcgct tccatccaac cgaagaggag      60
cttcttcact actatctcag gaagaaagtt tcatatgaga ggattgatct tgacgtcatt     120
cgagaggttg atcttaacaa gct                                             143

SEQ ID NO: 106          moltype = DNA  length = 103
FEATURE                 Location/Qualifiers
source                  1..103
                        mol_type = genomic DNA
                        organism = Rubus sp.
SEQUENCE: 106
ggtccctcct ggctttcgct tccatccaac cgaagaggag cttcttcact actatctcag      60
gaagaaagtt tcatatgaga ggattgatct tgacgtcatt cga                       103

SEQ ID NO: 107          moltype = DNA  length = 63
FEATURE                 Location/Qualifiers
source                  1..63
                        mol_type = genomic DNA
                        organism = Rubus sp.
SEQUENCE: 107
tccatccaac cgaagaggag cttcttcact actatctcag gaagaaagtt tcatatgaga      60
gga                                                                    63

SEQ ID NO: 108          moltype = DNA  length = 102
FEATURE                 Location/Qualifiers
source                  1..102
                        mol_type = genomic DNA
                        organism = Rubus sp.
SEQUENCE: 108
agaggatcat atgaatctat ccataaatgg tcagtctcag gtccctcctg gctttcgctt      60
ccatccaacc gaagaggagc ttcttcacta ctatctcagg aa                        102
```

```
SEQ ID NO: 109            moltype = DNA   length = 46
FEATURE                   Location/Qualifiers
source                    1..46
                          mol_type = genomic DNA
                          organism = Rubus sp.
SEQUENCE: 109
gcttccatcc aaccgaagag gagcttcttc actactatct caggaa                    46

SEQ ID NO: 110            moltype = DNA   length = 190
FEATURE                   Location/Qualifiers
source                    1..190
                          mol_type = genomic DNA
                          organism = Rubus sp.
SEQUENCE: 110
atgtctgcag aggatcatat gaatctatcc ataaatggtc agtctcaggt ccctcctggc     60
tttcgcttcc atccaaccga agaggagctt cttcactact atctcaggaa gaaagtttcc    120
tatgagagga ttgatcttga cgtcattcga gaggttgatc ttaacaagct cgagccatgg    180
gacattcaag                                                           190

SEQ ID NO: 111            moltype = DNA   length = 143
FEATURE                   Location/Qualifiers
source                    1..143
                          mol_type = genomic DNA
                          organism = Rubus sp.
SEQUENCE: 111
ccaaaaaaaa aaaagtgaaa aaaaagactt tcagtaggct agctaggcgc taatgtctgc     60
agaggatcat atgaatctat ccataaatgg tcagtctcag gtccctcctg gctttcgctt    120
ccatccaacc gaagaggagc ttc                                            143

SEQ ID NO: 112            moltype = DNA   length = 143
FEATURE                   Location/Qualifiers
source                    1..143
                          mol_type = genomic DNA
                          organism = Rubus sp.
SEQUENCE: 112
ctgcagagga tcatatgaat ctatccataa atggtcagtc tcaggtccct cctggctttc     60
gcttccatcc aaccgaagag gagcttcttc actactatct caggaagaaa gtttcctatg    120
agaggattga tcttgacgtc att                                            143

SEQ ID NO: 113            moltype = DNA   length = 103
FEATURE                   Location/Qualifiers
source                    1..103
                          mol_type = genomic DNA
                          organism = Rubus sp.
SEQUENCE: 113
ctatccataa atggtcagtc tcaggtccct cctggctttc gcttccatcc aaccgaagag     60
gagcttcttc actactatct caggaagaaa gtttcctatg aga                      103

SEQ ID NO: 114            moltype = DNA   length = 143
FEATURE                   Location/Qualifiers
source                    1..143
                          mol_type = genomic DNA
                          organism = Rubus sp.
SEQUENCE: 114
tccataaatg gtcagtctca ggtccctcct ggctttcgct tccatccaac cgaagaggag     60
cttcttcact actatctcag gaagaaagtt cctatgaga ggattgatct tgacgtcatt    120
cgagaggttg atcttaacaa gct                                            143

SEQ ID NO: 115            moltype = DNA   length = 103
FEATURE                   Location/Qualifiers
source                    1..103
                          mol_type = genomic DNA
                          organism = Rubus sp.
SEQUENCE: 115
ggtccctcct ggctttcgct tccatccaac cgaagaggag cttcttcact actatctcag     60
gaagaaagtt tcctatgaga ggattgatct tgacgtcatt cga                      103

SEQ ID NO: 116            moltype = DNA   length = 63
FEATURE                   Location/Qualifiers
source                    1..63
                          mol_type = genomic DNA
                          organism = Rubus sp.
SEQUENCE: 116
tccatccaac cgaagaggag cttcttcact actatctcag gaagaaagtt cctatgaga      60
gga                                                                   63

SEQ ID NO: 117            moltype = DNA   length = 23
FEATURE                   Location/Qualifiers
source                    1..23
```

```
                              mol_type = other DNA
                              organism = synthetic construct
SEQUENCE: 117
tggatagatt catatgatcc tct                                               23

SEQ ID NO: 118            moltype = DNA   length = 23
FEATURE                   Location/Qualifiers
source                    1..23
                          mol_type = other DNA
                          organism = synthetic construct
SEQUENCE: 118
gcttccatcc aaccgaagag gag                                               23

SEQ ID NO: 119            moltype = DNA   length = 23
FEATURE                   Location/Qualifiers
source                    1..23
                          mol_type = other DNA
                          organism = synthetic construct
SEQUENCE: 119
ttcctgagat agtagtgaag aag                                               23

SEQ ID NO: 120            moltype = DNA   length = 23
FEATURE                   Location/Qualifiers
source                    1..23
                          mol_type = other DNA
                          organism = synthetic construct
SEQUENCE: 120
atcaaaattc aaaatgactg aaa                                               23

SEQ ID NO: 121            moltype = DNA   length = 23
FEATURE                   Location/Qualifiers
source                    1..23
                          mol_type = other DNA
                          organism = synthetic construct
SEQUENCE: 121
atccaactga agaggagctc ttg                                               23

SEQ ID NO: 122            moltype = DNA   length = 23
FEATURE                   Location/Qualifiers
source                    1..23
                          mol_type = other DNA
                          organism = synthetic construct
SEQUENCE: 122
agatttcatc caactgaaga gga                                               23

SEQ ID NO: 123            moltype = AA   length = 61
FEATURE                   Location/Qualifiers
source                    1..61
                          mol_type = protein
                          organism = Rubus sp.
SEQUENCE: 123
MTENVSISVN GQSQVPPGFR FHPTEEELLQ YYLRKKVSNQ SIDLDVICDV DLNKLEPWDI        60
Q                                                                       61

SEQ ID NO: 124            moltype = AA   length = 41
FEATURE                   Location/Qualifiers
source                    1..41
                          mol_type = protein
                          organism = Rubus sp.
SEQUENCE: 124
GQSQVPPGFR FHPTEEELLQ YYLRKKVSNQ SIDLDVICDV D                           41

SEQ ID NO: 125            moltype = AA   length = 21
FEATURE                   Location/Qualifiers
source                    1..21
                          mol_type = protein
                          organism = Rubus sp.
SEQUENCE: 125
FHPTEEELLQ YYLRKKVSNQ S                                                 21

SEQ ID NO: 126            moltype = AA   length = 14
FEATURE                   Location/Qualifiers
source                    1..14
                          mol_type = protein
                          organism = Rubus sp.
SEQUENCE: 126
FHPTEEELLQ YYLR                                                         14

SEQ ID NO: 127            moltype = AA   length = 5
```

```
FEATURE                 Location/Qualifiers
source                  1..5
                        mol_type = protein
                        organism = Rubus sp.
SEQUENCE: 127
EEELL                                                                    5

SEQ ID NO: 128          moltype = AA  length = 61
FEATURE                 Location/Qualifiers
source                  1..61
                        mol_type = protein
                        organism = Rubus sp.
SEQUENCE: 128
MTENVSISVN GQSQVPPGFR FHPTEEELLQ YYLRKKVSNQ SIDLDVISDV DLNKLEPWDI    60
Q                                                                       61

SEQ ID NO: 129          moltype = AA  length = 41
FEATURE                 Location/Qualifiers
source                  1..41
                        mol_type = protein
                        organism = Rubus sp.
SEQUENCE: 129
GQSQVPPGFR FHPTEEELLQ YYLRKKVSNQ SIDLDVISDV D                            41

SEQ ID NO: 130          moltype = AA  length = 63
FEATURE                 Location/Qualifiers
source                  1..63
                        mol_type = protein
                        organism = Rubus sp.
SEQUENCE: 130
MSAEDHMNLS INGQSQVPPG FRFHPTEEEL LHYYLRKKVS YERIDLDVIR EVDLNKLEPW    60
DIQ                                                                     63

SEQ ID NO: 131          moltype = AA  length = 43
FEATURE                 Location/Qualifiers
source                  1..43
                        mol_type = protein
                        organism = Rubus sp.
SEQUENCE: 131
INGQSQVPPG FRFHPTEEEL LHYYLRKKVS YERIDLDVIR EVD                          43

SEQ ID NO: 132          moltype = AA  length = 23
FEATURE                 Location/Qualifiers
source                  1..23
                        mol_type = protein
                        organism = Rubus sp.
SEQUENCE: 132
FRFHPTEEEL LHYYLRKKVS YER                                                23

SEQ ID NO: 133          moltype = AA  length = 15
FEATURE                 Location/Qualifiers
source                  1..15
                        mol_type = protein
                        organism = Rubus sp.
SEQUENCE: 133
RFHPTEEELL HYYLR                                                         15

SEQ ID NO: 134          moltype = DNA  length = 23
FEATURE                 Location/Qualifiers
source                  1..23
                        mol_type = other DNA
                        organism = synthetic construct
SEQUENCE: 134
ttcttgaaga ttctgcaaac cac                                                23

SEQ ID NO: 135          moltype = DNA  length = 23
FEATURE                 Location/Qualifiers
source                  1..23
                        mol_type = other DNA
                        organism = synthetic construct
SEQUENCE: 135
ttctgtgata gatgaagaaa tag                                                23

SEQ ID NO: 136          moltype = DNA  length = 23
FEATURE                 Location/Qualifiers
source                  1..23
                        mol_type = other DNA
SEQUENCE: 136
```

```
ctcaaaagct ccctcatgat cat                                              23

SEQ ID NO: 137          moltype = DNA   length = 20
FEATURE                 Location/Qualifiers
source                  1..20
                        mol_type = other DNA
                        organism = synthetic construct
SEQUENCE: 137
tttcttgcag gtttctagtt                                                  20

SEQ ID NO: 138          moltype = DNA   length = 20
FEATURE                 Location/Qualifiers
source                  1..20
                        mol_type = other DNA
                        organism = synthetic construct
SEQUENCE: 138
ttgcaggttt ctagttcaat                                                  20

SEQ ID NO: 139          moltype = DNA   length = 20
FEATURE                 Location/Qualifiers
source                  1..20
                        mol_type = other DNA
                        organism = synthetic construct
SEQUENCE: 139
tggtagttct tcttcttgaa                                                  20

SEQ ID NO: 140          moltype = DNA   length = 20
FEATURE                 Location/Qualifiers
source                  1..20
                        mol_type = other DNA
                        organism = synthetic construct
SEQUENCE: 140
cagggtcttc aagaagaaga                                                  20

SEQ ID NO: 141          moltype = DNA   length = 20
FEATURE                 Location/Qualifiers
source                  1..20
                        mol_type = other DNA
                        organism = synthetic construct
SEQUENCE: 141
ggctctccaa ggctttctgg                                                  20

SEQ ID NO: 142          moltype = DNA   length = 20
FEATURE                 Location/Qualifiers
source                  1..20
                        mol_type = other DNA
                        organism = synthetic construct
SEQUENCE: 142
atgagtccat cgggtaggag                                                  20

SEQ ID NO: 143          moltype = DNA   length = 20
FEATURE                 Location/Qualifiers
source                  1..20
                        mol_type = other DNA
                        organism = synthetic construct
SEQUENCE: 143
gttgtttgat gagtccatcg                                                  20

SEQ ID NO: 144          moltype = DNA   length = 20
FEATURE                 Location/Qualifiers
source                  1..20
                        mol_type = other DNA
                        organism = synthetic construct
SEQUENCE: 144
tcgaaccacc cggtagcatt                                                  20

SEQ ID NO: 145          moltype = DNA   length = 347
FEATURE                 Location/Qualifiers
source                  1..347
                        mol_type = genomic DNA
                        organism = Rubus sp.
SEQUENCE: 145
tgagtttata gacatatcga tcgattgtta ttgaacagtt tccttttatt tgaatcaggt      60
ctcgatcacc gttgtgggag aggcagcgga ggaggggtgg gtggtttgca gaatcttcaa     120
gaagaaaaat ctccacaaga gcttgagtag tccaatcatg agcacttcta tttcttcatc     180
tatcacagaa gaaattacaa gaagctcaag ccaaatgttt gatgatgatc atgagggagc     240
ttttgaggaa atgcttcagt acataggatc aaggacctgc aaggaagaga ataatgaaca     300
ttatcatctt catcccatca acacaggtaa tagtgataag attaatg                  347
```

```
SEQ ID NO: 146          moltype = DNA    length = 267
FEATURE                 Location/Qualifiers
source                  1..267
                        mol_type = genomic DNA
                        organism = Rubus sp.
SEQUENCE: 146
tcctttatt tgaatcaggt ctcgatcacc gttgtgggag aggcagcgga ggaggggtgg    60
gtggtttgca gaatcttcaa gaagaaaaat ctccacaaga gcttgagtag tccaatcatg   120
agcacttcta tttcttcatc tatcacagaa gaaattacaa gaagctcaag ccaaatgttt   180
gatgatgatc atgagggagc ttttgaggaa atgcttcagt acataggatc aaggacctgc   240
aaggaagaga ataatgaaca ttatcat                                       267

SEQ ID NO: 147          moltype = DNA    length = 227
FEATURE                 Location/Qualifiers
source                  1..227
                        mol_type = genomic DNA
                        organism = Rubus sp.
SEQUENCE: 147
ctcgatcacc gttgtgggag aggcagcgga ggaggggtgg gtggtttgca gaatcttcaa    60
gaagaaaaat ctccacaaga gcttgagtag tccaatcatg agcacttcta tttcttcatc   120
tatcacagaa gaaattacaa gaagctcaag ccaaatgttt gatgatgatc atgagggagc   180
ttttgaggaa atgcttcagt acataggatc aaggacctgc aaggaag                 227

SEQ ID NO: 148          moltype = DNA    length = 187
FEATURE                 Location/Qualifiers
source                  1..187
                        mol_type = genomic DNA
                        organism = Rubus sp.
SEQUENCE: 148
aggcagcgga ggaggggtgg gtggtttgca gaatcttcaa gaagaaaaat ctccacaaga    60
gcttgagtag tccaatcatg agcacttcta tttcttcatc tatcacagaa gaaattacaa   120
gaagctcaag ccaaatgttt gatgatgatc atgagggagc ttttgaggaa atgcttcagt   180
acatagg                                                             187

SEQ ID NO: 149          moltype = DNA    length = 147
FEATURE                 Location/Qualifiers
source                  1..147
                        mol_type = genomic DNA
                        organism = Rubus sp.
SEQUENCE: 149
gtggtttgca gaatcttcaa gaagaaaaat ctccacaaga gcttgagtag tccaatcatg    60
agcacttcta tttcttcatc tatcacagaa gaaattacaa gaagctcaag ccaaatgttt   120
gatgatgatc atgagggagc ttttgag                                       147

SEQ ID NO: 150          moltype = DNA    length = 223
FEATURE                 Location/Qualifiers
source                  1..223
                        mol_type = genomic DNA
                        organism = Rubus sp.
SEQUENCE: 150
tgagtttata gacatatcga tcgattgtta ttgaacagtt tcctttatt tgaatcaggt     60
ctcgatcacc gttgtgggag aggcagcgga ggaggggtgg gtggtttgca gaatcttcaa   120
gaagaaaaat ctccacaaga gcttgagtag tccaatcatg agcacttcta tttcttcatc   180
tatcacagaa gaaattacaa gaagctcaag ccaaatgttt gat                     223

SEQ ID NO: 151          moltype = DNA    length = 143
FEATURE                 Location/Qualifiers
source                  1..143
                        mol_type = genomic DNA
                        organism = Rubus sp.
SEQUENCE: 151
tcctttatt tgaatcaggt ctcgatcacc gttgtgggag aggcagcgga ggaggggtgg     60
gtggtttgca gaatcttcaa gaagaaaaat ctccacaaga gcttgagtag tccaatcatg   120
agcacttcta tttcttcatc tat                                           143

SEQ ID NO: 152          moltype = DNA    length = 103
FEATURE                 Location/Qualifiers
source                  1..103
                        mol_type = genomic DNA
                        organism = Rubus sp.
SEQUENCE: 152
ctcgatcacc gttgtgggag aggcagcgga ggaggggtgg gtggtttgca gaatcttcaa    60
gaagaaaaat ctccacaaga gcttgagtag tccaatcatg agc                     103

SEQ ID NO: 153          moltype = DNA    length = 63
FEATURE                 Location/Qualifiers
source                  1..63
                        mol_type = genomic DNA
                        organism = Rubus sp.
```

-continued

```
SEQUENCE: 153
aggcagcgga ggaggggtgg gtggtttgca gaatcttcaa gaagaaaaat ctccacaaga    60
gct                                                                 63

SEQ ID NO: 154          moltype = DNA  length = 223
FEATURE                 Location/Qualifiers
source                  1..223
                        mol_type = genomic DNA
                        organism = Rubus sp.
SEQUENCE: 154
accgttgtgg gagaggcagc ggaggagggg tgggtggttt gcagaatctt caagaagaaa    60
aatctccaca agagcttgag tagtccaatc atgagcactt ctatttcttc atctatcaca   120
gaagaaatta caagaagctc aagccaaatg tttgatgatg atcatgaggg agcttttgag   180
gaaatgcttc agtacatagg atcaaggacc tgcaaggaag aga                    223

SEQ ID NO: 155          moltype = DNA  length = 143
FEATURE                 Location/Qualifiers
source                  1..143
                        mol_type = genomic DNA
                        organism = Rubus sp.
SEQUENCE: 155
gcagaatctt caagaagaaa aatctccaca agagcttgag tagtccaatc atgagcactt    60
ctatttcttc atctatcaca gaagaaatta caagaagctc aagccaaatg tttgatgatg   120
atcatgaggg agcttttgag gaa                                          143

SEQ ID NO: 156          moltype = DNA  length = 103
FEATURE                 Location/Qualifiers
source                  1..103
                        mol_type = genomic DNA
                        organism = Rubus sp.
SEQUENCE: 156
aatctccaca agagcttgag tagtccaatc atgagcactt ctatttcttc atctatcaca    60
gaagaaatta caagaagctc aagccaaatg tttgatgatg atc                    103

SEQ ID NO: 157          moltype = DNA  length = 63
FEATURE                 Location/Qualifiers
source                  1..63
                        mol_type = genomic DNA
                        organism = Rubus sp.
SEQUENCE: 157
tagtccaatc atgagcactt ctatttcttc atctatcaca gaagaaatta caagaagctc    60
aag                                                                 63

SEQ ID NO: 158          moltype = DNA  length = 223
FEATURE                 Location/Qualifiers
source                  1..223
                        mol_type = genomic DNA
                        organism = Rubus sp.
SEQUENCE: 158
aaaaatctcc acaagagctt gagtagtcca atcatgagca cttctatttc ttcatctatc    60
acagaagaaa ttacaagaag ctcaagccaa atgtttgatg atgatcatga gggagctttt   120
gaggaaatgc ttcagtacat aggatcaagg acctgcaagg aagagaataa tgaacattat   180
catcttcatc ccatcaacac aggtaatagt gataagatta atg                    223

SEQ ID NO: 159          moltype = DNA  length = 143
FEATURE                 Location/Qualifiers
source                  1..143
                        mol_type = genomic DNA
                        organism = Rubus sp.
SEQUENCE: 159
cttctatttc ttcatctatc acagaagaaa ttacaagaag ctcaagccaa atgtttgatg    60
atgatcatga gggagctttt gaggaaatgc ttcagtacat aggatcaagg acctgcaagg   120
aagagaataa tgaacattat cat                                          143

SEQ ID NO: 160          moltype = DNA  length = 103
FEATURE                 Location/Qualifiers
source                  1..103
                        mol_type = genomic DNA
                        organism = Rubus sp.
SEQUENCE: 160
acagaagaaa ttacaagaag ctcaagccaa atgtttgatg atgatcatga gggagctttt    60
gaggaaatgc ttcagtacat aggatcaagg acctgcaagg aag                    103

SEQ ID NO: 161          moltype = DNA  length = 63
FEATURE                 Location/Qualifiers
source                  1..63
                        mol_type = genomic DNA
                        organism = Rubus sp.
SEQUENCE: 161
```

```
ctcaagccaa atgtttgatg atgatcatga gggagctttt gaggaaatgc ttcagtacat   60
agg                                                                63

SEQ ID NO: 162          moltype = DNA  length = 347
FEATURE                 Location/Qualifiers
source                  1..347
                        mol_type = genomic DNA
                        organism = Rubus sp.
SEQUENCE: 162
tttatagaca tatcgatcga ttgttattga acagttaatt tccttttata tgaatcaggt   60
ctcgatcacc gttgtgggag acgcagcgga ggaggggtgg gtggtttgca gaatcttcaa  120
gaagaaaaat ctccacaaga gcttgagtag tccaatcatg agcacttcta tttcttcatc  180
tatcacagaa gaaattacaa gaagctcaag ccaaatgttt gatgatgatc atgagggagc  240
ttttgaggaa atgcttcagt acataggatc aaggacctgc aaggaagaga ataatgaaca  300
ttatcatctt catcccatca acacaggtaa tagtgataac attaatg                347

SEQ ID NO: 163          moltype = DNA  length = 267
FEATURE                 Location/Qualifiers
source                  1..267
                        mol_type = genomic DNA
                        organism = Rubus sp.
SEQUENCE: 163
tccttttata tgaatcaggt ctcgatcacc gttgtgggag acgcagcgga ggaggggtgg   60
gtggtttgca gaatcttcaa gaagaaaaat ctccacaaga gcttgagtag tccaatcatg  120
agcacttcta tttcttcatc tatcacagaa gaaattacaa gaagctcaag ccaaatgttt  180
gatgatgatc atgagggagc ttttgaggaa atgcttcagt acataggatc aaggacctgc  240
aaggaagaga ataatgaaca ttatcat                                      267

SEQ ID NO: 164          moltype = DNA  length = 227
FEATURE                 Location/Qualifiers
source                  1..227
                        mol_type = genomic DNA
                        organism = Rubus sp.
SEQUENCE: 164
ctcgatcacc gttgtgggag acgcagcgga ggaggggtgg gtggtttgca gaatcttcaa   60
gaagaaaaat ctccacaaga gcttgagtag tccaatcatg agcacttcta tttcttcatc  120
tatcacagaa gaaattacaa gaagctcaag ccaaatgttt gatgatgatc atgagggagc  180
ttttgaggaa atgcttcagt acataggatc aaggacctgc aaggaag                227

SEQ ID NO: 165          moltype = DNA  length = 187
FEATURE                 Location/Qualifiers
source                  1..187
                        mol_type = genomic DNA
                        organism = Rubus sp.
SEQUENCE: 165
acgcagcgga ggaggggtgg gtggtttgca gaatcttcaa gaagaaaaat ctccacaaga   60
gcttgagtag tccaatcatg agcacttcta tttcttcatc tatcacagaa gaaattacaa  120
gaagctcaag ccaaatgttt gatgatgatc atgagggagc ttttgaggaa atgcttcagt  180
acatagg                                                            187

SEQ ID NO: 166          moltype = DNA  length = 223
FEATURE                 Location/Qualifiers
source                  1..223
                        mol_type = genomic DNA
                        organism = Rubus sp.
SEQUENCE: 166
tttatagaca tatcgatcga ttgttattga acagttaatt tccttttata tgaatcaggt   60
ctcgatcacc gttgtgggag acgcagcgga ggaggggtgg gtggtttgca gaatcttcaa  120
gaagaaaaat ctccacaaga gcttgagtag tccaatcatg agcacttcta tttcttcatc  180
tatcacagaa gaaattacaa gaagctcaag ccaaatgttt gat                    223

SEQ ID NO: 167          moltype = DNA  length = 143
FEATURE                 Location/Qualifiers
source                  1..143
                        mol_type = genomic DNA
                        organism = Rubus sp.
SEQUENCE: 167
tccttttata tgaatcaggt ctcgatcacc gttgtgggag acgcagcgga ggaggggtgg   60
gtggtttgca gaatcttcaa gaagaaaaat ctccacaaga gcttgagtag tccaatcatg  120
agcacttcta tttcttcatc tat                                          143

SEQ ID NO: 168          moltype = DNA  length = 103
FEATURE                 Location/Qualifiers
source                  1..103
                        mol_type = genomic DNA
                        organism = Rubus sp.
SEQUENCE: 168
ctcgatcacc gttgtgggag acgcagcgga ggaggggtgg gtggtttgca gaatcttcaa   60
gaagaaaaat ctccacaaga gcttgagtag tccaatcatg agc                    103
```

```
SEQ ID NO: 169          moltype = DNA  length = 63
FEATURE                 Location/Qualifiers
source                  1..63
                        mol_type = genomic DNA
                        organism = Rubus sp.
SEQUENCE: 169
acgcagcgga ggaggggtgg gtggtttgca gaatcttcaa gaagaaaaat ctccacaaga    60
gct                                                                 63

SEQ ID NO: 170          moltype = DNA  length = 223
FEATURE                 Location/Qualifiers
source                  1..223
                        mol_type = genomic DNA
                        organism = Rubus sp.
SEQUENCE: 170
accgttgtgg gagacgcagc ggaggagggg tgggtggttt gcagaatctt caagaagaaa    60
aatctccaca agagcttgag tagtccaatc atgagcactt ctatttcttc atctatcaca   120
gaagaaatta caagaagctc aagccaaatg tttgatgatg atcatgaggg agcttttgag   180
gaaatgcttc agtacatagg atcaaggacc tgcaaggaag aga                    223

SEQ ID NO: 171          moltype = DNA  length = 223
FEATURE                 Location/Qualifiers
source                  1..223
                        mol_type = genomic DNA
                        organism = Rubus sp.
SEQUENCE: 171
aaaaatctcc acaagagctt gagtagtcca atcatgagca cttctatttc ttcatctatc    60
acagaagaaa ttacaagaag ctcaagccaa atgtttgatg atgatcatga gggagctttt   120
gaggaaatgc ttcagtacat aggatcaagg acctgcaagg aagagaataa tgaacattat   180
catcttcatc ccatcaacac aggtaatagt gataacatta atg                    223

SEQ ID NO: 172          moltype = AA  length = 96
FEATURE                 Location/Qualifiers
source                  1..96
                        mol_type = protein
                        organism = Rubus sp.
SEQUENCE: 172
SITVVGEAAE EGWVVCRIFK KKNLHKSLSS PIMSTSISSS ITEEITRSSS QMFDDDHEGA    60
FEEMLQYIGS RTCKEENNEH YHLHPINTGN SDKING                             96

SEQ ID NO: 173          moltype = AA  length = 85
FEATURE                 Location/Qualifiers
source                  1..85
                        mol_type = protein
                        organism = Rubus sp.
SEQUENCE: 173
AAEEGWVVCR IFKKKNLHKS LSSPIMSTSI SSSITEEITR SSSQMFDDDH EGAFEEMLQY    60
IGSRTCKEEN NEHYHLHPIN TGNSD                                         85

SEQ ID NO: 174          moltype = AA  length = 75
FEATURE                 Location/Qualifiers
source                  1..75
                        mol_type = protein
                        organism = Rubus sp.
SEQUENCE: 174
SITVVGEAAE EGWVVCRIFK KKNLHKSLSS PIMSTSISSS ITEEITRSSS QMFDDDHEGA    60
FEEMLQYIGS RTCKE                                                    75

SEQ ID NO: 175          moltype = AA  length = 55
FEATURE                 Location/Qualifiers
source                  1..55
                        mol_type = protein
                        organism = Rubus sp.
SEQUENCE: 175
EGWVVCRIFK KKNLHKSLSS PIMSTSISSS ITEEITRSSS QMFDDDHEGA FEEML         55

SEQ ID NO: 176          moltype = AA  length = 35
FEATURE                 Location/Qualifiers
source                  1..35
                        mol_type = protein
                        organism = Rubus sp.
SEQUENCE: 176
KKNLHKSLSS PIMSTSISSS ITEEITRSSS QMFDD                              35

SEQ ID NO: 177          moltype = AA  length = 55
FEATURE                 Location/Qualifiers
source                  1..55
                        mol_type = protein
```

-continued

```
                         organism = Rubus sp.
SEQUENCE: 177
IFKKKNLHKS LSSPIMSTSI SSSITEEITR SSSQMFDDDH EGAFEEMLQY IGSRT          55

SEQ ID NO: 178           moltype = AA   length = 35
FEATURE                  Location/Qualifiers
source                   1..35
                         mol_type = protein
                         organism = Rubus sp.
SEQUENCE: 178
LSSPIMSTSI SSSITEEITR SSSQMFDDDH EGAFE                                35

SEQ ID NO: 179           moltype = AA   length = 15
FEATURE                  Location/Qualifiers
source                   1..15
                         mol_type = protein
                         organism = Rubus sp.
SEQUENCE: 179
SSSITEEITR SSSQM                                                      15

SEQ ID NO: 180           moltype = AA   length = 96
FEATURE                  Location/Qualifiers
source                   1..96
                         mol_type = protein
                         organism = Rubus sp.
SEQUENCE: 180
SITVVGDAAE EGWVVCRIFK KKNLHKSLSS PIMSTSISSS ITEEITRSSS QMFDDDHEGA     60
FEEMLQYIGS RTCKEENNEH YHLHPINTGN SDNIND                               96

SEQ ID NO: 181           moltype = DNA   length = 361
FEATURE                  Location/Qualifiers
source                   1..361
                         mol_type = genomic DNA
                         organism = Rubus sp.
SEQUENCE: 181
cagccttgac accacagtat gttagctatt aattttcgaa ctcttcaaat atttctcatc     60
agagataaat tatcaaacac ttaattggaa tgtacttttc tttcttgcag gtttctagtt    120
caattgggga gtcaatgtca gaagatgggt gggtggtttg cagggtcttc aagaagaaga    180
actaccagaa agccttggag agcccaaaat cctcctaccc gatggactca tcaaacaacc    240
aaatgctacc gggtggttcg agaaacgacg gcgttgtcga tcagattctc ttgtacatgg    300
gaaggactag ttgcaagctc gaaaaccatg actcactcca tgacagattc atgcatcttc    360
c                                                                   361

SEQ ID NO: 182           moltype = DNA   length = 281
FEATURE                  Location/Qualifiers
source                   1..281
                         mol_type = genomic DNA
                         organism = Rubus sp.
SEQUENCE: 182
ctcttcaaat atttctcatc agagataaat tatcaaacac ttaattggaa tgtacttttc     60
tttcttgcag gtttctagtt caattgggga gtcaatgtca gaagatgggt gggtggtttg    120
cagggtcttc aagaagaaga actaccagaa agccttggag agcccaaaat cctcctaccc    180
gatggactca tcaaacaacc aaatgctacc gggtggttcg agaaacgacg gcgttgtcga    240
tcagattctc ttgtacatgg gaaggactag ttgcaagctc g                        281

SEQ ID NO: 183           moltype = DNA   length = 241
FEATURE                  Location/Qualifiers
source                   1..241
                         mol_type = genomic DNA
                         organism = Rubus sp.
SEQUENCE: 183
agagataaat tatcaaacac ttaattggaa tgtacttttc tttcttgcag gtttctagtt     60
caattgggga gtcaatgtca gaagatgggt gggtggtttg cagggtcttc aagaagaaga    120
actaccagaa agccttggag agcccaaaat cctcctaccc gatggactca tcaaacaacc    180
aaatgctacc gggtggttcg agaaacgacg gcgttgtcga tcagattctc ttgtacatgg    240
g                                                                   241

SEQ ID NO: 184           moltype = DNA   length = 201
FEATURE                  Location/Qualifiers
source                   1..201
                         mol_type = genomic DNA
                         organism = Rubus sp.
SEQUENCE: 184
ttaattggaa tgtacttttc tttcttgcag gtttctagtt caattgggga gtcaatgtca     60
gaagatgggt gggtggtttg cagggtcttc aagaagaaga actaccagaa agccttggag    120
agcccaaaat cctcctaccc gatggactca tcaaacaacc aaatgctacc gggtggttcg    180
agaaacgacg gcgttgtcga t                                              201

SEQ ID NO: 185           moltype = DNA   length = 160
```

```
FEATURE              Location/Qualifiers
source               1..160
                     mol_type = genomic DNA
                     organism = Rubus sp.
SEQUENCE: 185
tttcttgcag gtttctagtt caattgggga gtcaatgtca gaagatgggt gggtggtttg    60
cagggtcttc aagaagaaga actaccagaa agccttggag agcccaaaat cctcctaccc   120
gatggactca tcaaacaacc aaatgctacc gggtggttcg                         160

SEQ ID NO: 186       moltype = DNA   length = 100
FEATURE              Location/Qualifiers
source               1..100
                     mol_type = genomic DNA
                     organism = Rubus sp.
SEQUENCE: 186
cagggtcttc aagaagaaga actaccagaa agccttggag agcccaaaat cctcctaccc    60
gatggactca tcaaacaacc aaatgctacc gggtggttcg                         100

SEQ ID NO: 187       moltype = DNA   length = 49
FEATURE              Location/Qualifiers
source               1..49
                     mol_type = genomic DNA
                     organism = Rubus sp.
SEQUENCE: 187
ctcctacccg atggactcat caaacaacca aatgctaccg gtggttcg                 49

SEQ ID NO: 188       moltype = DNA   length = 44
FEATURE              Location/Qualifiers
source               1..44
                     mol_type = genomic DNA
                     organism = Rubus sp.
SEQUENCE: 188
cagggtcttc aagaagaaga actaccagaa agccttggag agcc                     44

SEQ ID NO: 189       moltype = DNA   length = 220
FEATURE              Location/Qualifiers
source               1..220
                     mol_type = genomic DNA
                     organism = Rubus sp.
SEQUENCE: 189
cagccttgac accacagtat gttagctatt aattttcgaa ctcttcaaat atttctcatc    60
agagataaat tatcaaacac ttaattggaa tgtacttttc tttcttgcag gtttctagtt   120
caattgggga gtcaatgtca gaagatgggt gggtggtttg cagggtcttc aagaagaaga   180
actaccagaa agccttggag agcccaaaat cctcctaccc                         220

SEQ ID NO: 190       moltype = DNA   length = 140
FEATURE              Location/Qualifiers
source               1..140
                     mol_type = genomic DNA
                     organism = Rubus sp.
SEQUENCE: 190
ctcttcaaat atttctcatc agagataaat tatcaaacac ttaattggaa tgtacttttc    60
tttcttgcag gtttctagtt caattgggga gtcaatgtca gaagatgggt gggtggtttg   120
cagggtcttc aagaagaaga                                               140

SEQ ID NO: 191       moltype = DNA   length = 100
FEATURE              Location/Qualifiers
source               1..100
                     mol_type = genomic DNA
                     organism = Rubus sp.
SEQUENCE: 191
agagataaat tatcaaacac ttaattggaa tgtacttttc tttcttgcag gtttctagtt    60
caattgggga gtcaatgtca gaagatgggt gggtggtttg                         100

SEQ ID NO: 192       moltype = DNA   length = 60
FEATURE              Location/Qualifiers
source               1..60
                     mol_type = genomic DNA
                     organism = Rubus sp.
SEQUENCE: 192
ttaattggaa tgtacttttc tttcttgcag gtttctagtt caattgggga gtcaatgtca    60

SEQ ID NO: 193       moltype = DNA   length = 221
FEATURE              Location/Qualifiers
source               1..221
                     mol_type = genomic DNA
                     organism = Rubus sp.
SEQUENCE: 193
cttgacacca cagtatgtta gctattaatt ttcgaactct tcaaatattt ctcatcagag    60
```

```
ataaattatc aaacacttaa ttggaatgta cttttctttc ttgcaggttt ctagttcaat    120
tggggagtca atgtcagaag atgggtgggt ggtttgcagg gtcttcaaga agaagaacta    180
ccagaaagcc ttggagagcc caaaatcctc tacccgatg g                        221

SEQ ID NO: 194          moltype = DNA   length = 141
FEATURE                 Location/Qualifiers
source                  1..141
                        mol_type = genomic DNA
                        organism = Rubus sp.
SEQUENCE: 194
tcaaatatttt ctcatcagag ataaattatc aaacacttaa ttggaatgta cttttctttc    60
ttgcaggttt ctagttcaat tggggagtca atgtcagaag atgggtgggt ggtttgcagg    120
gtcttcaaga agaagaacta c                                              141

SEQ ID NO: 195          moltype = DNA   length = 101
FEATURE                 Location/Qualifiers
source                  1..101
                        mol_type = genomic DNA
                        organism = Rubus sp.
SEQUENCE: 195
ataaattatc aaacacttaa ttggaatgta cttttctttc ttgcaggttt ctagttcaat    60
tggggagtca atgtcagaag atgggtgggt ggtttgcagg g                        101

SEQ ID NO: 196          moltype = DNA   length = 60
FEATURE                 Location/Qualifiers
source                  1..60
                        mol_type = genomic DNA
                        organism = Rubus sp.
SEQUENCE: 196
tggaatgtac ttttctttct tgcaggtttc tagttcaatt ggggagtcaa tgtcagaaga    60

SEQ ID NO: 197          moltype = DNA   length = 220
FEATURE                 Location/Qualifiers
source                  1..220
                        mol_type = genomic DNA
                        organism = Rubus sp.
SEQUENCE: 197
agagataaat tatcaaacac ttaattggaa tgtacttttc tttcttgcag gtttctagtt    60
caattgggga gtcaatgtca gaagatgggt gggtggtttg cagggtcttc aagaagaaga    120
actaccagaa agccttggag agcccaaaat cctcctaccc gatggactca tcaaacaacc    180
aaatgctacc gggtggttcg agaaacgacg gcgttgtcga                          220

SEQ ID NO: 198          moltype = DNA   length = 140
FEATURE                 Location/Qualifiers
source                  1..140
                        mol_type = genomic DNA
                        organism = Rubus sp.
SEQUENCE: 198
tttcttgcag gtttctagtt caattgggga gtcaatgtca gaagatgggt gggtggtttg    60
cagggtcttc aagaagaaga actaccagaa agccttggag agcccaaaat cctcctaccc    120
gatggactca tcaaacaacc                                                140

SEQ ID NO: 199          moltype = DNA   length = 100
FEATURE                 Location/Qualifiers
source                  1..100
                        mol_type = genomic DNA
                        organism = Rubus sp.
SEQUENCE: 199
caattgggga gtcaatgtca gaagatgggt gggtggtttg cagggtcttc aagaagaaga    60
actaccagaa agccttggag agcccaaaat cctcctaccc                          100

SEQ ID NO: 200          moltype = DNA   length = 60
FEATURE                 Location/Qualifiers
source                  1..60
                        mol_type = genomic DNA
                        organism = Rubus sp.
SEQUENCE: 200
gaagatgggt gggtggtttg cagggtcttc aagaagaaga actaccagaa agccttggag    60

SEQ ID NO: 201          moltype = DNA   length = 220
FEATURE                 Location/Qualifiers
source                  1..220
                        mol_type = genomic DNA
                        organism = Rubus sp.
SEQUENCE: 201
aattatcaaa cacttaattg gaatgtactt tctttcttg caggtttcta gttcaattg      60
ggagtcaatg tcagaagatg ggtgggtggt ttgcagggtc ttcaagaaga agaactacca    120
gaaagccttg gagagcccaa aatcctccta cccgatggac tcatcaaaca accaaatgct    180
accgggtggt tcgagaaacg acggcgttgt cgatcagatt                          220
```

```
SEQ ID NO: 202          moltype = DNA   length = 140
FEATURE                 Location/Qualifiers
source                  1..140
                        mol_type = genomic DNA
                        organism = Rubus sp.
SEQUENCE: 202
aggtttctag ttcaattggg gagtcaatgt cagaagatgg gtgggtggtt tgcagggtct   60
tcaagaagaa gaactaccag aaagccttgg agagcccaaa atcctcctac ccgatggact  120
catcaaacaa ccaaatgcta                                              140

SEQ ID NO: 203          moltype = DNA   length = 100
FEATURE                 Location/Qualifiers
source                  1..100
                        mol_type = genomic DNA
                        organism = Rubus sp.
SEQUENCE: 203
ggagtcaatg tcagaagatg ggtgggtggt ttgcagggtc ttcaagaaga agaactacca   60
gaaagccttg gagagcccaa aatcctccta cccgatggac                        100

SEQ ID NO: 204          moltype = DNA   length = 60
FEATURE                 Location/Qualifiers
source                  1..60
                        mol_type = genomic DNA
                        organism = Rubus sp.
SEQUENCE: 204
ggtgggtggt ttgcagggtc ttcaagaaga agaactacca gaaagccttg gagagcccaa   60

SEQ ID NO: 205          moltype = DNA   length = 220
FEATURE                 Location/Qualifiers
source                  1..220
                        mol_type = genomic DNA
                        organism = Rubus sp.
SEQUENCE: 205
ttggaatgta cttttctttc ttgcaggttt ctagttcaat tggggagtca atgtcagaag   60
atgggtgggt ggtttgcagg gtcttcaaga agaagaacta ccagaaagcc ttggagagcc  120
caaaatcctc ctacccgatg gactcatcaa acaaccaaat gctaccgggt ggttcgagaa  180
acgacggcgt tgtcgatcag attctcttgt acatgggaag                        220

SEQ ID NO: 206          moltype = DNA   length = 140
FEATURE                 Location/Qualifiers
source                  1..140
                        mol_type = genomic DNA
                        organism = Rubus sp.
SEQUENCE: 206
tggggagtca atgtcagaag atgggtgggt ggtttgcagg gtcttcaaga agaagaacta   60
ccagaaagcc ttggagagcc caaaatcctc ctacccgatg gactcatcaa acaaccaaat  120
gctaccgggt ggttcgagaa                                              140

SEQ ID NO: 207          moltype = DNA   length = 100
FEATURE                 Location/Qualifiers
source                  1..100
                        mol_type = genomic DNA
                        organism = Rubus sp.
SEQUENCE: 207
atgggtgggt ggtttgcagg gtcttcaaga agaagaacta ccagaaagcc ttggagagcc   60
caaaatcctc ctacccgatg gactcatcaa acaaccaaat                        100

SEQ ID NO: 208          moltype = DNA   length = 60
FEATURE                 Location/Qualifiers
source                  1..60
                        mol_type = genomic DNA
                        organism = Rubus sp.
SEQUENCE: 208
gtcttcaaga agaagaacta ccagaaagcc ttggagagcc caaaatcctc ctacccgatg   60

SEQ ID NO: 209          moltype = DNA   length = 220
FEATURE                 Location/Qualifiers
source                  1..220
                        mol_type = genomic DNA
                        organism = Rubus sp.
SEQUENCE: 209
tttctagttc aattggggag tcaatgtcag aagatgggtg gtggtttgc agggtcttca    60
agaagaagaa ctaccagaaa gccttggaga gcccaaaatc ctcctacccg atggactcat  120
caaacaacca aatgctaccg ggtggttcga gaaacgacgg cgttgtcgat cagattctct  180
tgtacatggg aaggactagt tgcaagctcg aaaaccatga                        220

SEQ ID NO: 210          moltype = DNA   length = 140
FEATURE                 Location/Qualifiers
```

```
                    source              1..140
                                        mol_type = genomic DNA
                                        organism = Rubus sp.
SEQUENCE: 210
ggtggtttgc agggtcttca agaagaagaa ctaccagaaa gccttggaga gcccaaaatc    60
ctcctacccg atggactcat caaacaacca aatgctaccg ggtggttcga gaaacgacgg   120
cgttgtcgat cagattctct                                               140

SEQ ID NO: 211              moltype = DNA   length = 100
FEATURE                     Location/Qualifiers
source                      1..100
                            mol_type = genomic DNA
                            organism = Rubus sp.
SEQUENCE: 211
agaagaagaa ctaccagaaa gccttggaga gcccaaaatc ctcctacccg atggactcat    60
caaacaacca aatgctaccg ggtggttcga gaaacgacgg                         100

SEQ ID NO: 212              moltype = DNA   length = 60
FEATURE                     Location/Qualifiers
source                      1..60
                            mol_type = genomic DNA
                            organism = Rubus sp.
SEQUENCE: 212
gccttggaga gcccaaaatc ctcctacccg atggactcat caaacaacca aatgctaccg    60

SEQ ID NO: 213              moltype = DNA   length = 220
FEATURE                     Location/Qualifiers
source                      1..220
                            mol_type = genomic DNA
                            organism = Rubus sp.
SEQUENCE: 213
tcaattgggg agtcaatgtc agaagatggg tgggtggttt gcagggtctt caagaagaag    60
aactaccaga aagccttgga gagcccaaaa tcctcctacc cgatggactc atcaaacaac   120
caaatgctac cgggtggttc gagaaacgac ggcgttgtcg atcagattct cttgtacatg   180
ggaaggacta gttgcaagct cgaaaaccat gactcactcc                         220

SEQ ID NO: 214              moltype = DNA   length = 140
FEATURE                     Location/Qualifiers
source                      1..140
                            mol_type = genomic DNA
                            organism = Rubus sp.
SEQUENCE: 214
gcagggtctt caagaagaag aactaccaga aagccttgga gagcccaaaa tcctcctacc    60
cgatggactc atcaaacaac caaatgctac cgggtggttc gagaaacgac ggcgttgtcg   120
atcagattct cttgtacatg                                               140

SEQ ID NO: 215              moltype = DNA   length = 101
FEATURE                     Location/Qualifiers
source                      1..101
                            mol_type = genomic DNA
                            organism = Rubus sp.
SEQUENCE: 215
aactaccaga aagccttgga gagcccaaaa tcctcctacc cgatggactc atcaaacaac    60
caaatgctac cgggtggttc gagaaacgac ggcgttgtcg a                       101

SEQ ID NO: 216              moltype = DNA   length = 60
FEATURE                     Location/Qualifiers
source                      1..60
                            mol_type = genomic DNA
                            organism = Rubus sp.
SEQUENCE: 216
gagcccaaaa tcctcctacc cgatggactc atcaaacaac caaatgctac cgggtggttc    60

SEQ ID NO: 217              moltype = DNA   length = 220
FEATURE                     Location/Qualifiers
source                      1..220
                            mol_type = genomic DNA
                            organism = Rubus sp.
SEQUENCE: 217
aagatgggtg ggtggtttgc agggtcttca agaagaagaa ctaccagaaa gccttggaga    60
gcccaaaatc ctcctacccg atggactcat caaacaacca aatgctaccg ggtggttcga   120
gaaacgacgg cgttgtcgat cagattctct tgtacatggg aaggactagt tgcaagctcg   180
aaaaccatga ctcactccat gacagattca tgcatcttcc                         220

SEQ ID NO: 218              moltype = DNA   length = 140
FEATURE                     Location/Qualifiers
source                      1..140
                            mol_type = genomic DNA
                            organism = Rubus sp.
```

-continued

```
SEQUENCE: 218
ctaccagaaa gccttggaga gcccaaaatc ctcctacccg atggactcat caaacaacca    60
aatgctaccg ggtggttcga gaaacgacgg cgttgtcgat cagattctct tgtacatggg   120
aaggactagt tgcaagctcg                                                140

SEQ ID NO: 219          moltype = DNA  length = 100
FEATURE                 Location/Qualifiers
source                  1..100
                        mol_type = genomic DNA
                        organism = Rubus sp.
SEQUENCE: 219
gcccaaaatc ctcctacccg atggactcat caaacaacca aatgctaccg ggtggttcga    60
gaaacgacgg cgttgtcgat cagattctct tgtacatggg                         100

SEQ ID NO: 220          moltype = DNA  length = 60
FEATURE                 Location/Qualifiers
source                  1..60
                        mol_type = genomic DNA
                        organism = Rubus sp.
SEQUENCE: 220
atggactcat caaacaacca aatgctaccg ggtggttcga gaaacgacgg cgttgtcgat    60

SEQ ID NO: 221          moltype = DNA  length = 339
FEATURE                 Location/Qualifiers
source                  1..339
                        mol_type = genomic DNA
                        organism = Rubus sp.
SEQUENCE: 221
cagccttgac accacagtaa gttagctatt aattttcgaa ctcttcaaat atttctcatc    60
agagataaat tatcaaacac ttaattggaa tgcacttttc tttcttgcag gtttctagtt   120
caattgggga gtcaatgtca gaagatgggt gggtggtttg cagggtcttc aagaagaaga   180
actaccagaa agccttggag agcccaaaat cctcctaccc gatggactca tcaaacaacc   240
aaatgctacc gggtggtatg agaaacgacg gcgttgtcga tcagattctc ttgtacatgg   300
gaaggactag ttgcaagctc gaaaaccatg actcactcc                          339

SEQ ID NO: 222          moltype = DNA  length = 259
FEATURE                 Location/Qualifiers
source                  1..259
                        mol_type = genomic DNA
                        organism = Rubus sp.
SEQUENCE: 222
ctcttcaaat atttctcatc agagataaat tatcaaacac ttaattggaa tgcacttttc    60
tttcttgcag gtttctagtt caattgggga gtcaatgtca gaagatgggt gggtggtttg   120
cagggtcttc aagaagaaga actaccagaa agccttggag agcccaaaat cctcctaccc   180
gatggactca tcaaacaacc aaatgctacc gggtggtatg agaaacgacg gcgttgtcga   240
tcagattctc ttgtacatg                                                259

SEQ ID NO: 223          moltype = DNA  length = 219
FEATURE                 Location/Qualifiers
source                  1..219
                        mol_type = genomic DNA
                        organism = Rubus sp.
SEQUENCE: 223
agagataaat tatcaaacac ttaattggaa tgcacttttc tttcttgcag gtttctagtt    60
caattgggga gtcaatgtca gaagatgggt gggtggtttg cagggtcttc aagaagaaga   120
actaccagaa agccttggag agcccaaaat cctcctaccc gatggactca tcaaacaacc   180
aaatgctacc gggtggtatg agaaacgacg gcgttgtcg                          219

SEQ ID NO: 224          moltype = DNA  length = 179
FEATURE                 Location/Qualifiers
source                  1..179
                        mol_type = genomic DNA
                        organism = Rubus sp.
SEQUENCE: 224
ttaattggaa tgcacttttc tttcttgcag gtttctagtt caattgggga gtcaatgtca    60
gaagatgggt gggtggtttg cagggtcttc aagaagaaga actaccagaa agccttggag   120
agcccaaaat cctcctaccc gatggactca tcaaacaacc aaatgctacc gggtggtat    179

SEQ ID NO: 225          moltype = DNA  length = 139
FEATURE                 Location/Qualifiers
source                  1..139
                        mol_type = genomic DNA
                        organism = Rubus sp.
SEQUENCE: 225
tttcttgcag gtttctagtt caattgggga gtcaatgtca gaagatgggt gggtggtttg    60
cagggtcttc aagaagaaga actaccagaa agccttggag agcccaaaat cctcctaccc   120
gatggactca tcaaacaac                                                139

SEQ ID NO: 226          moltype = DNA  length = 79
```

```
FEATURE                 Location/Qualifiers
source                  1..79
                        mol_type = genomic DNA
                        organism = Rubus sp.
SEQUENCE: 226
cagggtcttc aagaagaaga actaccagaa agccttggag agcccaaaat cctcctaccc    60
gatggactca tcaaacaac                                                 79

SEQ ID NO: 227          moltype = DNA   length = 64
FEATURE                 Location/Qualifiers
source                  1..64
                        mol_type = genomic DNA
                        organism = Rubus sp.
SEQUENCE: 227
ttcaagaaga agaactacca gaaagccttg gagagcccaa atcctcctac ccgatggac    60
tcat                                                                 64

SEQ ID NO: 228          moltype = DNA   length = 47
FEATURE                 Location/Qualifiers
source                  1..47
                        mol_type = genomic DNA
                        organism = Rubus sp.
SEQUENCE: 228
ccagaaagcc ttggagagcc caaaatcctc ctacccgatg gactcat                  47

SEQ ID NO: 229          moltype = DNA   length = 220
FEATURE                 Location/Qualifiers
source                  1..220
                        mol_type = genomic DNA
                        organism = Rubus sp.
SEQUENCE: 229
cagccttgac accacagtaa gttagctatt aattttcgaa ctcttcaaat atttctcatc    60
agagataaat tatcaaacac ttaattggaa tgcacttttc tttcttgcag gtttctagtt   120
caattgggga gtcaatgtca gaagatgggt gggtggtttg cagggtcttc aagaagaaga   180
actaccagaa agccttggag agcccaaaat cctcctaccc                         220

SEQ ID NO: 230          moltype = DNA   length = 140
FEATURE                 Location/Qualifiers
source                  1..140
                        mol_type = genomic DNA
                        organism = Rubus sp.
SEQUENCE: 230
ctcttcaaat atttctcatc agagataaat tatcaaacac ttaattggaa tgcacttttc    60
tttcttgcag gtttctagtt caattgggga gtcaatgtca gaagatgggt gggtggtttg   120
cagggtcttc aagaagaaga                                               140

SEQ ID NO: 231          moltype = DNA   length = 100
FEATURE                 Location/Qualifiers
source                  1..100
                        mol_type = genomic DNA
                        organism = Rubus sp.
SEQUENCE: 231
agagataaat tatcaaacac ttaattggaa tgcacttttc tttcttgcag gtttctagtt    60
caattgggga gtcaatgtca gaagatgggt gggtggtttg                         100

SEQ ID NO: 232          moltype = DNA   length = 60
FEATURE                 Location/Qualifiers
source                  1..60
                        mol_type = genomic DNA
                        organism = Rubus sp.
SEQUENCE: 232
ttaattggaa tgcacttttc tttcttgcag gtttctagtt caattgggga gtcaatgtca    60

SEQ ID NO: 233          moltype = DNA   length = 220
FEATURE                 Location/Qualifiers
source                  1..220
                        mol_type = genomic DNA
                        organism = Rubus sp.
SEQUENCE: 233
cttgacacca cagtaagtta gctattaatt ttcgaactct tcaaatattt ctcatcagag    60
ataaattatc aaacacttaa ttggaatgca cttttctttc ttgcaggttt ctagttcaat   120
tggggagtca atgtcagaag atgggtgggt ggtttgcagg gtcttcaaga agaagaacta   180
ccagaaagcc ttggagagcc caaaatcctc ctacccgatg                         220

SEQ ID NO: 234          moltype = DNA   length = 140
FEATURE                 Location/Qualifiers
source                  1..140
                        mol_type = genomic DNA
                        organism = Rubus sp.
```

-continued

```
SEQUENCE: 234
tcaaatattt ctcatcagag ataaattatc aaacacttaa ttggaatgca ctttctttc    60
ttgcaggttt ctagttcaat tggggagtca atgtcagaag atgggtgggt ggtttgcagg   120
gtcttcaaga agaagaacta                                               140

SEQ ID NO: 235          moltype = DNA   length = 100
FEATURE                 Location/Qualifiers
source                  1..100
                        mol_type = genomic DNA
                        organism = Rubus sp.
SEQUENCE: 235
ataaattatc aaacacttaa ttggaatgca ctttctttc ttgcaggttt ctagttcaat    60
tggggagtca atgtcagaag atgggtgggt ggtttgcagg                         100

SEQ ID NO: 236          moltype = DNA   length = 60
FEATURE                 Location/Qualifiers
source                  1..60
                        mol_type = genomic DNA
                        organism = Rubus sp.
SEQUENCE: 236
ttggaatgca ctttctttc ttgcaggttt ctagttcaat tggggagtca atgtcagaag    60

SEQ ID NO: 237          moltype = DNA   length = 220
FEATURE                 Location/Qualifiers
source                  1..220
                        mol_type = genomic DNA
                        organism = Rubus sp.
SEQUENCE: 237
agagataaat tatcaaacac ttaattggaa tgcactttc ttcttgcag gtttctagtt    60
caattgggga gtcaatgtca gaagatgggt gggtggtttg cagggtcttc aagaagaaga  120
actaccagaa agccttggag agcccaaaat cctcctaccc gatggactca tcaaacaacc  180
aaatgctacc gggtggtatg agaaacgacg gcgttgtcga                        220

SEQ ID NO: 238          moltype = DNA   length = 220
FEATURE                 Location/Qualifiers
source                  1..220
                        mol_type = genomic DNA
                        organism = Rubus sp.
SEQUENCE: 238
aattatcaaa cacttaattg gaatgcactt tctttcttg caggtttcta gttcaattgg    60
ggagtcaatg tcagaagatg ggtgggtggt ttgcagggtc ttcaagaaga agaactacca  120
gaaagccttg gagagcccaa aatcctccta cccgatggac tcatcaaaca accaaatgct  180
accgggtggt atgagaaacg acggcgttgt cgatcagatt                        220

SEQ ID NO: 239          moltype = DNA   length = 140
FEATURE                 Location/Qualifiers
source                  1..140
                        mol_type = genomic DNA
                        organism = Rubus sp.
SEQUENCE: 239
caggtttcta gttcaattgg ggagtcaatg tcagaagatg ggtgggtggt ttgcagggtc    60
ttcaagaaga agaactacca gaaagccttg gagagcccaa aatcctccta cccgatggac  120
tcatcaaaca accaaatgct                                               140

SEQ ID NO: 240          moltype = DNA   length = 220
FEATURE                 Location/Qualifiers
source                  1..220
                        mol_type = genomic DNA
                        organism = Rubus sp.
SEQUENCE: 240
ttggaatgca ctttctttc ttgcaggttt ctagttcaat tggggagtca atgtcagaag    60
atgggtgggt ggtttgcagg gtcttcaaga agaagaacta ccagaaagcc ttggagagcc  120
caaaatcctc ctacccgatg gactcatcaa acaaccaaat gctaccgggt ggtatgagaa  180
acgacggcgt tgtcgatcag attctcttgt acatgggaag                        220

SEQ ID NO: 241          moltype = DNA   length = 140
FEATURE                 Location/Qualifiers
source                  1..140
                        mol_type = genomic DNA
                        organism = Rubus sp.
SEQUENCE: 241
tggggagtca atgtcagaag atgggtgggt ggtttgcagg gtcttcaaga agaagaacta    60
ccagaaagcc ttggagagcc caaaatcctc ctacccgatg gactcatcaa acaaccaaat  120
gctaccgggt ggtatgagaa                                               140

SEQ ID NO: 242          moltype = DNA   length = 220
FEATURE                 Location/Qualifiers
source                  1..220
                        mol_type = genomic DNA
```

-continued

```
                        organism = Rubus sp.
SEQUENCE: 242
tttctagttc aattggggag tcaatgtcag aagatgggtg ggtggtttgc agggtcttca    60
agaagaagaa ctaccagaaa gccttggaga gcccaaaatc ctcctacccg atggactcat   120
caaacaacca aatgctaccg ggtggtatga gaaacgacgg cgttgtcgat cagattctct   180
tgtacatggg aaggactagt tgcaagctcg aaaaccatga                         220

SEQ ID NO: 243          moltype = DNA   length = 140
FEATURE                 Location/Qualifiers
source                  1..140
                        mol_type = genomic DNA
                        organism = Rubus sp.
SEQUENCE: 243
ggtggtttgc agggtcttca agaagaagaa ctaccagaaa gccttggaga gcccaaaatc    60
ctcctacccg atggactcat caaacaacca aatgctaccg ggtggtatga gaaacgacgg   120
cgttgtcgat cagattctct                                               140

SEQ ID NO: 244          moltype = DNA   length = 100
FEATURE                 Location/Qualifiers
source                  1..100
                        mol_type = genomic DNA
                        organism = Rubus sp.
SEQUENCE: 244
agaagaagaa ctaccagaaa gccttggaga gcccaaaatc ctcctacccg atggactcat    60
caaacaacca aatgctaccg ggtggtatga gaaacgacgg                         100

SEQ ID NO: 245          moltype = DNA   length = 220
FEATURE                 Location/Qualifiers
source                  1..220
                        mol_type = genomic DNA
                        organism = Rubus sp.
SEQUENCE: 245
tcaattgggg agtcaatgtc agaagatggg tgggtggttt gcagggtctt caagaagaag    60
aactaccaga aagccttgga gagcccaaaa tcctcctacc cgatggactc atcaaacaac   120
caaatgctac cgggtggtat gagaaacgac ggcgttgtcg atcagattct cttgtacatg   180
ggaaggacta gttgcaagct cgaaaaccat gactcactcc                         220

SEQ ID NO: 246          moltype = DNA   length = 140
FEATURE                 Location/Qualifiers
source                  1..140
                        mol_type = genomic DNA
                        organism = Rubus sp.
SEQUENCE: 246
gcagggtctt caagaagaag aactaccaga aagccttgga gagcccaaaa tcctcctacc    60
cgatggactc atcaaacaac caaatgctac cgggtggtat gagaaacgac ggcgttgtcg   120
atcagattct cttgtacatg                                               140

SEQ ID NO: 247          moltype = DNA   length = 100
FEATURE                 Location/Qualifiers
source                  1..100
                        mol_type = genomic DNA
                        organism = Rubus sp.
SEQUENCE: 247
aactaccaga aagccttgga gagcccaaaa tcctcctacc cgatggactc atcaaacaac    60
caaatgctac cgggtggtat gagaaacgac ggcgttgtcg                         100

SEQ ID NO: 248          moltype = DNA   length = 60
FEATURE                 Location/Qualifiers
source                  1..60
                        mol_type = genomic DNA
                        organism = Rubus sp.
SEQUENCE: 248
gagcccaaaa tcctcctacc cgatggactc atcaaacaac caaatgctac cgggtggtat    60

SEQ ID NO: 249          moltype = AA   length = 238
FEATURE                 Location/Qualifiers
source                  1..238
                        mol_type = protein
                        organism = Rubus sp.
SEQUENCE: 249
SSSIGESMSE DGWVVCRVFK KKNYQKALES PKSSYPMDSS NNQMLPGGSR NDGVVDQILL    60
YMGRTSCKLE NHDSLHDRFM HLPRLESQTS LPSLAVHFDH DRSFKGCYHD QTIDDMLIET   120
DHQQPSPTTN QPNDPVDHDD PKTRIVNDWA TIHQLVASQL NGHEDTSKHL SCFGDPNMAF   180
CSSPPSNDED LQLSYPYLRP GRISQNQPEV YNSENDLWSF TKSSPSPSSS DPLCHLSV     238

SEQ ID NO: 250          moltype = AA   length = 62
FEATURE                 Location/Qualifiers
source                  1..62
                        mol_type = protein
```

```
                            organism   = Rubus sp.
SEQUENCE: 250
SSSIGESMSE DGWVVCRVFK KKNYQKALES PKSSYPMDSS NNQMLPGGSR NDGVVDQILL      60
YM                                                                    62

SEQ ID NO: 251          moltype = AA  length = 42
FEATURE                 Location/Qualifiers
source                  1..42
                        mol_type  = protein
                        organism  = Rubus sp.
SEQUENCE: 251
SSSIGESMSE DGWVVCRVFK KKNYQKALES PKSSYPMDSS NN                         42

SEQ ID NO: 252          moltype = AA  length = 32
FEATURE                 Location/Qualifiers
source                  1..32
                        mol_type  = protein
                        organism  = Rubus sp.
SEQUENCE: 252
ESMSEDGWVV CRVFKKKNYQ KALESPKSSY PM                                    32

SEQ ID NO: 253          moltype = AA  length = 21
FEATURE                 Location/Qualifiers
source                  1..21
                        mol_type  = protein
                        organism  = Rubus sp.
SEQUENCE: 253
GWVVCRVFKK KNYQKALESP K                                                21

SEQ ID NO: 254          moltype = AA  length = 238
FEATURE                 Location/Qualifiers
source                  1..238
                        mol_type  = protein
                        organism  = Rubus sp.
SEQUENCE: 254
SSSIGESMSE DGWVVCRVFK KKNYQKALES PKSSYPMDSS NNQMLPGGMR NDGVVDQILL      60
YMGRTSCKLE NHDSLHDRFM HLPRLESQTS LPSLAVHFDH DRSFKACYHD QTIDDMLIET     120
DHQQPSPTTN QPNDPVDHDD PKTRIVNDWA TIHQLVASQL NGHEDTSKHL SCFGDPNMAF     180
CSSPPSNDED LQLSYPYLRP GRISQNQPEV YNSENDLWSF TKSSPSPSSS DPLCHLSV       238

SEQ ID NO: 255          moltype = AA  length = 62
FEATURE                 Location/Qualifiers
source                  1..62
                        mol_type  = protein
                        organism  = Rubus sp.
SEQUENCE: 255
SSSIGESMSE DGWVVCRVFK KKNYQKALES PKSSYPMDSS NNQMLPGGMR NDGVVDQILL      60
YM                                                                    62

SEQ ID NO: 256          moltype = DNA  length = 1560
FEATURE                 Location/Qualifiers
source                  1..1560
                        mol_type  = genomic DNA
                        organism  = Rubus sp.
SEQUENCE: 256
atgactgaaa acgtgagtat atctgtgaat gggcaatctc aagtccctcc tggtttcaga      60
tttcatccaa ctgaagagga gctcttgcag tactacttga ggaagaaggt ctccaatcag     120
agcattgatc tcgatgtcat ctgcgatgta gatctcaata gcttgagcc atgggatata      180
caaggtacgt acgtacataa atgatatggg aaatatttaa ttcagtctag tagttctccg     240
acaagttatg tatccacaat aaatatgaatt aatccaagtt ttgatgttgg ttttgcagag    300
aagtgtaaga taggaaccac accgcaaaat gattggtatt tcttcagcca caaagacaag     360
aaatacccta ccggaacacg tacaaaccgt gcaacggctg ccggattctg aaggccacc      420
gggcgtgata aggtgataag cagcaactgc aggcggatcg gtatgaggaa gactcttgtg     480
ttctacaaag gccgagctcc ccacggccaa aagtccgatt ggatcatgca cgagtataga    540
ctcgacgaca cactagcag catcactaat gtaagtcatt taattcaaac cagagtttca    600
gtcctcggga aatgttcaag tgcggacttt gcagaccttg tgtctacaga acgtttgcaa    660
agtctgcagt ctgcagtata gatgtccaca cttgaacatt ttgagtttat agacatatcg    720
atcgattgtt cttgaacagt ttccttttat atgaatcagg tctctatcac cgttgtggga    780
gaggcagcag aggagggatg ggtggtttgc agaatcttca agaagaaaaa tctccacaag    840
agcttgagta gtccaatcat gagcacttct atttcttcat ctatcacagc agaaattaca    900
agaagctcaa gccaaatgtt tgatgatgat gatcaggagg gagcttttga ggaaatgctt    960
cagtacatag gatcaaggac ctgcaaggaa gagattaatg aacattatca tcttcatccc   1020
atcaacacag gtaatagtga taacatgaat ggctaccatg atcatggtga taggttcttg   1080
aaacttccga gccttgagag ccccaactcc accagtagcc aaaacggtta tcagcccatt   1140
atcaatcatg aagacatggt catagatcag aatgaaggca caattgctaa ccagcatctg   1200
ggttatcagc acgtggacga ctcagccagc ctcaccaact gggcagcgct tgatcgtttg   1260
gtggcttcac aactcaatgg cggccatgaa acggggtcgt ctaggcaatt tcttgctta    1320
attgaaccca ctcttaatgt ttactgcact agtactactg ataatgagct tcagttaccg   1380
agtacattac gatcgtcaac ttcttcgaat tcatccagca aatcatacca cgccacccaa   1440
```

```
ccggaataca acaatagcga gattgacctg tggactactt ttggtgctgc tcgactacaa 1500
tcatcatccc ctttgtcatc ctccgacgca ctatgccacg tgtcgaacgc tcctatataa 1560

SEQ ID NO: 257           moltype = AA  length = 418
FEATURE                  Location/Qualifiers
source                   1..418
                         mol_type = protein
                         organism = Rubus sp.
SEQUENCE: 257
MTENVSISVN GQSQVPPGFR FHPTEEELLQ YYLRKKVSNQ SIDLDVICDV DLNKLEPWDI  60
QEKCKIGTTP QNDWYFFSHK DKKYPTGTRT NRATAAGFWK ATGRDKVISS NCRRIGMRKT 120
LVFYKGRAPH GQKSDWIMHE YRLDDNTSSI TNVSITVVGE AAEEGWVVCR IFKKKNLHKS 180
LSSPIMSTSI SSSITAEITR SSSQMFDDDD QEGAFEEMLQ YIGSRTCKEE INEHYHLHPI 240
NTGNSDNMNG YHDHGDRFLK LPSLESPNST SSQNGYQPII NHEDMVIDQN EGTIANQHLG 300
YQHVDDSASL TNWAALDRLV ASQLNGGHET GSSRQFSCLI EPTLNVYCTS TTDNELQLPS 360
TLRSSTSSNS SSKSYHATQP EYNNSEIDLW TTFGAARLQS SSPLSSSDAL CHVSNAPI   418

SEQ ID NO: 258           moltype = DNA  length = 1556
FEATURE                  Location/Qualifiers
source                   1..1556
                         mol_type = genomic DNA
                         organism = Rubus sp.
SEQUENCE: 258
atgactgaaa acgtgagtat atctgtgaat gggcaatctc aagtccctcc tggtttcaga   60
tttcatccaa ctgaagagga gctcttgcag tactacttga ggaagaaggt ctccaatcag  120
agcagttgatc tcgatgtcat ctgcgatgta gatctcaata agcttgagcc atgggatata  180
caaggtacgt acgtacataa atgatatggg aaatatttaa ttcagtctag tagttctccg  240
acaagttatg tatcacaatt aatatgaatt aatccaagtt ttgatgttgg ttttgcagag  300
aagtgtaaga taggaaccac accgcaaaat gattggtatt tcttcagcca caagacaag   360
aaatacccta ccggaaacacg tacaaaccgt gcaacggctg ccggattctg gaaggccacc  420
gggcgtgata aggtgataag cagcaactgc aggcggatcg gtatgaggaa gactcttgtg  480
ttctacaaag gccgagctcc ccacggcaa aagtccgatt ggatcatgca cgagtataga   540
ctcgacgaca cactagcag catcactaat gtaagtcatt taatttaaac cagagtttca  600
gtcctcggga aatgttcaag tgcggacttt gcagaccttg tgtctacaga acgtttgcac  660
aatctgcagt ctgcagtaca gatgtccaca cttgaacatt ttgagtttat agacatatcg  720
atcgattgtt cttgaacagt ttccttatga atcaggtctc tatcaccgtt gtgggagagg  780
cagcagagga gggatgggtg gtttgcagaa tcttcaagaa gaaaaatctc cacaagagct  840
tgagtagtcc aatcatgagc acttctattt cttcatctat cacagcagaa attacaagaa  900
gctcaagcca aatgtttgac gatgatgatc aggacggagc ttttgaggaa atgcttcagt  960
acataggatc aaggacctgc aaggaagaga ttaatgaaca ttatcatctt catcccatca 1020
acacagataa tagtgataac atgaatggct accatgatca tggtgatagg ttcttgaaac 1080
ttccgagcct tgagagcccc aactccacca gtagccaaaa cggttatcag cccattatca 1140
atcatgaaga catggtcata gatcagaatg aaggcacaat tgctaaccag catctgggtt 1200
atcagcacgt ggacgactca gccagcctca ccaactgggc agcgcttgat cgtttggtgg 1260
cttcacaact caatgcggc catgaaacgg ggtcgtctag gcaattttct tgcttaattg 1320
aacccactct taatgtttac tgcactagta ctactgataa tgagcttcag ttaccgagta 1380
cattacgatc atcaacttct tcgaattcat ccagcaaatc ataccacgcc acccaaccgg 1440
aatacaacaa tagcgagatt gacctgtgga ctacttttgg tgctgctcga ctacaatcat 1500
catcccttt gtcatcctcc gacgcactat gccacgtgtc gaactctcct atataa      1556

SEQ ID NO: 259           moltype = AA  length = 418
FEATURE                  Location/Qualifiers
source                   1..418
                         mol_type = protein
                         organism = Rubus sp.
SEQUENCE: 259
MTENVSISVN GQSQVPPGFR FHPTEEELLQ YYLRKKVSNQ SIDLDVICDV DLNKLEPWDI  60
QEKCKIGTTP QNDWYFFSHK DKKYPTGTRT NRATAAGFWK ATGRDKVISS NCRRIGMRKT 120
LVFYKGRAPH GQKSDWIMHE YRLDDNTSSI TNVSITVVGE AAEEGWVVCR IFKKKNLHKS 180
LSSPIMSTSI SSSITAEITR SSSQMFDDDD QDGAFEEMLQ YIGSRTCKEE INEHYHLHPI 240
NTDNSDNMNG YHDHGDRFLK LPSLESPNST SSQNGYQPII NHEDMVIDQN EGTIANQHLG 300
YQHVDDSASL TNWAALDRLV ASQLNGGHET GSSRQFSCLI EPTLNVYCTS TTDNELQLPS 360
TLRSSTSSNS SSKSYHATQP EYNNSEIDLW TTFGAARLQS SSPLSSSDAL CHVSNSPI   418

SEQ ID NO: 260           moltype = DNA  length = 1446
FEATURE                  Location/Qualifiers
source                   1..1446
                         mol_type = genomic DNA
                         organism = Rubus sp.
SEQUENCE: 260
atgtctgcgg aggatcatat gaatctatcc ataaatggtc agtcccaggt ccctcctggc   60
tttcgcttcc atccaaccga agaggagctt cttcactact atctcaggaa gaaagtttcc  120
tatgagagga ttgatcttga cgtcattcga gaggttgatc ttaacaagct tgagccatgg  180
gacattcaag gtactccagg cttcattccc ctcgttcttt agcttaaagt gattccactt  240
tccaacgagc taatcctaat tatcattagt atcgagattc aaaactagtt attataacat  300
gctagacggt ctgaaatgac tcattggttt gtggttttga catgtagaga agtgcaagat  360
aggttccacc ccacagaacg attggtattt cttcagccac aaagacaaga aatacctac   420
aggtactcga accaatcgcg caaccgctgc agggttttgg aaggctaccg gccgcgacaa  480
gatcatctac agcggcattc gaagaatcgg attgagaaag acgcttgtgt tttacaaggg  540
```

```
acgagctccg cacggacaaa agtctgattg gatcatgcat gaatacagac tagatgaaag  600
cagcagcagc agcagccttg acaccacagt atgctagcta ttaattttcg atctcttcaa  660
atagttctca tcggagacaa attatcaaac acttaattgg aatgcacttg attttctttc  720
ttgcaggttt ctagtttaat tggagagtca atgtccgaag atgggtgggt ggtttgcagg  780
gtcttcaaga agaagaacta ccagaaagcc ttggagagca caaaagcctc ctacccgatg  840
gactcatcaa acaaccaaat gctaccgggt ggttcgagaa acgacggcgt tgtcgatcag  900
attctcttgt acatggggaag gactagttgc aagctcgaaa accatgactc actccatgac  960
aggttcatgc atcttccaag gctcgagagc caaacttctc ttccctcact tgcggtccac  1020
ttcgatcatg accgtagctt caaagcttgt tatcatgctg agaccattga tgacatgctc  1080
atagaaacag atcatcaaca accttctcca acaacaaacc aacccaacga cccggttgat  1140
cacgacgacc ccaaaacaag gattgtaaat gactgggcta ctatccatca gctcgtggcc  1200
tctcaactca atggccatga agacacatca aagcacttgt cctgtttcgg tgacccaaac  1260
atggcctttt gttcttctcc tccttctaat gatgaggact tacagttgtc ctatccatat  1320
ctacgtccag gtagaaatatc acagaatcaa cccgaagtct acaacagcga gaacgatctg  1380
tggagcttca caaaatcgtc gccgtcgccg tcatcatcag acccattatg ccacctgtcg  1440
gtataa                                                              1446

SEQ ID NO: 261          moltype = AA  length = 396
FEATURE                 Location/Qualifiers
source                  1..396
                        mol_type = protein
                        organism = Rubus sp.
SEQUENCE: 261
MSAEDHMNLS INGQSQVPPG FRFHPTEEEL LHYYLRKKVS YERIDLDVIR EVDLNKLEPW  60
DIQEKCKIGS TPQNDWYFFS HKDKKYPTGT RTNRATAAGF WKATGRDKII YSGIRRIGLR  120
KTLVFYKGRA PHGQKSDWIM HEYRLDESSS SSSLDTTVSS LIGESMSEDG WVVCRVFKKK  180
NYQKALESPK ASYPMDSSNN QMLPGGSRND GVVDQILLYM GRTSCKLENH DSLHDRFMHL  240
PRLESQTSLP SLAVHFDHDR SFKACYHDQT IDDMLIETDH QQPSPTTNQP NDPVDHDDPK  300
TRIVNDWATI HQLVASQLNG HEDTSKHLSC FGDPNMAFCS SPPSNDEDLQ LSYPYLRPGR  360
ISQNQPEVYN SENDLWSFTK SSPSPSSSDP LCHLSV                            396

SEQ ID NO: 262          moltype = DNA  length = 1447
FEATURE                 Location/Qualifiers
source                  1..1447
                        mol_type = genomic DNA
                        organism = Rubus sp.
SEQUENCE: 262
atgtctgcag aggatcatat gaatctatcc ataaatggtc agtcccaggt ccctcctggc  60
tttcgcttcc atccaaccga agaggagctt cttcactact atctccaggaa gaaagtttcc  120
tatgagagga ttgatcttga cgtcattcga gaggttgatc ttaacaagct cgagccatgg  180
gacattcaag gtactcacgg cttcattccc ctcgttcttt agcttaaagt gattccactt  240
tccaacgagc taatcctaat tatcattagt atatatcgag attcaaaact agttattata  300
acatgctaga cggtctgaaa tgactcattg gtttgtggtt ttgacatgta gagaagtgca  360
agataggttc cacccacag aacgattggt atttcttcag ccacaaagac aagaaatacc  420
ctacaggtac tcgaaccaat cgcgcaaccg ctgcagggtt ttggaaggct accggccgcg  480
acaagatcat ctacagcggc attcgaagaa tcggattgag aaagacgcta gtgttttaca  540
agggacggtc tccgcacgga caaaagtcag attggatcat gcatgaatac agactagatg  600
aaagcagcag cagcagcctt gacaccacag tatgctagct attaattttc gatctcttca  660
aatagttctc atcggagaca attatcaaac acttaattg gaatgcactt gattttctttt  720
gttgcaggtt tctagttcaa ttggagagtc aatgtccgaa gatgggtggg tggtttgcag  780
agtcttcaag aagaagaact accagaaagc ctttggagagc ccaaaagcct cctaccggat  840
ggactcatca acaaccaaa tgctaccggg tggttcgaga acgacggcg ttgtcgatca  900
gattctcttg tacatgggaa ggactagttg caagctcgaa aaccatgact cactccatga  960
caggttcatg catcttccaa ggctcgagag ccaaacttct cttccttcac ttgcggtcca  1020
cttcgatcat gaccgtagct tcaaagcttg ttatcatgct cagaccattg atgacatgct  1080
catagaaaca gatcatcaac aaccttctcc aacaacaaac caacccaacg acccggttga  1140
tcatgacgac cccaaaacaa ggattgtaaa tgactgggct actatccatc agctcgtggc  1200
ctctcaactc aatggccatg aagacacatc aaagcacttg tcctgtttcg gtgacccaaa  1260
catggccttt tgttcttctc ctccttctaa tgatgaggac ttacagttgt cctatccata  1320
tctacgtcca ggtagaaat acacagaatca acccgaagtc tacaacagcg agaacgatct  1380
gtggagcttc acaaaatcgt cgccgtcgcc gtcatcatca gacccattat gccacctgtc  1440
ggtataa                                                             1447

SEQ ID NO: 263          moltype = AA  length = 395
FEATURE                 Location/Qualifiers
source                  1..395
                        mol_type = protein
                        organism = Rubus sp.
SEQUENCE: 263
MSAEDHMNLS INGQSQVPPG FRFHPTEEEL LHYYLRKKVS YERIDLDVIR EVDLNKLEPW  60
DIQEKCKIGS TPQNDWYFFS HKDKKYPTGT RTNRATAAGF WKATGRDKII YSGIRRIGLR  120
KTLVFYKGRA PHGQKSDWIM HEYRLDESSS SSLDTTVSSS IGESMSEDGW VVCRVFKKKN  180
YQKALESPKA SYPMDSSNNQ MLPGGSRNDG VVDQILLYMG RTSCKLENHD SLHDRFMHLP  240
RLESQTSLPS LAVHFDHDRS FKACYHDQTI DDMLIETDHQ QPSPTTNQPN DPVDHDDPKT  300
RIVNDWATIH QLVASQLNGH EDTSKHLSCF GDPNMAFCSS PPSNDEDLQL SYPYLRPGRI  360
SQNQPEVYNS ENDLWSFTKS SPSPSSSDPL CHLSV                              395

SEQ ID NO: 264          moltype = AA  length = 97
FEATURE                 Location/Qualifiers
```

```
source                   1..97
                         mol_type = protein
                         organism = Rubus sp.
SEQUENCE: 264
SITVVGEAAE EGWVVCRIFK KKNLHKSLSS PIMSTSISSS ITAEITRSSS QMFDDDDQEG    60
AFEEMLQYIG SRTCKEEINE HYHLHPINTG NSDNMNG                             97

SEQ ID NO: 265           moltype = AA   length = 77
FEATURE                  Location/Qualifiers
source                   1..77
                         mol_type = protein
                         organism = Rubus sp.
SEQUENCE: 265
EGWVVCRIFK KKNLHKSLSS PIMSTSISSS ITAEITRSSS QMFDDDDQEG AFEEMLQYIG    60
SRTCKEEINE HYHLHPI                                                   77

SEQ ID NO: 266           moltype = AA   length = 57
FEATURE                  Location/Qualifiers
source                   1..57
                         mol_type = protein
                         organism = Rubus sp.
SEQUENCE: 266
KKNLHKSLSS PIMSTSISSS ITAEITRSSS QMFDDDDQEG AFEEMLQYIG SRTCKEE       57

SEQ ID NO: 267           moltype = AA   length = 49
FEATURE                  Location/Qualifiers
source                   1..49
                         mol_type = protein
                         organism = Rubus sp.
SEQUENCE: 267
IFKKKNLHKS LSSPIMSTSI SSITAEITR SSSQMFDDDD QEGAFEEML                 49

SEQ ID NO: 268           moltype = AA   length = 15
FEATURE                  Location/Qualifiers
source                   1..15
                         mol_type = protein
                         organism = Rubus sp.
SEQUENCE: 268
SSSITAEITR SSSQM                                                     15

SEQ ID NO: 269           moltype = AA   length = 97
FEATURE                  Location/Qualifiers
source                   1..97
                         mol_type = protein
                         organism = Rubus sp.
SEQUENCE: 269
SITVVGEAAE EGWVVCRIFK KKNLHKSLSS PIMSTSISSS ITAEITRSSS QMFDDDDQDG    60
AFEEMLQYIG SRTCKEEINE HYHLHPINTD NSDNMNG                             97

SEQ ID NO: 270           moltype = AA   length = 77
FEATURE                  Location/Qualifiers
source                   1..77
                         mol_type = protein
                         organism = Rubus sp.
SEQUENCE: 270
EGWVVCRIFK KKNLHKSLSS PIMSTSISSS ITAEITRSSS QMFDDDDQDG AFEEMLQYIG    60
SRTCKEEINE HYHLHPI                                                   77

SEQ ID NO: 271           moltype = AA   length = 57
FEATURE                  Location/Qualifiers
source                   1..57
                         mol_type = protein
                         organism = Rubus sp.
SEQUENCE: 271
KKNLHKSLSS PIMSTSISSS ITAEITRSSS QMFDDDDQDG AFEEMLQYIG SRTCKEE       57

SEQ ID NO: 272           moltype = AA   length = 49
FEATURE                  Location/Qualifiers
source                   1..49
                         mol_type = protein
                         organism = Rubus sp.
SEQUENCE: 272
IFKKKNLHKS LSSPIMSTSI SSITAEITR SSSQMFDDDD QDGAFEEML                 49

SEQ ID NO: 273           moltype = AA   length = 36
FEATURE                  Location/Qualifiers
source                   1..36
                         mol_type = protein
                         organism = Rubus sp.
```

```
SEQUENCE: 273
LSSPIMSTSI SSSITAEITR SSSQMFDDDD QDGAFE                                36

SEQ ID NO: 274          moltype = AA  length = 417
FEATURE                 Location/Qualifiers
source                  1..417
                        mol_type = protein
                        organism = synthetic construct
VARIANT                 48
                        note = Xaa may be Cys or Ser
VARIANT                 107
                        note = Xaa may be Met or Val
VARIANT                 160
                        note = Xaa may be Glu or Asp
VARIANT                 246
                        note = Xaa may be Lys or Asn
VARIANT                 249
                        note = Xaa may be Gly or Asp
VARIANT                 262
                        note = Xaa may be Ser or Arg
VARIANT                 284
                        note = Xaa may be Met or Leu
VARIANT                 326
                        note = Xaa may be Val or Gly
VARIANT                 336
                        note = Xaa may be Ser, Thr, or Ala
VARIANT                 337
                        note = Xaa may be Cys or Phe
VARIANT                 350
                        note = Xaa may be Ile or Thr
VARIANT                 376
                        note = Xaa may be Ala or Ser
VARIANT                 381
                        note = Xaa may be Cys or Tyr
VARIANT                 401
                        note = Xaa may be Phe or Ser
SEQUENCE: 274
MTENVSISVN GQSQVPPGFR FHPTEEELLQ YYLRKKVSNQ SIDLDVIXDV DLNKLEPWDI    60
QEKCKIGTTP QNDWYFFSHK DKKYPTGTRT NRATAAGFWK ATGRDKXISS NCRRIGMRKT   120
LVFYKGRAPH GQKSDWIMHE YRLDDNTSNI TNVSITVVGX AAEEGWVVCR IFKKKNLHKS   180
LSSPIMSTSI SSSITEEITR SSSQMFDDDH EGAFEEMLQY IGSRTCKEEN NEHYHLHPIN   240
TGNSDXINXY HDHGDRFLKL PXLESPNSTS SQNGYQPIIS HEDXVIDQNE GTIANQHLGY   300
QHVDDSASLT NWAALDRLVA SQLNGXHETG SSRQFXXLIE PIRDVYCTSX TDNELQLPST   360
LRSSTSSNSS SKSYHXTQPE XNNSEIDLWT TFAAARLQSS XPLSSSDALC HVSNAPI      417

SEQ ID NO: 275          moltype = AA  length = 418
FEATURE                 Location/Qualifiers
source                  1..418
                        mol_type = protein
                        organism = synthetic construct
VARIANT                 48
                        note = Xaa may be Cys or Ser
VARIANT                 107
                        note = Xaa may be Met or Val
VARIANT                 149
                        note = Xaa may be Ser or Asn
VARIANT                 160
                        note = Xaa may be Glu or Asp
VARIANT                 196
                        note = Xaa may be Ala or Glu
VARIANT                 209
                        note = Xaa may be present or absent and when present is Asp
VARIANT                 211
                        note = Xaa may be Gln or His
VARIANT                 212
                        note = Xaa may be Glu or Asp
VARIANT                 230
                        note = Xaa may be Ile or Asn
VARIANT                 243
                        note = Xaa may be Gly or Asp
VARIANT                 247
                        note = Xaa may be Lys or Asn
VARIANT                 248
                        note = Xaa may be Met or Ile
VARIANT                 250
                        note = Xaa may be Gly or Asp
VARIANT                 263
                        note = Xaa may be Ser or Arg
VARIANT                 281
```

```
VARIANT          285
                 note = Xaa may be Ser or Asn
VARIANT          327
                 note = Xaa may be Met or Leu
VARIANT          337
                 note = Xaa may be Val or Gly
VARIANT          338
                 note = Xaa may be Ser, Thr, or Ala
VARIANT          343
                 note = Xaa may be Cys or Phe
VARIANT          344
                 note = Xaa may be Thr or Ile
VARIANT          345
                 note = Xaa may be Leu or Arg
VARIANT          351
                 note = Xaa may be Asn or Asp
VARIANT          377
                 note = Xaa may be Thr or Ile
VARIANT          382
                 note = Xaa may be Ala or Ser
VARIANT          394
                 note = Xaa may be Tyr or Cys
VARIANT          402
                 note = Xaa may be Gly or Ala
VARIANT          416
                 note = Xaa may be Ser or Phe
                 note = Xaa may be Ala or Ser
SEQUENCE: 275
MTENVSISVN GQSQVPPGFR FHPTEEELLQ YYLRKKVSNQ SIDLDVIXDV DLNKLEPWDI    60
QEKCKIGTTP QNDWYFFSHK DKKYPTGTRT NRATAAGFWK ATGRDKXISS NCRRIGMRKT   120
LVFYKGRAPH GQKSDWIMHE YRLDDNTSXI TNVSITVVGX AAEEGWVVCR IFKKKNLHKS   180
LSSPIMSTSI SSSITXEITR SSSQMFDDXD XXGAFEEMLQ YIGSRTCKEE XNEHYHLHPI   240
NTXNSDXXNX YHDHGDRFLK LPXLESPNST SSQNGYQPII XHEDXVIDQN EGTIANQHLG   300
YQHVDDSASL TNWAALDRLV ASQLNGXHET GSSRQFXXLI EPXXXVYCTS XTDNELQLPS   360
TLRSSTSSNS SSKSYHXTQP EXNNSEIDLW TTFXAARLQS SXPLSSSDAL CHVSNXPI    418

SEQ ID NO: 276           moltype = AA  length = 397
FEATURE                  Location/Qualifiers
source                   1..397
                         mol_type = protein
                         organism = synthetic construct
VARIANT                  151
                         note = Xaa may be present or absent and when present is Ser
VARIANT                  208
                         note = Xaa may be Ser or Met
VARIANT                  265
                         note = Xaa may be Gly or Ala
SEQUENCE: 276
MSAEDHMNLS INGQSQVPPG FRFHPTEEEL LHYYLRKKVS YERIDLDVIR EVDLNKLEPW    60
DIQEKCKIGS TPQNDWYFFS HKDKKYPTGT RTNRATAAGF WKATGRDKII YSGIRRIGLR   120
KTLVFYKGRA PHGQKSDWIM HEYRLDESSS XSSSLDTTVS SSIGESMSED GWVVCRVFKK   180
KNYQKALESP KSSYPMDSSN NQMLPGGXRN DGVVDQILLY MGRTSCKLEN HDSLHDRFMH   240
LPRLESQTSL PSLAVHFDHD RSFKXCYHDQ TIDDMLIETD HQQPSPTTNQ PNDPVDHDDP   300
KTRIVNDWAT IHQLVASQLN GHEDTSKHLS CFGDPNMAFC SSPPSNDEDL QLSYPYLRPG   360
RISQNQPEVY NSENDLWSFT KSSPSPSSSD PLCHLSV                            397

SEQ ID NO: 277           moltype = AA  length = 397
FEATURE                  Location/Qualifiers
source                   1..397
                         mol_type = protein
                         organism = synthetic construct
VARIANT                  150
                         note = Xaa may be present or absent and when present is Ser
VARIANT                  151
                         note = Xaa may be present or absent and when present is Ser
VARIANT                  162
                         note = Xaa may be Ser or Leu
VARIANT                  192
                         note = Xaa may be Ser or Ala
VARIANT                  208
                         note = Xaa may be Met or Ser
VARIANT                  265
                         note = Xaa may be Ala or Gly
SEQUENCE: 277
MSAEDHMNLS INGQSQVPPG FRFHPTEEEL LHYYLRKKVS YERIDLDVIR EVDLNKLEPW    60
DIQEKCKIGS TPQNDWYFFS HKDKKYPTGT RTNRATAAGF WKATGRDKII YSGIRRIGLR   120
KTLVFYKGRA PHGQKSDWIM HEYRLDESSX XSSSLDTTVS SXIGESMSED GWVVCRVFKK   180
KNYQKALESP KXSYPMDSSN NQMLPGGXRN DGVVDQILLY MGRTSCKLEN HDSLHDRFMH   240
LPRLESQTSL PSLAVHFDHD RSFKXCYHDQ TIDDMLIETD HQQPSPTTNQ PNDPVDHDDP   300
```

```
KTRIVNDWAT IHQLVASQLN GHEDTSKHLS CFGDPNMAFC SSPPSNDEDL QLSYPYLRPG   360
RISQNQPEVY NSENDLWSFT KSSPSPSSSD PLCHLSV                           397

SEQ ID NO: 278          moltype = AA  length = 417
FEATURE                 Location/Qualifiers
source                  1..417
                        mol_type = protein
                        organism = synthetic construct
VARIANT                 48
                        note = Xaa may be any amino acid residue
VARIANT                 107
                        note = Xaa may be any amino acid residue
VARIANT                 160
                        note = Xaa may be any amino acid residue
VARIANT                 246
                        note = Xaa may be any amino acid residue
VARIANT                 249
                        note = Xaa may be any amino acid residue
VARIANT                 262
                        note = Xaa may be any amino acid residue
VARIANT                 284
                        note = Xaa may be any amino acid residue
VARIANT                 326
                        note = Xaa may be any amino acid residue
VARIANT                 336
                        note = Xaa may be any amino acid residue
VARIANT                 337
                        note = Xaa may be any amino acid residue
VARIANT                 350
                        note = Xaa may be any amino acid residue
VARIANT                 376
                        note = Xaa may be any amino acid residue
VARIANT                 381
                        note = Xaa may be any amino acid residue
VARIANT                 401
                        note = Xaa may be any amino acid residue
SEQUENCE: 278
MTENVSISVN GQSQVPPGFR FHPTEEELLQ YYLRKKVSNQ SIDLDVIXDV DLNKLEPWDI   60
QEKCKIGTTP QNDWYFFSHK DKKYPTGTRT NRATAAGFWK ATGRDKXISS NCRRIGMRKT   120
LVFYKGRAPH GQKSDWIMHE YRLDDNTSNI TNVSITVVGX AAEEGWVVCR IFKKKNLHKS   180
LSSPIMSTSI SSSITEEITR SSSQMFDDDH EGAFEEMLQY IGSRTCKEEN NEHYHLHPIN   240
TGNSDXINXY HDHGDRFLKL PXLESPNSTS SQNGYQPIIS HEDXVIDQNE GTIANQHLGY   300
QHVDDSASLT NWAALDRLVA SQLNGXHETG SSRQFXXLIE PIRDVYCTSX TDNELQLPST   360
LRSSTSSNSS SKSYHXTQPE XNNSEIDLWT TFAAARLQSS XPLSSSDALC HVSNAPI     417

SEQ ID NO: 279          moltype = AA  length = 418
FEATURE                 Location/Qualifiers
source                  1..418
                        mol_type = protein
                        organism = synthetic construct
VARIANT                 48
                        note = Xaa may be any amino acid residue
VARIANT                 107
                        note = Xaa may be any amino acid residue
VARIANT                 160
                        note = Xaa may be any amino acid residue
VARIANT                 149
                        note = Xaa may be any amino acid residue
VARIANT                 196
                        note = Xaa may be any amino acid residue
VARIANT                 209
                        note = Xaa may be present or absent and when present may be
                          any amino acid residue
VARIANT                 211
                        note = Xaa may be any amino acid residue
VARIANT                 212
                        note = Xaa may be any amino acid residue
VARIANT                 230
                        note = Xaa may be any amino acid residue
VARIANT                 243
                        note = Xaa may be any amino acid residue
VARIANT                 247
                        note = Xaa may be any amino acid residue
VARIANT                 248
                        note = Xaa may be any amino acid residue
VARIANT                 250
                        note = Xaa may be any amino acid residue
VARIANT                 263
                        note = Xaa may be any amino acid residue
```

```
VARIANT                 281
                        note = Xaa may be any amino acid residue
VARIANT                 285
                        note = Xaa may be any amino acid residue
VARIANT                 327
                        note = Xaa may be any amino acid residue
VARIANT                 337
                        note = Xaa may be any amino acid residue
VARIANT                 338
                        note = Xaa may be any amino acid residue
VARIANT                 343
                        note = Xaa may be any amino acid residue
VARIANT                 344
                        note = Xaa may be any amino acid residue
VARIANT                 345
                        note = Xaa may be any amino acid residue
VARIANT                 351
                        note = Xaa may be any amino acid residue
VARIANT                 377
                        note = Xaa may be any amino acid residue
VARIANT                 382
                        note = Xaa may be any amino acid residue
VARIANT                 394
                        note = Xaa may be any amino acid residue
VARIANT                 402
                        note = Xaa may be any amino acid residue
VARIANT                 416
                        note = Xaa may be any amino acid residue
SEQUENCE: 279
MTENVSISVN GQSQVPPGFR FHPTEEELLQ YYLRKKVSNQ SIDLDVIXDV DLNKLEPWDI   60
QEKCKIGTTP QNDWYFFSHK DKKYPTGTRT NRATAAGFWK ATGRDKXISS NCRRIGMRKT  120
LVFYKGRAPH GQKSDWIMHE YRLDDNTSXI TNVSITVVGX AAEEGWVVCR IPKKKNLHKS  180
LSSPIMSTSI SSSITXEITR SSSQMFDDXD XXGAFEEMLQ YIGSRTCKEE XNEHYHLHPI  240
NTXNSDXXNX YHDHGDRFLK LPXLESPNST SSQNGYQPII XHEDXVIDQN EGTIANQHLG  300
YQHVDDSASL TNWAALDRLV ASQLNGXHET GSSRQFXXLI EPXXXVYCTS XTDNELQLPS  360
TLRSSTSSNS SSKSYHXTQP EXNNSEIDLW TTFXAARLQS SXPLSSSDAL CHVSNXPI    418

SEQ ID NO: 280          moltype = AA  length = 397
FEATURE                 Location/Qualifiers
source                  1..397
                        mol_type = protein
                        organism = synthetic construct
VARIANT                 151
                        note = Xaa may be present or absent and when present is any
                         amino acid residue
VARIANT                 208
                        note = Xaa may be any amino acid residue
VARIANT                 265
                        note = Xaa may be any amino acid residue
SEQUENCE: 280
MSAEDHMNLS INGQSQVPPG FRFHPTEEEL LHYYLRKKVS YERIDLDVIR EVDLNKLEPW   60
DIQEKCKIGS TPQNDWYFFS HKDKKYPTGT RTNRATAAGF WKATGRDKII YSGIRRIGLR  120
KTLVFYKGRA PHGQKSDWIM HEYRLDESSS XSSSLDTTVS SSIGESMSED GWVVCRVFKK  180
KNYQKALESP KSSYPMDSSN NQMLPGGXRN DGVVDQILLY MGRTSCKLEN HDSLHDRFMH  240
LPRLESQTSL PSLAVHFDHD RSFKXCYHDQ TIDDMLIETD HQQPSPTTNQ PNDPVDHDDP  300
KTRIVNDWAT IHQLVASQLN GHEDTSKHLS CFGDPNMAFC SSPPSNDEDL QLSYPYLRPG  360
RISQNQPEVY NSENDLWSFT KSSPSPSSSD PLCHLSV                           397

SEQ ID NO: 281          moltype = AA  length = 397
FEATURE                 Location/Qualifiers
source                  1..397
                        mol_type = protein
                        organism = synthetic construct
VARIANT                 150
                        note = Xaa may be present or absent and when present is any
                         amino acid residue
VARIANT                 151
                        note = Xaa may be present or absent and when present is any
                         amino acid residue
VARIANT                 162
                        note = Xaa may be any amino acid residue
VARIANT                 192
                        note = Xaa may be any amino acid residue
VARIANT                 208
                        note = Xaa may be any amino acid residue
VARIANT                 265
                        note = Xaa may be any amino acid residue
SEQUENCE: 281
MSAEDHMNLS INGQSQVPPG FRFHPTEEEL LHYYLRKKVS YERIDLDVIR EVDLNKLEPW   60
```

```
DIQEKCKIGS TPQNDWYFFS HKDKKYPTGT RTNRATAAGF WKATGRDKII YSGIRRIGLR    120
KTLVFYKGRA PHGQKSDWIM HEYRLDESSX XSSSLDTTVS SXIGESMSED GWVVCRVFKK    180
KNYQKALESP KXSYPMDSSN NQMLPGGXRN DGVVDQILLY MGRTSCKLEN HDSLHDRFMH    240
LPRLESQTSL PSLAVHFDHD RSFKXCYHDQ TIDDMLIETD HQQPSPTTNQ PNDPVDHDDP    300
KTRIVNDWAT IHQLVASQLN GHEDTSKHLS CFGDPNMAFC SSPPSNDEDL QLSYPYLRPG    360
RISQNQPEVY NSENDLWSFT KSSPSPSSSD PLCHLSV                             397

SEQ ID NO: 282          moltype = AA  length = 19
FEATURE                 Location/Qualifiers
source                  1..19
                        mol_type = protein
                        organism = Rubus sp.
SEQUENCE: 282
VPPGFRFHPT EEELLQYYL                                                 19

SEQ ID NO: 283          moltype = AA  length = 19
FEATURE                 Location/Qualifiers
source                  1..19
                        mol_type = protein
                        organism = Rubus sp.
SEQUENCE: 283
VPPGFRFHPT EEELLHYYL                                                 19
```